US010725023B2

(12) United States Patent
Abassi et al.

(10) Patent No.: US 10,725,023 B2
(45) Date of Patent: *Jul. 28, 2020

(54) METHOD OF MEASURING CELL-SUBSTRATE IMPEDANCE IN LIVING CELLS TO IDENTIFY COMPOUNDS AFFECTING RECEPTOR TYROSINE KINASE (RTK) ACTIVITY AND PATHWAYS FOR THE TREATMENT OF CANCER

(71) Applicant: ACEA Biosciences, Inc., San Diego, CA (US)

(72) Inventors: Yama A. Abassi, San Diego, CA (US); Naichen Yu, San Diego, CA (US); Josephine Atienza, San Diego, CA (US); Xiao Xu, San Diego, CA (US); Xiaobo Wang, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/237,382

(22) Filed: Dec. 31, 2018

(65) Prior Publication Data
US 2019/0195861 A1 Jun. 27, 2019

Related U.S. Application Data

(60) Continuation of application No. 15/613,052, filed on Jun. 2, 2017, now Pat. No. 10,168,318, which is a continuation of application No. 14/541,024, filed on Nov. 13, 2014, now Pat. No. 10,067,121, which is a division of application No. 13/569,156, filed on Aug. 7, 2012, now Pat. No. 8,916,357, which is a division of application No. 11/198,831, filed on Aug. 4, 2005, now Pat. No. 8,263,375, which is a continuation-in-part of application No. PCT/US2005/004481, filed on Feb. 9, 2005, and a continuation-in-part of application No. 11/055,639, filed on Feb. 9, 2005, now Pat. No. 7,560,269, and a continuation-in-part of application No. PCT/US2004/037696, filed on Nov. 12, 2004, said application No. 11/055,639 is a continuation-in-part of application No. 10/987,732, filed on Nov. 12, 2004, now Pat. No. 7,192,752, which is a continuation-in-part of application No. 10/705,447, filed on Nov. 10, 2003, now Pat. No. 7,470,533, and a continuation-in-part of application No. 10/705,615, filed on Nov. 10, 2003, now Pat. No. 7,459,303, said application No. 10/705,447 is a continuation of application No. PCT/US03/22557, filed on Jul. 18, 2003, and a continuation of application No. PCT/US03/22537, filed on Jul. 18, 2003, said (Continued)

(51) Int. Cl.
*G01N 33/50* (2006.01)
*G01N 33/543* (2006.01)
*G01N 27/02* (2006.01)
*C12Q 1/00* (2006.01)

(52) U.S. Cl.
CPC ........ *G01N 33/5041* (2013.01); *C12Q 1/002* (2013.01); *G01N 27/021* (2013.01); *G01N 33/5014* (2013.01); *G01N 33/5438* (2013.01); *G01N 2333/4716* (2013.01); *G01N 2333/705* (2013.01); *G01N 2333/91205* (2013.01); *G01N 2500/04* (2013.01); *G01N 2500/10* (2013.01)

(58) Field of Classification Search
CPC .......... G01N 33/5014; G01N 33/5041; G01N 33/5438; G01N 27/021; G01N 2500/04; G01N 2500/10; G01N 2333/705; G01N 2333/4716; G01N 2333/91205; C12Q 1/002
See application file for complete search history.

(56) References Cited

U.S. PATENT DOCUMENTS 2,656,508 A 10/1953 Coulter
3,259,842 A 7/1966 Coulter et al.
(Continued)

FOREIGN PATENT DOCUMENTS

EP 1138758 A1 10/2001
EP 1195432 B1 6/2004
(Continued)

OTHER PUBLICATIONS

EP05786773 Extended European Search Report dated Mar. 21, 2013.
(Continued)

*Primary Examiner* — Robert S Landsman
(74) *Attorney, Agent, or Firm* — Wagenknecht IP Law Group PC

(57) ABSTRACT

A method of identifying a therapeutic compound for treating cancer in a human subject, the method including: providing a device that measures cell-substrate impedance; culturing cancer cells in the at least two wells, wherein the cancer cells are obtained from a human subject and have a receptor tyrosine kinase (RTK) pathway; adding to a first well a proposed therapeutic compound that affects an RTK pathway and an RTK stimulating factor for the RTK pathway to form a test well, and adding to another well the RTK stimulating factor to form a control well; continuously monitoring cell-substrate impedance of the at least two wells; and determining a difference in impedance or optionally in cell index between the test well and control well; and if significantly different, concluding the proposed therapeutic compound is therapeutically active in the RTK pathway within the cancer cells of the human subject.

15 Claims, 67 Drawing Sheets

Related U.S. Application Data application No. 10/705,615 is a continuation of application No. PCT/US03/22537.

(60) Provisional application No. 60/689,422, filed on Jun. 10, 2005, provisional application No. 60/660,898, filed on Mar. 10, 2005, provisional application No. 60/660,829, filed on Mar. 10, 2005, provisional application No. 60/647,189, filed on Jan. 26, 2005, provisional application No. 60/647,075, filed on Jan. 26, 2005, provisional application No. 60/630,071, filed on Nov. 22, 2004, provisional application No. 60/614,601, filed on Sep. 29, 2004, provisional application No. 60/613,872, filed on Sep. 27, 2004, provisional application No. 60/598,608, filed on Aug. 4, 2004, provisional application No. 60/598,609, filed on Aug. 4, 2004, provisional application No. 60/548,713, filed on Feb. 27, 2004, provisional application No. 60/542,927, filed on Feb. 9, 2004, provisional application No. 60/519,567, filed on Nov. 12, 2003, provisional application No. 60/469,572, filed on May 9, 2003, provisional application No. 60/435,400, filed on Dec. 20, 2002.

(56) References Cited

U.S. PATENT DOCUMENTS

| | | |
|---|---|---|
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,559,310 A | 12/1985 | Cantor et al. |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin, Jr. |
| 5,514,555 A | 5/1996 | Springer et al. |
| 5,563,067 A | 10/1996 | Sugihara et al. |
| 5,601,997 A | 2/1997 | Tchao |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenback et al. |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti et al. |
| 6,368,851 B1 | 4/2002 | Baumann et al. |
| 6,376,233 B1 | 4/2002 | Wolf et al. |
| 6,377,057 B1 | 4/2002 | Borkholder et al. |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Mueller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhullar et al. |
| 7,510,699 B2 | 3/2009 | Black et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadter et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Wang et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 9,399,787 B2 | 7/2016 | Abassi et al. |
| 9,612,234 B2 | 4/2017 | Li et al. |
| 9,625,472 B2 | 4/2017 | Ku et al. |
| 9,709,548 B2 | 7/2017 | Wang et al. |
| 10,012,636 B2 | 7/2018 | Wang et al. |
| 10,067,121 B2 | 9/2018 | Abassi et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge et al. |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2004/0152067 A1 | 8/2004 | Wang et al. |
| 2005/0014130 A1 | 1/2005 | Liu et al. |
| 2005/0153425 A1 | 7/2005 | Xu et al. |
| 2005/0182447 A1 | 8/2005 | Schecter |
| 2005/0287065 A1 | 12/2005 | Suddarth et al. |
| 2006/0023559 A1 | 2/2006 | Xu et al. |
| 2006/0050596 A1 | 3/2006 | Abassi et al. |
| 2006/0057771 A1 | 3/2006 | Kovacs et al. |
| 2006/0121446 A1 | 6/2006 | Abassi et al. |
| 2006/0161073 A1 | 7/2006 | Singer |
| 2006/0216203 A1 | 9/2006 | Fuller et al. |
| 2006/0240490 A1 | 10/2006 | Lee |

(56) References Cited

U.S. PATENT DOCUMENTS

| | | |
|---|---|---|
| 2006/0252054 A1 | 11/2006 | Lin et al. |
| 2007/0042347 A1 | 2/2007 | Rosen et al. |
| 2007/0087333 A1 | 4/2007 | Gruters et al. |
| 2007/0172939 A1 | 7/2007 | Xu et al. |
| 2007/0212423 A1 | 9/2007 | Epstein et al. |
| 2008/0190783 A1 | 8/2008 | Hyland |
| 2008/0286750 A1 | 11/2008 | Xu et al. |
| 2009/0017465 A1 | 1/2009 | Xu |
| 2009/0142790 A1 | 6/2009 | Fang et al. |
| 2009/0155821 A1 | 6/2009 | Kunich et al. |
| 2009/0241698 A1 | 10/2009 | Biksacky |
| 2009/0325213 A1 | 12/2009 | Gambari et al. |
| 2010/0029506 A1 | 2/2010 | Wang et al. |
| 2011/0039294 A1 | 2/2011 | Wang et al. |
| 2011/0231103 A1 | 9/2011 | Fang |
| 2011/0300569 A1 | 12/2011 | Li et al. |
| 2012/0142031 A1 | 6/2012 | Ku et al. |
| 2012/0295253 A1 | 11/2012 | Abassi et al. |
| 2012/0322050 A1 | 12/2012 | Abassi et al. |
| 2013/0123136 A1 | 5/2013 | Abassi et al. |
| 2014/0203818 A1 | 7/2014 | Wang et al. |
| 2015/0125894 A1 | 5/2015 | Laing et al. |
| 2015/0185206 A1 | 7/2015 | Abassi et al. |
| 2015/0231634 A1 | 8/2015 | Szita et al. |
| 2017/0205391 A1 | 7/2017 | Li et al. |
| 2017/0269062 A1 | 9/2017 | Abassi et al. |
| 2017/0315131 A1 | 11/2017 | Xu et al. |
| 2017/0370907 A1 | 12/2017 | Abassi et al. |
| 2018/0246079 A1 | 8/2018 | Wang et al. |

FOREIGN PATENT DOCUMENTS

| | | |
|---|---|---|
| EP | 1040345 B1 | 3/2006 |
| EP | 2213721 | 8/2010 |
| EP | 2291645 | 9/2015 |
| WO | 1996/001836 A1 | 1/1996 |
| WO | 1999/066329 A1 | 12/1999 |
| WO | 2000/037628 A1 | 6/2000 |
| WO | 2000/070343 A2 | 11/2000 |
| WO | 2000/071669 A1 | 11/2000 |
| WO | 2001/025769 A3 | 4/2001 |
| WO | 2001/038873 A3 | 5/2001 |
| WO | 2001/079529 A1 | 10/2001 |
| WO | 2002/004943 A3 | 1/2002 |
| WO | 2002/042766 A3 | 5/2002 |
| WO | 2003/016887 A3 | 2/2003 |
| WO | 2004/010103 A2 | 1/2004 |
| WO | 2005/005979 A1 | 1/2005 |
| WO | 2005/047482 A2 | 5/2005 |
| WO | 2005/077104 A2 | 8/2005 |
| WO | 2006/017762 A2 | 2/2006 |
| WO | 2009/137440 A1 | 11/2009 |
| WO | 2010/129725 A1 | 11/2010 |
| WO | 2011/146531 A1 | 11/2011 |
| WO | 2012/043820 A1 | 4/2012 |
| WO | 2014/085727 A1 | 6/2014 |
| WO | 2017/068421 A1 | 4/2017 |
| WO | 2017/087945 A1 | 5/2017 |

OTHER PUBLICATIONS

EP05852157 Extended European Search Report dated Sep. 13, 2011.
EP058122680 Extended European Search Report dated Sep. 7, 2011.
EP03748948 Extended European Search Report dated Mar. 12, 2007.
EP09743420 European Search Report dated Nov. 26, 2013.
EP10772804.0 Extended European Search Report dated Oct. 27, 2017.
PCT/US2009/033801 International Search Report and Written Opinion dated Jul. 9, 2010.
PCT/US2009/042787 International Search Report and Written Opinion dated Jun. 24, 2009.
PCT/US2011/036877 International Search Report dated Sep. 2, 2011.
PCT/US2013/072439 International Search Report dated Feb. 19, 2014.
PCT/US2005/034561 International Preliminary Report on Patentability dated Mar. 27, 2007.
PCT/US2005/034561 International Search Report dated Sep. 27, 2006.
PCT/US2005/027943 International Preliminary Report on Patentability dated Apr. 11, 2007.
PCT/US2005/027943 International Search Report and Written Opinion dated Mar. 21, 2007.
PCT/US2004/037696 International Search Report dated May 16, 2005.
PCT/US2005/04481 International Search Report dated Sep. 12, 2005.
PCT/US2016/063066 ISR and WO mailed Jan. 30, 2017.
PCT/US2018/044774 ISR and WO mailed Oct. 23, 2018.
Miyata et al. "New Wound-Healing Model Using Cultured Corneal Endothelial Cells." Japan Journal of Opthalmology, 1990, 34:257-266.
Mohr et al. "Performance of a Thin Film Microelectrode Array for Monitoring Electrogenic Cells in Vitro." Sensors and Actuators, B34:265-269 (1996).
Nieher, Erwin, "Molecular Biology Meets Microelectronics." Nature Biotechnology, 2001; 19:114.
Nierurkar et al. "The Use of Surfactants to Enhance the Permeability of Peptides Through Caco-2 Cells by Inhibition of an Apically Polarized Efflux System." Pharmaceutical Research, 1996,13(4):528-534.
Nicolazzi et al. "Cationic Lipids for Transfection." Current Medicinal Chemistry, 2003, 10:1263-1277.
Oka et al. "A New Planar Multielectrode Array for Extracellular Recording: Application to Hippocampal Acute Slice." Journal of Neuroscience Methods, 1999, 93:61-67, Elsevier Science, B.V.
Ong et al. "Remote Query Resonant-Circuit Sensors for Monitoring of Bacterial Growth: Application to Food Quality Control." Sensors 2002; 2:219-232.
Pancrazio et al. "Portable Cell-Based Biosensor System for Toxin Detection." Sensors and Actuators 1998; 53:179-185.
Patolsky et al. "Detection of Single-Base DNA Mutations by Enzyme-Amplified Electronic Transduction." Nature Biotechnology, 2001, 19:253-257.
Pethig et al. "Positive and Negative Dielectrophoretic Collection of Colloidal Particles Using Interdigitated Castellated Microelectrodes." Applied Physics, 1992, 24:881-888.
Qiu et al. "Real-Time Monitoring Primary Cardiomyocyte Adhesion Based on Electrochemical Impedance Spectroscopy and Electrical Cell-Substrate Impedance Sensing" Analytical Chemistry, 2008, 80:990-996.
Rabow et al. "Mining the National Cancer Institute's Tumor-Screening Database: Identification of Compounds with Similar Cellular Activities." Journal of Medicinal Chemistry, 2002, 45:818-840.
Richards et al. "A Modified Microchamber Method for Chemotaxis and Chemokinesis." Immunological Communications, 1984, 13(1):49-62.
Rishpon et al. "An Amperometric Enzyme-channeling Immunosensor." Biosensors & Bioelectronics, 1997, 12(3):195-204.
Simpson et al. "Whole-Cell Biocomputing." Trends in Biotechnology, 2001, 19(9):317-323.
Slaughter et al. "Artificial Neural Network for Temporal Impedance Recognition of Neurotoxins." 2006 International Joint Conference on Neural Networks Jul. 16-21, 2006: 2001-2008.
Sohn et al. "Capacitance Cytometry: Measuring Biological Cells One by One." Proceedings of the National Academy of Sciences, 2000, 97(20):10687-10690.
Steinem et al. "Impedance and Shear Wave Resonance Analysis of Ligand-Receptor Interactions at Functionalized Surfaces and of Cell Monolayers." Biosensors & Bioelectronics, 1997, 12(8):787-808.

(56) References Cited

OTHER PUBLICATIONS

Stenger et al. "Detection of Physiologically Active Compounds Using Cell-Based Biosensors." Trends in Biotechnology, 2001; 19(8):304-309.
Svetlicic et al. "Charge Displacement by Adhesion and Spreading of a Cell." Bioelectrochemistry, 2000, 53:79-86.
Tiruppathi et al. "Electrical Method for Detection of Endothelial Cell Shape Change in Time: Assessment of Endothelial Barrier Function." Proceedings of the National Academy of Sciences, USA, 1992, 89:7919-7923.
Wang et al. "Selective Dielectrophoretic Confinement of Bioparticles in Potential Energy Wells." Applied Physics, 1993, 26:1278-1285.
Wang et al. "Cell Separation by Dielectrophoretic Field-Flow-Fractionation." Analyitcal Chemistry., 2000, 72:832-839.
Wang et al. "Dielectrophoretic Manipulation of Cells with Spiral Electrodes." Biophysical Journal, 1997, 72:1887-1899.
Wang et al. "Separation of Polystyrene Microbeads Using Dielectrophoretic/Gravitational Field-Flow-Fractionation." Biophysical Journal, 1998, 74:2689-2701.
Wang et al. "Electronic Manipulation of Cells on Microchip-Based Devices." in Biochip Technology (eds), 2001, pp. 135-159, Harwood Academic Publishers, PA, USA.
Wang et al. "A Theoretical Method of Electrical Field Analysis for Dielectrophoretic Electrode Arrays Using Green's Theorem" Journal of Phyics D: Applied Physics, 1996; 29:1649-1660.
Warburg Ueber die Polarisationscapacitat des Platins. Annals of Physics, 6:125-135 (1901).
Wegener et al. "Electric Cell-Substrate Impedance Sensing (ECIS) as Noninvasive Means to Monitor the Kinetics of Cell Spreading to Artificial Surfaces." Experimental Cell Research 2000; 259:158-166.
Wegener et al., Use of Electrochemical Impedance Measurements to Monitor Beta-Adrenergic Stimulation of Bovine Aortic Endothelial Cells. European Journal of Physiology, 437:925-934 (1999).
Wolf et al. "Monitoring of Cellular Signalling and Metabolism with Modular Sensor-Technique: The PhysioControl-Microsystem (PCM)." Biosensors and Bioelectronics 1998; 13:501-509.
Xiao et al. "Assessment of Cytotoxicity Using Electric Cell-Substrate Impedance Sensing: Concentration and Time Response Function Approach." Analytical Chemistry, 2002, 74:5748-5753.
Xiao et al. "An In-Depth Analysis of Electric Cell-Substrate Impedance Sensing to Study the Attachment and Spreading of Mammalian Cells." Analytical Chemistry, 2002; 74(6):1333-1339.
Xiao et al. "On-Line Monitoring of Cell Growth and Cytotoxicity Using Electric Cell-Substrate Impedance Sensing (ECIS)." Biotechnology Progress, 2003; 19:1000-1005.
Xing et al. "Dynamic Monitoring of Cytotoxicity on Microelectronic Sensors" Chemical Research in Toxicology., 2005, 18 (2):154-161.
Yamauchi et al. "Spatially and Temporally Controlled Gene Transfer by Electroporation into Adherent Cells on Plasmid DNA-Loaded Electrodes." Nucleic Acids Research, 2004, 32(22):1-8.
Yang et al. "Celli Separation on Microfabricated Electrodes Using Dielectrophoretic/Gravitational field-flow Fractionation." Analytical Chemistry, 1999, 71:911-918.
Yang et al. "A Novel Microfluidic Impedance Assay for Monitoring Endothelin-Induced Cardiomyocyte Hypertrophy." Biosensors and Bioelectronics, 2007, 22:1688-1693.
Yu et al. "Real-Time Monitoring of Morphological Changes in Living Cells by Electronic Cell Sensor Arrays: An Approach to Study G Protein-Coupled Receptors." Analytical Chemistry, 2006, 78:35-43.
"Automated Cell Monitoring Instrument." Applied BioPhysics, 2002, [retrieved from the internet] http://www.biophysics.com/pages/front.html, 1 page.
"Cell Migration Studies with TECAN Systems." TECAN., Sep. 1999, [retrieved from the internet] http://www.tecan.com/migration_introl.pdf, 10 pgs.
"Detect Cell Migration and Invasion in a Homogeneous Fluorescent Assay System." BD Biosciences, http://www.bdbiosciences.com/discovery_labware/Products/inserts/BD_Falcon_HTS_fluoroblok_inserts/individual_fluoroblok_inserts/index.html, 2004.
HP 4284A Precision LCR Meter Operation Manual, Aug. 1998, Hewlett Packard, 6th Edition, p. 1-460.
"Molecular Viewer" New Products page. Science 298:2409 (2002).
CA2556219 Office Action dated Aug. 9, 2010.
CA2575573 Office Action dated Apr. 4, 2012.
EP05722991 Extended European Search Report dated Apr. 3, 2009.
EP11193882 Extended European Search Report dated Apr. 5, 2012.
EP13171137 Extended European Search Report dated Aug. 16, 2013.
Aravanis et al. "A Genetically Engineered Cell-Based Biosensor for Functional Classification of Agents." Biosensors & Bioelectronics, 2001, 16:571-577.
Banach et al. "Development of Electrical Activity in Cardiac Myocyte Aggregates Derived from Mouse Embryonic Stem Cells." Amerocam Journal of Physiology-Heart Circulatoy Physiology, 2003, 284: H2114-H2123.
Baumann et al, "Microelectronic Sensor System for Microphysical Application on Living Cells", Sensors and Actuators, 1999:77-89.
Becker et al. "Separation of Human Breast Cancer Cells from Blood by Differential Dielectric Affinity." Cell Biology, 1995, 92:960-964.
Berdondini et al. "High-Density Electrode Array for Imaging in Vitro Electrophysiological Activity." Biosensors and Bioelectronics, 2005, 21:167-174.
Berens et al. "The Role of Extracelluar Matrix in Human Astrocytoma Migration and Proliferation Studied in a Microliter Scale Assay." Clinical and Experimental Metastasis, 1994; 12(6):405-415.
Bergveld, P. "A Critical Evaluation of Direct Electrical Protein Detection Methods." Biosensors & Bioelectronics. 6:55-72 (1991).
Bieberich et al. "Neuronal Differentiation and Synapse Formation of PC12 and Embryonic Stem Cells on Interdigitated Microelectrode Arrays," Biosensors and Bioelectronics 2004; 19:923-931.
Blagbrough et al. "Polyamines and Novel Polyamine Conjugates Interact with DNA in Ways That Can Be Exploited in Non-Viral Gene Therapy" Biochemical Society Transactions, 2003, 31, Part 2, pp. 397-406.
Bonetta, Laura. "The Inside Scoop-Evaluating Gene Delivery Methods." Nature Methods, Nov. 2005, 2(11):875-883.
Burnett et al. "Fluorescent Imaginng of Electrically Stimulated Cells." Journal of Biomolecular Screening 2003; 8(6):660-667.
Burns et al. "Neutrophil Transendothelial Migration Is Independent of Tight Junctions and Occurs Preferentially at Tricellular Corners." Journal of Immunology, 1997, 2893-2903.
Cady et al. "Electrical Impedance Measurements: Rapid Method for Detecting and Monitoring Microorganisms," Journal of Clinical Mirobiology, 1978; 7(3):265-272.
Cartellieri et al. "Chimeric Antigen Receptor-Engineered T Cells for Immunotherapy of Cancer." Journal of Biomedicine and Biotechnology, 2010, 1-13.
Chang et al. "Impedimetric Monitoring of Cell Attachment on Interdigitated Microelectrodes." Sensors and Actuators, 2005, B 105:159-163.
Ciambrone et al. "Cellular Dielectric Spectroscopy: A Powerful New Approach to Label-Free Cellular Analysis." Journal of Biomolecular Screening, 2004, 9(6):467-480.
Connolly et al. "An Extracellular Microelectrode Array for Monitoring Electrogenic Cells in Culture," Biosensors and Biolectronics, 1190, 5:223-234, (1990).
Duan et al. "Separation-Free Sandwich Enzyme Immunoassays Using Microporous Gold Electrodes and Self-Assembled Monolayer/Immobilized Capture Antibodies." Analytical Chemistry, 1994, 66:1369-1377.
Ehret et al. "Monitoring of Cellular Behaviour by Impedance Measurements on Interdigitated Electrode Structures." Biosensors and Bioelectronics 1997; 12(1):29-41.
Ehret et al. "On-Line Control of Cellular Adhesion with Impedance Measurements Using Interdigitated Electrode Structures", Medical & Biological Engineering & Computing, 1998; 36:365-370.
Falk et al. "A 48-well Micro Chemotaxis Assembly for Rapid and Accurate Measurement of Leukocyte Migration." Journal of Immunological Methods., 1980, 33:239-247.

(56) References Cited

OTHER PUBLICATIONS

Fuhr et al. "Positioning and Manipulation of Cells and Microparticles Using Miniaturized Electric Field Traps and Travelling Waves." Sensors and Materials 7(2):131-146 (1995).

Fusenig et al. "The Need for a Worldwide Consensus for Cell Line Authentication: Experience Implementing a Mandatory Requirement at the Internation Journal of Cancer". PLOS Biologiy, Apr. 17, 2017, 15(4) p. e2001438 pp. 1-13.

Giaever et al, "Monitoring Fibroblast Behavior in Tissue Culture with an Applied Electric Field." Proceedings of the National Academy of Sciences. USA; 1984; 81(June):3761-3764.

Giaever et al. "Micromotion of Mammalian Cells Measured Electrically." Proceedings of the National Academy of Sciences, USA, 1991; 8(Sept.):7896-7900.

Gutmann et al. "Evidence for Different ABC-Transporters in Caco-2 Cells Modulating Drug Uptake." Pharmaceutical Research, 1999, 16(3):402-407.

Hadjout et al. "Automated Real-Time Measurement of Chemotactic Cell Motility." BioTechniques, 2001, 31:1130-1138.

Hapala, Ivan. "Breaking the Barrier: Methods for Reversible Permeabilization of Cellular Membranes." Critical Reviews in Biotechnology, 1997, 17(2):105-122.

Henning et al. "Approach to a Mutliparametric Sensor-Chip-Based Tumor Chemosensitivity Assay," Anti-Cancer Drugs 2001; 12:21-32.

Hescheler et al. "Determination of Electrical Properties of ES Cell-derived Cardiomyocytes Using MEAs." Journal of Electrocardiology, 2004, vol. 37, Suppl.

Hidalgo et al. "Characterization of the Human Colon Carcinoma Cell Line (Caco-2) as a Model System for Intestinal Epithelial Permeability," Gastroenterology, 1989; 96:736-749.

Horvath et al. "Monitoring of Living Cell Attachment and Spreading Using Reverse Symmetry Waveguide Sensing." Applied Physics Letters, 2005, 86:071101.

Huang et al. "Dielectrophoretic Cell Separation and Gene Expression Profiling on Microelectronic Chip Arrays." Analytical Chemistry, 2002, 74:3362-3371.

Hug, Thomas, "Biophysical Methods for Monitoring Cell-Substrate Interactions in Drug Discovery." Assay and Drug Development Technologies, 2003; 1(3):479-488.

Keese et al. "Real-time Impedance Assay to Follow the Invasive Activities of Metastatic Cells in Culture." BioTechniques, 2002, 33:842-850.

Klauke et al. "Extracellular Recordings of Field Potentials from Single Cardiomyocytes." Biophysical Journal, Oct. 2006, 91:2543-2551.

Kleinman et al. "Basement Membrane Complexes with Biological Activity." Biochemistry 1986; 25(2):312-318.

Kloss et al. "Microcavity Array (MCA)-Based Biosensor Chip for Functional Drug Screening of 3D Tissue Models." Biosensors and Bioelectronics, 2008, 23:1473-1480.

Kowolenko et al. "Measurement of Macrophage Adherence and Spreading with Weak Electric Fields." Journal of Immunological Methods, 1990; 127:71-77.

Larsen et al. "Somatic Cell Counting with Silicon Apertures." Micro Total Analysis Systems, 2000, 103-106.

Lin et al. "Electroporation Microchips for In Vitro Gene Transfection." Journal of Micromechanics and Microengineering, 2001, 11:542-547.

Lin et al. "Simulation and Experimental Demonstration of the Electric Field Assisted Electroporation Microchip for In Vitro Gene Delivery Enhancement." Miniaturisation for Chemistry, Biology & Bioengineerin., 2004, 4:104-108.

Lo et al. American Physical Society Mar. Meeting 2010, Portland Oregon, vol. 55, No. 2, Poter Session Abstract, BAPS, Mar. 2010 C1 268.

Lo et al. "Monitoring Motion of Confluent Cells in Tissue Culture." Experimental Cell Research 1983; 204:102-109.

Lo et al. "Impedance Analysis of Mdck Cells Measured by Electric Cell-Substrate Impedance Sensing." Biophysical Journal, 1995, 69:2800-2807.

Lo et al. "pH Changes in pulsed CO2 incubators cause periodic changes in cell morphology." Experimental Cell Research, 1994, 213:391-397.

Loffert et al. "Multiplex PCR with QIAGEN: Taq DNA Plymerase and PCR Buffer." QIAGENews, 1994, 4:15-18.

Luan et al. "Clustering of Time-Course Gene Expression Data Using a Mixed-Effects Model with B-Splines." Bioinformatics, 2003, 19(4):474-482.

Luong et al. "Monitoring Motility, Spreading and Mortality of Adherent Insect Cells Using an Impedance Sensor.", Analytical Chemistry, 2001, 73(8):1844-1848.

Mitra et al. "Electric Measurements Can Be Used to Monitor the Attachment and Spreading of Cells in Tissue Culture." Biotechniques, 1991, 11(4):504-510.

Shade-coding Scheme

CCI >> 0.7/DT:

CCI ~ 0.7/DT:

0< CCI < 0.7/DT:

CCI ~ 0:

CCI < 0:

CCI << 0:

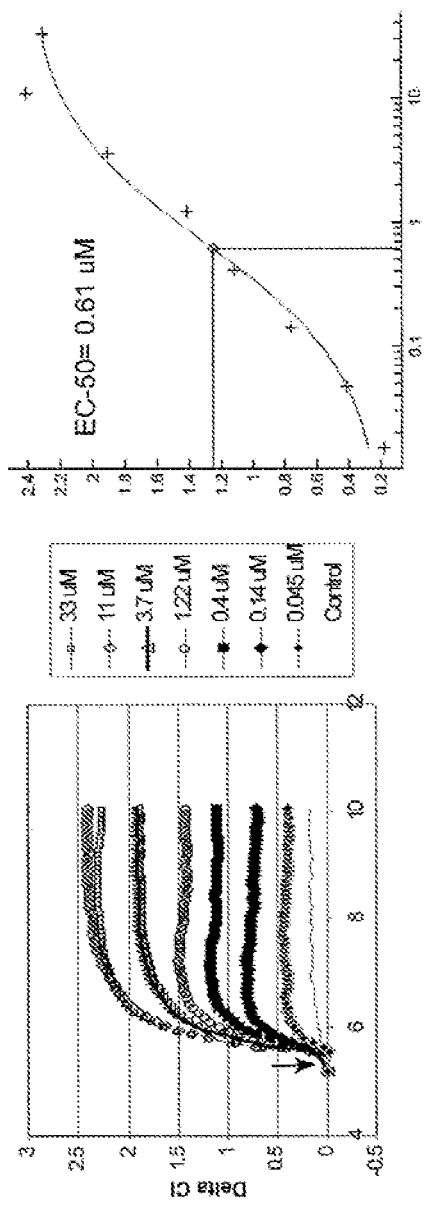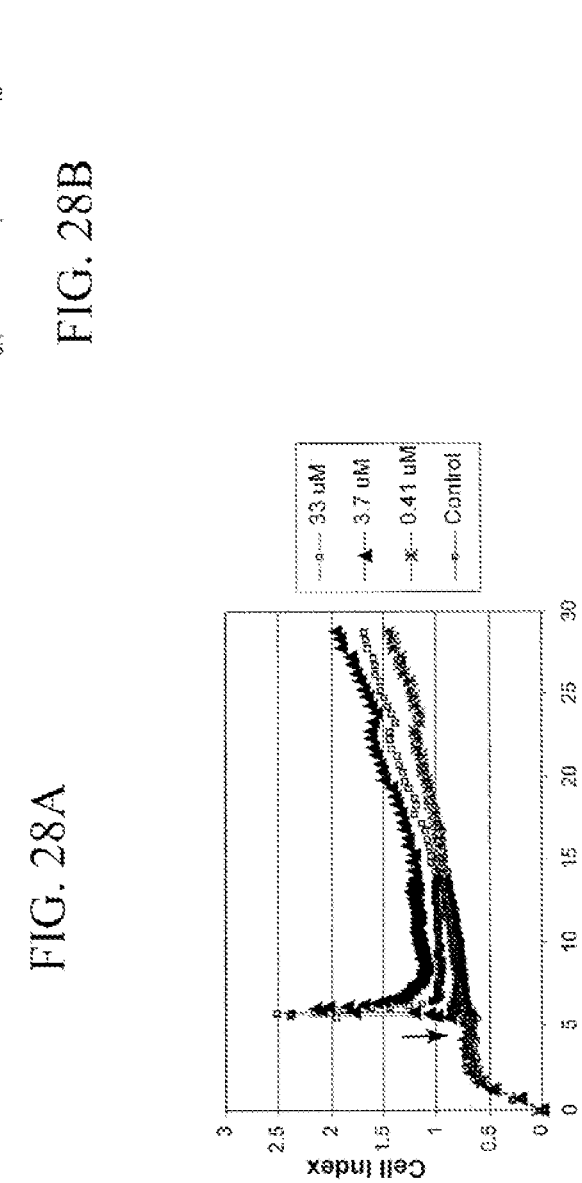
FIG. 28A
FIG. 28B
FIG. 28C

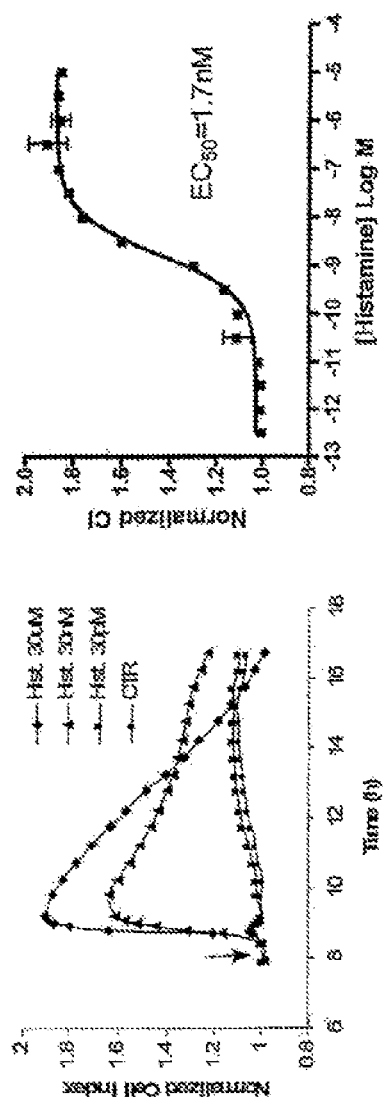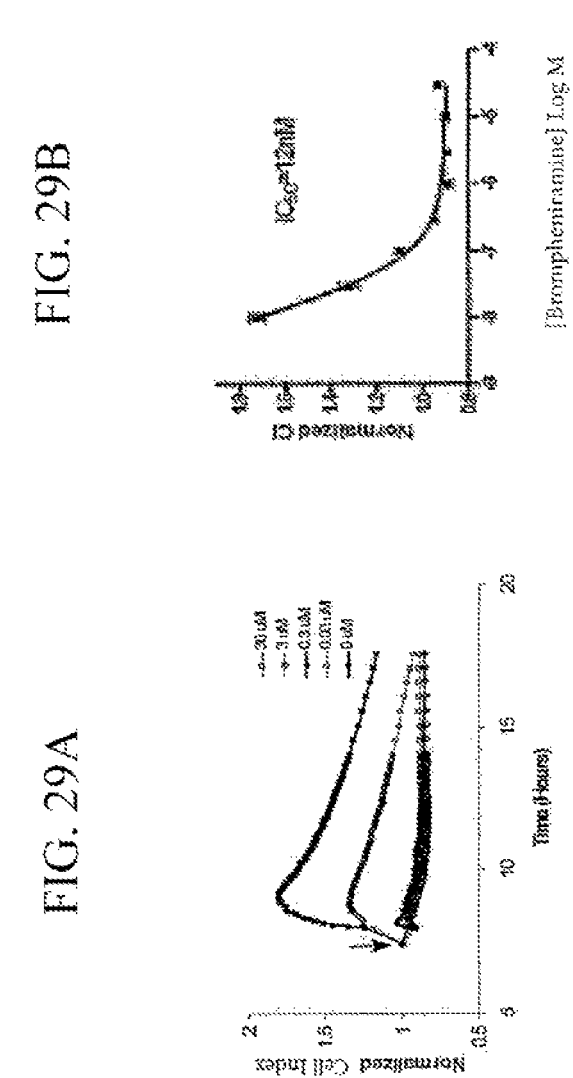
FIG. 29A
FIG. 29B
FIG. 29C
FIG. 29D

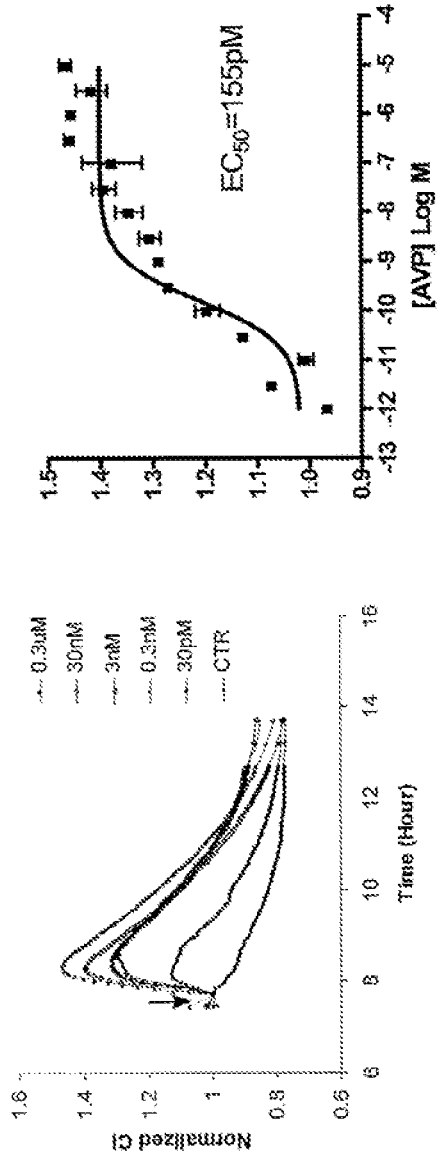
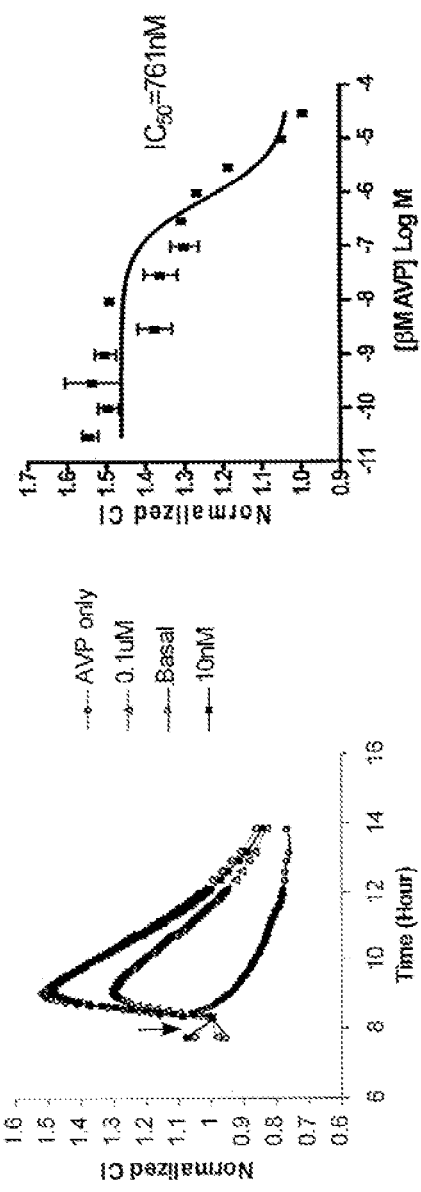
FIG. 30A
FIG. 30B
FIG. 30C
FIG. 30D

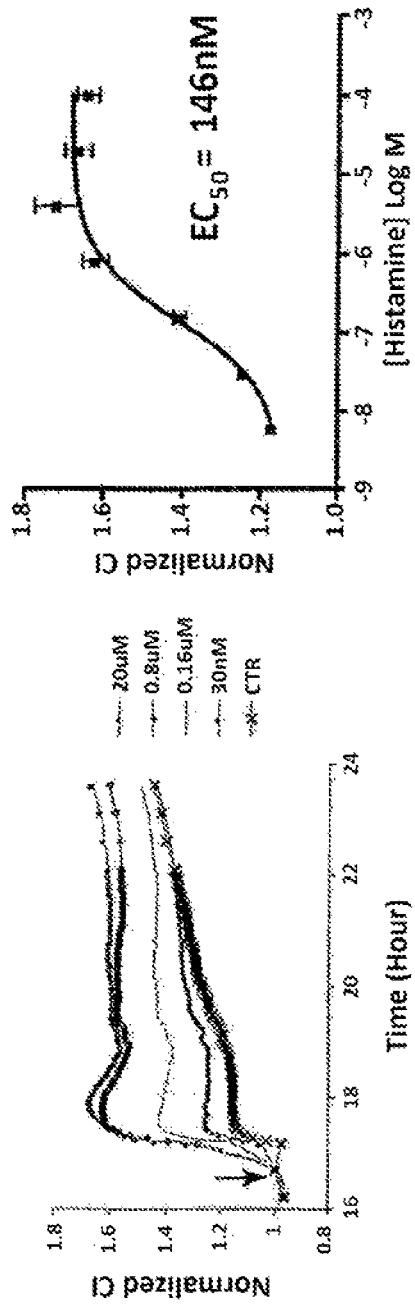
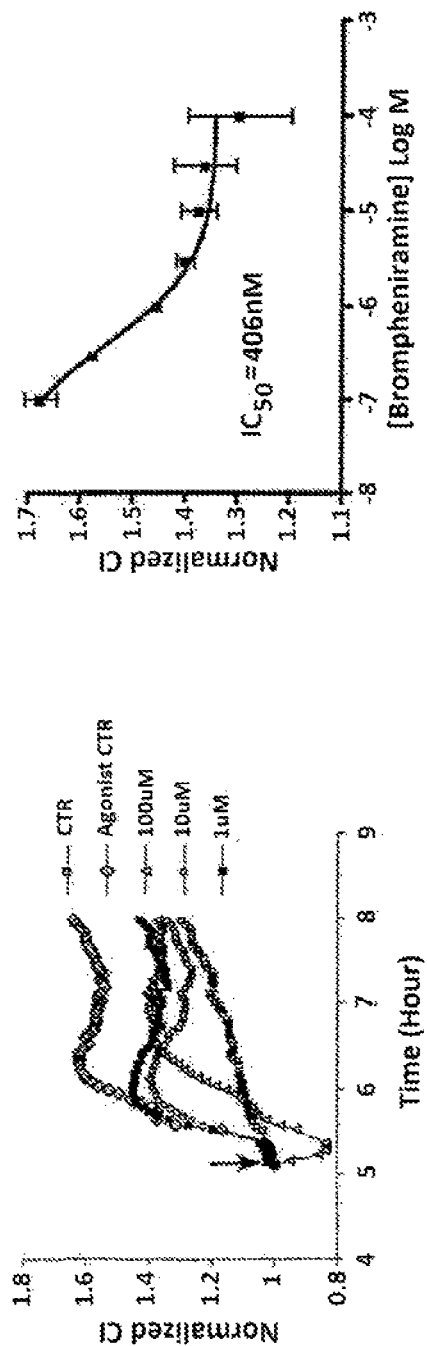
FIG. 31A
FIG. 31B
FIG. 31C
FIG. 31D

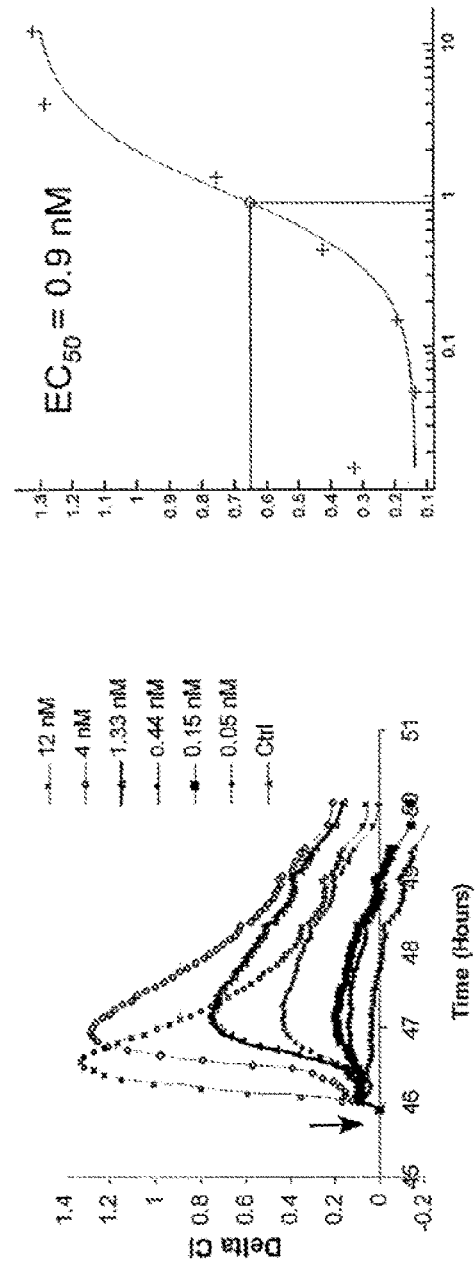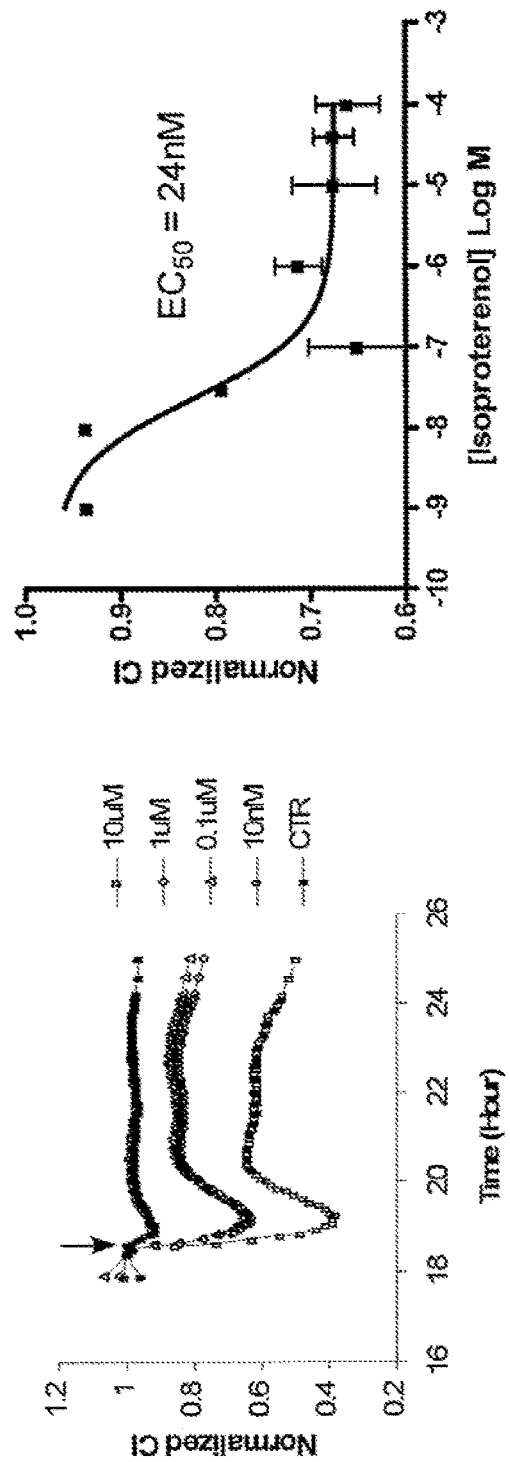
FIG. 32A  FIG. 32B
FIG. 33A  FIG. 33B

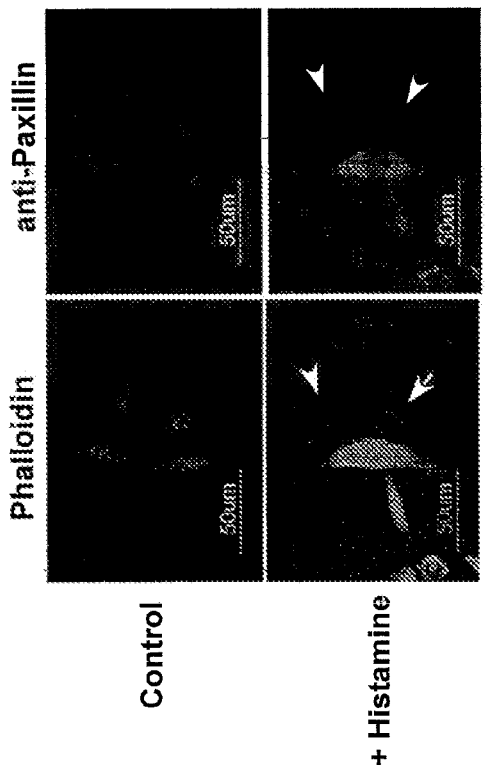
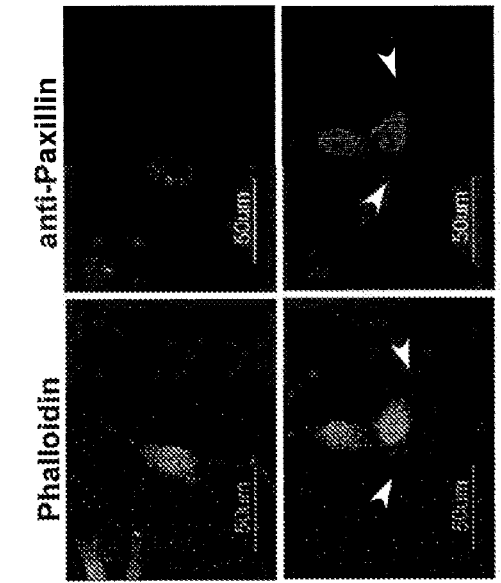
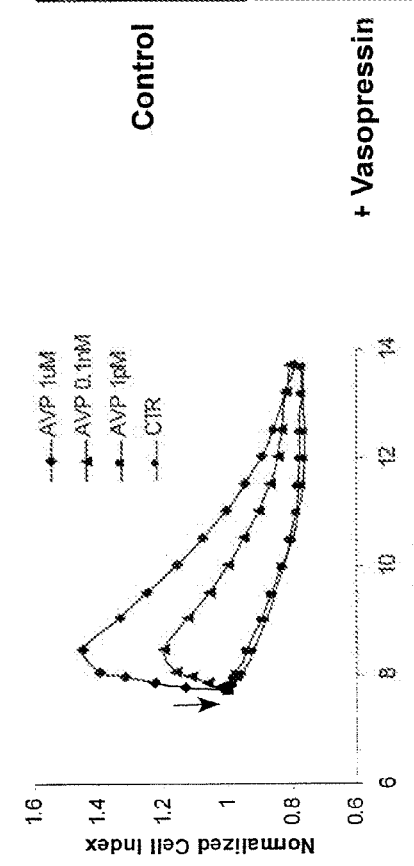
FIG. 40A
FIG. 40B
FIG. 40C
FIG. 40D

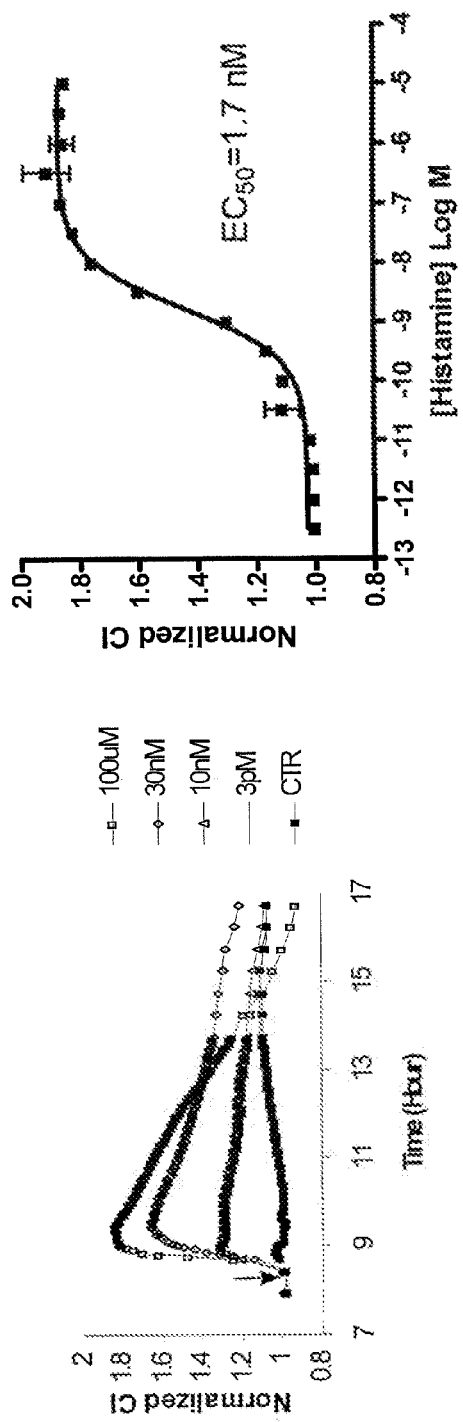
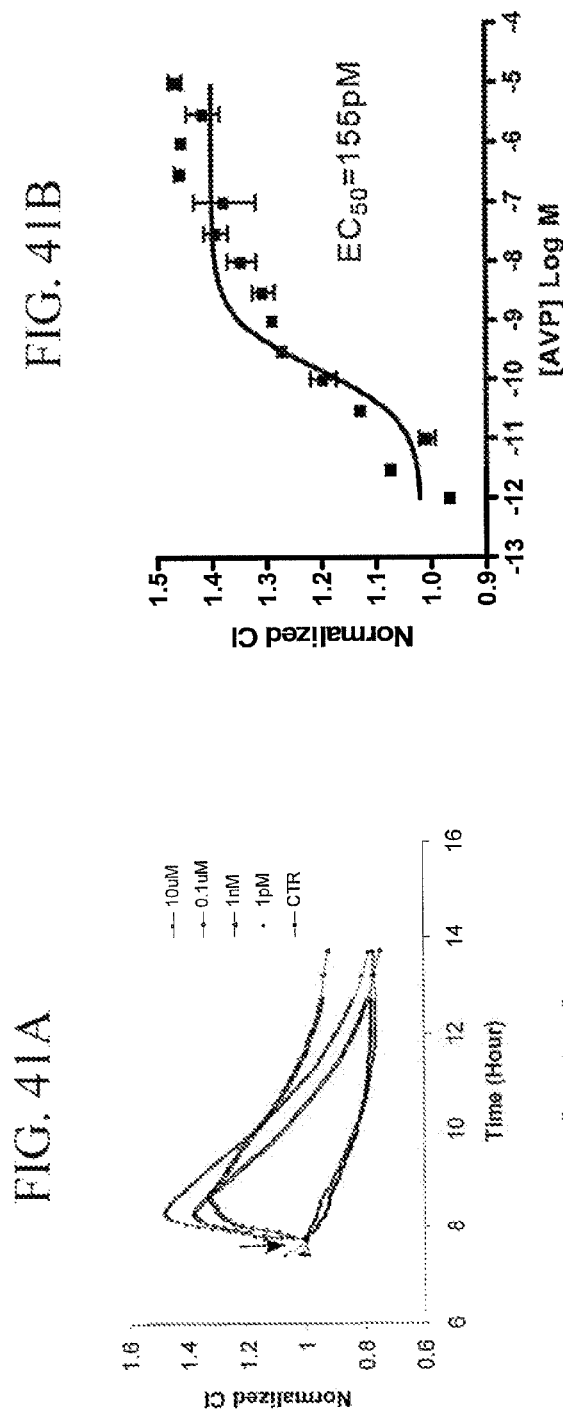
FIG. 41A
FIG. 41B
FIG. 41C
FIG. 41D

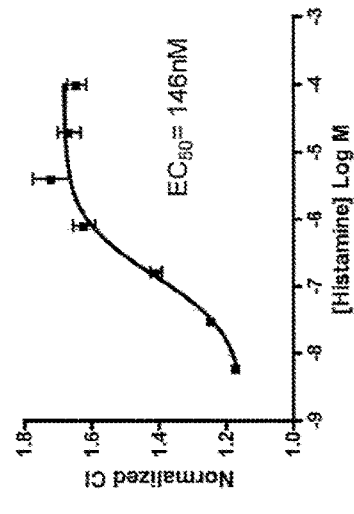
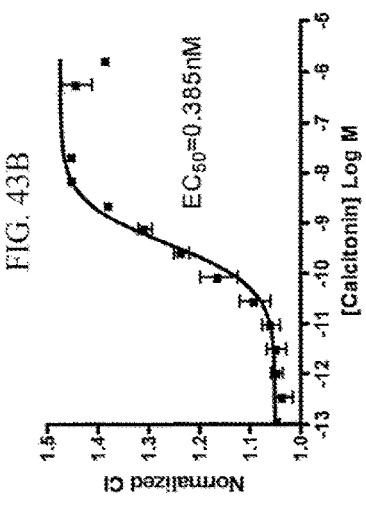
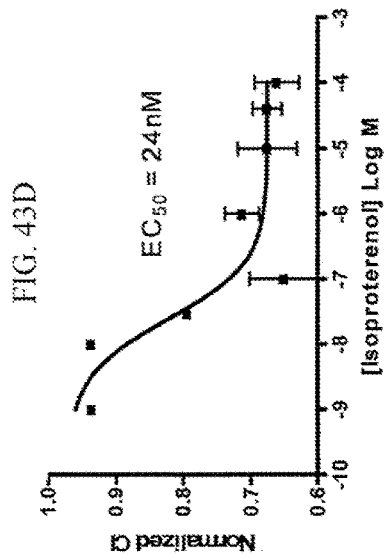
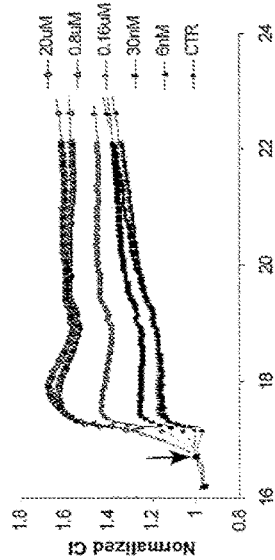
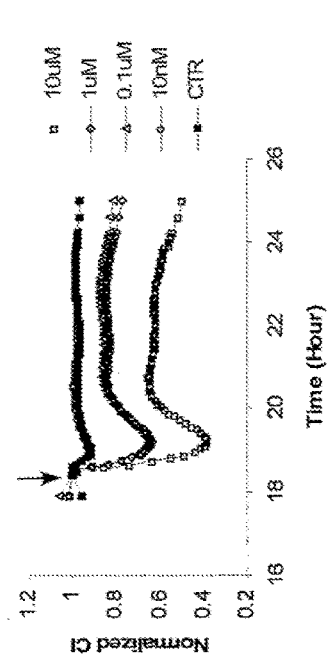
FIG. 43A  FIG. 43B  FIG. 43C  FIG. 43D  FIG. 43E  FIG. 43F

METHOD OF MEASURING CELL-SUBSTRATE IMPEDANCE IN LIVING CELLS TO IDENTIFY COMPOUNDS AFFECTING RECEPTOR TYROSINE KINASE (RTK) ACTIVITY AND PATHWAYS FOR THE TREATMENT OF CANCER

CROSS REFERENCE TO RELATED APPLICATIONS

This application is a continuation of U.S. patent application Ser. No. 15/613,052, now U.S. Pat. No. 10,168,318, filed Jun. 2, 2017, which is a continuation of U.S. patent application Ser. No. 14/541,024, now U.S. Pat. No. 10,067,121, filed Nov. 13, 2014, which is a divisional of U.S. patent application Ser. No. 13/569,156, now U.S. Pat. No. 8,916,357, filed Aug. 7, 2012, which is itself a divisional of U.S. patent application Ser. No. 11/198,831, now U.S. Pat. No. 8,263,375, filed Aug. 4, 2005, which is a continuation-in-part of U.S. patent application Ser. No. 11/055,639, now U.S. Pat. No. 7,560,269, filed Feb. 9, 2005, which is a continuation-in-part of U.S. patent application Ser. No. 10/987,732, now U.S. Pat. No. 7,192,752, filed Nov. 12, 2004, which claims priority to U.S. provisional patent application 60/519,567, filed Nov. 12, 2003. All of the applications referred to in this paragraph are incorporated by reference in their entireties herein.

U.S. patent application Ser. No. 10/987,732, now U.S. Pat. No. 7,192,752 is itself a continuation-in-part of U.S. patent application Ser. No. 10/705,447, now U.S. Pat. No. 7,470,533, filed Nov. 10, 2003, which claims priority to U.S. provisional patent application 60/435,400, filed Dec. 20, 2002; and U.S. provisional application 60/469,572, filed on May 9, 2003; and is a continuation of PCT/US2003/022557 filed Jul. 18, 2003. All of the applications referred to in this paragraph are incorporated by reference in their entireties herein.

U.S. patent application Ser. No. 10/987,732, now U.S. Pat. No. 7,192,752, is also a continuation-in-part of U.S. patent application Ser. No. 10/705,615, now U.S. Pat. No. 7,459,303, filed Nov. 10, 2003, which claims priority to U.S. provisional application 60/435,400, filed Dec. 20, 2002; U.S. provisional application 60/469,572, filed May 9, 2003; and is a continuation of PCT/US2003/022537 filed Jul. 18, 2003. All of the applications referred to in this paragraph are incorporated by reference in their entireties herein.

U.S. patent application Ser. No. 11/055,639, now U.S. Pat. No. 7,560,269, also claims priority to U.S. provisional patent application 60/542,927 filed Feb. 9, 2004; U.S. provisional patent application 60/548,713, filed Feb. 27, 2004, and US provisional application 60/614,601, filed Sep. 29, 2004. All of the applications referred to in this paragraph are incorporated by reference in their entireties herein.

U.S. patent application Ser. No. 11/198,831, now U.S. Pat. No. 8,263,375, is also a continuation-in-part of PCT patent application PCT/US05/04481, filed Feb. 9, 2005, and a continuation-in-part of PCT patent application PCT/US04/37696, filed Nov. 12, 2004. All of the applications referred to in this paragraph are incorporated by reference in their entireties herein.

U.S. patent application Ser. No. 11/198,831, now U.S. Pat. No. 8,263,375 also claims benefit of priority to U.S. provisional patent application 60/598,608, filed Aug. 4, 2004, U.S. provisional patent application 60/630,071, filed Nov. 22, 2004, U.S. provisional patent application 60/689,422, filed Jun. 10, 2005, U.S. provisional patent application 60/598,609, filed Aug. 4, 2004, U.S. provisional patent application 60/613,872, filed Sep. 27, 2004, U.S. provisional patent application 60/647,189, filed Jan. 26, 2005, U.S. provisional patent application 60/647,075 filed Jan. 26, 2005, U.S. provisional patent application 60/660,829 filed Mar. 10, 2005, and U.S. provisional patent application 60/660,898, filed Mar. 10, 2005. All of the applications referred to in this paragraph are incorporated by reference in their entireties herein.

TECHNICAL FIELD

This invention relates to the field of cell-based assays. In particular, the invention provides impedance-based devices, apparatuses and systems for analyzing cells and for conducting cell-based assays.

BACKGROUND OF THE INVENTION

A. Electronic Analysis of Cells

Bioelectronics is a progressing interdisciplinary research field that involves the integration of biomaterials with electronic devices. Bioelectronic methods have been used for analyzing cells and assaying biological molecules and cells. In one type of application, cells are cultured on microelectrodes and cell-electrode impedance is measured and determined to monitor cellular changes.

In PCT Application No. PCT/US03/22557, entitled "IMPEDANCE BASED DEVICES AND METHODS FOR USE IN ASSAYS", filed on Jul. 18, 2003, a device for detecting cells and/or molecules on an electrode surface is disclosed. The device detects cells and/or molecules through measurement of impedance changes resulting from the attachment or binding of cells and/or molecules to the electrode surfaces. A number of embodiments of the device is disclosed, together with the apparatuses, system for using such devices to perform certain cell based assays.

In PCT Application No. PCT/US04/037696, entitled "REAL TIME ELECTRONIC CELL SENSING SYSTEM AND APPLICATION FOR CELL-BASED ASSAYS", filed on Nov. 12, 2004, devices, systems and methods for assaying cells using cell-substrate impedance monitoring are disclosed. In one aspect, the disclosed cell-substrate monitoring devices comprise electrode arrays on a nonconducting substrate, in which each of the arrays has an approximately uniform electrode resistance across the entire array. In another aspect, the disclosed cell-substrate monitoring systems comprise one or more cell-substrate devices comprising multiple wells each having an electrode array, an impedance analyzer, a device station that connects arrays of individual wells to the impedance analyzer, and software for controlling the device station and impedance analyzer. In another aspect, the disclosed cellular assays use impedance monitoring to detect changes in cell behavior or state.

In PCT Application No. PCT/US05/004481, entitled "REAL TIME ELECTRONIC CELL SENSING SYSTEM AND APPLICATIONS FOR CYTOTOXICITY PROFILING AND COMPOUND ASSAYS", filed on Feb. 9, 2005, devices, systems and methods for assaying cells using cell-substrate impedance monitoring are disclosed. In one aspect, the disclosed cellular assays use impedance monitoring to detect changes in cell behavior or state. The methods can be used to test the effects of compounds on cells, such as in cytotoxicity assays. Methods of cytotoxicity profiling of compounds were also provided.

B. GPCR Assay

Eukaryotic cells from unicellular and multicellular organisms have devised evolutionarily conserved mechanisms for responding to environmental cues by utilizing specific cell surface receptors. These membrane-bound receptors recognize and bind to their cognate ligand and turn on biochemical cascades inside the cell that culminate in a specific cellular response. Members of the G-protein coupled receptor (GPCR) family are one of the main classes of cell surface receptors that participate in a variety of cellular pathways that result in different cellular responses such as proliferation, chemotaxis, and cytoskeletal dynamics. GPCRs have the ability to recognize a wide range of extracellular molecules including amino acids, hormones, growth factors, light, peptide and non-peptide neurotransmitters and a number of odorant molecules. Because GPCRs and their cognate ligands participate in important physiological and pathophysiological settings, including but not limited to inflammation, hypertension, diabetes and autoimmunity they are extremely attractive targets for the pharmaceutical industry. More than 50% of the current therapeutic agents on the market are targeted at GPCRs and as more GPCRs and their ligands are being discovered this number will likely rise even further in the coming years. Therefore, GPCRs occupy a unique position as a pharmaceutical target because it far exceeds any other pharmaceutically relevant target.

As the name implies, GPCRs are associated with a heterotrimeric guanine nucleotide binding-protein complex (G-proteins). Ligand binding to the GPCR induces a conformational change which promotes exchange of GTP for GDP on the G-protein α-subunit which allows for dissociation of the G-protein α-subunit from Gβγ-subunits. Subsequently, the activated Gα subunit and Gβγ subunit positively and/or negatively impact the activity of effector enzymes and proteins. Furthermore, in recent years it has come to light that there is a feedback mechanism in place which negatively regulates or modulates GPCR-mediated signaling by a variety of mechanisms such as post-translational modification, protein-protein interaction or receptor endocytosis. Thus, the activity of GPCR is determined by the fine balance of receptor de-sensitization and re-sensitization which is dictated by the ligand concentration and numerous other inputs that the cell receives simultaneously.

The human genome project has identified a number of proteins which can be categorized into GPCRs based on sequence. The number of GPCRs encoded by the human genome is estimated to be between 800-1000 and thus far approximately 650 GPCR have been identified from the effort of the human genome project, 200 of which are classified as known GPCR because the activating ligands for these receptors are known (Nambi, P and Aiyar N, G-protein coupled receptors in drug discovery, in *Assay and Drug Development Technologies* (2003) 1, 305-310). The remaining receptors for which the ligands are not known are considered "orphan receptors" and they are the subject of intense scrutiny as potential medically relevant targets. There are a number of in vitro and cell-based assays available which are used to screen for potential agonist or antagonist of GPCRs. The in vitro assays are based on binding studies with labeled ligand and receptor. (Nambi, P and Aiyar N, G-protein coupled receptors in drug discovery, in *Assay and Drug Development Technologies* (2003) 1, 305-310) The cell-based assays are based on engineering cell lines to express exogenous GPCRs alone or together with a reporter plasmid. Calcium sensitive dyes have been used extensively to screen for GPCRs that increase intracellular calcium levels in response to agonists challenge. Alternatively, a fluorescent or luminescent-based reporter assay co-transfected with the appropriate GPCR and G-protein has also been used to identify potential agonists or antagonists of the transfected GPCR (Nambi, P and Aiyar N, 2003, G-protein coupled receptors in drug discovery, in *Assay and Drug Development Technologies* Vol: 1, pp 305-310). While these assays are extremely useful in high throughput screening to identify potential agonists and antagonists, they do involve pre-labeling the cells with fluorescent dyes in the case of calcium-based assays or lysing the cells to measure the activity of reporter genes.

C. Receptor Protein Tyrosine Kinases

All of the cells in our body are constantly and simultaneously exposed to hundreds of different stimuli. The cells need to recognize these stimuli, mobilize its biochemical machinery and respond in an appropriate and coordinated fashion. Polypeptide growth factors such as the epidermal growth factor (EGF), platelet derived growth factor (PDGF), nerve growth factor (NGF) and a whole host of other growth factors constitute a large family of growth factors which is used by the cells in the body to communicate and regulate cell growth, proliferation, differentiation, migration and cell death. These polypeptide growth factors interact with specific receptors present at the cell surface called receptor protein tyrosine kinases. These receptors are single pass transmembrane receptors, composed of an extracellular domain, a transmembrane domain and a cytoplasmic domain containing tyrosine kinase activity. Upon binding their cognate ligand the receptor undergoes a conformational change which leads to dimerization, cross phosphorylation and activation of the cytoplasmic tyrosine kinase domain. The activated kinase domain binds to ATP and transfers and covalently links the terminal phosphate of ATP to specific tyrosine residues of signaling proteins inside the cell. Tyrosine phosphorylation of target proteins allows specific protein-protein interactions inside the cell leading to biochemical, structural, morphological and gene expression changes and finally culminating in cellular response such as proliferation and migration.

Because polypeptide growth factors and their receptors control crucial cellular processes such as proliferation, differentiation and migration it is absolutely imperative that these growth factors and the signaling pathways they trigger inside the cell is coordinated in a very controlled and precise manner. Failure to regulate these growth factors or their signaling pathways can lead to cancer, degenerative diseases and inflammation. A number of cancers, especially those of the breast and lung have been shown to be associated with dysregulation of growth factors and their signaling pathways due to mutations that constitutively activate the receptors or due to overexpression of the receptors. Because growth factors and their receptors play a central role in certain diseases and disease progression, they have become highly valued and pursued targets for the pharmaceutical and biotech industries. Recent years has witnessed a surge of protein-based and compound-based drugs which seek to inhibit or block receptor protein tyrosine kinase signaling involved in certain cancers.

Several different approaches, including antibody-based drugs as well as small molecular-based drugs have been developed to block the action of polypeptide growth factors and their receptors which may be involved in cancer. Herceptin, a monoclonal antibody targeted to the c-erB-2/Her-2 receptor, a member of the EGF receptor family, is now an approved therapy for breast cancer (Roberto E. Favoni and Alessandra De Cupis, 2000, The role of polypeptide growth factors in human carcinomas: new targets for a novel pharmacological approach, in *Pharmacological Reviews*, Vol:52, pp 179-205). Also, Gefitinib, a small molecular inhibitor of the EGF receptor has been shown to be efficacious against certain kinds of lung cancer (El-Rayes BF and LoRusso P M, 2004, Targeting the epidermal growth factor receptor, in *British Journal of Cancer*, Vol: 91, pp: 418-424). Both in vitro kinase assays and cell-based assays based on proliferation, reporter-based assays, and migration have been established and utilized to screen for potential inhibitor of receptor tyrosine kinases involved in cancer progression. There are several advantages for using cell-based assays to screen for receptor protein tyrosine kinase inhibitors, regardless of whether they are protein-based or compound-based inhibitors. Cell-based assays allow for a more physiological setting to test the selectivity and efficacy of the inhibitor of interest. Furthermore, since in some cases the inhibitors need to traverse the membrane in order to inhibit the kinase activity of the receptor, the cell-based assay allows for assessment of both the stability and solubility of the compound of interest.

The present invention further expands the inventions disclosed in PCT Application No. PCT/US03/22557, entitled "IMPEDANCE BASED DEVICES AND METHODS FOR USE IN ASSAYS", filed on Jul. 18, 2003, and disclosed in U.S. patent application Ser. No. 10/705,447, entitled "IMPEDANCE BASED DEVICES AND METHODS FOR USE IN ASSAYS," filed on Nov. 10, 2003, and disclosed in PCT Application No. PCT/US05/004481, entitled "REAL TIME ELECTRONIC CELL SENSING SYSTEM AND APPLICATIONS FOR CYTOTOXICITY PROFILING AND COMPOUND ASSAYS", filed on Feb. 9, 2005, and disclosed in U.S. patent application Ser. No. 11/055,639, entitled "REAL TIME ELECTRONIC CELL SENSING SYSTEM AND APPLICATIONS FOR CYTOTOXICITY PROFILING AND COMPOUND ASSAYS" filed on Feb. 9, 2005, and disclosed in PCT Application No. PCT/US04/037696, entitled "REAL TIME ELECTRONIC CELL SENSING SYSTEM AND APPLICATION FOR CELL-BASED ASSAYS", filed on Nov. 12, 2004, and disclosed in U.S. patent application Ser. No. 10/987,732, entitled "REAL TIME ELECTRONIC CELL SENSING SYSTEM AND APPLICATION FOR CELL-BASED ASSAYS" filed on Nov. 12, 2004. The present invention provides a real time cell electronic sensing system for conducting cell-based assays based on measurement of cell-substrate impedance and provides the method for dynamic monitoring of G-Protein Coupled Receptor activation and Receptor Tyrosine Kinase activation using real-time microelectronic cell sensing technology.

SUMMARY OF THE INVENTION

In one aspect, the present invention is directed to a device for monitoring cell-substrate impedance, which device comprises: a) a nonconducting substrate; b) two or more electrode arrays fabricated on the substrate, where each of the two or more electrode arrays comprises two electrode structures; and c) at least two connection pads, each of which is located on an edge of the substrate. Each electrode array of the device has an approximately uniform electrode resistance distribution across the entire array. The substrate of the device has a surface suitable for cell attachment or growth; where cell attachment or growth on said substrate can result in a detectable change in impedance between or among the electrode structures within each electrode array. In preferred embodiments, each electrode array on the substrate of a device of the present invention is associated with a fluid-impermeable container.

In another aspect, the present invention is directed to a cell-substrate impedance measurement system comprising: a) at least one multiple-well device monitoring cell-substrate impedance, in which at least two of the multiple wells each comprise an electrode array at the bottom of the well; b) an impedance analyzer; c) a device station capable of engaging the one or more multiple-well devices and capable of selecting and electrically connecting electrode arrays within any of the multiple wells in to the impedance analyzer; and d) a software program to control the device station and perform data acquisition and data analysis on impedance values measured by the impedance analyzer. In preferred embodiments of this aspect of the present invention, each electrode array of the multiple-well device is individually addressed.

In yet another aspect, the present invention provides a method for monitoring cell-substrate impedance using a device of the present invention. The method includes: providing a multiple array device of the present invention; connecting said multiple array device to an impedance analyzer; depositing cells on at least one of the two or more arrays of the device; and monitoring cell-substrate impedance on one or more arrays of the device.

In yet another aspect, the present invention provides methods for calculating a Cell Change Index for quantifying and comparing cell-substrate impedance.

In yet another aspect, the present invention provides methods for calculating resistance of electrical traces connecting an array of a cell-substrate monitoring device with a connection pad. Such calculations of electrical trace resistance can be used for calculating Cell Index.

In yet another aspect, the present invention provides a method for monitoring cell-substrate impedance using a cell-substrate impedance measurement system of the present invention. The method includes: providing a cell-substrate impedance measurement system of the present invention, adding cells to at least one well of the multiple-well device that comprises an electrode array, and monitoring cell-substrate impedance from one or more of the wells that comprise cells. Impedance can be monitored at regular or irregular time intervals. In preferred embodiments, cell-substrate impedance is monitored in at least two wells of a multiple-well device.

In yet another aspect, the present invention provides a method for performing real-time cell-based assays investigating the effects of one or more compound on cells, comprising: providing an above described cell-substrate impedance measurement system; introducing cells into at least one well of the system that comprises an electrode array; adding one or more compounds to one or more of the wells containing cells; and monitoring cell-substrate impedance over the electrode array of the one or more wells before and after adding the one or more compounds. Preferably, cell-substrate impedance is monitored at regular or irregular time intervals after adding one or more compounds to the one or more of the wells containing cells. The time dependent impedance change can provide information about time dependent cell status before addition of the compound and about time dependent cell status under the interaction of the compound. This information can be used to determine the effect of a compound on the cells.

In yet another aspect, the present invention provides a method for performing real-time cytotoxicity assays of at least one compound, comprising: providing an above described cell-substrate impedance measurement system; introducing cells into one or more wells of the system that comprise an electrode array; adding one or more compounds to the one or more wells containing cells; and monitoring cell-substrate impedance of the one or more wells before and after adding the one or more compounds, wherein the time dependent impedance change provides information about time dependent cytotoxicity of the compound or compounds. Preferably, cell-substrate impedance is monitored at regular or irregular time intervals after adding one or more compounds to the one or more of the wells containing cells. The time dependent impedance change can provide information about any potential cytotoxic effects of the compound.

In one embodiment of the above methods, multiple wells with same cell types are used, wherein different concentrations of a compound are added to different wells that comprise cells. The method can monitor and quantitate time-dependent and concentration-dependent cellular responses.

In yet another aspect, the present invention provides a method for analyzing and comparing time-dependent effects of a first compound and a second compound on a cell type, comprising: a) performing a real-time assay on a cell type with the first compound using the method described above; b) performing a real-time assay on said cell type with the second compound using the method described above; and c) comparing the time-dependent responses of the first compound and the second compound.

In one embodiment of this method, time-dependent cellular responses are determined for a first compound at multiple dose concentrations. In another embodiment, time-dependent responses are determined for a second compound at multiple dose concentrations. In yet another embodiment, time-dependent cellular responses are determined for both a first compound and a second compound at multiple dose concentrations.

In yet another aspect, the present invention provides methods for cytotoxicity profiling for a compound on multiple cell types, comprising: a) performing real-time cytotoxicity assays on different cell types with the compound using the method described above, and b) analyzing real-time cytotoxic responses of different cell types to the compound to provide a cytotoxicity profile of the compound. In yet another embodiment, the above methods are applied to perform cytotoxicity profiling of multiple compounds on multiple cell types.

In yet another aspect, the present invention provides methods for identifying a compound capable of interacting with a G-Protein Coupled Receptor (GPCR) comprising: (a) providing a device capable of measuring cell-substrate impedance; wherein the device comprises at least two wells, further wherein the device is operably connected to an impedance analyzer; (b) adding test cells to at least two wells, wherein the test cells express a GPCR; (c) measuring first impedances of the at least two wells immediately preceding step d) and optionally determining first cell indices from the first impedances; (d) adding a compound to at least one well containing the test cells to form at least one compound well and adding a vehicle control to at least another well containing test cells to form at least one control well; (e) measuring second impedances of the at least one compound well and of the at least one control well after step d) and optionally determining second cell indices from the second impedances; (f) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the at least one control well; (g) comparing the change in impedance or cell index between the at least one compound well and the at least one control well; and (h) identifying the compound interacts with the GPCR if the comparison demonstrates a significant difference between the change in impedance or cell index of the at least one compound well and the change in impedance or cell index of the at least one control well.

In yet another aspect, the present invention provides methods for of identifying a compound capable of interacting with a G-Protein Coupled Receptor (GPCR) comprising: (a) providing a device capable of measuring cell-substrate impedance; wherein the device comprises at least two wells, further wherein the device is operably connected to an impedance analyzer; (b) adding test cells to at least one of the at least two wells to form at least one test well, and adding control cells to at least another well to form at least one control well, wherein the test cells express a GPCR and the control cells do not express the GPCR or express the GPCR at a significantly lesser level that the test cells; (c) measuring first impedances of the at least one test well and of the at least one control well immediately preceding step d) and optionally determining first cell indices from the first impedances; (d) adding a compound to the at least one test well and to the at least one control well; (e) measuring second impedances from the at least one test well and from the at least one control well after step d) and optionally determining second cell indices from the second impedances; (f) determining the change in the impedance or cell index of the at least one test well by comparing the second impedance or the second cell index of the at least one test well to the first impedance or the first cell index of the the at least one test well, and determining the change in the impedance or cell index of the at least one control well by comparing the second impedance or the second cell index of the at least one control well to the first impedance or the first cell index of the the at least one control well; (g) comparing the changes in impedance or in cell index between the at least one test well and the at least one control well; and (h) identifying the compound interacts with the GPCR if the comparison demonstrates a significant difference between the change in impedance or cell index for the at least one test well and the change in impedance or cell index for the at least one control well.

In yet another aspect, the present invention provides methods for screening for an antagonist for a G-Protein Coupled Receptor (GPCR) with a known ligand comprising: (a) providing a device capable of measuring cell-substrate impedance, wherein the device comprises at least two wells, further wherein the device is operably connected to an impedance analyzer; (b) adding test cells to each of at least two of the at least two wells, wherein the test cells express a GPCR; (c) adding a compound suspected of being a GPCR antagonist to at least one of the at least two wells to form at least one compound well, adding a vehicle control to at least another well of the at least two wells to form at least one control well; (d) measuring first impedances of the at least one compound well and the at least one control well immediately preceding step e), and optionally determining first cell indices from the first impedances; (e) adding a GPCR ligand to the at least one compound well and to the at least one control well; (f) measuring second impedances of the at least one compound well and the at least one control well after step e) and optionally determining second cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the at least one control well; (h) comparing the change in impedance or cell index between the at least one compound well and the at least one control well; and (i) identifying the compound is an antagonist for the GPCR if the comparison demonstrates a significant difference between the change in impedance or cell index of the at least one compound well and the change in impedance or cell index of the at least one control well.

In yet another aspect, the present invention provides methods for identifying a compound that affects a G-Protein Coupled Receptor (GPCR) pathway comprising: (a) providing a device capable of measuring cell-substrate impedance, wherein the device comprises at least two wells, further wherein the device is operably connected to an impedance analyzer; (b) adding test cells to at least two of the at least two wells, wherein the test cells express a GPCR; (c) adding a compound suspected of being capable of affecting a GPCR pathway to at least one of the at least two wells containing the test cells to form at least one compound well, adding a vehicle control to at least another well of the at least two wells containing the test cells to form at least one control well; (d) measuring first impedances of the at least one compound well and the at least one control well immediately preceding step e), and optionally determining first cell indices from the first impedances; (e) adding a GPCR activating compound to the at least one compound well and to the at least one control well; (f) measuring second impedances of the at least one compound well and the at least one control well after step e) and optionally determining second cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the at least one control well; (h) comparing the change in impedance or cell index between the at least one compound well and the at least one control well; and (i) identifying the compound effects the GPCR pathway if the comparison demonstrates a significant difference between the change in impedance or cell index of the at least one compound well and the change in impedance or cell index of the at least one control well.

In yet another aspect, the present invention provides methods for validating a molecular target involved in the GPCR signaling pathway leading from GPCR activation comprising: (a) providing a device capable of measuring cell-substrate impedance, wherein the device comprises two or more wells, further wherein the device is operably connected to an impedance analyzer; (b) adding test cells to at least one well to form a test well and adding confirmation cells to at least another well to form a confirmation well, wherein the test cells express a GPCR and the confirmation cells comprise: (i) a dominant negative of protein of interest, or (ii) an siRNA targeting a protein of interest, or (iii) a gene knockout of protein of interest, or (iv) a chemical or protein inhibitor of the protein of interest; (c) measuring first impedances of the at least one test well and the at least one confirmation well immediately preceding step d), and optionally determining first cell indices from the first impedances; (d) adding a GPCR activating compound to the at least one test well and to the at least one confirmation well; (e) measuring second impedances of the at least one test well and the at least one confirmation well after step d) and optionally determining second cell indices from the second impedances; (f) determining the change in the impedance or cell index for the at least one test well by comparing the second impedance or the second cell index of the at least one test well to the first impedance or the first cell index of the at least one test well, and determining the change in the impedance or cell index of the at least one confirmation well by comparing the second impedance or the second cell index of the at least one confirmation well to the first impedance or the first cell index of the at least one confirmation well; (g) comparing the change in impedance or cell index between the at least one test well and the at least one confirmation well; and (h) validating the molecular target if the comparison demonstrates a significant difference between the change in impedance or cell index of the at least one test well and the change in impedance or cell index of the at least one confirmation well.

In a preferred embodiment of the above method for validating a molecular target involved in the GPCR signaling pathway leading from GPCR activation, the activating compound is a GPCR ligand or a GPCR agonist.

In yet another aspect, the present invention provides methods for monitoring dose-dependent functional activation of a G-Protein Coupled Receptor (GPCR) comprising: (a) providing a device capable of measuring cell-substrate impedance; wherein the device comprises at least two wells, further wherein the device is operably connected to an impedance analyzer; (b) adding test cells to the at least two wells, wherein the test cells express a GPCR; (c) measuring first impedances from the at least two wells immediately preceding step d) and optionally determining first cell indices from the first impedances; (d) adding a compound capable of activating the GPCR to at least two wells in at least at two different concentrations forming compound wells 1 through x, wherein x equals the number of the at least two different concentrations; (e) measuring a series of impedances for each of the compound wells 1 through x after step d) and optionally determining a series of cell indices from the series of impedances, wherein the series comprise at least three impedance measurements; (f) determining the change in the impedance or cell index for each of the compound wells 1 through x by comparing the series of impedances or the series of cell indices for each of the compound wells 1 through x to the first impedance or the first cell index of each well corresponding to the compound wells 1 through x; and (g) comparing the changes in impedances or in cell indices between the compound wells 1 through x at a given time point.

In a preferred embodiment of the above method for monitoring dose-dependent functional activation of a G-Protein Coupled Receptor (GPCR), the method further comprises establishing a dose curve, wherein the dose curve is determined by plotting a maximum change in impedance or a maximum change in cell index for each concentration of the compound versus the corresponding concentration. In another embodiment, the dose curve is determined by measuring the area under the cell-index curve or impedance curve for each of the concentrations and plotting the area under the cell-index curve or impedance curve versus the corresponding concentration. Preferably, the EC50 of the compound is determined from the dose curve, wherein the EC50 is the molar concentration of the compound capable of inducing 50% of maximum responses in impedance or cell index or 50% of maximum change in area under the cell-index curve or impedance curve.

In yet another aspect, the present invention provides methods to determine desensitization of a GPCR comprising: (a) providing a device capable of measuring cell-substrate impedance of a test cell expressing a GPCR, wherein the device comprises at least one well, further wherein the device is operably connected to an impedance analyzer; (b) adding test cells to the at least one well, wherein the test cells expresses a GPCR; (c) measuring a first impedance of the at least one well immediately preceding step d) and optionally determining a first cell index; (d) introducing an agonist to the at least one well; (e) measuring a second impedance of the at least one well and optionally determining a second cell index; (f) comparing the second impedance or the second cell index to the first impedance or the first cell index; (g) allowing the cell-substrate impedance to return about to the first impedance; (h) washing the test cells with an appropriate wash solution; (i) introducing an agonist to the at least one well after the washing the test cells; (j) measuring a third impedance of the at least one well and optionally determining a third cell index; (k) comparing the third impedance or the third cell index to to the first impedance or the first cell index; (l) comparing the third impedance or the third cell index to the second impedance or the second cell index; and (m) determining the GPCR is fully desensitized if the third impedance or the third cell index does not significantly vary from the first impedance or the first cell index, or determining the GPCR is not desensitized if the third impedance or third cell index does not significantly vary from the second impedance or the second cell index, or determining the GPCR is partially desensitized if the third impedance or third cell index does vary from the first impedance or the first cell index.

Preferably, in one embodiment of the above method for determine desensitization of a GPCR, if the GPCR is not fully desensitized, the steps h) through m) are repeated.

In yet another aspect, the present invention provides methods for identifying a factor capable of interacting with a receptor tyrosine kinase (RTK) comprising: (a) providing a device capable of measuring cell-substrate impedance; wherein the device comprises at least two wells, further wherein the device is operably connected to an impedance analyzer; (b) adding test cells to at least two wells, wherein the test cells express a RTK; (c) measuring first impedances of the at least two wells immediately preceding step d) and optionally determining first cell indices from the first impedances; (d) adding a compound suspected of being a factor capable of interacting with a RTK to at least one well containing the test cells to form at least one compound well and adding a vehicle control to at least another well containing test cells to form at least one control well; (e) measuring second impedances of the at least one compound well and of the at least one control well after step d) and optionally determining second cell indices from the second impedance; (f) determining the change in the impedance or cell index for the at least one compound well by comparing the second impedance or the second cell index of the at least one compound well to the first impedance or the first cell index of the at least one compound well, and determining the change in the impedance or cell index for the at least one control well by comparing the second impedance or the second cell index of the at least one control well to the first impedance or the first cell index of the the at least one control well; (g) comparing the changes in impedances or in cell indices between the at least one compound well and the at least one control well; and (h) identifying the compound is a factor that interacts with the RTK and affects cell morphology if the comparison demonstrates a significant difference between the change in impedance or cell index for the at least one compound well and the change in impedance or cell index for the at least one control well.

In a preferred embodiment of the above method for identifying a factor capable of interacting with a receptor tyrosine kinase (RTK), the test cells are in a serum free medium.

In yet another aspect, the present invention provides methods for identifying a factor capable of interacting with a receptor tyrosine kinase (RTK) comprising (a) providing a device capable of measuring cell-substrate impedance; wherein the device comprises at least two wells, further wherein the device is operably connected to an impedance analyzer; (b) adding test cells to at least one well to form at least one test well, wherein the test cells express a RTK, and adding control cells to at least another well to form at least one control well, wherein the control cells do not express the RTK or express the RTK at a significantly lesser level that the test cells; (c) measuring first impedances from the at least one test well and from the at least one control well immediately preceding step d) and optionally determining first cell indices from the first impedances; (d) adding a compound to the at least one test well and to the at least one control well; (e) measuring second impedances from the at least one test well and from the at least one control well after step d) and optionally determining second cell indices from the second impedances; (f) determining the change in the impedance or cell index for the at least one test well by comparing the second impedance or the second cell index of the at least one test well to the first impedance or the first cell index of the at least one test well, and determining the change in the impedance or cell index for the at least one control well by comparing the second impedance or the second cell index of the at least one control well to the first impedance or the first cell index of the at least one control well; (g) comparing the changes in impedance or in cell index between the at least one test well and the at least one control well; and (h) identifying the compound interacts with the RTK if the comparison demonstrates a significant difference between the change in impedance or cell index for the at least one test well and the change in impedance or cell index for the at least one control well.

In yet another aspect, the present invention provides methods for screening for an inhibitor for a Receptor Tyrosine Kinase (RTK) in response to activation of RTK with a stimulating factor comprising: (a) providing a device capable of measuring cell-substrate impedance, wherein the device comprises at least two wells, further wherein the device is operably connected to an impedance analyzer; (b) adding test cells to each of at least two of the at least two wells, wherein the test cells expresses a RTK; (c) adding a compound suspected of being a RTK inhibitor to at least one of the at least two wells containing test cells to form at least one compound well, adding a vehicle control to at least another well of the at least two wells containing test cells to form at least one control well; (d) measuring first impedances of the at least one compound well and the at least one control well immediately preceding step e), and optionally determining first cell indices from the first impedances; (e) adding a RTK stimulating factor to the compound well and the control well; (f) measuring second impedances of the at least one compound well and the at least one control well after step e) and optionally determining third cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the the at least one control well; (h) comparing the change in impedance or cell index between the at least one compound well and the at least one control well; and (i) identifying the compound is an inhibitor for the RTK if the comparison demonstrates a significant difference between the change in impedance or cell index for the at least one compound well and the change in impedance or cell index for the at least one control well.

In yet another aspect, the present invention provides methods for identifying a compound that affects a Receptor Tyrosine Kinase (RTK) pathway comprising: (a) providing a device capable of measuring cell-substrate impedance, wherein the device comprises at least two wells, further wherein the device is operably connected to an impedance analyzer; (b) adding test cells to at least two of the at least two wells, wherein the test cells expresses a RTK; (c) adding a compound suspected of being capable of effecting a RTK pathway to at least one of the at least two wells to form at least one compound well, adding a vehicle control to at least another well of the at least two wells to form at least one control well; (d) measuring first impedances of the at least one compound well and the at least one control well immediately preceding step e), and optionally determining first cell indices from the first impedances; (e) adding a RTK stimulating factor to the at least one compound well and to the at least one control well; (f) measuring second impedances of the at least one compound well and the at least one control well after the adding the RTK stimulating factor and optionally determining second cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the at least one control well; (h) comparing the change in impedance or cell index between the at least one compound well and the at least one control well; (i) identifying the compound effects the RTK pathway if the comparison demonstrates a significant difference between the change in impedance or cell index for the at least one compound well and the change in impedance or cell index for the at least one control well.

In one embodiment of the above methods for identifying a compound that affects receptor tyrosine kinase (RTK) pathway, the stimulating factor is a growth factor capable of activating RTK. In a preferred embodiments, the growth factor is selected from the group consisting of epidermal growth factor (EGF), platelet derived growth factor (PDGF), a nerve growth factor (NGF), and an antibody capable of activating RTK.

In yet another aspect, the present invention provides methods for validating a molecular target involved in the Receptor Tyrosine Kinase (RTK) signaling pathway leading from RTK activation comprising: (a) providing a device capable of measuring cell-substrate impedance, wherein the device comprises at least two wells, further wherein the device is operably connected to an impedance analyzer; (b) adding test cells to at least one well to form a test well and adding control cells to at least another well to form a control well, wherein the control cells express a RTK and the test cells comprise: (1) a dominant negative version of protein of interest, or (2) an siRNA targeting a protein of interest; or (3) a gene knockout of a protein of interest; or (4) a chemical or protein inhibitor specific for target of interest; (c) measuring first impedances of the at least one test well and the at least one control well immediately preceding step d), and optionally determining first cell indices from the first impedances; (d) adding a compound to the at least one test well and to the at least one control well; (e) measuring second impedances of the at least one test well and the at least one control well after step d) and optionally determining second cell indices from the second impedances; (f) determining the change in the impedance or cell index for the at least one test well by comparing the second impedance or the second cell index of the at least one test well to the first impedance or the first cell index of the at least one test well, and determining the change in the impedance or cell index of the at least one control well by comparing the second impedance or the second cell index of the at least one control well to the first impedance or the first cell index of the at least one control well; (g) comparing the change in impedance or cell index between the at least one test well and the at least one control well; and (h) validating the molecular target if the comparison demonstrates a significant difference between the change in impedance or cell index of the at least one test well and the change in impedance or cell index of the at least one control well.

In yet another aspect, the present invention provides methods for monitoring dose-dependent functional activation of a Receptor Tyrosine Kinase (RTK) comprising: (a) providing a device capable of measuring cell-substrate impedance; wherein the device comprises at least two wells, further wherein the device is operably connected to an impedance analyzer; (b) adding test cells to the at least two wells, wherein the test cells express a RTK; (c) measuring first impedances from the at least two wells immediately preceding step d) and optionally determining first cell indices from the first impedances; (d) adding a compound capable of activating the RTK to at least two wells in at least at two different concentrations forming compound wells 1 through x, wherein x equals the number of the at least two different concentrations; (e) measuring a series of impedances for each of the compound wells 1 through x after step d) and optionally determining a series of cell indices from the series of impedances, wherein the series comprise at least three impedance measurements; (f) determining the change in the impedance or cell index for each of the compound wells 1 through x by comparing the series of impedances or the series of cell indices for each of the compound wells 1 through x to the first impedance or the first cell index of each well corresponding to compound wells 1 through x; and (g) comparing the changes in impedances or in cell indices between the compound wells 1 through x at a given time point.

In one embodiment of the above method for monitoring dose-dependent functional activation of a Receptor Tyrosine Kinase (RTK), the method further comprises establishing a dose curve, wherein the dose curve is determined by plotting a maximum change in impedance or a maximum change in cell index for each concentration of the compound versus the corresponding concentration, or the dose curve is determined by measuring the area under the cell-index curve or impedance curve for each of the concentrations and plotting the area under the cell-index curve or impedance curve versus the corresponding concentration. In a preferred embodiment of the above method, the method further comprise determining an EC50 of the compound, wherein the EC50 is the molar concentration of the compound capable of inducing 50% of a maximum response in impedance or cell index or 50% of a maximum change in area under the cell-index curve or impedance curve.

In yet another aspect, the present invention provides methods for identifying a compound capable of affecting Receptor Tyrosine Kinase (RTK) activity in cancer cell proliferation comprising: (a) providing a device capable of measuring cell-substrate impedance, wherein the device comprises at least two wells, further wherein the device is operably connected to an impedance analyzer; (b) adding cancer cells expressing a receptor tyrosine kinase (RTK) to at least two of the at least two wells; (c) measuring first impedances of the at least two wells before step d) and optionally determining first cell indices; (d) introducing a compound suspected of being an RTK inhibitor to the at least one well to form at least one compound well and adding a vehicle control to at least another well to form a control well; (e) measuring a series of second impedances of the compound well and the control well after step d) and optionally determining second cell indices; (f) determining the change in the impedance or cell index for the at least one compound well by comparing the series of second impedances or the second cell indices of the at least one compound well to the first impedance or the first cell index of the at least one compound well, and determining the change in the impedance or cell index of the at least one control well by comparing the series of second impedances or the second cell indices of the at least one control well to the first impedance or the first cell index of the the at least one control well; (g) comparing the change in impedance or cell index between the at least one compound well and the at least one control well; and (h) identifying the compound is capable of affecting cancer cell proliferation if the comparison demonstrates the change in impedance or cell index of the at least one control well is greater than the change in impedance or cell index at least one compound well.

In one embodiment of the above method for identifying a compound capable of affecting Receptor Tyrosine Kinase (RTK) activity in cancer cell proliferation, the second impedances are measured during a period occurring after an initial spike in impedance. In another embodiment of the above method, the method further comprise adding a RTK stimulating factor after step d) and before step e), wherein the cancer cells are in serum-free medium in the at least compound well and in the at least one control well.

In one embodiment of the above methods for dynamic monitoring of activation of G-Protein coupled receptor (GPCR) and receptor tyrosine kinase (RTK) in living cells, the device capable of measuring or monitoring cell-substrate impedance may comprise, a) a nonconducting substrate; b) two or more electrode arrays fabricated on the substrate, wherein each of the two or more electrode arrays comprises two electrode structures; c) the two or more wells on the substrate, wherein each of the two or more arrays is associated with one of the two or more wells; and d) at least two connection pads, each of which is located on an edge of the substrate; wherein for each of the two or more electrode arrays, each of the two electrode structures comprises multiple electrode elements and the first of the two electrode structures of each of the at least two electrode arrays is connected to one of the at least two connection pads, and the second of the two electrode structures of each of the at least two electrode arrays is connected to another of the at least two connection pads; further wherein at least two of the two or more electrode arrays share one common connection pad; further wherein each electrode array has an approximately uniform electrode resistance distribution across the entire array; and further wherein the substrate has a surface suitable for cell attachment or growth; wherein the cell attachment or growth on the substrate can result in a detectable change in impedance between or among the electrode structures within each electrode array.

In one embodiment of the above methods for monitoring activation of a G-Protein Coupled Receptor (GPCR) or a receptor tyrosine kinase, the device capable of measuring cell-substrate impedance may comprise (a) a nonconductive substrate; and (b) a conductive electrode array fabricated on said nonconductive substrate; wherein a cell is capable of attaching to said electrode array. In a preferred embodiment of the methods, the device is in the format of a multi-well plate; wherein each of said at least two wells comprises said conductive electrode array. Preferably, the multi-well plate is selected from the group consisting of a 16 well plate, a 24 well plate, a 96 well plate, a 384 well plate, and a 1536 well plate.

In a preferred embodiment of the above methods for monitoring the activation of a G-Protein Coupled Receptor (GPCR) or a Receptor Tyrosine Kinase (RTK), the cell substrate impedance measures a cell's morphology or a characteristic of the cytoskeleton of a cell.

In preferred embodiments of the above methods for monitoring the activation of a G-Protein Coupled Receptor (GPCR), the GPCR is selected from the group consisting of a recombinant GPCR, an endogenous GPCR, an orphan GPCR, a constitutively active GPCR, and chimeric GPCR, or other chimeric receptor containing GPCR property.

In a preferred embodiment of the above methods for monitoring the activation of a G-Protein Coupled Receptor (GPCR) or a Receptor Tyrosine Kinase (RTK), the cell index is a normalized cell index wherein normalization is at a time point a short time before adding a compound, or a vehicle control, or an agonist, or a ligand, or a GPCR activating compound, or a RTK stimulator factor, wherein the short time is selected from the group consisting of less than 1 minute, less than 2 minutes, less than 5 minutes, less than 10 minutes, less than 30 minutes, less than 1 hour, less than 2 hours, less than 5 hours, less than 10 hours and less than 24 hours.

In some preferred embodiments of the above methods for monitoring the activation of a G-Protein Coupled Receptor (GPCR) or a Receptor Tyrosine Kinase (RTK), each of the first impedances are a series of impedance measurements prior to adding a compound, a vehicle control, or an agonist, or a ligand, or a GPCR activating compound or a RTK stimulator factor, and each of the first cell indices are a series of cell indices, wherein each of the first cell indices corresponds to a distinct impedance measurement within the series of impedance measurements. In some embodiments of the above methods, the measurement of the first impedances occurs at a time selected from the group consisting of less than 1 minute, less than 5 minutes, less than 30 minutes, less than 1 hour, less 2 hours, less than 5 hours, less than 10 hours, and less than 24 hours prior to said adding a compound, or a vehicle control, or an agonist, or a ligand, or a GPCR activating compound or a RTK stimulator factor.

In some preferred embodiments of the above methods for monitoring the activation of a G-Protein Coupled Receptor (GPCR) or a Receptor Tyrosine Kinase (RTK), each of the second impedances are a series of impedance measurements after the adding a compound, a vehicle control, or an agonist, or a ligand, or a GPCR activating compound or a RTK stimulator factor, and each of the second cell indices are a series of cell indices, wherein each of the second cell indices correspond to a distinct impedance measurement within the series of impedance measurements. In some embodiments of the above methods, the measurement of the second impedances occurs at a time point selected from the group consisting of more than 1 minute, more than 5 minute, more than 30 minute, more than 1 hour, more than 2 hours, more than 5 hours, more than 10 hours, and more than 24 hours after adding a compound, or a vehicle control, or an agonist, or a ligand, or a GPCR activating compound or a RTK stimulator factor.

In a preferred embodiment, the compound is selected from a library of compounds. A compound may be any molecules or biomolecules, including but not limited to a small molecule, a large molecule, a molecular complex, an organic molecule, an inorganic molecule, a lipid, a steroid, a carbohydrate, a fatty acid, an amino acid, a peptide, a protein, an antibody, a nucleic acid, or any combination of these. Preferably, a compound is capable of, or is suspected of, interacting with cells (for example, binding to cell surface receptor, or inhibiting certain intracellular signal transduction pathway, or activating cells). A compound may be a ligand, an agonist, an inverse agonist, an antagonist, an inhibitor, a RTK activating factor. Preferably, the compound is added to multiple wells at multiple, different concentrations.

In some embodiments of the above methods for monitoring the activation of a G-Protein Coupled Receptor (GPCR) or a Receptor Tyrosine Kinase (RTK), the changes in impedances or cell indices are absolute changes in impedances or cell indices. In some other embodiments, the changes in impedances or cell indices are relative changes in impedances or cell indices.

In a preferred embodiment of the above methods for monitoring the activation of a G-Protein Coupled Receptor (GPCR) or a Receptor Tyrosine Kinase (RTK), the compound is added to at least two wells in at least two different concentrations. In some embodiments of the above methods, a dose curve is determined by plotting a maximum change in impedance or a maximum change in cell index for each concentration of the compound versus the corresponding concentration. In other embodiments, a dose curve is established by determining the area under the cell-index curve or impedance curve for the different concentrations of the compound and plotting the area under the cell-index curve or impedance curve for each of the compound concentrations versus the corresponding concentration.

If a compound is identified as a ligand or an agonist or an activating compound for a G-Protein Coupled Receptor (GPCR), or a stimulating factor for a Receptor Tyrosine Kinase (RTK), preferably, EC50 of the compound is determined from a dose response curve. If a compound is identified as an antagonist for a GPCR, or as an inhibitor for a Receptor Tyrosine Kinase (RTK) in response to activation of RTK with a stimulating factor, preferably, IC50 of the compound is determined from a dose response curve.

BRIEF DESCRIPTION OF THE DRAWINGS

FIG. 1A depicts the substrate having 16 electrode arrays (or 16 electrode structure units) that are arranged in a 2-row by 8-column configuration on a substrate. FIG. 1B depicts a single electrode array of a device. FIG. 1C shows a schematic drawing of an electrode array, illustrating the requirement of approximately uniform distribution of electrode resistance across the array.

FIG. 15B: Paclitaxel; FIG. 15C: Olomoucine; FIG. 15D: Tamoxifan) for the indicated cell lines as estimated at 5 hr intervals from the cell index curves obtained using a cell-substrate impedance monitoring system of the present invention.

(FIG. 19A) Increasing numbers of NIH3T3 ranging from 100 cells all the way up to 10,000 cells were seeded in a device of the present invention and the cells were monitored for 10 hours at which point the Cell Index was obtained. The Cell Index value was plotted against the corresponding number of cells. (FIG. 19B) The cells described in FIG. 19A were assayed by MTT assay at the end of the experiment and the optical density at 590 nm was plotted against the number of cells seeded.

(FIG. 20A) A549 cells were seeded in a device of present invention at a density of 10,000 cells per well and the cells were continuously monitored up to 24 hours at which point paclitaxel was added at the indicated final concentrations. (FIG. 20B) Annexin V staining of A549 cells treated with DMSO or 12.5 nM paclitaxel for 20 hours. The cells were observed with fluorescence microscope and images were captured with an attached digital camera.

(FIG. 23A) CHO-M1 cells expressing the muscarinic M1 receptor were seeded in the wells of ACEA 16× device (16× E-Plate, 16 well microtiter plate that has incorporated microelectrode arrays at the bottom of the wells) and continuously monitored using the RT-CES™ system. At 24 hours post seeding the cells were stimulated with different doses of carbacol between 500 uM and 31.25 uM cabacol, plus media control. (FIG. 23B) The cells were seeded and monitored as described in (FIG. 23A). However, prior to stimulation with indicated doses of carbacol, the cells were incubated with the M1 receptor antagonist, pirenzipine at a final concentration of 50 uM.

FIG. 28A-C depict the carbachol-evoked increases of Cell Index (CI) of rat basophilic leukemia (RBL-2H3) cells expressing M3 and M2 receptors. M3 and M2 muscarinic receptor cell lines were seeded at 50,000 cells per well of ACEA E-plates. The cells were continuously monitored using the RT-CES system. At the indicated time point, increasing concentrations of carbachol (from 0 to 33 µM) were added to the cells and the cell response was monitored every 3 minutes by the RT-CES system. Carbachol leads to a dose-dependent and transient increase in CI in M3 (FIG. 28A) and M2 (FIG. 28C). Plotting the peak cell index response versus the corresponding log concentration allows for calculation of the $EC_{50}$ of carbachol for M3 (FIG. 28B). Delta cell index shown in (FIG. 28A) at a given time point was calculated by subtracting the cell index at a standard time point from the cell index at the given time point. Here the standard time point was the last time point of the measurement before adding carbachol to the cells (the first time point on the traces in FIG. 28A).

FIG. 29A-D depict histamine-evoked increases of Cell Index (CI) of CHO-K1 cells expressing the human recombinant H1 receptor (hH1-C1): pharmacologic characterization. Cell lines were seeded at 50,000 cells per well of ACEA E-plates. The cells were continuously monitored using the RT-CES system. At the indicated time point, increasing concentrations of histamine (from 0 (CTR) to 30 µM) were added to the cells and the cell response was monitored every 3 minutes by the RT-CES system. Histamine leads to a dose-dependent and transient increase in CI in hH-C1 cells shown in traces (FIG. 29A). Plotting the peak normalized cell index response versus the corresponding log concentration allows for calculation of the $EC_{50}$ of histamine (FIG. 29B). For blocking experiment, various concentrations of brompheniramine (histamine receptor antagonist, between 0 µM and 30 µM) were added to the cells 10 min prior to the addition of a fixed concentration histamine (20 nM)) and the cell response was monitored every 3 minutes by the RT-CES system. Brompheniramine blocked histamine-induced normalized-CI increase in a concentration-dependent manner as shown in traces (FIG. 29C). Plotting the maximal blocking effects on cell index response versus the corresponding log concentration allows for calculation of the $IC_{50}$ of brompheniramine (FIG. 29D). Normalized cell index shown in (FIG. 29A) and (FIG. 29C) at a given time point was calculated by dividing the Cell Index at the time point by the Cell Index at a reference time point. Here the reference time point was the last time point of the measurement before adding histamine to the cells. Note that sometime, we refer the reference time point for calculating normalized cell index as the time point at which the normalization is (i.e., normalization is at the reference time point).

FIGS. 30A-D depict an example of [Arg] Vasopressin (AVP)-evoked increases of Cell Index (CI) of 1321-N1 cells expressing the human recombinant vasopressin (V1a) receptor (V1a-C1): Blockage by selective non-active analogue [β-Mercapto-β, β-cyclopentamethylene-propionyl1, O-Et-Tyr$^2$, Val$^4$, Arg$^8$]Vasopressin (13M AVP). V1a-C1 cells were seeded at 50,000 cells per well of ACEA E-plates. The cells were continuously monitored using the RT-CES system. At the indicated time point, increasing concentrations of AVP were added to the cells and the cell response was monitored every 3 minutes by the RT-CES system. AVP leads to a dose-dependent and transient increase in CI in V1a-C1 cells shown in traces (FIG. 30A). Plotting the peak normalized-cell-index response versus the corresponding log concentration allows for calculation of the $EC_{50}$ of AVP (FIG. 30B). For blocking experiment, various concentrations of βM AVP were added to the cells 10 min prior to the addition of a fixed concentration of AVP (1 uM) and the cell response was monitored every 3 minutes by the RT-CES system. βM AVP blocked AVP-induced CI increases in a concentration-dependant manner as shown in traces (FIG. 30C). Plotting the maximal blocking effects on cell index response versus the corresponding log concentration allows for calculation of the $IC_{50}$ of βM AVP (FIG. 30D). Normalized cell index shown in (FIG. 30A) and (FIG. 30C) at a given time point was calculated by dividing the Cell Index at the time point by the Cell Index at a reference time point. Here the reference time point was the last time point of the measurement before adding AVP to the cells. Note that sometime, we refer the reference time point for calculating normalized cell index as the time point at which the normalization is (i.e., normalization is at the reference time point).

FIGS. 31A-D depict histamine-evoked increases of Cell Index (CI) of HeLa cells which express the endogenous histamine receptors: Blockage by antagonist brompheniramine. HeLa cells were seeded at 50,000 cells per well of ACEA E-plates. The cells were continuously monitored using the RT-CES system. At the indicated time point, increasing concentrations of histamine were added to the cells and the cell response was monitored every 3 minutes by the RT-CES system. Histamine leads to a dose-dependent and transient increase in CI in HeLa cells shown in traces (FIG. 31A). Plotting the peak cell index response versus the corresponding log concentration allows for calculation of the $EC_{50}$ of histamine (FIG. 31B). For the antagonist study, increasing concentrations of brompheniramine were added to the cells 10 min prior to the application of a fixed concentration histamine (5 uM) and the cell response was monitored every 3 minutes by the RT-CES system. Brompheniramine blocked histamine-induced CI increases in a concentration-dependent manner as shown in traces (FIG. 31C). Plotting the maximal blocking effects on cell index response versus the corresponding log concentration allows for calculation of the $IC_{50}$ of brompheniramine (FIG. 31D). Normalized cell index shown in (FIG. 31A) and (FIG. 31C) at a given time point was calculated by dividing the Cell Index at the time point by the Cell Index at a reference time point. Here the reference time point was the last time point of the measurement before adding histamine to the cells. Note that sometime, we refer the reference time point for calculating normalized cell index as the time point at which the normalization is (i.e., normalization is at the reference time point).

FIGS. 32A-B depict Endothelin 1-evoked increases of Cell Index (CI) of HeLa cells which express the endogenous endothelin receptors. HeLa cells were seeded at 50,000 cells per well of ACEA E-plates. The cells were continuously monitored using the RT-CES system. At the indicated time point, increasing concentrations of histamine were added to the cells and the cell response was monitored every 3 minutes by the RT-CES system. Endothelin 1 leads to a dose-dependent and transient increase in CI in HeLa cells shown in traces (FIG. 32A). Plotting the peak cell index response versus the corresponding log concentration allows for calculation of the $EC_{50}$ of endothelin 1 (FIG. 32B). Delta cell index shown in (FIG. 32A) at a given time point was calculated by subtracting the cell index at a standard time point from the cell index at the given time point. Here the standard time point was the last time point of the measurement before adding Endothelin to the cells (the first time point on the traces in FIG. 32A).

FIGS. 40A-D depict the characterization of activation of overexpressed GPCRs by RT-CES system. Human recombinant histamine 1 receptor (H1) and human recombinant vasopressin 1a (V1a) receptor (FIGS. 40A and 40C, respectively) were seeded at 50,000 cells per well of ACEA E-plates. The cells were continuously monitored using the RT-CES system. At the indicated time point, increasing concentrations of histamine were added to the cells and the cell response was monitored every 3 min. A typical set of CI traces by H1 cell line and V1a cell line were shown. Arrows indicate the addition of the ligand. Plotting the peak cell index response versus the corresponding log concentration allows for calculation of the $EC_{50}$. FIG. 40B demonstrates cell ruffling and cell adhesion enhancement after 5 min application of respective ligand. Histamine increase cell ruffling (c, arrow head) and cell adhesion assembly (d, arrow head) in H1 cells and AVP increase cell ruffling (g, arrow head) and cell adhesion assembly (h, arrow head) in V1a cell.

FIGS. 41A-D depict a pharmacological study of H1 cell line and V1a cell line coupled to Gq: Generation of $EC_{50s}$. H1 or V1a cell lines were seeded at 50,000 cells per well of ACEA E-plates. The cells were continuously monitored using the RT-CES system. At the indicated time point (arrows), increasing concentrations of histamine (FIG. 41A) or AVP (FIG. 41C) were added to the cells and the cell response was monitored every 3 min by the RT-CES system. A typical set of CI traces were shown. Plotting the peak cell index responses versus the corresponding log concentrations allows for calculation of the $EC_{50}$ of histamine (FIG. 41B) and AVP (FIG. 41D). Normalized cell index shown in (FIG. 41A and FIG. 41C) at a given time point was calculated by dividing the Cell Index at the time point by the Cell Index at a reference time point. Here the reference time point was the last time point of the measurement before adding histamine (FIG. 41A) or AVP (FIG. 41C) to the cells.

FIGS. 43A-F depict a pharmacological study of endogenous GPCRs by various ligands: Generation of $EC_{50s}$. HeLa cells (FIG. 43A) CHO cells (FIG. 43C) and C6 cells (FIG. 43E) were seeded at 50,000 cells per well of ACEA E-plates. The cells were continuously monitored using the RT-CES system. At the indicated time point (arrows), increasing concentrations of histamine (FIG. 43A), calcitonin (FIG. 43C) or isoproterenol (FIG. 43E) were added to the cells and the cell response was monitored every 3 min by the RT-CES system. Plotting the peak cell index responses versus the corresponding log concentrations allows for calculation of the $EC_{50s}$ of histamine (FIG. 43B) calcitonin (FIG. 43D) and isoproterenol (FIG. 43F) respectively. Normalized cell index shown in (FIG. 43A, FIG. 43C and FIG. 43E) at a given time point was calculated by dividing the Cell Index at the time point by the Cell Index at a reference time point. Here the reference time point was the last time point of the measurement before adding histamine (FIG. 43A) or calcitonin (FIG. 43C) or isoproterenol (FIG. 43E) to the cells.

(FIG. 44A) Cells treated with insulin or EGF showed a characteristic rise in cell index. (FIG. 44B) When pretreated with 10 µM EGFR inhibitor, 4557 W, the EGF response is inhibited while the insulin response remains intact. Normalized cell index shown in (FIGS. 44A and 44B) at a given time point was calculated by dividing the Cell Index at the time point by the Cell Index at a reference time point. Here the reference time point was the last time point of measurement before treatment of the cells with EGF or insulin.

(FIG. 45C) ELISA assay of phosphorylated EGFR were performed on COS7 cells treated with varying concentrations of EGF. Dose response curves were generated by plotting % control (relative to the response of the sample treated with maximum ligand concentration) of absorbance readings versus ligand concentration. Normalized cell index shown in (FIGS. 45A and 45B) at a given time point was calculated by dividing the Cell Index at the time point by the Cell Index at a reference time point. Here the reference time point was the last time point before adding EGF (FIG. 45A) or HGF (FIG. 45B).

(FIG. 46A) Increasing number of COS7 cells were plated, treated with EGF and cell indexes measured every minute over several hours. (FIG. 46B) Statistical evaluation of label-free EGFR inhibitor screening assay. Z', S/N, S/B and % CV were determined to assess quality of assay.

DETAILED DESCRIPTION OF THE INVENTION

A. Definitions

Figure 1A:
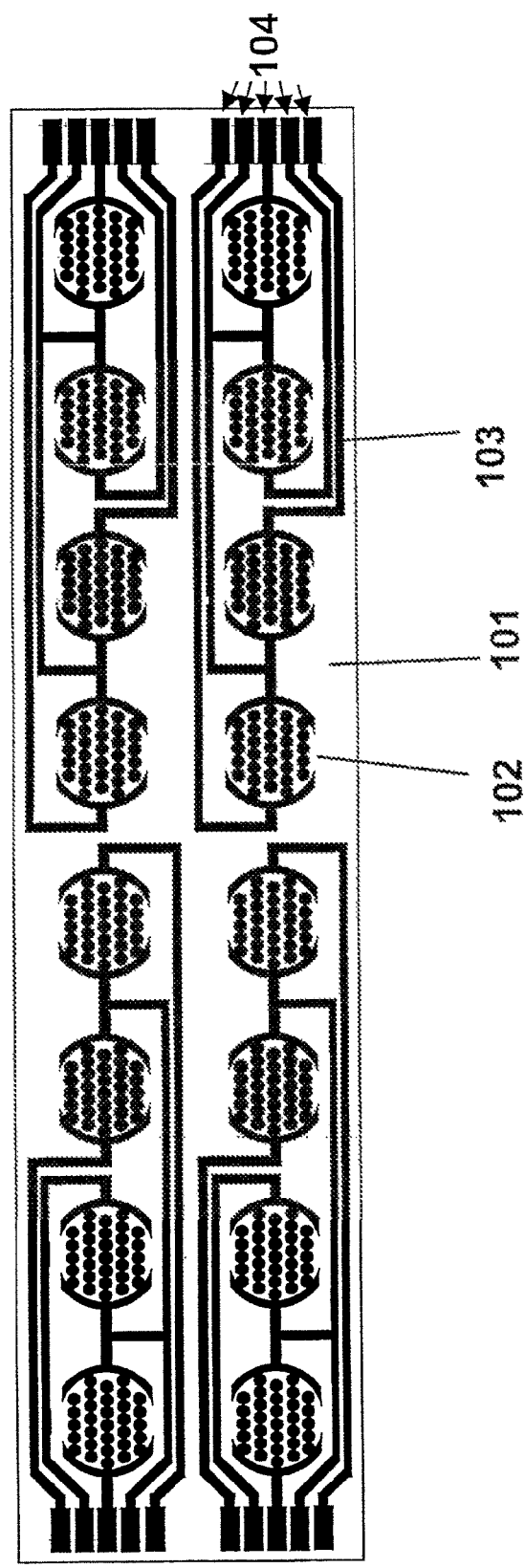
FIGS. 1A-C show schematic drawings of one design of a cell-substrate impedance measurement device of the present invention.

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible membrane" means a membrane that does not have deleterious effects on cells, including the viability, attachment, spreading, motility, growth, or cell division.

When a suspension of viable, unimpaired, epithelial or endothelial cells is added to a vessel, a surface of the vessel "is suitable for cell attachment" when a significant percentage of the cells are adhering to the surface of the vessel within twelve hours. Preferably, at least 50% of the cells are adhering to the surface of the vessel within twelve hours. More preferably, a surface that is suitable for cell attachment has surface properties so that at least 70% of the cells are adhering to the surface within twelve hours of plating (i.e., adding cells to the vessel). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a membrane) preferably is suitable for the attachment of cells of the type that are to be used in an assay that uses the biocompatible surface (e.g., membrane), and most preferably, allows the attachment of at least 90% of the cells that contact the biocompatible surface during the assay.

A "biomolecular coating" is a coating on a surface that comprises a molecule that is a naturally occurring biomolecule or biochemical, or a biochemical derived from or based on one or more naturally occurring biomolecules or biochemicals. For example, a biomolecular coating can comprise an extracellular matrix component (e.g., fibronectin, collagens), or a derivative thereof, or can comprise a biochemical such as polylysine or polyornithine, which are polymeric molecules based on the naturally occurring biochemicals lysine and ornithine. Polymeric molecules based on naturally occurring biochemicals such as amino acids can use isomers or enantiomers of the naturally-occurring biochemicals.

An "extracellular matrix component" is a molecule that occurs in the extracellular matrix of an animal. It can be a component of an extracellular matrix from any species and from any tissue type. Nonlimiting examples of extracellular matrix components include laminins, collagens fibronectins, other glycoproteins, peptides, glycosaminoglycans, proteoglycans, etc. Extracellular matrix components can also include growth factors.

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "at least two electrodes fabricated on said substrate" means that the at least two electrodes are fabricated or made or produced on the substrate. The at least two electrodes can be on the same side of the substrate or on the different side of the substrate. The substrate may have multiple layers, the at least two electrodes can be either on the same or on the different layers of the substrate.

As used herein, "at least two electrodes fabricated to a same side of said substrate" means that the at least two electrodes are fabricated on the same side of the substrate.

As used herein, "at least two electrodes fabricated to a same plane of said substrate" means that, if the nonconducting substrate has multiple layers, the at least two electrodes are fabricated to the same layer of the substrate.

As used herein, "said . . . electrodes [or electrode structures] have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "said device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among said electrodes" (or "detectable change in impedance between or among said electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the dose concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus doss concentration provides information not only about number of cells but also about their physiological status (e.g. cell morphology and cell adhesion). Furthermore, an important advantage offered by the system and devices of the present application is that in a single experiment, one can obtain "dose-response curves" at multiple time points since the system allows for the continuous monitoring of cells and provides impedance measurement at many time points over a time range as short as a few minutes to as long as days or weeks. In another example, a test compound may result in a change in cell morphology, which can be monitored or measured by cell-substrate impedance. Thus, cell-substrate impedance and cell index may follow a dose-dependent relationship on the concentration of the test compound. One may construct dose-response by plotting the maximum change in cell-substrate impedance or maximum change in cell index after adding the test compound at each compound concentration to the cells with respect to the cell-substrate impedance or cell index prior to the addition of the test compound. From such dose-response curve, one may derive important parameters such as EC50 or IC50 of the test compound.

As used herein, "the electrodes have, along the length of the microchannel, a length that is substantially less than the largest single-dimension of a particle to be analyzed" means that the electrodes have, along the length of the microchannel, a length that is at least less than 90% of the largest single-dimension of a particle to be analyzed. Preferably, the electrodes have, along the length of the microchannel, a length that is at least less than 80%, 70%, 60%, 50%, 40%, 30%, 20%, 10%, 5% of the largest single-dimension of a particle to be analyzed.

As used herein, "the microelectrodes span the entire height of the microchannel" means that the microelectrodes span at least 70% of the entire height of the microchannel. Preferably, microelectrodes span at least 80%, 90%, 95% of the entire height of the microchannel. More preferably, microelectrodes span at least 100% of the entire height of the microchannel.

As used herein, "an aperture having a pore size that equals to or is slightly larger than size of said particle" means that aperture has a pore size that at least equals to the particle size but less than 300% of the particle size. Here both pore size and particle size are measured in terms of single dimension value.

As used herein, "microelectrode strip or electrode strip" means that a non-conducting substrate strip on which electrodes or electrode structure units are fabricated or incorporated. The non-limiting examples of the non-conducting substrate strips include polymer membrane, glass, plastic sheets, ceramics, insulator-on-semiconductor, fiber glass (like those for manufacturing printed-circuits-board). Electrode structure units having different geometries can be fabricated or made on the substrate strip by any suitable microfabrication, micromachining, or other methods. Non-limiting examples of electrode geometries include interdigitated electrodes, circle-on-line electrodes, diamond-on-line electrodes, castellated electrodes, or sinusoidal electrodes. Characteristic dimensions of these electrode geometries may vary from as small as less than 5 micron, or less than 10 micron, to as large as over 200 micron, over 500 micron, over 1 mm. The characteristic dimensions of the electrode geometries refer to the smallest width of the electrode elements, or smallest gaps between the adjacent electrode elements, or size of a repeating feature on the electrode geometries. The microelectrode strip can be of any geometry for the present invention. One exemplary geometry for the microelectrode strips is rectangular shape—having the width of the strip between less than 50 micron to over 10 mm, and having the length of the strip between less than 60 micron to over 15 mm. An exemplary geometry of the microelectrode strips may have a geometry having a width of 200 micron and a length of 20 mm. A single microelectrode strip may have two electrodes serving as a measurement unit, or multiple such two-electrodes serving as multiple measurement units, or a single electrode structure unit as a measurement unit, or multiple electrode structure units serving as multiple electrode structure units. In one exemplary embodiment, when multiple electrode structure units are fabricated on a single microelectrode strip, these electrode structure units are positioned along the length direction of the strip. The electrode structure units may be of squared-shape, or rectangular-shape, or circle shapes. Each of electrode structure units may occupy size from less than 50 micron by 50 micron, to larger than 2 mm×2 mm.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

A "compound" or "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule such as but not limited to a lipid, a steroid, a carbohydrate, a fatty acid, an amino acid, a peptide, a protein, an antibody, a nucleic acid, or any combination of these. A test compound can be a synthetic compound, a naturally occurring compound, a derivative of a naturally-occurring compound, etc. The structure of a test compound can be known or unknown. In one application of the present invention, a compound is capable of, or is suspected of, inducing cytotoxicity. In another application of present invention, a compound is capable of, or is suspected of, stimulating effector cells. In still another application, a compound is capable of, or is suspected of, interacting with cells (for example, binding to cell surface receptor, or inhibiting certain intracellular signal transduction pathway, or activating cells).

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell viability, cell adhesion, apoptosis, cell differentiation, cell proliferation, cell morphology, cell cycle, IgE-mediated cell activation or stimulation, receptor-ligand binding, cell number, cell quality, cell cycling, etc.

An "impedance value" is the impedance measured for electrodes in a well with or without cell present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

A "Cell Index" or "CI" is a parameter that can derived from measured impedance values and that can be used to reflect the change in impedance values. There are a number of methods to derive or calculate Cell Index.

A "Normalized Cell Index" at a given time point is calculated by dividing the Cell Index at the time point by the Cell Index at a reference time point. Thus, the Normalized Cell Index is 1 at the reference time point.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the $1^{st}$ order derive of the Cell Index with respect to time, divided by the Cell Index at the time point. In other words, CCI is calculated as $$CCI(t) = \frac{dCI(t)}{CI(t) \cdot dt}.$$

B. Devices and Systems for Monitoring Cell-Substrate Impedance

Devices for Measuring Cell-Substrate Impedance

The present invention includes devices for measuring cell-substrate impedance that comprise a nonconducting substrate; two or more electrode arrays fabricated on the substrate, where each of the two or more electrode arrays comprises two electrode structures; and at least two connection pads, each of which is located on an edge of the substrate. Each electrode array of the device has approximately uniform electrode resistance across the entire array. The substrate of the device has a surface suitable for cell attachment or growth; where cell attachment or growth on said substrate can result in a detectable change in impedance between or among the electrode structures within each electrode array.

An electrode array is two or more electrode structures that are constructed to have dimensions and spacing such that they can, when connected to a signal source, operate as a unit to generate an electrical field in the region of spaces around the electrode structures. An electrode structure refers to a single electrode, particularly one with a complex structure. (For example, an electrode structure can comprise two or more electrode elements that are electrically connected together.) In devices of the present invention, an electrode array comprises two electrode structures, each of which comprises multiple electrode elements, or substructures. In preferred embodiments of the present invention, the electrode structures of each of the two or more electrode arrays of a device have substantially the same surface area. In preferred embodiments of a device of the present invention, each of the two or more electrode arrays of a device comprise two electrode structures, and each electrode structure comprises multiple electrode elements. Each of the two electrode structures of an electrode array is connected to a separate connection pad that is located at the edge of the substrate.

Thus, in devices of the present invention, for each of the two or more electrode arrays of the device, the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time by using switches (such as electronic switches).

Each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

For a device of the present invention, preferred arrangements for the electrode elements, gaps between the electrodes and electrode buses in a given electrode array are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in parent U.S. patent application Ser. No. 10/705,447, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. patent application Ser. No. 10/705,447, herein incorporated by reference for all description and disclosure of the design, features, and manufacture of impedance device comprising electrode arrays.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups.

Descriptions of electrode arrays used for impedance measurement that apply to the devices of the present invention are described in parent U.S. patent application Ser. No. 10/705,447, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure.

Preferably, the electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an array of the present device of the present invention are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

A device of the present invention can include one or more fluid-impermeable receptacles which serve as fluid containers. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in parent U.S. patent application Ser. No. 10/705,447, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in parent U.S. patent application Ser. No. 10/705,447, and also in parent application U.S. patent application Ser. No. 10/987,732, both herein incorporated by reference for disclosure of multiwell impedance measurement devices, including their design, composition, and manufacture. A device of the present invention preferably has between 2 and 1,536 wells, more preferably between 4 and 384 wells, and even more preferably, between 16 and 96 wells, all or less than all or which are associated with electrode arrays.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

Methods of Use

The present invention also includes methods of using a device of the present invention that comprises fluid containers situated over electrode arrays to measure cell-substrate impedance. Such methods include: providing a device of the present invention that comprises fluid containers situated over electrode arrays, attaching an impedance analyzer to a device of the present invention, adding cells to one or more fluid containers of the device, and measuring impedance over one or more arrays of the device. Methods of performing cell assays using impedance measurement devices can be found in parent U.S. patent application Ser. No. 10/987,732 and U.S. patent application Ser. No. 10/705,447, both herein incorporated by reference for all disclosure of methods of using impedance measurement devices, as well as in Sections D and E of the present application.

Cell-Substrate Impedance Measurement Systems

In another aspect, the present invention is directed to a cell-substrate impedance measurement system comprising a) at least one multiple-well cell-substrate impedance measuring device, in which at least two of the multiple wells comprise an electrode array at the bottom of the well; b) an impedance analyzer electronically connected to the multiple-well cell-substrate impedance measuring device; c) a device station capable of engaging the one or more multiple-well devices and comprising electronic circuitry capable of selecting and connecting electrode arrays within any of the multiple wells to the impedance analyzer; and d) a software program connected to the device station and impedance analyzer to control the device station and perform data acquisition and data analysis from the impedance analyzer.

In a cell-substrate impedance measurement system of the present invention, the impedance analyzer engages connection pads of one or more multi-well devices to measure impedance. In one embodiment of the above system, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 0.1 ohm and $10^3$ ohm in frequency range of 100 Hz to 100 kHz.

A cell-substrate measurement system can be used to efficiently and simultaneously perform multiple assays by using circuitry of the device station to digitally switch from recording from measuring impedance over an array in one well to measuring impedance over an array in another well. In one embodiment of the above system, the system under software control is capable of completing an impedance measurement for an individual well at a single frequency within less than ten seconds. In another embodiment, the averaged time used by the system to complete an impedance measurement for an individual well at a single frequency is less than one second.

A multiple-well cell-substrate impedance measuring device in a system of the present invention can be any multiple-well cell-substrate impedance measuring device in which at least two of the multiple wells comprise an electrode array at the bottom of the well, and in which at least two of the multiple wells comprise an electrode array are individually addressed. In one embodiment of the above system, the multi-well device takes the form of a specialized microtiter plate which has microelectronic sensor arrays integrated into the bottom of the wells.

A device used in a system of the present invention, when connected to an impedance analyzer, can measure differences in impedance values that relate to cell behavior. For example, a cell-substrate impedance measuring device used in a system of the present invention can measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes.

Preferred devices that can be part of a cell-substrate impedance monitoring system can be those described in parent U.S. patent application Ser. No. 10/705,447, and in U.S. patent application Ser. No. 10/987,732, both herein incorporated by reference for disclosure of cell-substrate impedance monitoring devices that comprise electrode arrays, including disclosure of their design, composition, and manufacture. Preferred devices that can be part of a cell-substrate impedance monitoring system can also be those described in the present application.

Preferably a multi-well device of a system of the present invention comprises between 4 and 1,536 wells, some or all of which can comprise electrode arrays. In some embodiments of the present invention, a device station can comprise one or more platforms or one or more slots for positioning one or more multiwell devices. The one or more platforms or one or more slots can comprise sockets, pins or other devices for electrically connecting the device to the device station. The device station preferably can be positioned in a tissue culture incubator during cell impedance measurement assays. It can be electrically connected to an impedance analyzer and computer that are preferably located outside the tissue culture incubator.

The device station comprises electronic circuitry that can connect to an impedance monitoring device and an impedance analyzer and electronic switches that can switch on and off connections to each of the two or more electrode arrays of the multiwell devices used in the system. The switches of the device station are controlled by a software program. The software program directs the device station to connect arrays of the device to an impedance analyzer and monitor impedance from one or more of the electrode arrays. During impedance monitoring, the impedance analyzer can monitor impedance at one frequency or at more than one frequency. Preferably, impedance monitoring is performed at more than one time point for a given assay, and preferably, impedance is monitored at least three time points. The device station can connect individual arrays of a device to an impedance analyzer to monitor one, some, or all of the arrays of a device for a measurement time point. The switches of the device station allow the selected individual arrays to be monitored in rapid succession for each desired monitoring time point. Each monitoring time point is in fact a narrow time frame (for example from less than one second to minutes) of measurement in the assay during which impedance monitoring is performed. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc.

Preferably, the software can also analyze impedance data. In preferred embodiments, the software can calculate a cell index (CI) for one or more time points for one or more wells of the multiwell device. In some preferred embodiments, the software can calculate a cell change index (CCI) from impedance measurements of one or more wells of the multiwell device. The software can preferably generate plots of impedance data and impedance values, such as but not limited to CI or CCI, with respect to time. The software may perform other analysis as well, such as calculate cell number from CI, generate dose-response curves based on impedance data, calculate IC values based on impedance values, and calculate kinetic parameters of cell growth or behavior based on impedance values and impedance value curves. The software of the impedance monitoring system can also store and display analyses of the data, such as calculated impedance values and kinetic parameters derived therefrom, Data can be displayed on a screen, as printed data, or both.

C. Methods for Calculating Cell Index (CI) and Cell Change Index (CCI)

Cell Index

Based on the dependent relationship between the measured impedance, cell number (more accurately, the viable cell number, or attached cell number) and cell attachment status, it is possible to derive a so-called "cell number index" or "cell index" from the measured impedance frequency spectra that provides a useful index for quantitating and comparing cell behavior in the impedance-based assays of the present invention. In some applications of the present invention, "cell index" in the present application is the same as "cell number index" in PCT Application No. PCT/US03/22557, entitled "IMPEDANCE BASED DEVICES AND METHODS FOR USE IN ASSAYS", filed on Jul. 18, 2003 and in U.S. patent application Ser. No. 10/705,447, entitled "IMPEDANCE BASED DEVICES AND METHODS FOR USE IN ASSAYS," filed on Nov. 10, 2003, U.S. patent application Ser. No. 10/987,732, filed Nov. 12, 2004, U.S. patent application Ser. No. 10/705,447 and PCT Application No. PCT/US03/22557 are hereby incorporated by reference for the discussions and disclosures of cell index and cell number index they contain.

Various methods for calculating such a cell number index can be used, some of which are novel methods disclosed herein.

The present invention provides several methods of calculating cell index numbers for cells attached to two or more essentially identical arrays of a cell-substrate impedance device, where the cells are monitored for impedance changes. In preferred embodiments of the present invention, the methods calculate cell index number with better accuracy than previous methods of calculating cell index for cells on two or more arrays of a cell-substrate monitoring device. In some preferred methods of the present invention, methods of calculating a cell index rely on novel methods for calculating the resistances of electrical traces leading to two or more essentially identical arrays. The present invention therefore also includes methods of calculating resistances of electrical traces leading to two or more essentially identical arrays on a substrate.

By "essentially identical electrode arrays" or "essentially identical arrays" is meant that the dimensions and arrangement of electrodes, electrode structures, and electrode elements is the same for the referenced arrays. Thus, two essentially identical electrode arrays will have electrode structures of the same dimensions (length, width, thickness), where the electrode structures have the same number of electrode elements, and the arrangement of electrode structures and electrode elements in each array are the same. By arrangement is meant the distance between structures or elements (gap width), their physical position with respect to one another, and their geometry (angles, degree of curvature, circle-on-line or castellated geometries, etc.), including the same features of any electrode buses that may be connected to electrode structures or electrode elements. Electrodes of essentially identical arrays also comprise the same materials. For the purposes of calculating trace resistances and cell index number, a substrate can have any number of essentially identical arrays.

The following discussion provides novel methods of calculating cell index of cells adhered to arrays of a cell-substrate impedance monitoring device and novel methods for the calculation of the resistances of the electrical connection traces leading to two or more electrode arrays of a cell-substrate impedance monitoring device.

Impedance (Z) has two components, namely the resistance Rs and reactance Xs. Mathematically, the impedance Z is expressed as follows, $$Z = Rs + j\, Xs, \tag{2}$$

where $j = \sqrt{-1}$, depicting that for the (serial) reactance component Xs, the voltage applied over it is 90 degree phased-out from the current going through it. For the (serial) resistance, the voltage applied over it is in phase with the current going through it. As it is well-known in electronic and electrical engineering, the impedance can also be expressed in terms of parallel resistance Rp and parallel reactance Xp, as follows, $$Z = Rp^*(j\, Xp)/(Rp + j\, Xp), \tag{3}$$

where $j = \sqrt{-1}$. Nevertheless, these expressions (serial resistance and serial reactance, or parallel resistance and parallel reactance) are equivalent. Those who are skilled in electrical and electronic engineering can readily derive one form of expression from the parameter values in the other expression. For the sake of clarity and consistency, the description and discussion in the present invention utilizes the expression of serial resistance and serial reactance. For simplicity, serial resistance and serial reactance are simply called resistance and reactance.

As described in U.S. patent application Ser. No. 10/705, 447, entitled "Impedance based devices and methods for use in assays", filed on Nov. 10, 2003 and PCT application number PCT/US03/22557, entitled "Impedance based devices and methods for use in assays", filed on Jul. 18, 2003, both of which are herein incorporated by reference for disclosures relating to cell-substrate impedance monitoring, monitoring cell-substrate impedance for detection or measurement of change in impedance can be done by measuring impedance in any suitable range of frequencies. For example, the impedance can be measured in a frequency range from about 1 Hz to about 100 MHz. In another example, the impedance can be measured in a frequency range from about 100 Hz to about 2 MHz. The impedance is typically a function of the frequency, i.e., the impedance values change as frequency changes. Monitoring cell-substrate impedance can be done either in a single frequency or multiple frequencies. If the impedance measurement is performed at multiple frequencies, then a frequency-dependent impedance spectrum is obtained—i.e., there is an impedance value at each measured frequency. As mentioned above, the impedance has two components—a resistance component and a reactance component. A change in either resistance component or reactance component or both components can constitute a change in impedance.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, herein incorporated by reference for disclosure of methods of measuring electrical impedance, the method for the measurement of electrical (or electronic) impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. As it is well-known in electrical and electronic engineering, in such calculations (e.g. divisions mentioned above), the current amplitude and voltage amplitude are expressed in the form of complex numbers, which take into account of how big the current and the voltage are and what the phase difference between the sinusoidal waves of the current and the voltage is. Similarly, the impedance value is also expressed in a complex form, having both resistance and reactance component, as shown in equations above.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, both incorporated herein by reference for disclosure relating to Cell Index or Cell Number Index, the measured cell-substrate impedance can be used to calculate a parameter termed Cell Index or Cell Number Index. Various methods for calculating such a cell number index can be used based on the changes in resistance or reactance when cells are attached to the electrode structures with respect to the cases no cells are attached to the electrode structures. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example (A), the cell index or cell number index can be calculated by:

(A1) at each measured frequency, calculating the resistance ratio by dividing the resistance of the electrode arrays when cells are present and/or attached to the electrodes by the baseline resistance, (A2) finding or determining the maximum value in the resistance ratio over the frequency spectrum, (A3) and subtracting one from the maximum value in the resistance ratio.

Using a mathematically formula, Cell Index is derived as $$\text{Cell Index} = \max_{i=1,2,\ldots N}\left(\frac{R_{cell}(f_i)}{R_b(f_i)} - 1\right) \qquad (4)$$

Where N is the number of the frequency points at which the impedance is measured. For example, if the frequencies used for the measurements are at 10 kHz, 25 kHz and 50 kHz, then N=3, $f_1$=10 kHz, $f_2$=25 kHz, $f_3 \times$50 kHz. $R_{cell}(f_i)$ is the resistance (cell-substrate resistance) of the electrode arrays or electrode structures when the cells are present on the electrodes at the frequency $f_i$ and $R_b(f_i)$ is the baseline resistance of the electrode array or structures at the frequency $f_i$.

The cell index obtained for a given well reflects: 1) how many cells are attached to the electrode surfaces in this well, 2) how well cells are attached to the electrode surfaces in the well. In this case, a zero or near-zero "cell index or cell number index" indicates that no cells or very small number of cells are present on or attached to the electrode surfaces. In other words, if no cells are present on the electrodes, or if the cells are not well-attached onto the electrodes, $R_{cell}(f_i)$ is about the same as $R_b(f_i)$, leading to Cell Index=0. A higher value of "cell number index" indicates that, for same type of the cells and cells under similar physiological conditions, more cells are attached to the electrode surfaces. In other words, under same physiological conditions, more cells attached on the electrodes, the larger the values $R_{cell}(f_i)$ is, leading to a large value for Cell Index. Thus Cell Index is a quantitative measure of cell number present in a well. A higher value of "cell index" may also indicate that, for same type of the cells and same number of the cells, cells are attached better (for example, cells spread out more, or cell adhesion to the electrode surfaces is stronger) on the electrode surfaces.

Thus, for same number of the cells present in the well, change in a cell status will lead to a change in cell index. For example, an increase in cell adhesion or a cell spread leading to large cell/electrode contact area will result in an increase in $R_{cell}(f_i)$ and a larger Cell Index. On the other hand, a cell death or toxicity induced cell detachment, cell rounding up, will lead to smaller $R_{cell}(f_i)$ and thus smaller Cell Index.

In another example (B), the cell number index can be calculated by:
(B1) at each measured frequency, calculating the reactance ratio by dividing the reactance of the electrode arrays when cells are present on and/or attached to the electrodes by the baseline reactance,
(B2) finding or determining the maximum value in the reactance ratio over the frequency spectrum,
(B3) and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example (C), the cell index can be calculated by:
(C1) at each measured frequency, subtracting the baseline resistance from the resistance of the electrode arrays when cells are present or attached to the electrodes to determine the change in the resistance with the cells present relative to the baseline resistance;
(C2) then finding or determining the maximum value in the change of the resistance.

In this case, "cell-number index" is derived based on the maximum change in the resistance across the measured frequency range with the cells present relative to the baseline resistance. This cell index would have a dimension of ohm.

In yet another example (D), the cell index can be calculated by:
(D1) at each measured frequency, calculating the magnitude of the impedance (equaling to $\sqrt{R_s^2+X_s^2}$, where $R_s$ and $X_s$ are the serial resistance and reactance, respectively).
(D2) subtracting the magnitude of the baseline impedance from the magnitude of the impedance of the electrode arrays when cells are present or attached to the electrodes to determine the change in the magnitude of the impedance with the cells present relative to the baseline impedance;
(D3) then finding or determining the maximum value in the change of the magnitude of the impedance.

In this case, "cell-number index" is derived based on the maximum change in the magnitude of the impedance across the measured frequency range with the cells present relative to the baseline impedance. This cell index would have a dimension of ohm.

In yet another example (E), the index can be calculated by:
(E1) at each measured frequency, calculating the resistance ratio by dividing the resistance of electrode arrays when cells are present or attached to the electrodes by the baseline resistance,
(E2) then calculating the relative change in resistance in each measured frequency by subtracting one from the resistance ratio,
(E3) then integrating all the relative-change value (i.e., summing together all the relative-change values at different frequencies).

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

In yet another example (F), the cell index can be calculated by:
(F1) at each measured frequency, subtracting the baseline resistance from the resistance of the electrode arrays when cells are attached to the electrodes to determine the change in the resistance with the cells present relative to the baseline impedance; (here the change in the resistance is given by $\Delta R(f_i)=R_{s\text{-}cell}(f_i)-R_{s\text{-}baseline}(f_i)$ for the frequency $f_i$, $R_{s\text{-}cell}$ and $R_{s\text{-}baseline}$ are the serial resistances with the cells present on the electrode array and the baseline serial resistances, respectively);
(F3) analyzing the frequency dependency of the change of the resistance to derive certain parameters that can quantify such dependency. In one example, such parameters can be calculated as $$\sqrt{\sum_i [\Delta R(f_i)]^2}.$$

In another example, such parameter can be calculated as $$\sum_i |\Delta R(f_i)|.$$

The parameter(s) are used as cell index or cell number index.

In this case, "cell-number index" is derived based on the analysis of the frequency spectrum of the change in the resistance. Depending how the parameters are calculated, the cell index may have a dimension of ohm.

In yet another example (G), the cell index can be calculated by:
(G1) at each measured frequency, calculating the magnitude of the impedance (equaling to $\sqrt{R_s^2+X_s^2}$, where $R_s$ and $X_s$ are the serial resistance and reactance, respectively).
(G2) subtracting the magnitude of the baseline impedance from the magnitude of the impedance of the electrode arrays when cells are attached to the electrodes to determine the change in the magnitude of the impedance with the cells present relative to the baseline impedance; (here, the change in the magnitude of the impedance is given by $\Delta Z(f_i)=|Z_{cell}(f_i)|-|Z_{baseline}(f_i)|$ for the frequency $f_i$, $|Z_{cell}(f_i)|=\sqrt{R_{s\text{-}cell}(f_i)^2+X_{s\text{-}cell}(f_i)^2}$, $R_{s\text{-}cell}$ and $X_{s\text{-}cell}$ being the serial resistance and reactance with the cells present on the electrode arrays, respectively, $|Z_{cell}(f_i)|$ is the magnitude of the impedance of the electrode array with cells present on the electrode arrays, $|Z_{baseline}(f_i)|$ is the magnitude of the baseline impedance of the electrode array);

(G3) analyzing the frequency dependency of the change of the magnitude of the impedance to derive certain parameters that can quantify such dependency. In one example, such parameters can be calculated as $$\sqrt{\sum_i [\Delta Z(f_i)]^2}.$$

In another example, such parameter can be calculated as $$\sum_i |\Delta Z(f_i)|.$$

The parameter(s) are used as cell index or cell number index.

In this case, "cell-number index" is derived based on the analysis of the frequency spectrum of the change in the magnitude of the impedance. Depending how the parameters are calculated, the cell index may have a dimension of ohm.

As described in the U.S. patent application Ser. No. 10/705,447, entitled "Impedance based devices and methods for use in assays", filed on Nov. 10, 2003 and PCT application number PCT/US03/22557, entitled "Impedance based devices and methods for use in assays", filed on Jul. 18, 2003, and U.S. patent application Ser. No. 10/987,732, all herein incorporated by reference for disclosure of Cell Index or Cell Number Index and its calculation, there are different methods for calculating the parameter termed Cell Index or Cell Number Index from the measured cell-substrate impedance (resistance or reactance). Cell Index or Cell Number Index is a quantitative measure of cells in the wells under cell-substrate impedance measurement.

It is worthwhile to point out that it is not necessary to derive such a "cell number index" for utilizing the impedance information for monitoring cell conditions over the electrodes. Actually, one may choose to directly use measured impedance (e.g., at a single fixed frequency; or at a maximum relative-change frequency, or at multiple frequencies) as an indicator of cell conditions. If measured impedance values are directly used for monitoring cell conditions, then resistance, or reactance or both resistance and reactance can be used.

Still, deriving "cell index" or "cell number index" and using such index to monitor cell conditions may have advantages. There are several advantages of using "cell number index" to monitor cell growth and/or attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

As shown above, for some methods of calculating cell index or cell number index, it is important to know the impedance (resistance and/or reactance) of the electrode structures with and without cells present on them. Based on the equation (1), the impedance of the electrode array (with or without cells present on the electrodes) is given by $$Z_{electrode-array} = Z_{total} - Z_{trace} - Z_{switch} \quad (5)$$

Where $Z_{switch}$ is the impedance of electronic switch at its on stage, $Z_{trace}$ is the impedance of the electrical connection traces (or electrical conductive traces) on the substrate between the connection pads and the electrode buses, $Z_{total}$ is the total impedance measured at the impedance analyzer. By choosing electronic switches with good quality, it is possible to have all the electronic switches have a consistent on-impedance (mainly resistance). For example, the on-resistance of electronic switches can be about 3 ohm (+/- 10%) with the on reactance being negligible (for example, less than 0.2 ohm in the frequency range of interest). Thus, if the trace impedance is determined or calculated, then formula (5) can be used to calculate the impedance of the electrode arrays with or without cells present.

Figure 1B:
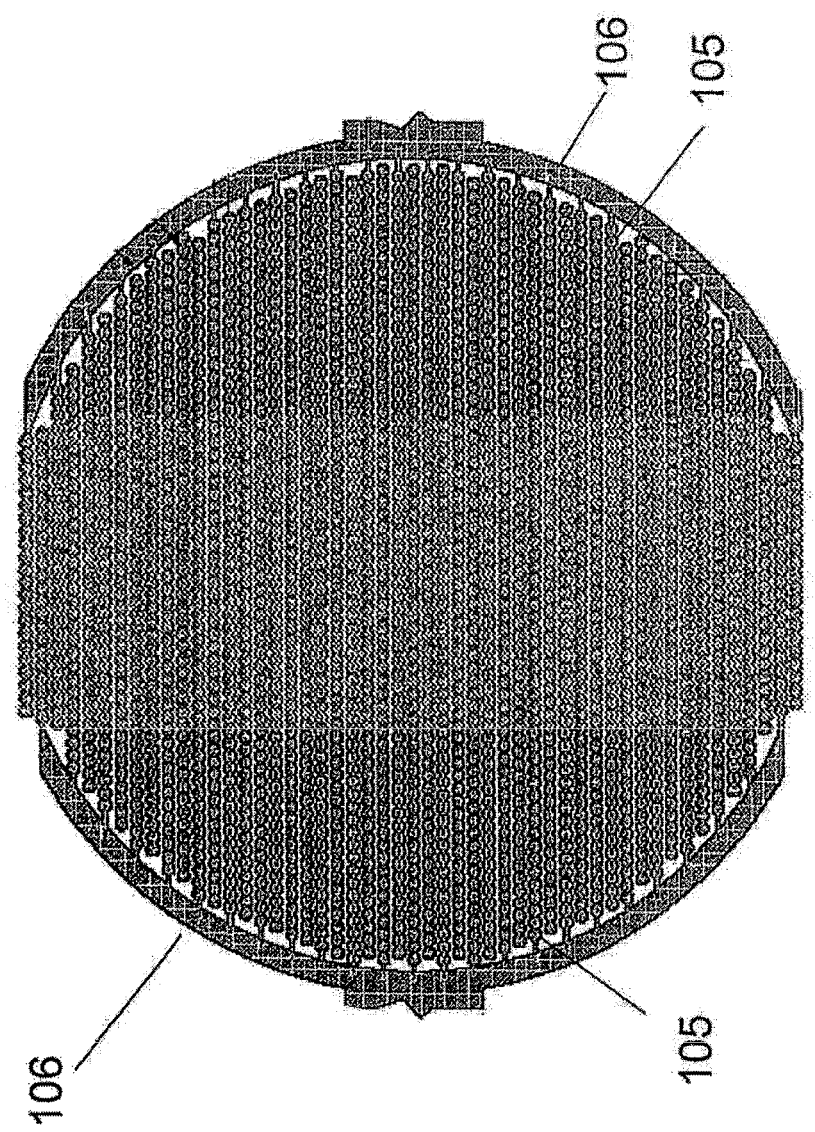
Figure 1C:
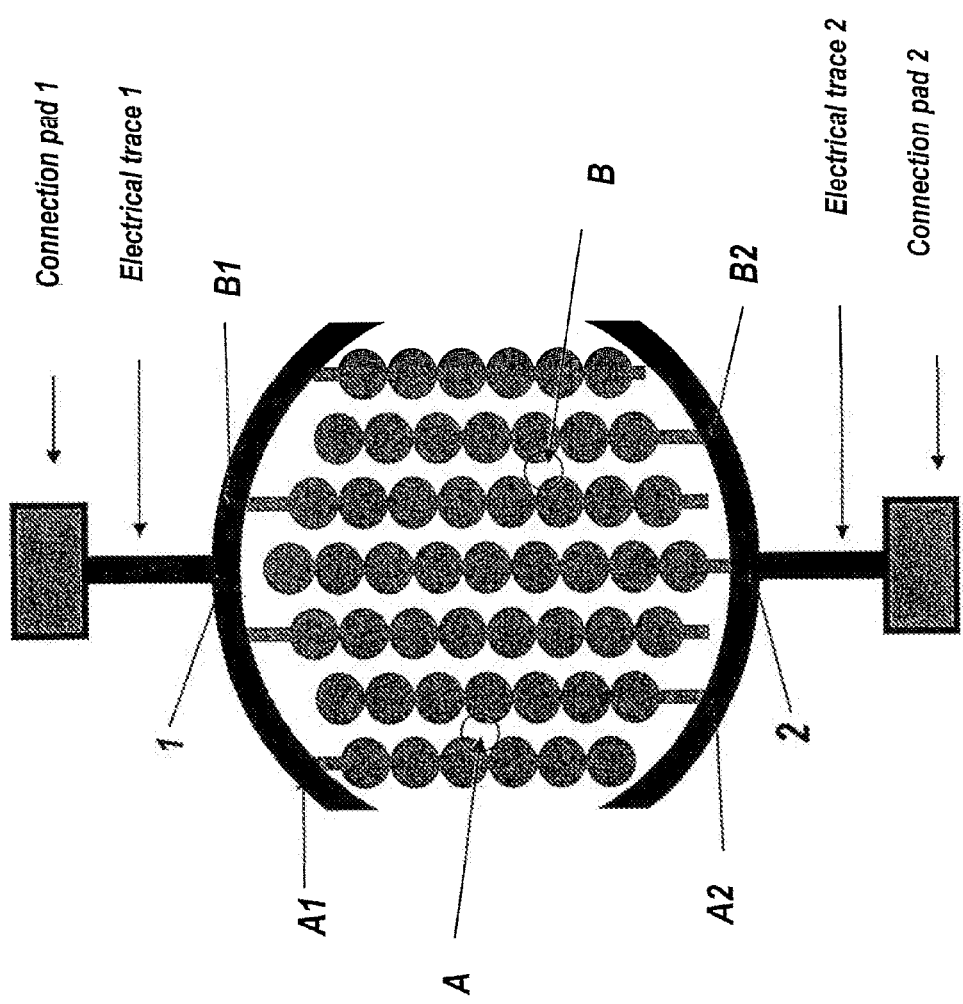

A method is invented in the present application to determine the impedance of electrical conductive (electrical connection) traces (mainly trace resistance, trace reactance is very small for the thin conductive film trace) based on the relationships among two or more essentially identical arrays on a cell-substrate impedance monitoring device. In the following, the electrode arrays as indicated in FIGS. 1A-C, are used to illustrate this method. The electrical reactance (serial reactance) of the electronic switches and the electrical reactance (serial reactance) of the electrical connection traces are small as compared with the corresponding electrical resistances (serial resistances). Thus, we focus on the analysis of the resistance of the electrical connection traces. The impedance determined from the impedance analyzer does contain both resistance (serial resistance, $R_{total}$) and reactance (serial reactance). For the electrode arrays A-D, the measured total resistance $R_{total}$, the resistance ($R_{trace}$) of electrical conductive (connection) trace, the switch resistance ($R_{switch}$) and the resistance ($R_{e-array}$) of the electrode array satisfy the following equations:

$$R_{e-array-A} = R_{total-A} - R_{trace-A} - R_{switch-A} \quad (6A)$$

$$R_{e-array-B} = R_{total-B} - R_{trace-B} - R_{switch-B} \quad (6B)$$

$$R_{e-array-C} = R_{total-C} - R_{trace-C} - R_{switch-C} \quad (6C)$$

$$R_{e-array-D} = R_{total-D} - R_{trace-D} - R_{switch-D} \quad (6D)$$

With chosen electronic switches having consistent switch-on resistance, $R_{switch-A}$, $R_{switch-B}$, $R_{switch-C}$ and $R_{switch-D}$ have very similar values and can be assumed to be the same, $R_{switch}$. Thus, in above equations, the known parameters are $R_{total-A}$, $R_{total-B}$, $R_{total-C}$, and $R_{total-D}$, and $R_{switch-A}$, $R_{switch-B}$, $R_{switch-C}$ and $R_{switch-D}$, and there are eight unknown parameters $R_{e-array-A}$, $R_{e-array-B}$, $R_{e-array-C}$, and $R_{e-array-D}$, and $R_{trace-A}$, $R_{trace-B}$, $R_{trace-C}$ and $R_{trace-D}$. It is impossible to solve these equations for the eight unknown variables from these four equations directly. Additional relationships between these variables are needed to solve for them. Each trace resistance ($R_{trace-A}$, $R_{trace-B}$, $R_{trace-C}$ and $R_{trace-D}$) depends on the metal film type used, and the geometry of the trace such as the how many rectangular segments the trace has, the film thickness(es) of the segments, the width(s) of the segments, the length(s) of the segment(s). For example, $$R_{trace-A} = \sum_{i=1}^{N} \rho \frac{L_{A-i}}{t_{A-i} * d_{A-i}} \quad (7)$$

where N is the number of the segments of the trace-A, $t_{A-i}$, $d_{A-i}$ and $L_{A-i}$ is the thickness, width and length of the i-th segment of the traces for the electrode array A, and ρ is the resistivity of the thin film. The equation here applies to the film comprising a single type of metal. The equation can be readily modified to be applicable to the film comprising two or more metal types (e.g. gold film over chromium adhesion layer).

If the film thickness is reasonably uniform (for example, less than 10% in thickness variation) across the substrate, then the relationship among the trace resistances is simply determined by the pre-determined geometrical shapes (e.g. the length, width of the segments). For example, it would be straightforward to calculate the ratio $\alpha_{A-D}$ between the resistance of the electrically conductive traces for the electrode array A to the resistance of the electrically conductive traces for the electrode array D as below, where the film thickness is assumed to be the same everywhere on these traces and the resistivity is also the same everywhere on these traces, $$\alpha_{A-D} = \frac{R_{trace\_A}}{R_{trace\_D}} = \frac{\sum_{i=1}^{N} \rho \frac{L_{A-i}}{t_{A-i} * d_{A-i}}}{\sum_{i=1}^{M} \rho \frac{L_{D-i}}{t_{D-i} * d_{D-i}}} = \frac{\sum_{i=1}^{N} \frac{L_{A-i}}{d_{A-i}}}{\sum_{i=1}^{M} \frac{L_{D-i}}{d_{D-i}}}. \quad (8)$$

Similarly, one can determine the ratio $\alpha_{B-D}$ and $\alpha_{C-D}$ based on the pre-determined geometrical relationships for the traces of the electrode arrays B, C and D. Note that above equations can be similarly derived for the cases where the thin film in these traces comprises more than one metal type. Thus, based on the equalities $$R_{switch-A} = R_{switch-B} = R_{switch-C} = R_{switch-D} = R_{switch} \quad (9A)$$

$$R_{trace-A} = \alpha_{A-D} \cdot R_{trace-D}, \quad (9B)$$

$$R_{trace-B} = \alpha_{B-D} \cdot R_{trace-D}, \quad (9B)$$

$$R_{trace-C} = \alpha_{C-D} \cdot R_{trace-D}, \quad (9C)$$

and $R_{trace-D} = \alpha_{D-D} \cdot R_{trace-D}$, \quad (9D)

equations (6A)-(6D) can be re-written in the following format:

$$R_{e\text{-}array\text{-}A} = R_{total\text{-}A} - \alpha_{A\text{-}D} \cdot R_{trace\text{-}D} - R_{switch} \quad (10A)$$

$$R_{e\text{-}array\text{-}B} = R_{total\text{-}B} - \alpha_{B\text{-}D} \cdot R_{trace\text{-}D} - R_{switch} \quad (10B)$$

$$R_{e\text{-}array\text{-}C} = R_{total\text{-}C} - \alpha_{C\text{-}D} \cdot R_{trace\text{-}D} - R_{switch} \quad (10C)$$

$$R_{e\text{-}array\text{-}D} = R_{total\text{-}D} - \alpha_{D\text{-}D} \cdot R_{trace\text{-}D} - R_{switch} \quad (10D)$$

For equations (10A) through (10D), there are five unknown variables, $R_{e\text{-}array\text{-}A}$, $R_{e\text{-}array\text{-}B}$, $R_{e\text{-}array\text{-}C}$, and $R_{e\text{-}array\text{-}D}$ and $R_{trace\text{-}D}$. Mathematically, these unknown variables cannot be determined from these equations. Additional information is needed to solve for these variables $R_{e\text{-}array\text{-}A}$, $R_{e\text{-}array\text{-}B}$, $R_{e\text{-}array\text{-}C}$, and $R_{e\text{-}array\text{-}D}$ and $R_{array\text{-}D}$.

One approach is invented and described in the present invention. In this approach, same biological or chemical solutions or suspensions are applied to the electrode-arrays A through D. Because the electrode arrays A through D have essentially identical electrode structures, the electrode array resistances $R_{e\text{-}array\text{-}A}$, $R_{e\text{-}array\text{-}B}$, $R_{e\text{-}array\text{-}C}$ and $R_{e\text{-}array\text{-}D}$ should be of same, or very similar value for such a condition when all the electrode arrays are exposed to the same biological or chemical solutions or suspensions, i.e.: $R_{e\text{-}array\text{-}A} \approx R_{e\text{-}array\text{-}B} \approx R_{e\text{-}array\text{-}C} \approx R_{e\text{-}array\text{-}D}$. If we assume the averaged electrode array resistance is $R_{e\text{-}array}$, then these approximate relationship exists $R_{e\text{-}array\text{-}A} \approx R_{e\text{-}array\text{-}B} \approx R_{e\text{-}array\text{-}C} \approx R_{e\text{-}array\text{-}D} \approx R_{e\text{-}array}$. Thus, equations (10A-10D) can be changed to the following:

$$R_{e\text{-}array} \approx R_{total\text{-}A} - \alpha_{A\text{-}D} \cdot R_{trace\text{-}D} - R_{switch} \quad (11A)$$

$$R_{e\text{-}array} \approx R_{total\text{-}B} - \alpha_{B\text{-}D} \cdot R_{trace\text{-}D} - R_{switch} \quad (11B)$$

$$R_{e\text{-}array} \approx R_{total\text{-}C} - \alpha_{C\text{-}D} \cdot R_{trace\text{-}D} - R_{switch} \quad (11C)$$

$$R_{e\text{-}array} \approx R_{total\text{-}D} - \alpha_{D\text{-}D} \cdot R_{trace\text{-}D} - R_{switch} \quad (11D)$$

Thus, we would need to find $R_{trace\text{-}D}$ and $R_{e\text{-}array}$ that satisfy the above approximate equality as close as possible. One mathematical approach is to find $R_{trace\text{-}D}$ and $R_{e\text{-}array}$ that would result in the minimum value for the following expression—an expression that quantifies the differences between the two sides of the approximate equality in (11A, 11B, 11C and 11D), $$F(R_{trace\text{-}D}, R_{e\text{-}array}) = [R_{e\text{-}array} - (R_{total\text{-}A} - \alpha_{A\text{-}D} R_{trace\text{-}D} - R_{switch})]^2 + [R_{e\text{-}array} - (R_{total\text{-}B} - \alpha_{B\text{-}D} R_{trace\text{-}D} - R_{switch})]^2 + [R_{e\text{-}array} - (R_{total\text{-}C} - \alpha_{C\text{-}D} R_{trace\text{-}D} - R_{switch})]^2 + [R_{e\text{-}array} - (R_{total\text{-}D} - R_{trace\text{-}D} - R_{switch})]^2 \quad (12)$$

The expression $F(R_{trace\text{-}D}, R_{e\text{-}array})$ is the sum of the squared-differences between the two-sides of the approximate equality in (11A, 11B, 11C and 11D). The smaller $F(R_{trace\text{-}D}, R_{e\text{-}array})$, the closer the two sides of the approximate equality (11A, 11B, 11C and 11D). Thus, values of $R_{trace\text{-}D}$ and $R_{e\text{-}array}$ that result in the minimum value of $F(R_{trace\text{-}D}, R_{e\text{-}array})$ should be determined. Mathematical approach involves in the calculation of the first order derivative of $F(R_{trace\text{-}D}, R_{e\text{-}array})$ to $R_{trace\text{-}D}$ and to $R_{e\text{-}array}$ and let such first order derivatives equal to zero. The values of $R_{trace\text{-}D}$ and $R_{e\text{-}array}$ that result in zero for these first-order-derivatives are those that result in the minimum value of $F(R_{trace\text{-}D}, R_{e\text{-}array})$. The first order derivatives are as follows:

$$\frac{\partial [F(R_{trace\text{-}D}, R_{e\text{-}array})]}{\partial R_{trace\text{-}D}} = \quad (13A)$$

$$2 \cdot \alpha_{A\text{-}D} \cdot [R_{e\text{-}array} - (R_{total\text{-}A} - \alpha_{A\text{-}D} R_{trace\text{-}D} - R_{switch})] +$$
$$2 \cdot \alpha_{B\text{-}D} \cdot [R_{e\text{-}array} - (R_{total\text{-}B} - \alpha_{B\text{-}D} R_{trace\text{-}D} - R_{switch})] +$$
$$2 \cdot \alpha_{C\text{-}D} \cdot [R_{e\text{-}array} - (R_{total\text{-}C} - \alpha_{C\text{-}D} R_{trace\text{-}D} - R_{swich})] +$$
$$2 \cdot [R_{e\text{-}array} - (R_{total\text{-}D} - R_{trace\text{-}D} - R_{switch})] = 0;$$

$$\frac{\partial [F(R_{trace\text{-}D}, R_{e\text{-}array})]}{\partial R_{e\text{-}array}} = \quad (13B)$$

$$2 \cdot [R_{e\text{-}array} - (R_{total\text{-}A} - \alpha_{A\text{-}D} R_{trace\text{-}D} - R_{switch})] +$$
$$2 \cdot [R_{e\text{-}array} - (R_{total\text{-}B} - \alpha_{B\text{-}D} R_{trace\text{-}D} - R_{switch})] +$$
$$2 \cdot [R_{e\text{-}array} - (R_{total\text{-}C} - \alpha_{C\text{-}D} R_{trace\text{-}D} - R_{swich})] +$$
$$2 \cdot [R_{e\text{-}array} - (R_{total\text{-}D} - R_{trace\text{-}D} - R_{switch})] = 0.$$

Equations (13A) and (13B) can be re-written as $$R_{e\text{-}array} \cdot [\alpha_{A\text{-}D}+\alpha_{B\text{-}D}+\alpha_{C\text{-}D}+1]+R_{trace\text{-}D}[\alpha_{A\text{-}D}^2+\alpha_{B\text{-}D}^2+\alpha_{C\text{-}D}^2+1]=\alpha_{A\text{-}D}\cdot[R_{total\text{-}A}-R_{switch}]+\alpha_{B\text{-}D}\cdot[R_{total\text{-}A}-R_{switch}]+\alpha_{C\text{-}D}\cdot[R_{total\text{-}C}-R_{switch}]+[R_{total\text{-}D}-R_{switch}] \quad (14A)$$

$$4 \cdot R_{e\text{-}array}+R_{trace\text{-}D}\cdot[\alpha_{A\text{-}D}+\alpha_{B\text{-}D}+\alpha_{B\text{-}D}+\alpha_{C\text{-}D}+1]=[R_{total\text{-}A}-R_{switch}]+[R_{total\text{-}B}-R_{switch}]+[R_{total\text{-}C}-R_{switch}]+[R_{total\text{-}D}-R_{switch}] \quad (14B)$$

Thus, we can solve for $R_{trace\text{-}D}$ as follows:

$$R_{trace\text{-}D} = \frac{4 \cdot S_1 - A_{11} \cdot S_2}{4 \cdot A_{12} - A_{11} \cdot B_{12}} \quad (15)$$

where $A_{11} = [\alpha_{A\text{-}D} + \alpha_{B\text{-}D} + \alpha_{C\text{-}D} + 1]$;

$A_{12} = [\alpha_{A\text{-}D}^2 + \alpha_{B\text{-}D}^2 + \alpha_{C\text{-}D}^2 + 1]$;

$S_1 = \alpha_{A\text{-}D} \cdot [R_{total\text{-}A} - R_{switch}] + \alpha_{B\text{-}D} \cdot [R_{total\text{-}B} - R_{switch}] + \alpha_{C\text{-}D} \cdot [R_{total\text{-}C} - R_{switch}] + [R_{total\text{-}D} - R_{switch}]$;

$B_{12} = [\alpha_{A\text{-}D} + \alpha_{B\text{-}D} + \alpha_{C\text{-}D} + 1]$;

$S_2 = [R_{total\text{-}A} - R_{switch}] + [R_{total\text{-}B} - R_{switch}] + [R_{total\text{-}C} - R_{switch}] + [R_{total\text{-}D} - R_{switch}]$.

Thus, with the determined $R_{trace\text{-}D}$, the trace resistances of $R_{trace\text{-}A}$, $R_{trace\text{-}B}$, and $R_{trace\text{-}C}$ can be calculated using equations (9B), (9C) and (9D). Furthermore, the electrode array resistance $R_{e\text{-}array\text{-}A}$, $R_{e\text{-}array\text{-}B}$, $R_{e\text{-}array\text{-}C}$ and $R_{e\text{-}array\text{-}D}$ can be calculated from the measured resistance $R_{total\text{-}A}$, $R_{total\text{-}B}$, $R_{total\text{-}C}$ and $R_{total\text{-}D}$ respectively using equations (10A), (10B), (10C) and (10D).

Thus, one aspect of the present invention is directed to a method of calculation of the resistances of the electrical connection traces s from the measured, total resistances for two or more essentially identical electrode arrays (such as, for example arrays in FIGS. 1A-C), comprising the following steps:
(1) exposing the electrode arrays to the solutions having same or similar solutions or suspensions;
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIGS. 1A-C), and the resistance of the electrode array with the solutions or suspensions present;
(3) solving for the resistances of electrical connection traces using equation (15) and equations (9B), (9C) and (9D), noting in the calculation with equation (15), the geometrical relationships between the electrode arrays are used to determine the factor $\alpha_{A\text{-}D}$, $\alpha_{B\text{-}D}$ and $\alpha_{C\text{-}D}$.

Another aspect of the present invention is directed to a method of calculating the resistance of the electrode arrays from the measured, total electrode resistances for two or more essentially identical electrode arrays (such as, for example arrays in FIGS. 1A-C) if the same or similar solutions or suspensions are added to be in contact with the electrode assays, comprising the following steps:
(1) exposing the electrode arrays to the solutions having same or similar solutions or suspensions;
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIGS. 1A-C) and the resistance of the electrode arrays with the solutions or suspensions present;
(3) solving for the resistances of electrical connection traces using equation (15) and equations (9B), (9C) and (9D), noting in the calculation with equation (15), the geometrical relationships between the electrode arrays are used to determine the factor $\alpha_{A\text{-}D}$, $\alpha_{B\text{-}D}$ and $\alpha_{C\text{-}D}$;
(4) calculating the resistances of the electrode arrays using equations (10A, 10B, 10C and 10D)).

In many applications, the solutions or suspensions (for example, cell suspension) applied to each electrode array may have different compositions. For example, cell suspensions of different cell numbers may be used so that the suspensions applied to each electrode array are quite different. Under such cases, the determination of the resistance of the electrode arrays with the cells present would require the determination of the resistance of the electrical connection traces by performing a "reference run" or "calibration run" in which the electrode arrays are exposed to a same, reference solution. From the "reference run", the resistances of the electrical connection traces can be determined. In a separate test, the electrode arrays are exposed to the solutions or cell suspensions of interest and the resistances for the electrode arrays under such conditions are measured with an impedance analyzer or impedance measuring circuit. The resistance of the electrode arrays with such cell suspensions present can be determined (or continuously determined) from the measured resistance by subtracting the sum of the resistance of the electronic switches and the resistance of the electrical connection traces for corresponding electrode arrays from the measured resistances.

Thus, another aspect of the present invention is directed to a method of calculating the resistance of the electrode arrays from the total electrical resistances measured at an impedance analyzer for essentially identical electrode arrays (such as electrode arrays in FIGS. 1A-C used as an example) if different solutions or suspensions of interest are applied to the electrode assays, comprising the following steps:
(1) exposing the electrode arrays to the solutions having same or similar solutions or suspensions (reference solutions);
(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIGS. 1A-C) and the resistance of the electrode arrays with the reference solutions present;
(3) solving for the resistances of electrical connection traces using equation (15) and equations (9B), (9C) and (9D), noting in the calculation with equation (15), the geometrical relationships between the electrode arrays of FIGS. 1A-C are used to determine the factor $\alpha_{A\text{-}D}$, $\alpha_{B\text{-}D}$ and $\alpha_{C\text{-}D}$;
(4) applying the solutions or suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the solutions or suspensions of the interest present, (5) Calculating the resistance of the electrode arrays using equations (10A), (10B), (10C) and (10D) by subtracting the electronic switch resistances and the resistances of electrical connection traces from the measured resistances in the step (4).

Note that in above method, the steps of exposing the electrode arrays to reference solutions for the determination of the resistances of electrically conductive traces (step (1), (2) and (3)) may be performed before or after the steps of applying the solutions or suspensions of interest to the electrode arrays and measuring the total electrical resistance (step (4)). For example, step (4) may be performed first. After that, the solutions or suspensions of the interest may be removed from the electrode array. The reference solutions can then be added to the electrode arrays (step (1)). Step (2) and step (3) can be then performed to determine the resistances of electrical connection traces. Finally, Step (5) can be done.

In another approach, step (1) and (2) can be performed ahead of step (4).

Another aspect of the present invention is directed to a method of determining the resistance of the electrode arrays with the cells present for a cell-based assay based on the total electrical resistance measured at an impedance analyzer for essentially identical electrode arrays. In this method, the electrode arrays are exposed to a same, reference solution (for example, a same cell culture medium that does not contain any cells) and electrical measurement is conducted to determine the resistance of electrical connection traces. With the resistances of the electrical connection traces determined, electrical resistances of the electrode arrays with cell suspensions added to electrode arrays can be calculated from the total electrical resistances measured at an impedance analyzer. Such total electrical resistance would include the resistance of the electrode arrays with cells present, the resistance of electronic switches and the resistance of electrical connection traces. The method comprises following steps (1) exposing the electrode arrays to the solutions having same or similar solutions or suspensions (reference solutions);

(2) with an impedance analyzer or impedance measurement circuit, measuring the resistance (serial resistance) for each electrode array, such resistance being the sum of the resistance of electronic switches, the resistance of the electrical connection traces between the connection pads and the electrode structures (for example, between the connection pads and the electrode buses, for the electrode structures in FIGS. 1A-C) and the resistance of the electrode arrays with the reference solutions present;

(3) solving for the resistances of electrical connection traces using equation (15) and equations (9B), (9C) and (9D), noting in the calculation with equation (15), the geometrical relationships between the electrode arrays in FIGS. 1A-C are used to determine the factor $\alpha_{A-D}$, $\alpha_{B-D}$ and $\alpha_{C-D}$;

(4) applying the cell suspensions of interest to each electrode array; and with an impedance analyzer or impedance measurement circuit, measuring the resistance (serial resistance) of each electrode array, such resistance being the sum of the resistance of electronic switches, the resistance of the electrical connection traces between the connection pads and the electrode structures, the resistance of the electrode arrays with the cell suspensions of the interest present, (5) Calculating the resistance of the electrode arrays using equations (10A), (10B), (10C) and (10D) by subtracting the electronic switch resistances and the resistances of electrical connection traces from the measured resistances in step (4).

Note that in above method, the steps of exposing the electrode arrays to reference solution for the determination of the electrical resistance of electrically conductive traces (step (1), (2) and (3)) may be performed before or after the steps of applying the solutions of interest or cell suspensions of interest to the electrode arrays and measuring the total electrical resistance (step (4)). For example, step (4) may be performed first, followed by steps (1) and (2). In one approach, after step (4), the cell suspensions of the interest may be removed from the electrode array. Then reference solutions can be added to the electrode arrays. In another approach, after step (4), the cells are all lysed with some cell lysis solutions so that the electrodes are exposed to the same, reference solutions for the measurement and calculation of step (2) and (3). And then, step (5) is performed to determine the electrical resistance of electrode arrays with the cell suspensions of interest present.

The determination of the resistances of the electrical conductive traces for the electrode arrays that essentially identical electrode arrays may be, or may not be, part of the monitoring of cell-substrate impedance for cell-based assays. It depends on how the impedance data (measured at a single frequency or multiple frequencies, measured at multiple time points) of the electrode arrays is analyzed.

In some assays, one is interested in the relative change in the resistance or impedance of the electrode arrays with the cells present relative to the baseline resistance or impedance. For such cases, it is preferred to determine the resistance (or impedance) of the electrode arrays from the total, measures resistance (or impedance) by subtracting the resistance of the electrical conductive traces and the resistance of electronic switches. Thus, determination of the resistances or impedance of the electrically conductive traces may be required.

In some other assays, one is interested in the absolute changes in the resistance (or impedance) of the electrode arrays with cells present relative to the baseline resistance (or impedance). In these cases, one can directly subtract the measured resistance or impedance for the baseline condition from the measured resistance or impedance for the condition that the cells are present on the electrode arrays. The contribution of the resistance (or impedance) of the electronic switches and the resistance (or impedance) of the electrically conductive traces to the total measured resistance (or impedance) values is cancelled out in such subtractions. Thus, there is no need for determining the resistances of the electrically conductive traces.

In some assays, one is interested in calculating the Cell Index or Cell Number Index based on the monitored impedance values. Depending on which method is used for calculating the Cell Index, it may, or may not, be necessary to determine the resistances of the electrically conductive traces. For example, for the Cell Index calculation method (A) described above, the resistances of the electrically conductive traces are needed, in order to remove the effect of the resistance of the electrically conductive traces on the analysis of the relative change of the resistance or impedance. In another example, for the Cell Index calculation method (F) described above, there is no need to determine the resistances of the electrically conductive traces since the effect of the resistance of the electrically conductive traces is canceled out in the calculations.

The monitoring of the cell-substrate impedance may be or may not be based on the change with respect to the baseline impedance (or resistance). For example, a cell-based assay is performed to assess the effect of a test compound on the cells. One method in performing such an assay is by monitoring of the cell-substrate impedance and determining the change in the cell-substrate impedance before and after the addition of the test compound to the cells. The monitoring of cell-substrate impedance can be performed at a single frequency point or multiple frequency points, at a single time point or multiple time points after drug addition. For example, the impedance is first measured at a single frequency or multiple frequencies for the electrode arrays with the cells present just before addition of test compound. The test compound is then added to the cells. The impedance is then measured again at the same single frequency or multiple frequencies for the electrode arrays with the cells after the addition of test compound.

Such post-compound addition measurement may be performed for many time points continuously in a regular or irregular time intervals. The change in the cell-substrate impedances can be determined or quantified by subtracting the impedance(s) (resistance and/or reactance) measured before addition of the test compound from the impedance(s) (resistance and/or reactance) measured after addition of the test compound. If the measurement is done at multiple frequencies, a single parameter or multiple parameters may be further derived for each time point after compound addition based on the calculated change in the cell-substrate impedances. Such parameters are used to quantify the cell changes after compound addition. Such approaches can be used further to analyze the responses of the cells to a test compound at multiple concentrations to derive dose-dependent response curves.

Normalized Cell Index, Delta Cell Index

A "Normalized Cell Index" at a given time point is calculated by dividing the Cell Index at the time point by the Cell Index at a reference time point. Thus, the Normalized Cell Index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

A "delta cell index" at a given time point is calculated by subtracting the cell index at a standard time point from the cell index at the given time point. Thus, the delta cell index is the absolute change in the cell index from an initial time (the standard time point) to the measurement time.

Cell Change Index

The time-dependent cellular response (including cytotoxicity response) may be analyzed by deriving parameters that directly reflect the changes in cell status. For example, time dependent cellular response may be analyzed by calculating the slope of change in the measured impedance responses (that is equivalent to the first order derivative of the impedance response with respect to time, impedance response here can be measured impedance data or derived values such as cell index, normalized cell index or delta cell index). In another example, the time-dependent cellular responses (including cytotoxicresposnes) responses may be analyzed for their higher order derivatives with respect to time. Such high order derivatives may provide additional information as for how cells responding to different compounds and as for the mechanisms of compound action.

As an example, we describe how one can to derive a parameter, called Cell Change Index, based on the real time, quantitative information (i.e., cell index, CI) about biological status of cells in the wells provided from RT-CES system. This new parameter, Cell Change Index (CCI), can effectively link time dependent cell index I with cell status, is calculated as, $$CCI(t) = \frac{dCI(t)}{CI(t) \cdot dt}. \qquad (5)$$

Thus CCI is the normalized rate of change in cell index. CCI values can be used to quantify the cell status change. For cells in an exponential growth under regular cell culture condition, the cell index determined by a cell-substrate impedance monitoring system described herein is expected to be a proportionate measure of the cell number in the well since the cell morphology and average extent of cell adhesion to the electrode surfaces among the whole cell population do not exhibit significant changes over time. Thus, the cell index (CI) increase with time following an exponential function, such that $$CI(t) = CI(0) * 2^{\frac{t}{DT}} \qquad (6)$$

where DT is the cell doubling time. For such exponential growth culture, CCI(t) is a constant, giving $$CCI(t) = \frac{0.693}{DT} \approx \frac{0.7}{DT}. \qquad (7)$$

Thus, several types of CCI(t) can be classified as:
  (1) If CCI is about 0.7/DT, cell index increases in the same rate as that expected for an exponential growth of the cells.
  (2) If CCI>>0.7/DT, cell index increases faster than that expected for an exponential growth (or log growth) of the cells. This indicates that cells may grow faster than regular exponential growth, or cells may exhibit some morphology change (e.g. cell spreading out or adhering better to the electrode surfaces), leading to large impedance signal, or both of above effects, or there may be other cell behaviors occurring particular to the assay or culture conditions.
  (3) If CCI is more than zero but somewhat smaller than 0.7/DT, then cell index increases in the rate slowed than that expected for an exponential growth. This indicates that cell growth rate may be slowed down relative to exponential growth, or cell growth may be somewhat inhibited by chemical compounds added to the culture media or by other cell culture parameters, or that certain populations of cells are dying off and detaching from the electrode surfaces, or there may be other cell behaviors occurring particular to the assay or culture conditions.

(4) If CCI is about zero, then cell index shows a near constant value. This may indicate that the cell growth is nearly-completely inhibited. For example, all the cells are arrested at certain points of cell cycle and are not progressing further. Or, this may indicate that the number of cells dying off in the culture is nearly as the number of newly-divided cells. Alternatively this may indicate that cells reach stationary phase of cell culture. Alternatively this may indicate that number of cells are above the detection upper limit of the cell-substrate impedance monitoring system. There is also the possibility of other cell behaviors occurring particular to the assay or culture conditions.

(5) If CCI is negative, then the cell index is decreasing with time, showing the cells losing attachment to the electrode surface or changing their morphology.

(6) If CCI is very negative, then the cell index decreases rapidly with time, showing that either cells lose attachment to the electrode surfaces quickly or cells change their morphology very quickly.

D. Methods for Performing Real-Time Cell-Based Assays

The present invention provide cell-based assays that can be performed in real time to assess cell proliferation, cell growth, cell death, cell morphology, cell membrane properties (for example, size, morphology, or composition of the cell membrane) cell adhesion, and cell motility. Thus the assays can be cytotoxicity assays, proliferation assays, apoptosis assays, cell adhesion assays, cell activation or stimulation assays, anti-cancer compound efficacy assays, receptor-ligand binding or signal transduction analysis, assays of cytoskeletal changes, assays of cell structural changes (including but not limited to, changes in cell membrane size, morphology, or composition), cell quantification, cell quality control, time-dependent cytotoxicity profiling, assays of cell differentiation or de-differentiation, detection or quantitation of neutralizing antibodies, specific T-cell mediated cytotoxic effect assays, assays of cell adhesivity, assays of cell-cell interactions, analysis of microbial, viral, or environmental toxins, etc.

The assays are real-time assays in the sense that cell behavior or cell status being assayed can be assessed continuously at regular or irregular intervals. Cell behaviors, cell responses, or cell status can be assayed and the results recorded or displayed within seconds to minutes of their occurrence. The cell response during an assay can be monitored essentially continuously over a selected time period. For example, a culture can be monitored every five to fifteen minutes for several hours to several days after addition of a reagent. The interval between impedance monitoring, whether impedance monitoring is performed at regular or irregular intervals, and the duration of the impedance monitoring assay can be determined by the experimenter.

Thus, the cell-based impedance assays of the present invention avoid inadvertently biased or misleading evaluation of cell responses due to the time point or time points chosen for sampling or assaying the cells. In addition, the assays do not require sampling of cell cultures or addition of reagents and thus eliminate the inconvenience, delay in obtaining results, and error introduced by many assays.

Descriptions of cell-substrate monitoring and associated devices, systems and methods of use have been provided in U.S. provisional application No. 60/379,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, entitled "Impedance based devices and methods for use in assays", filed on Jul. 18, 2003; PCT application number PCT/US03/22537, entitled "Impedance based apparatuses and methods for analyzing cells and particles", filed on Jul. 18, 2003; U.S. patent application Ser. No. 10/705,447, entitled "Impedance based devices and methods for use in assays", filed on Nov. 10, 2003; U.S. patent application Ser. No. 10/987,732 U.S. patent application Ser. No. 10/705,615, entitled "Impedance based apparatuses and methods for analyzing cells and particles", filed on Nov. 10, 2003, all incorporated herein by reference for their disclosure of cell-substrate impedance devices, systems, and methods of use. Additional details of cell-substrate impedance monitoring technology is further disclosed in the present invention.

In brief, for measurement of cell-substrate or cell-electrode impedance using the technology of the present invention, cell-substrate impedance monitoring devices are used that have microelectrode arrays with appropriate geometries fabricated onto the bottom surfaces of wells such as microtiter plate wells, or have a similar design of having multiple fluid containers (such as wells) having electrodes fabricated on their bottom surfaces facing into the fluid containers. Cells are introduced into the fluid containers of the devices, and make contact with and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue electronic readout signals can be measured automatically and in real time, and can be converted to digital signals for processing and for analysis.

Preferably, cell-substrate impedance assays are performed using a system of the present invention that comprises a device of the present invention, an impedance monitor, a device station that comprises electronic circuitry and engages the device and the impedance analyzer, and a software program that controls the device station and records and analyzes impedance data.

Using a system of the present invention, a cell index can optionally be automatically derived and provided based on measured electrode impedance values. The cell index obtained for a given well reflects: 1) how many cells are attached to the electrode surfaces in this well, and 2) how well (tightly or extensively) cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

In one aspect of the present invention, a method is provided for performing cell-based assays, comprising: a) providing a cell-substrate impedance monitoring device of the present invention that comprises two or more electrode arrays, each of which is associated with a fluid container of the device; b) attaching the device to an impedance monitor; c) introducing cells into one or more fluid containers of the device; and d) monitoring cell-substrate impedance of at least one of the fluid containers that comprises an electrode array and cells. Preferably, impedance is monitored from the at least one fluid container to obtain impedance measurements at at least three time points. Preferably, impedance measurements or impedance values derived from impedance measurements from at least three time points are plotted versus time to generate one or more impedance curves for the one or more fluid containers.

In a related aspect of the present invention, a method is provided for performing cell-based assays in an impedance-monitoring system, comprising: a) providing a cell-substrate impedance monitoring system of the present invention that comprises a device having two or more electrode arrays, each of which is associated with a well of the device; b) introducing cells into one or more wells of the device; and c) monitoring cell-substrate impedance of at least one of the wells that comprises an electrode array and cells. Preferably, impedance is monitored from the one or more wells of the device to obtain impedance measurements at at least three time points. Preferably, impedance measurements or impedance values derived from impedance measurements from at least three time points are plotted versus time to generate one or more impedance curves for the one or more wells.

The method can be used to assay cell status, where cell status includes, but is not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. The cell-based assays that be performed with above methods include, but are not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, and cell-based assays for screening and measuring ligand-receptor binding.

In preferred embodiments of this aspect of the present invention, cells are added to at least two fluid containers of a device, each of which comprises an electrode array, and impedance is monitored from at least two wells that comprise cells and an electrode array.

The cells used in the assay can be primary cells isolated from any species or cells of cell lines. Primary cells can be from blood or tissue. The cells can be engineered cells into which nucleic acids or proteins have been introduced. In some embodiments, different cell types are added to different wells and the behavior of the cell types is compared.

An impedance monitoring assay can be from minutes to days or even weeks in duration. Preferably, impedance is monitored at three or more time points, although this is not a requirement of the present invention. Impedance can be monitored at regular or irregular time intervals, or a combination of irregular and regular time intervals. In one embodiment of a cell-based impedance assay, the cell-substrate impedance is monitored at regular time intervals. In some embodiments of the present invention, impedance is monitored at irregular intervals and then at regular intervals during a particular time window of the assay. Impedance can be monitored at one frequency or at more than one frequency. For example, in some preferred embodiments, impedance is monitored over a range of frequencies for each time point at which impedance is monitored. Preferably, impedance is monitored at least one frequency between about 1 Hz and about 100 MHz, more preferably at least one frequency between about 100 Hz and about 2 MHz.

In yet another aspect, the present invention provides a method for performing real-time cell-based assay investigating the effect of a compound on cells, comprising: a) providing an above described system; b) seeding the cells to the wells of multiple-well devices; c) adding the compound to the wells containing cells; d) monitoring cell-substrate impedance before and after adding the compound at a regular or irregular time interval; wherein the time dependent impedance change provides information about time dependent cell status before addition of the compound and about time dependent cell status under the interaction of the compound. Information about cell status includes, not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

In one embodiment of the above cell-based assay, the cell-substrate impedance is monitored at regular time intervals. In exemplary embodiments, the impedance is measured at a regular 2 hour, 1 hour, 30 min or 15 min time interval before and after adding the compound. In the present application, a real-time assay means that one can perform the measurement on cell-substrate impedance with various time resolutions, for example, measurement taking place at a longer time interval such as every hour or every two hours, or at a shorter time interval every minute or a few minutes. Real-time assay does not mean that the measurements are provided in a continuous, uninterrupted fashion. In another word, real-time assay does not mean that the measurements are performed at every single moment.

Figure 2:
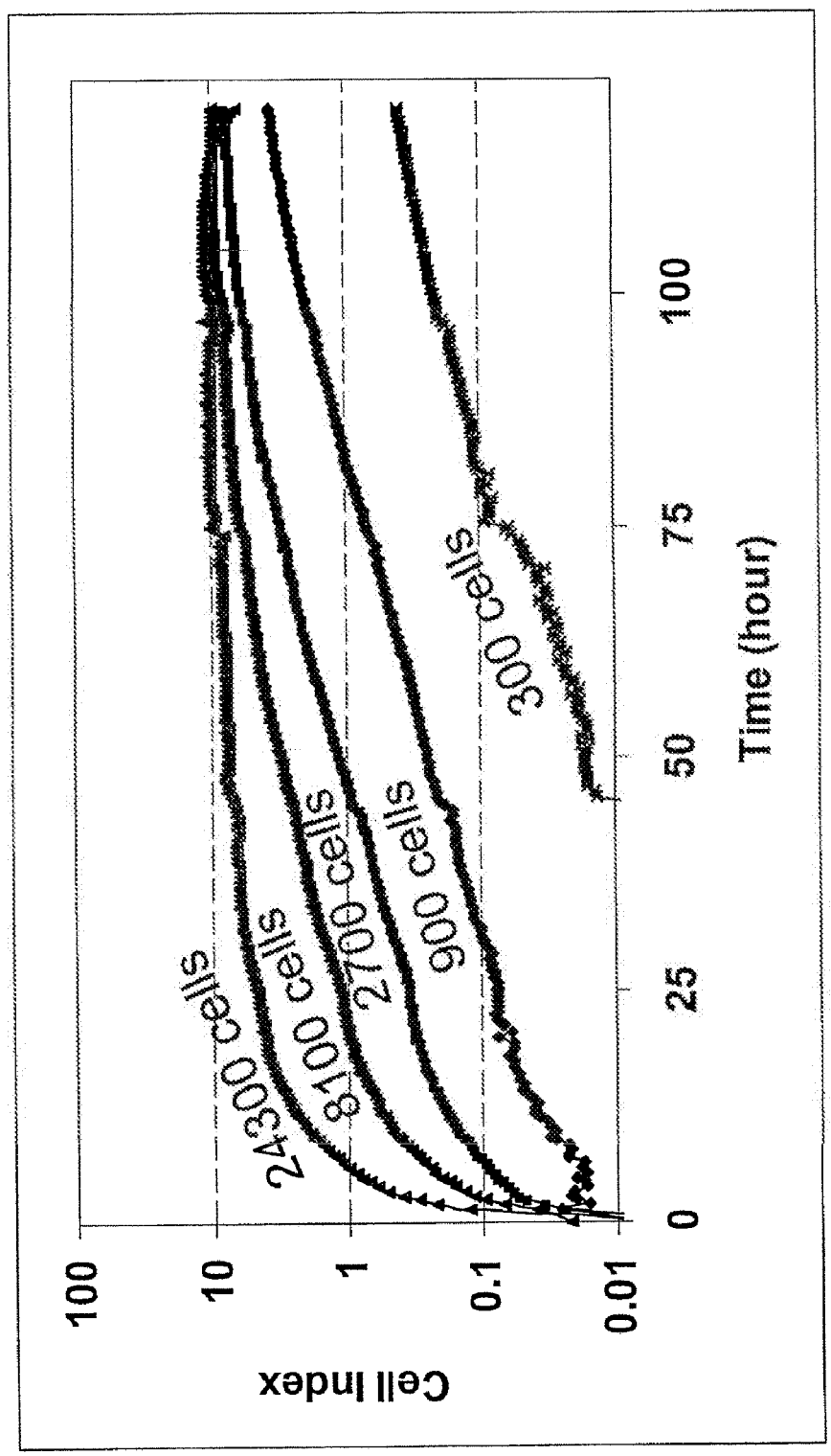
FIG. 2 shows real-time monitoring of proliferation of H460 cells seeded at different initial cell seeding numbers on a cell substrate impedance monitoring system of the present invention. The cell proliferation was continuously recorded every 15 minutes for over 125 hours. The cell growth curves in the log scale show exponential cell growth or cells in the stationary phase.

FIG. 2 depicts results of the use of methods of the present invention to monitor cell proliferation. In this experiment, H460 cells were introduced into wells of a 16 well device of a cell-substrate impedance monitoring system of the present invention, with different wells receiving different initial cell seeding numbers. The device was engaged with a device station of the system that was in a tissue culture incubator that kept a temperature of 37 degrees C. and an atmosphere of 5% $CO_2$. Cell-substrate impedance was monitored at 15 minute intervals for 125 hours. The cell index was calculated by the system for each time point and displayed as a function of time to give cell growth (proliferation) curves for each cell seeding number. The cell growth curves were plotted on a log scale showing exponential growth phases and stationary phases.

Figure 3:
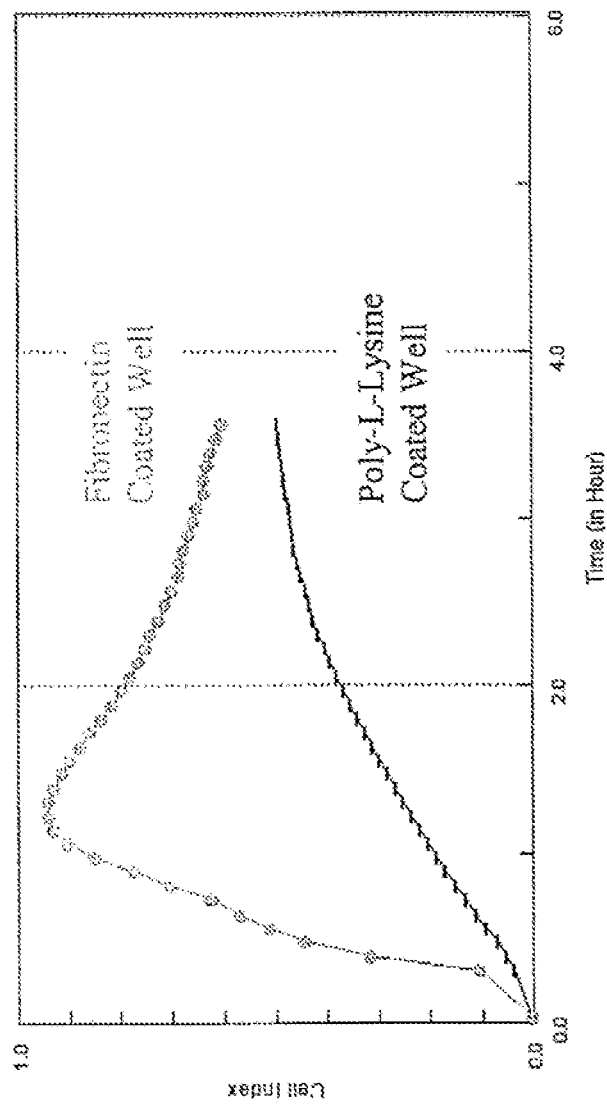
FIG. 3 shows real time monitoring of cell attachment and spreading of NIH3T3 cells using a cell-substrate impedance monitoring system of the present invention. The cells were seeded onto devices coated with either poly-L-lysine or fibronectin. The cell attachment and cell spreading processes on the different coating surfaces were monitored every 3 minutes for over 3 hours in real time.

FIG. 3 depicts results of real-time monitoring of cell attachment and spreading of NIH3T3 cells. The cells were seeded onto cell-substrate impedance monitoring devices of the present invention that were coated with either poly-L-lysine or fibronectin. The device was connected to a device station that was in a tissue culture incubator that kept a temperature of 37 degrees C. and an atmosphere of 5% $CO_2$. Cell attachment and cell spreading on the difference coating surfaces were monitored by measuring impedance on the cell-substrate monitoring system. Impedance was monitored in real time every 3 minutes for 3 hours. The cell index for each time point was calculated by the impedance monitoring system and plotted as a function of time.

Figure 4:
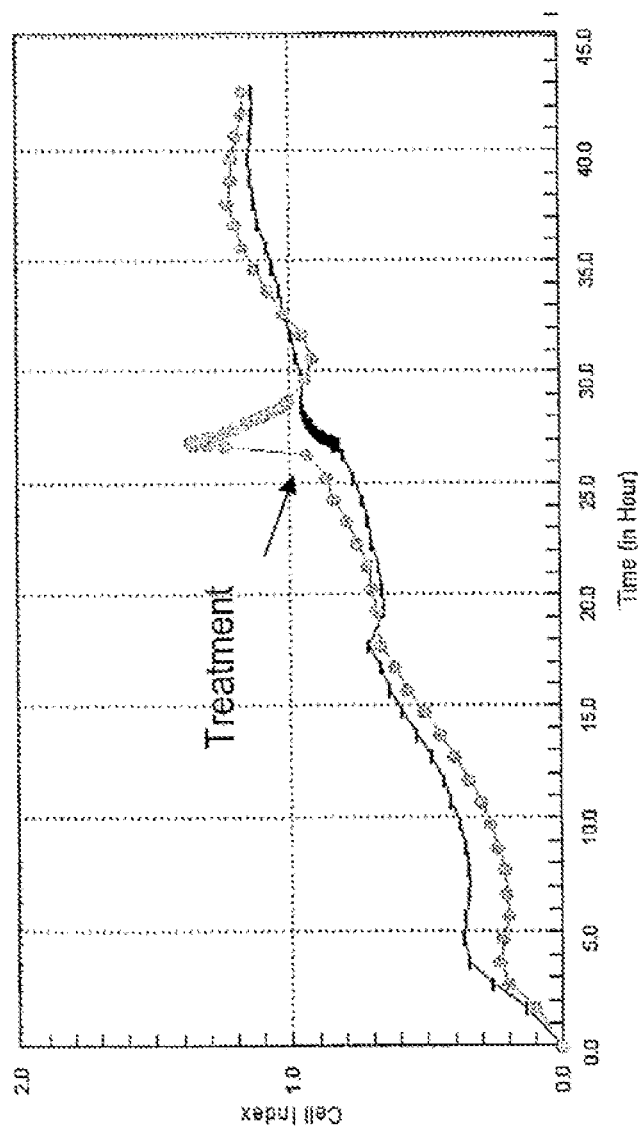
FIG. 4 shows real-time monitoring of morphological changes in Cos-7 cells using a cell-substrate impedance monitoring system of the present invention. The cells were serum starved for 8 hours and stimulated with or without 50 ng/mL EGF. Changes in cell morphology were monitored at 3 min intervals for 2 hours and then 1 hour interval for 14 hours. The initial jump in the signal in EGF-treated cells is due to membrane ruffling and actin dynamics in response to EGF. The arrow indicates the point of EGF stimulation.

FIG. 4 shows the results of an experiment monitoring morphological changes in Cos-7 cells in response to stimulation with epidermal growth factor (EGF). Cells were seeded in wells of a 16 well monitoring device of the present invention that engaged a device station of a cell-substrate monitoring system. The device station was positioned in an incubator held at 37 degrees C. and 5% $CO_2$. The cells were serum starved for 8 hours and then stimulated with 50 nanograms/mL of EGF. Control cells did not receive EGF. Impedance was monitored at 3 minute intervals for 2 hours and then at 1 hour intervals for 14 hours. The cell index was calculated by the system and plotted as a function of time. An initial jump in cell index is seen in EGF-treated cells due to membrane ruffling and actin dynamics in response to EGF. The arrow indicates the point of EGF addition.

D.1. Cell Proliferation Assays

The present invention provides methods for performing cell proliferation assays. In these assays, an increase in monitored impedance is indicative of an increases cell number. The impedance measurements or impedance values derived from impedance measurements can be plotted versus time to obtain growth curves for cells growing in a fluid container of a cell-substrate monitoring device of the present invention.

The present invention provides a method of generating at least one cell growth curve, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at three or more time points after adding the cells to the one or fluid containers; and plotting the impedance measurements or values for the three or more time points versus time to generate at least one growth curve for the cells in the one or more fluid containers.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells to one or more wells of the system; monitoring impedance from the one or more wells to obtain impedance measurements at three or more time points after adding cells to the one or more wells; and plotting impedance measurements or impedance values for the three or more time points versus time to generate a growth curve for the cells in the one or more wells.

Preferably, using a device or system of the present invention, impedance is monitored at four or more time points, in which at least one of the four or more time points is measured from a fluid container prior to adding cells to the fluid container. Preferably, impedance is monitored at regular or irregular time intervals for an assay period of from minutes to days. In many cases, proliferation assays can be performed by monitoring impedance for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

A growth curve can be generated by plotting impedance measurements versus time, or by plotting cell index values that are calculated from impedance measurements, such as normalized cell index values or delta cell index values versus time. The impedance measurement or cell index axis (typically the y-axis) can optionally use a log scale.

An impedance value can be any indices of impedance derived from impedance measurement, including, as non-limiting examples, a cell index, a normalized cell index or a delta cell index. In certain embodiment, impedance value can also be a "raw" measured or monitored impedance value. Cell index (including normalized and delta cell index) can be a useful value for plotting growth curves, as it relates impedance measurements to cell number. For cell growth curves, a delta cell index for a given time point can be derived by subtracting the cell index at a baseline point, such as a time point after cell attachment and just before log phase growth, from the cell index measurement at the given time point. Preferably, determinations of impedance values and generating growth curves based on impedance measurements or values can be performed by software, and preferably by software that interfaces directly with the impedance analyzer. For example, where the growth assays are performed by a system of the present invention, impedance values (where used) can be measured or derived or calculated and growth curves generated by a software program that controls and receives data from the impedance analyzer.

A growth curve generated from impedance measurements or cell index values (including normalized cell index values and delta cell index values) can optionally be used to calculate one or more kinetic parameters of cell growth or behavior. For example, a growth curve can be used to calculate the length of a lag phase, cell attachment time, cell attachment rate, or a cell doubling time.

FIG. 2 shows real-time monitoring of proliferation of H460 cells seeded at different initial cell seeding numbers on a cell substrate impedance monitoring system of the present invention. The cell proliferation was continuously recorded every 15 minutes for over 125 hours. The cell growth curves in the log scale show exponential cell growth or cells in the stationary phase. The cell index curve shown here can be used to calculate cell doubling time (DT). For example, taking the cell index for initial seeding density of 900 cells. It took approximately 57 hrs (from about 55 hr to about 112 hr) for cell index to increase from 0.3 to 3.0. Thus, the cell index doubling time is about 17.2 hrs (=log(2)*57). Assuming that there is a linear correlation between cell number and cell index in this range, then cell doubling time is the same as the cell index doubling time. Thus, the cell doubling time (DT) is about 17.2 hrs. Another simple method to calculate the cell index doubling time is just to figure out how long t takes cell index to double. For example, for the cell index curve with initial seeding density of 900 cells. It took about 17 hrs for cell index to change from 1.0 (at about 82 hrs) to 2.0 (at about 99 hrs). Thus the cell index doubling time is 17 hrs.

FIG. 3 shows real time monitoring of cell attachment and spreading of NIH3T3 cells using a cell-substrate impedance monitoring system of the present invention. The cells were seeded onto devices coated with either poly-L-lysine or fibronectin. The cell attachment and cell spreading processes on the different coating surfaces were monitored every 3 minutes for over 3 hours in real time. Using the cell index curve showing in FIG. 3, we can calculate the cell attachment time and cell attachment rate. Initial cell index increase immediately following cell addition to the ells (at time=0 in FIG. 3) reflects the cell spreading and attachment process. The time it takes for cell index to increase from zero to a maximum value or a some-what constant value (assuming that there is no cell division or growth in this initial time period following cell seeding) is the cell attachment time. For NIH3T3 cells, cell attachment time in a fibronectin coated well is about 1.2 hrs, as compared with the attachment time of about 3.5 hrs for the same cells in a poly-L-lysine coated well. Cell attachment rate is defined as 1 over the cell attachment time. Thus, cell attachment rate is about 0.83 $hr^{-1}$ and about 0.29 $hr^{-1}$, respectively, for NIH3T3 cells attaching to a fibronectin-coated well and a poly-L-lysine coated well.

FIG. 4 shows real-time monitoring of morphological changes in Cos-7 cells using a cell-substrate impedance monitoring system of the present invention. The cells were serum starved for 8 hours and stimulated with or without 50 ng/mL EGF. Changes in cell morphology were monitored at 3 min intervals for 2 hours and then 1 hour interval for 14 hours. The initial jump in the signal in EGF-treated cells is due to membrane ruffling and actin dynamics in response to EGF. The arrow indicates the point of EGF stimulation. Using the cell index curve showing in FIG. 4, we can calculate the cell attachment time and cell attachment rate. Initial cell index increase immediately following cell addition to the ells (at time=0 in FIG. 4) reflects the cell spreading and attachment process. The time it takes for cell index to increase from zero to a maximum value or a somewhat constant value (assuming that there is no cell division or growth in this initial time period following cell seeding) is the cell attachment time. For Cos-7 cells shown here, the cell attachment time is about 4 hrs. Cell attachment rate, as defined: 1 over the cell attachment time, is about 0.25 $hr^{-1}$ for Cos-7 cells. Furthermore, we can also calculate the length of lag phase. The lag phase corresponds to the time it takes for cells to enter the growth phase after the completion of cell attachment process. Based on the cell index curve in FIG. 4, cell attachment was complete at about 4 hrs. The cells showed significant increase in cell index—indicating cell growth, at around 9 hrs. Thus, the length of lag phase is about 5 hrs (=9 hr-4 hr).

Comparing Growth Curves of Two of More Cell Types

Two or more cell types can be seeded to separate wells in a proliferation assay using the methods of the present invention to generate growth curves of the two or more cell types. The growth curves or kinetic parameters derived from the growth curves of the cell types can be compared.

In this aspect, the invention includes a method of generating growth curves for at least two cell types, comprising: providing a device of the present invention having two or more electrode arrays, each of which is associated with a fluid container of the device; attaching the device to an impedance analyzer; adding cells of two or more cell types to two or more fluid containers of the device, in which at least one of the two or more fluid containers receives one cell type and at least one other of the two or more fluid containers receives a different cell type, to provide two or more fluid containers comprising two or more different cell types; monitoring impedance from the two or more fluid containers comprising different cell types at three or more time points after adding the two or more cell types to the two or more fluid containers; and plotting impedance measurements or impedance values for the three or more time points versus time to generate a growth curve for the two or more cell types.

The present invention also provides a method of generating at least one growth curve using a system of the present invention, where the system includes a multi-well cell-substrate impedance monitoring device, an impedance analyzer, a device station, and a software program. The method includes; providing a multi-well cell-substrate impedance measuring system; adding cells of two or more cell types to two or more wells of the device, in which at least one of the two or more wells receives one cell type and at least one other of the two or more wells receives a different cell type, to provide two or more wells comprising two or more different cell types; monitoring impedance from the two or more wells comprising different cell types at three or more time points after adding the two or more cell types to the two or more wells; and plotting impedance measurements or impedance values for the three or more time points versus time to generate a growth curve for the two or more cell types.

As, described above for proliferation assays, impedance is preferably monitored using an impedance monitoring device or system at four or more time points, in which at least one of the four or more time points is measured from fluid containers prior to adding cells to the fluid containers. Preferably, impedance is monitored at regular or irregular time intervals for an assay period of from minutes to days, for example, for a period of between several hours and several days.

It is preferable to perform replicate proliferation assays in which more than one fluid container is seeded with same number of cells of the same type. In this case, a plot can optionally be generated by plotting averaged impedance measurements of values at assayed time points for replicate wells versus time. Preferably, a standard deviation for the averaged values is also calculated.

Growth curves for different cell types can be generated as described above. Impedance or impedance values, such as cell index, normalized cell index, or delta cell index can be plotted versus time. The impedance measurement or cell index axis (typically the y-axis) can optionally use a log scale.

A growth curve generated from impedance measurements or cell index values (including normalized cell index values and delta cell index values) can optionally be used to calculate one or more kinetic parameters of cell growth or behavior. For example, a growth curve can be used to calculate the duration of a lag phase, cell attachment time, cell attachment rate, or a cell doubling time.

Preferably, the growth curves of the two or more different cell types, or kinetic parameters derived from the growth curves of the two or more different cell types, are compared to determine differences among the cell types in proliferation patterns or rates, or in kinetic parameters that can be derived from growth curves. The different cell types used can be any cell types, including primary cells isolated from blood or tissue of an animal or human, or cells from cell lines. For example, proliferation rates of two types of primary cancer cell can be compared, or of primary cancer cells of the same type but different grades. In another example, primary cells of individuals of different genotypes can be compared. In another example, proliferation rates of primary or cell line stem cells can be compared. In yet another example, growth curves or parameters of control and genetically modified cells of a cell line can be compared. In yet another example, growth curves or parameters of cells infected with virus and control cells can be compared.

D.2. Quantifying Cells Using Cell-Substrate Impedance Devices

The present invention also includes a method of quantifying cells, comprising: providing a device of the present invention having two or more electrode arrays, each of which is associated with a fluid container of the device; attaching the device to an impedance analyzer; adding cells to one or more fluid containers of the device; monitoring impedance from the one or more fluid containers to obtain impedance measurements at one or more time points after adding the cells to the one or more fluid containers; deriving a cell index for the one or more time points; and using the cell index to determine the number of cells in the one or more fluid containers at at least one of the one or more time points. The cell index is used to determine the number of cells using a formula that relates cell index to cell number, in which the formula is obtained by: providing a device for cell-substrate monitoring, attaching the device to an impedance monitor; adding cells to one or more fluid containers of the device; measuring impedance of the one or more fluid containers comprising cells; calculating a cell index from the impedance measurements; determining the number of cells of said at least one fluid container at the time of impedance monitoring by a means other than impedance monitoring; and deriving a formula that relates the number of cells of the one or more fluid containers at the two or more time points with the impedance measurements at the two or more time points.

In the embodiment of above method for obtaining the formula, sometimes, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemocytometer counting, flow cytometry, or Coulter counting.

The method can also be practiced using an impedance monitoring system of the present invention, where the system includes a multi-well cell-substrate impedance monitoring device, an impedance analyzer, a device station, and a software program. The method includes; providing a multi-well cell-substrate impedance measuring system; adding cells one or more wells of the system; monitoring impedance from the one or more wells comprising cells at one or more time points after adding the cells to the one or more wells; deriving a cell index for the one or more time points; and using the cell index to determine the number of cells in said at least well at least one of said one or more time points.

The cell index is used to determine the number of cells using a formula that relates cell index to cell number, in which the formula is obtained by: providing a system for cell-substrate monitoring, where the system comprises at least one multi-well cell-substrate impedance monitoring device, adding cells to one or more wells of a device of the system; measuring impedance of the one or more wells comprising cells at two or more time points; calculating a cell index from the impedance measurement at the two or more time points; determining the number of cells of the one or more wells at the two or more time points by a means other than impedance monitoring; and deriving a formula that relates the number of cells of the one or more wells at the two or more time points with the impedance measurements at the two or more time points.

In the embodiment of above method for obtaining the formula, sometimes, the number of cells introduced to the wells are pre-known or predetermined before cells are added in to the wells. Under such conditions, one assumes that there will be no change in cell number or little change in cell number when the impedance measurement for obtaining the formula is performed.

The number of cells determined by a method other than impedance monitoring can be determined by, for example, cell plating, hemocytometer counting, flow cytometry, or Coulter counting.

Formulas relating cell index (including normalized cell index and delta cell index, which can also be used) to cell number for a given cell type can be used to quantitate cells of that type in assays using a cell-substrate impedance monitoring device, such as a device described herein. Generally, for a give cell type and for cells under similar physiological conditions, the derived formulas relating cell index to cell number can be used in subsequent assays. There is no need to obtain the formula each time when an assay is performed. However, it is worthwhile to point that the formula can only be valid as long as the cells are under same physiological conditions in the assays where the formula was derived and where the formula is used. If the cell condition is different, for example, the composition of culture medias changed, or the cell attachment surface is altered, then the formula will not hold. In another example, if cells are in log-growth phase in one assay and are in stationary phase in another assay, then the formula may not hold. Another point worth mentioning here is that relates the fact the derived cell index or impedance also depends on cell attachment quality on the surface as well as cell morphology. If cell morphology or cell attachment changes during an assay, then one need to distinguish between the changes caused by change in cell number or in cell morphology or in cell attachment.

Figure 8:
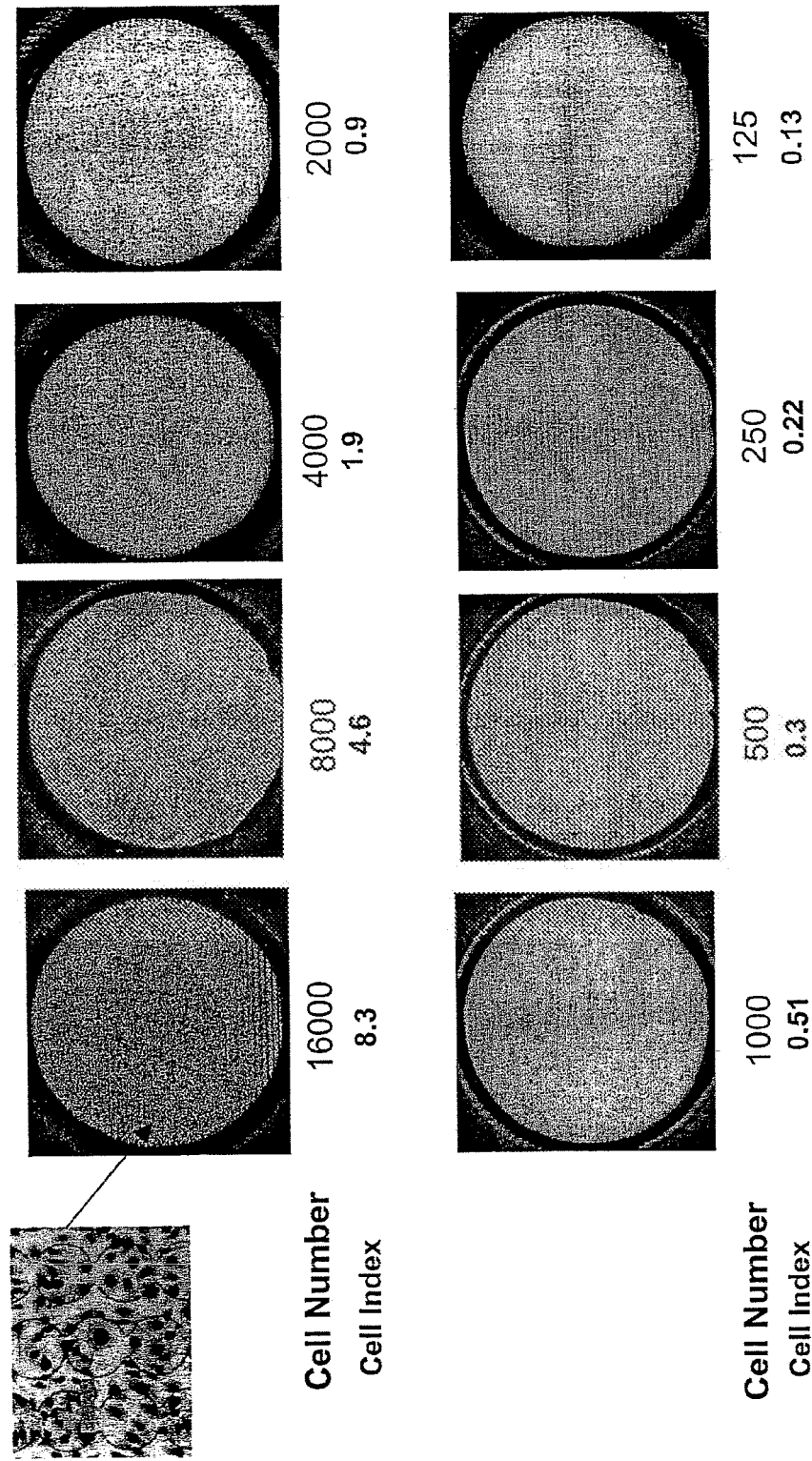
FIG. 8 shows titration of NIH3T3 cells on the devices of the present invention. The indicated cell number of cells were seeded into microtiter devices fabricated with electronic sensor arrays shown in FIG. 1B. The electronic sensor arrays were precoated with fibronectin. Two hours after seeding, the cell index number was determined using a cell-substrate impedance monitoring system of the present invention.

As an example, we can derive the correlation formula between cell index and cell number for NIH3T3 cells under the experimental conditions. The formula for converting cell index to cell number for this particular case is: Cell number=2000*Cell index−145. To test this formula, we found the error in estimating cell number based on the cell index data shown in FIG. 8 as compared to the seeded cell number is less than 20%.

D.3. Cell-Based Assays to Test the Effects of Compounds on Cells

In yet another aspect, the present invention provides a method for performing a cell-based assay investigating the effect of one or more test compounds on cells, comprising: providing a device of the present invention having two or more electrode arrays, each of which is associated with a fluid container of the device; attaching the device to an impedance analyzer; introducing cells into two or more fluid containers of the device that comprise an electrode array; adding at least one test compound to at least one of the one or more of the fluid containers comprising cells and an electrode array to provide at least one test compound fluid container; providing at least one control fluid container to which cells are added that does not receive test compound; and monitoring cell-substrate impedance of the one or more test compound fluid containers and the one or more control fluid containers at least three time points after adding the one or more test compounds, and analyzing impedance measurements from the one or more test compound fluid containers and the one or more control fluid containers at at least three time points after adding the one or more test compounds, in which changes in impedance can provide information about cell responses to the one or more test compounds.

In a related aspect the present invention also provides a method for performing a cell-based assay investigating the effect of one or more test compounds on cells, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes; providing a multi-well cell-substrate impedance measuring system; introducing cells into two or more wells of the device; adding at least one test compound to at least one of the one or more of the wells comprising cells to provide at least one test compound well; providing at least one control well to which cells are added that does not receive test compound; monitoring cell-substrate impedance of the one or more test compound wells and the one or more control wells at at least three time points after adding the one or more test compounds; and analyzing impedance measurements from the one or more test compound wells and the one or more control wells at at least three time points after adding the one or more test compounds, in which changes in impedance can provide information about cell responses to the one or more test compounds.

A test compound can be any compound, including a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc. The structure of a test compound can be known or unknown.

Information about cell responses to the one or more test compounds includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance.

The cells used in the assay can be primary cells isolated from any species or can be cells of cell lines. The cells can be genetically engineered cells (For example, cells from a genetically modified organism, such as for example from a "gene knockout" organism, or cells that have been engineered to over-express an endogenous gene or a transgene, or cells whose normal gene expression has been manipulated by use of antisense molecules or silencing RNA.) In some embodiments, different cell types are added to different wells and the behavior of the different cell types in response to one or more compounds is compared.

The cell-based assays that be performed with above methods include, but are not limited to, cell adhesion, apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral, bacterial, or environmental toxin mediated cell pathologic changes or cell death, detection or quantification of neutralizing antibodies, specific T-cell mediated cytotoxic effect, and cell-based assay for screening or measuring ligand-receptor binding.

In the methods of the present invention that investigate test compound effects on cells, impedance is preferably monitored from at least one test compound well at at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

It is preferable to perform replicate test compound assays in which more than one fluid container of cells receives the same compound at the same concentration. In this case, impedance measurements or values can be averaged for the assayed time points for replicate wells. Preferably, a standard deviation for the averaged values is also calculated.

In the methods of the present invention, analyzing impedance can comprise plotting cell impedance versus time to obtain at least one test compound impedance curve and at least one control impedance curve. Preferably, at least one test compound impedance curve and said at least one control impedance curve are compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Preferably, data from impedance monitoring of a well that comprises cells and a test compound is compared with data from impedance monitoring of a well that comprises cells in the absence of a test compound, however, this is not a requirement of the present invention. For example, it is also possible to compare impedance measurements from one or more time points prior to the addition of compound to compare impedance measurements from one or more time points after the addition of compound. Such comparisons can be used directly to assess the cells' response to a compound. It is also possible to calculate a cell index (or cell number index) using the impedance values obtained.

Methods of calculating a cell index (cell number index) are disclosed herein as well as in parent application U.S. patent application Ser. No. 10/705,447, U.S. patent application Ser. No. 10/987,732, both herein incorporated by reference for disclosures relating to cell number index and its calculation. The cell index calculated from impedance measurements of wells receiving compound can be compared with the cell index calculated from impedance measurements of control wells to assess the effect of a compound on cells. Alternatively, cell index calculated from impedance measurements of wells from one or more time points after the addition of a compound can be compared with the cell index calculated from impedance measurements of wells from one or more time points prior to the addition of a compound to assess the effect of a compound on cells. In some preferred embodiments, the cell index can be used as an indicator of cytotoxicity.

The derivation of cell index from impedance measurements is provided in Section C of the present application. Cell index values (including normalized cell index values and delta cell index values) from at least three time points from at least one test compound well and at least one control well can be plotted versus time to obtain one or more test compound cell index curve and one or more control cell index curves. The one or more test compound cell index curves and the one or more control cell index curves can be compared to identify a time frame, if any, in which a test compound curve differs significantly from a control curve, indicating a time frame of an effect of a test compound on cells. For example, depending on the time frame at which a test compound curve differs significantly from a control curve, the test compound can be hypothesized to affect one or more of, for example, cell attachment or adhesion, cell growth or proliferation, cytoskeleton organization or function, or apoptosis or cell death.

Cell index values at three or more assay time points for one or more test compound wells and one or more control wells can be used to derive cell change index (CCI) values or a second order derivatives of cell index at three or more assay time points. The calculation of cell change index is provided in Section C of the present application. The value of CCI at a given time point can be determined to be either approximately equal to 0.7, much greater than 0.7, greater than zero and less than 0.7, approximately equal to zero, less than zero, or much less than zero. These values can indicate cell behavior at an assay time point, as CCI approximately equal to 0.7 indicates log rate growth, a CCI much greater than 0.7 indicates faster than log rate growth, a CCI greater than zero and less than 0.7 indicates slower than log rate growth, a CCI approximately equal to zero indicates no growth (a constant cell index), a CCI less than zero indicates cells are detaching from the substrate, and a CCI much less than zero indicates cell are detaching rapidly from the substrate.

For a given assay time point, differences in CCI value between control and compound treated wells can indicate a time at which the compound has an effect on cells, as well as providing information on the type of effect the compound has.

The CCI can further be used to obtain information on the effect of a test compound by plotting CCI versus time for at least three assay time points to obtain a cell change index curve (CCI curve) for at least one control container or well and at least one test compound container or well. One or more test compound CCI curves can be compared with one or more control CCI curves to obtain information on cell status or behavior in response to said at least one test compound, wherein said cellular status or behavior is at least one of: cell attachment or adhesion status; cell growth or proliferation status; the number of viable cells or dead cells; cytoskeleton change or re-organization; or the number of cells going through apoptosis or necrosis.

Cell-Based Assays with More than One Cell Type

The present invention also provides methods of comparing the effects of a compound on two or more cell types. In one aspect, the method comprises: providing a device of the present invention having two or more electrode arrays, each of which is associated with a fluid container of the device; attaching the device to an impedance analyzer; introducing cells into two or more fluid containers of the device that comprise an electrode array, wherein at least one of the two or more fluid containers receives one cell type and at least one other of the two or more fluid containers receives a different cell type; adding a test compound to the one or more fluid containers receiving one cell type and adding the test compound to the one or more fluid containers receiving a different cell type to provide at least two test compound fluid containers that comprise cells of different types; providing at least two control fluid containers that do not receive test compound, in which at least one of the control fluid containers receives cells of the one type and at least one of the control fluid containers receives cells of the different type; monitoring cell-substrate impedance of the two or more test compound fluid containers that comprise different cell types and the one or more control fluid containers at at least three time points after adding the one or more test compounds; and analyzing impedance measurements from the two or more test compound fluid containers comprising different cell types and from the one or more control fluid containers at at least three time points after adding the one or more test compounds, in which changes in impedance can provide information about cell responses to the one or more test compounds.

In a related aspect the present invention also provides a method for performing a cell-based assay investigating the effect of one or more test compounds on cells using a cell-substrate impedance monitoring system of the present invention, where the system includes a multi-well cell-substrate impedance monitoring device, an impedance analyzer, a device station comprising electronic circuitry that engages the device and connects the two or more electrode arrays of the device to the impedance analyzer, and a software program that controls the device station and can record and analyze data from the impedance analyzer. The method includes: providing a multi-well cell-substrate impedance measuring system; introducing cells into two or more wells of the device that comprise an electrode array, wherein at least one of the two or more wells receives one cell type and at least one other of the two or more wells receives a different cell type; adding a test compound to the one or more wells receiving one cell type and adding the test compound to the one or more wells receiving a different cell type to provide at least two test compound wells that comprise cells of different types; providing at least two control wells that do not receive test compound, in which at least one of the wells receives cells of the one type and at least one of the control wells receives cells of the different type; monitoring cell-substrate impedance of the two or more test compound wells that comprise different cell types and the one or more control wells at least three time points after adding the one or more test compounds; and analyzing impedance measurements from the two or more test compound wells comprising different cell types and from the one or more control wells at least three time points after adding the one or more test compounds, in which changes in impedance can provide information about cell responses to the one or more test compounds.

In the methods of the present invention that investigate test compound effects on cells, impedance is preferably monitored from at least two test compound wells comprising different cell types at least one time point before adding test compound to the at least one two compound wells. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at least one frequency between about 1 Hz and about 100 MHz, more preferably at least one frequency between about 100 Hz and about 2 MHz.

As disclosed in an earlier section on compound assays, a test compound can be any compound whose effect on cells can be investigated. A test compound used in assays comparing cell responses can be a compound whose effect on one or more of the cell types to be assayed is known, or can be a compound whose effects on any of the cell types to be assayed are unknown. In preferred methods of the present invention, cells are introduced into at least three wells of the device that each comprise an electrode array, and at least one well that comprises an electrode array and comprises cells does not receive a test compound. A control well that does not receive a test compound can be monitored, and its impedance data can be compared with that of wells that receive a compound to determine the effect of the test compounds on cells.

As disclosed in a previous section for compound assays, the cell types used in the assay can be primary cells isolated from any species or can be cells of cell lines. In some preferred embodiments, the different cell types are the same type of cell from different individuals, and thus have different genotypes. One or more of the cell types can be genetically engineered (For example, cells from a genetically modified organism, such as for example from a "gene knockout" organism, or cells that have been engineered to overexpress an endogenous gene or a transgene, or cells whose normal gene expression has been manipulated by use of antisense molecules or silencing RNA.) In these cases, genetically modified cells can be compared with control cells. In another example the cells can be, for example, stem cells from different stages of differentiation or of different genotypes whose response to growth factors is being compared. In other examples the cells can be cancer cells where the test compound is tested for its cytotoxic effects. The cells can be primary cancer cells of the same type isolated from different individuals, for example, or different cancer cell lines, or cancer cells of the same type but of different grades. In some embodiments, three or more different cell types are added to different wells and the behavior of the three or more different cell types in response to one or more compounds is compared. In preferred embodiments of the present invention, for each cell type tested there is a control performed in which the control does not receive test compound.

A variety of assays can be employed, where the effect of a test compound on the behavior of two or more cell types in the assay is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Preferably, time-dependent responses of the first and second types of cells are compared to see how similar or different the responses from the two types of cells are. In one method of the present invention, impedance from a first cell type well is plotted versus time to give a first cell type impedance curve and impedance from a second cell type well is plotted versus time to give a second cell type impedance curve. Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration of a cells response to a compound are similar or different. Preferably, impedance curves or cell index curves generated from control wells comprising each cell type in the absence of compound are compared with the test compound curves to assess the compound-specific effects on each cell type. The effects of the compounds on one or more of the two or more cell types can be effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect of a compound on at least one of the cell types used in the assay may be known. The mechanism of action of a compound on at least one of the cell types used in the assay may be known. In such cases, comparison of the compound response of one or more different cell types with the compound response of a cell type whose response to the compound is characterized can give information as to the similarity or difference in response of a different cell type to the compound.

In one preferred embodiment of this method, time-dependent cytotoxic responses of particular cell types to a compound are compared. Cytotoxicity assays can provide information on the sensitivity of one or more cell type to a compound.

Figure 9A:
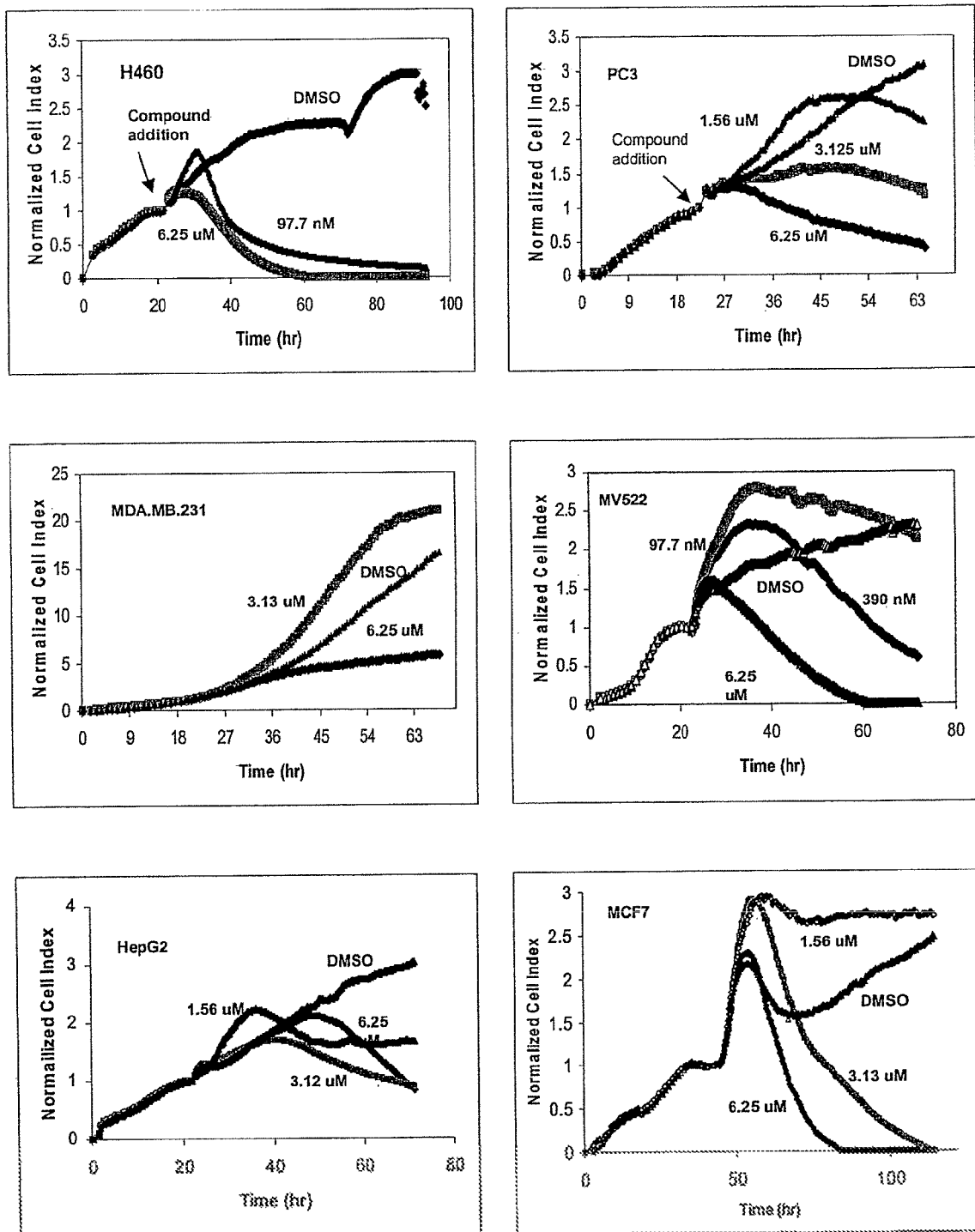
FIGS. 9A and 9B show the responses of various cell types (listed in Table 1) to doxorubicin treatment as monitored using a cell-substrate impedance monitoring system of the present invention. The indicated cell lines were seeded onto microtiter devices fabricated with electronic sensor arrays shown in FIGS. 1A-C. The cellular responses were continuously monitored at 15 or 30 or 60 minutes time interval before and after treatment with doxorubicin.
Figure 9B:
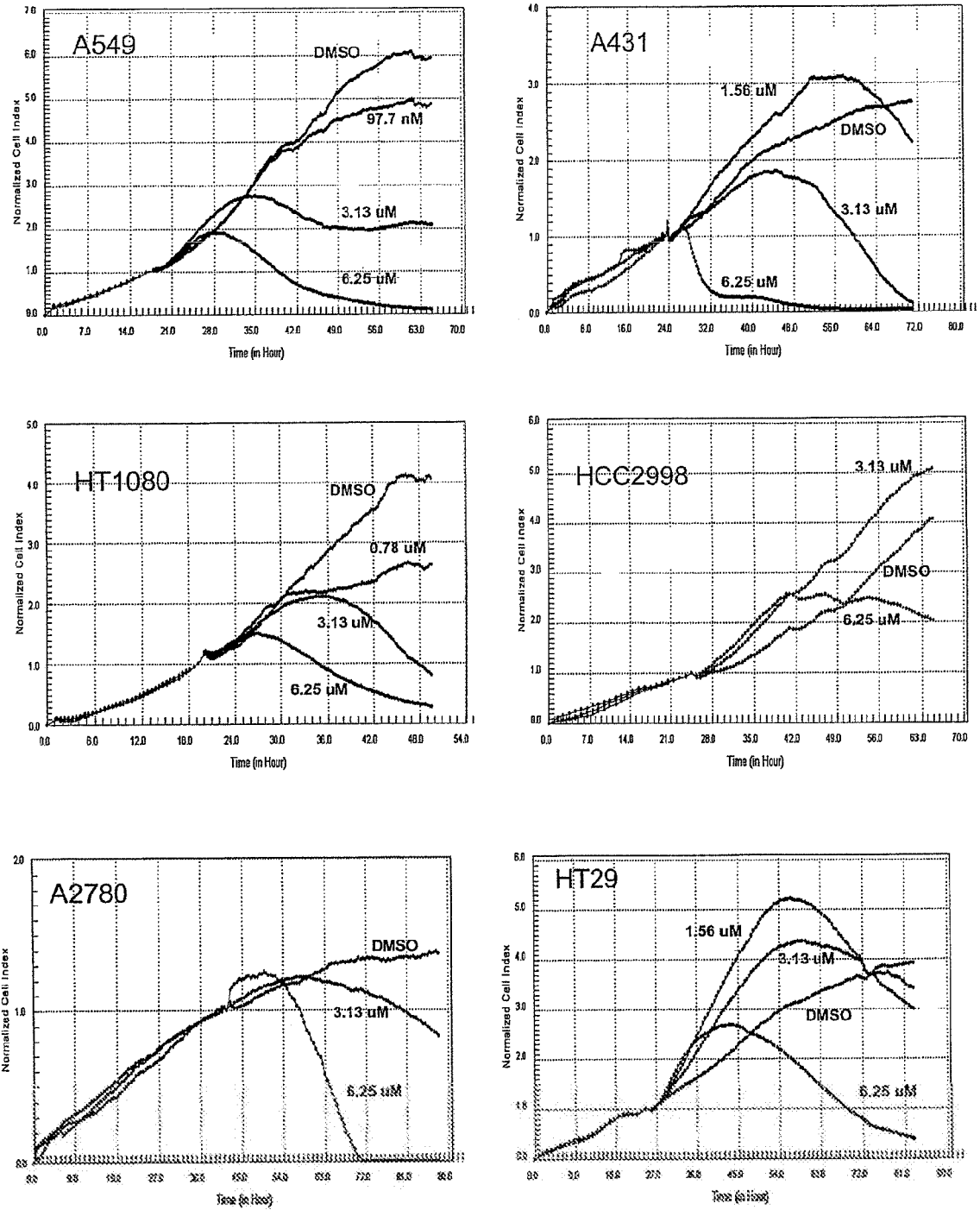
Figure 10A:
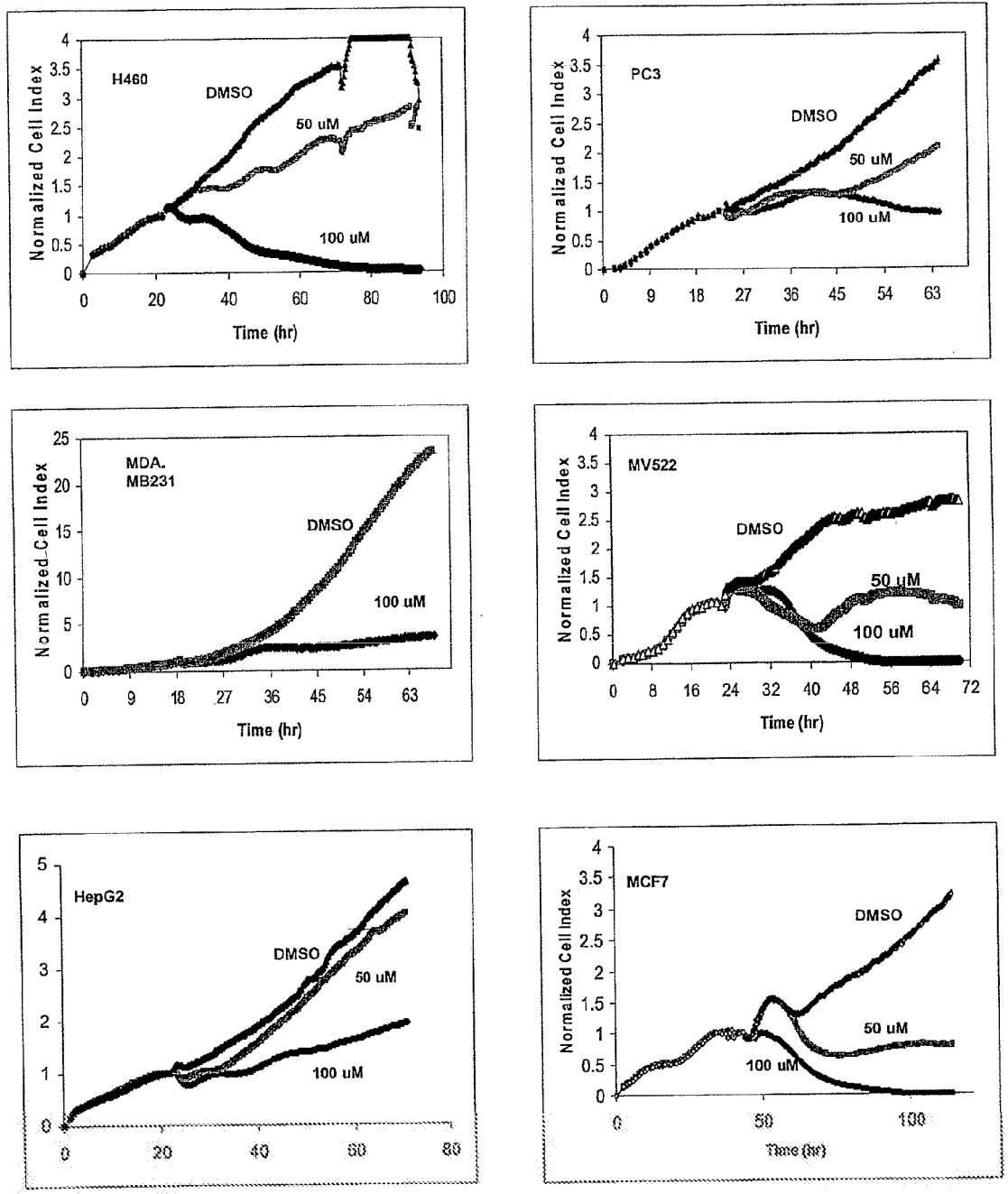
FIGS. 10A and 10B shows the responses of various cell types (listed in Table 1) to olomoucine treatment as monitored using a cell-substrate impedance monitoring system of the present invention. The indicated cell lines were seeded onto microtiter devices fabricated with electronic sensor arrays shown in FIG. 1B. The cellular responses were continuously monitored at 15 or 30 or 60 minutes time interval before and after treatment with olomoucine.
Figure 10B:
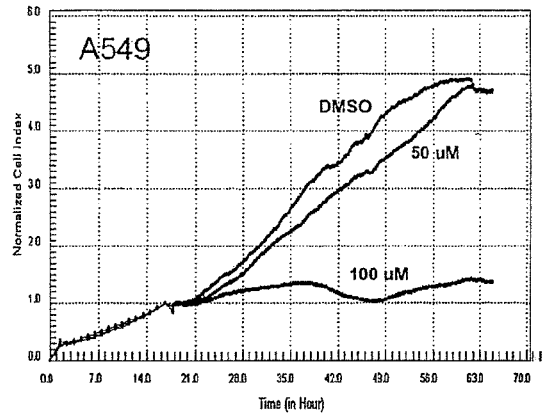
Figure 10B:
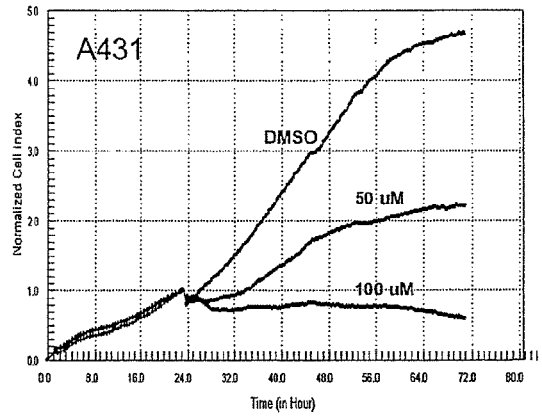
Figure 10B:
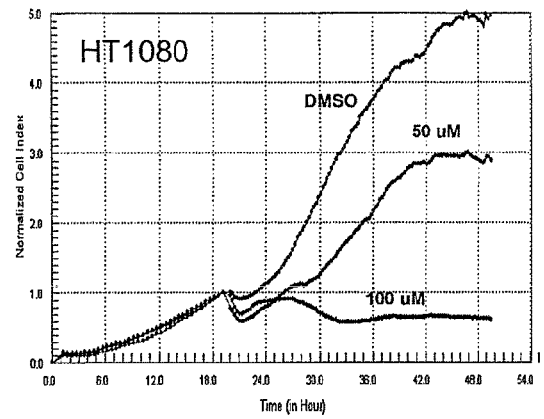
Figure 10B:
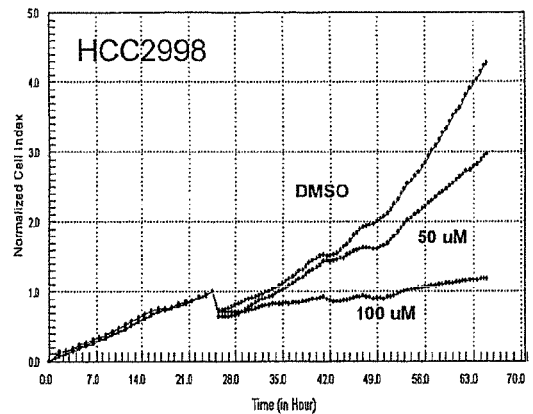
Figure 10B:
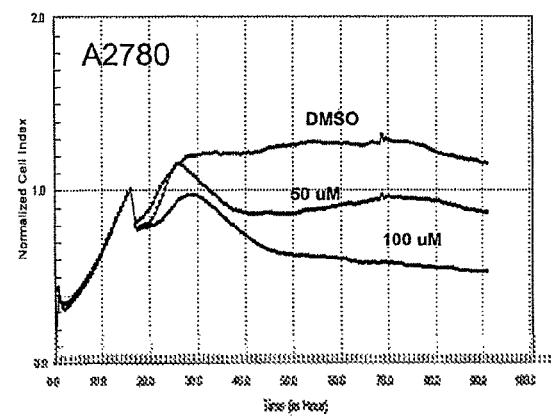
Figure 10B:
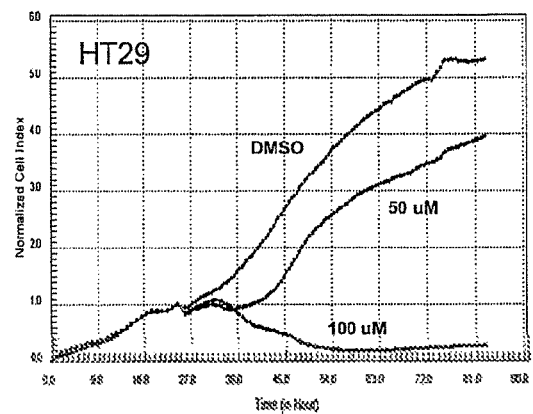

FIGS. 10A and 10B show the responses of various cell types (listed in Table 1) to olomoucine treatment as monitored using a cell-substrate impedance monitoring system of the present invention. The indicated cell lines were seeded onto microtiter devices fabricated with electronic sensor arrays shown in FIGS. 1A-C. The cellular responses were continuously monitored at 15 or 30 or 60 minutes time interval before and after treatment with olomoucine. Comparison among these cell index curves showed that certain similarity does exist. Take the treatment of olomoucine at 100 uM as an example. For a significant number of cell types tested, olomoucine treatment resulted in a near-constant cell index for some length of time (for example: 10, 20 or 30 hrs) a long time. This relates to the fact olomoucine is a cell cycle resting compound and for some time period following compound addition, cells do not divide any more and so cell number does not change but cells remain "live". Thus, for such time period, cell index did not change with time. The "near-constant" cell index curves were also observed for cells treated with roscovitine, which is another compound causing cell cycle arrest. The cell index curves shown in FIGS. 10A and 10B are strikingly different from the cell index curves shown in FIGS. 9A and 9B, and FIGS. 11A and 11B, where compounds follow different mechanism of compound action.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

Cell-Based Assays with More than One Compound

The present invention also provides methods of comparing the effects of two or more different compounds on cells. In one aspect, the method comprises: providing a device of the present invention having three or more electrode arrays, each of which is associated with a fluid container of the device; attaching the device to an impedance analyzer; introducing cells into three or more fluid containers of the device that comprise an electrode array; adding at least one test compound to at least one of the three or more fluid containers comprising cells and adding at least one different test compound to at least one other of the three or more fluid containers comprising cells to provide at least two different test compound fluid containers; providing as a control fluid container at least one of the three or more fluid containers, in which the control fluid container receives cells but does not receive compound; attaching an impedance analyzer to the device; monitoring cell-substrate impedance of the two or more different test compound fluid containers that comprise different compounds and the one or more control fluid containers at least three time points after adding the one or more test compounds; and analyzing impedance measurements from the two or more different test compound fluid containers and from the one or more control fluid containers at least three time points after adding the one or more test compounds, in which changes in impedance can provide information about cell responses to the one or more test compounds.

In a related aspect, the present invention provides a method for performing a cell-based assay investigating the effect of two or more test compounds on cells using a cell-substrate impedance monitoring system. The method includes: a) providing a cell-substrate impedance monitoring system of the present invention; b) introducing cells into at least two wells of the device that each comprise an electrode array; c) adding to at least one well of the device comprising cells and an electrode array a first test compound; d) adding to at least one other well of the device comprising cells and an electrode array a second test compound; and e) monitoring cell-substrate impedance of at least one well comprising cells and a first compound and at least one well comprising cells and a second compound, in which changes in impedance can provide information about cell responses to the first and second compounds.

Preferably, time-dependent responses of cells to the first compound and the second compound are compared to see how similar or different the responses from the two compounds are. In one preferred embodiment of this method, time-dependent cytotoxic responses are compared.

The cells and test compound that can be used in the assay can be any as described above for assays testing effects of test compounds.

In the assays of the present invention is preferable to perform replicate test compound assays in which more than one fluid container of cells of the same type receives the same compound at the same concentration. In this case, impedance measurements or values can optionally be averaged for the assayed time points for replicate wells. Preferably, a standard deviation for the averaged values is also calculated.

Impedance monitoring can be as described above for assays testing effects of test compounds. Preferably impedance is monitored from the at least two different test compound wells and at least one control well at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurement taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at least one frequency between about 1 Hz and about 100 MHz, more preferably at least one frequency between about 100 Hz and about 2 MHz.

Preferably, data from impedance monitoring of wells that comprise different test compounds are compared.

In one embodiment, for at least two different compound wells, impedance at three or more assay time points can be plotted versus time. Preferably, for a control well that does not receive compound, impedance at the same three or more assay time points is also plotted versus time. The impedance curves of different compound wells can be compared with the control impedance curve to determine whether the compounds have a similar or different effect on cells.

Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration of the response of cells to different compounds are similar or different. Preferably, impedance curves or cell index curves generated from one or more control wells comprising cells in the absence of compound are compared with the test compound curves to assess the compound-specific effects of each compound. The effects of the compounds on cells can be for example, effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect on cells of one or more of the compounds used in the assay may be known. The mechanism of action of one or more compounds used in the assay may be known. In such cases, comparison of the responses of cells to other test compounds used in the assay with cellular responses to the one or more compounds whose effects are characterized can give information as to the similarity or difference in response of different compounds to a known compound.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

A plurality of compounds can be assayed with multiple cell types. In one preferred embodiment of this method, time-dependent cytotoxic responses of different cell types to a set of compounds are compared.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

For example, the time frame, magnitude, and duration of a difference in response as evidenced by the curves can indicate a difference in efficacy or mechanism of compounds. The impedance differences can reflect differences in, for example, cell attachment or adhesion, cell growth or proliferation; the number of viable cells or dead cells; cytoskeleton organization or function; or the number of cells going through apoptosis or necrosis in response to a test compound.

A variety of assays can be employed, where the effect of two or more test compound on the behavior cells is under investigation. Such assays include, as nonlimiting examples, cell adhesion assays, apoptosis assays, cell differentiation assays, cell proliferation assays, cell survival assays, cytotoxicity assays, cell morphology detection assays, cell quantification assays, cell quality control assays, time-dependent cytotoxicity profiling assays, IgE-mediated cell activation or stimulation assays, receptor-ligand binding assays, viral, bacterial, or environmental toxin mediated cell pathologic changes or cell death assays, detection or quantification of neutralizing antibodies, specific T-cell mediated cytotoxic effect assays, and cell-based assays for screening or measuring ligand-receptor binding.

In one preferred embodiment of this method, time-dependent cytotoxic responses of cells to a set of compounds are compared. "Cytotoxicity profiling" in which the impedance responses of cells in response to a plurality of potentially cytotoxic compounds are compared, can provide information on the efficacy and mechanism of a test compound. Cytotoxicity profiling can be performed by comparing any combination of impedance plots, kinetic parameters derived from impedance plots, CI plots, CCI values, and CCI plots.

In one embodiment of the method, analyzing the cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Evaluating the Effect of Different Concentrations of a Compound on Cells

The present invention also includes methods of performing assays to test the effect of different concentrations of one or more test compounds on cells.

In one aspect, a method for testing different concentrations of a test compound on cells comprises: providing a device of the present invention having three or more electrode arrays, each of which is associated with a fluid container of the device; attaching the device to an impedance analyzer; introducing cells into at least two of the three or more fluid containers of the device that comprise an electrode array; adding different concentrations of a test compound to the two or more fluid containers of the device that comprise cells; providing a control fluid container that comprises cells but does not receive compound; monitoring cell-substrate impedance of the two or more different test compound fluid containers that comprise different concentrations of a test compound and of the one or more control fluid containers at at least three time points after adding a test compound; and analyzing impedance measurements from the two or more different test compound fluid containers and one or more control fluid containers at at least three time points after adding a test compound, in which changes in impedance can provide information about cell responses to the test compounds.

In a related aspect, the present invention provides a method for performing a cell-based assay investigating the effect of two or more concentrations of a test compound on cells using a cell-substrate impedance monitoring system. The method includes: providing a cell-substrate impedance monitoring system of the present invention; introducing cells into at least two of the three or more wells of the device that comprise an electrode array; adding different concentrations of a test compound to the two or more wells of the device that comprise cells; providing a control well that comprises cells but does not receive test compound; monitoring cell-substrate impedance of the two or more different test compound wells that comprise different concentrations of a test compound and the one or more control wells at at least three time points after adding a test compound; and analyzing impedance measurements from the two or more different test compound wells and the one or more control wells at at least three time points after adding a test compound, in which changes in impedance can provide information about cell responses to the test compounds.

The cells and test compound that can be used in the assay can be any as described above for assays testing effects of test compounds.

Impedance monitoring can be as described above for assays testing effects of test compounds. Preferably impedance is monitored from the at least two different test compound wells and at least one control well at least one time point before adding said at least one test compound to said at least one test compound well. Preferably, impedance is monitored at four or more time points, at least one of which is prior to the addition of one or more test compounds. Preferably, impedance is monitored at regular or irregular time intervals for an assay period of from minutes to days, for example, for a period of between several hours and several days. In one embodiment of the above cell-based assay, the cell-substrate impedance is monitored at least one time point prior to addition of the test compound, and at regular time intervals thereafter. For example, impedance can be measured at one or more intervals before adding the compound and at a regular 2 hour, 1 hour, 30 min or 15 min time intervals after adding the compound. Preferably, impedance is measured at three or more time points spaced at regular intervals. In the present application, a real-time assay means allows one to perform the measurement on cell-substrate impedance with various time resolutions, for example, measurements taking place at a longer time interval such as every hour or every two hours, or at a shorter time interval every minute or a few minutes.

Impedance can be monitored at one frequency or at more than one frequency. For example, in some preferred embodiments, impedance is monitored over a range of frequencies for each time point at which impedance is monitored. Preferably, impedance is monitored at at least one frequency between about 1 Hz and about 100 MHz, more preferably at at least one frequency between about 100 Hz and about 2 MHz.

In one embodiment, for at least two different compound concentrations, impedance or, preferably, cell index (including normalized cell index or delta cell index), at three or more assay time points is be plotted versus time. Preferably, for a control well that does not receive compound, impedance at the same three or more assay time points is also plotted versus time. An impedance curve or cell index curve can give an indication of the time frame at which a compound affects cell response. In some preferred embodiments, the cell index can be used as an indicator of cytotoxicity.

FIGS. 9A and 9B shows the responses of various cell types (listed in Table 1) to doxorubicin treatment as monitored using a cell-substrate impedance monitoring system of the present invention. The indicated cell lines were seeded onto microtiter devices fabricated with electronic sensor arrays shown in FIGS. 1A-C. The cellular responses were continuously monitored at 15 or 30 or 60 minutes time interval before and after treatment with doxorubicin. Comparison among these cell index curves showed that certain similarity does exist. Take the treatment of doxoorubincin at 3.13 uM as an example. For most of cell types tested, initially after the treatment, cell index increased with time in similar way to the cell index from DMSO control wells. After 10-20 hrs, depending on cell type, the cell index reached a peak and started decreasing with time. From that time on, the cell index monotonically decreases. Such cell index curves—characterized by "going up first and then going down"-were also observed for the cells treated with 5-Fluorouracil. Both Doxorubicin and 5-Fluorouacil act on cells through effects on DNA replication or topology.

Furthermore, such cell index curves are strikingly different from the cell index curves shown in FIGS. 10A and 10B, where 100 μM of olomoucine resulted in a nearly constant cell index value for 10, 20 even 30 hrs after compound addition. The cell index curves shown in FIG. 9 are also strikingly different from the cell index curves in FIG. 11, where nM concentration of paclitaxel caused an initial cell index decrease for about 15 hrs (it varies between cell types) and then a cell index increase. These dynamic changes in cell index curves reflect the fact that these different compounds interacts with the cells differently. Compounds that interact with cells in similar way or following same mechanism would result in a similar cell index response curves. One application of this is to investigate the mechanism of compound action based on the observed cell index curves. If cell index responses follow a certain pattern, then one may be able to deduce the mechanism of compound action. Alternatively, if two compounds showed similar, dynamic cell index response curves, then these two compounds may act on the cells with similar or same mechanism of compound action.

Figure 11A:
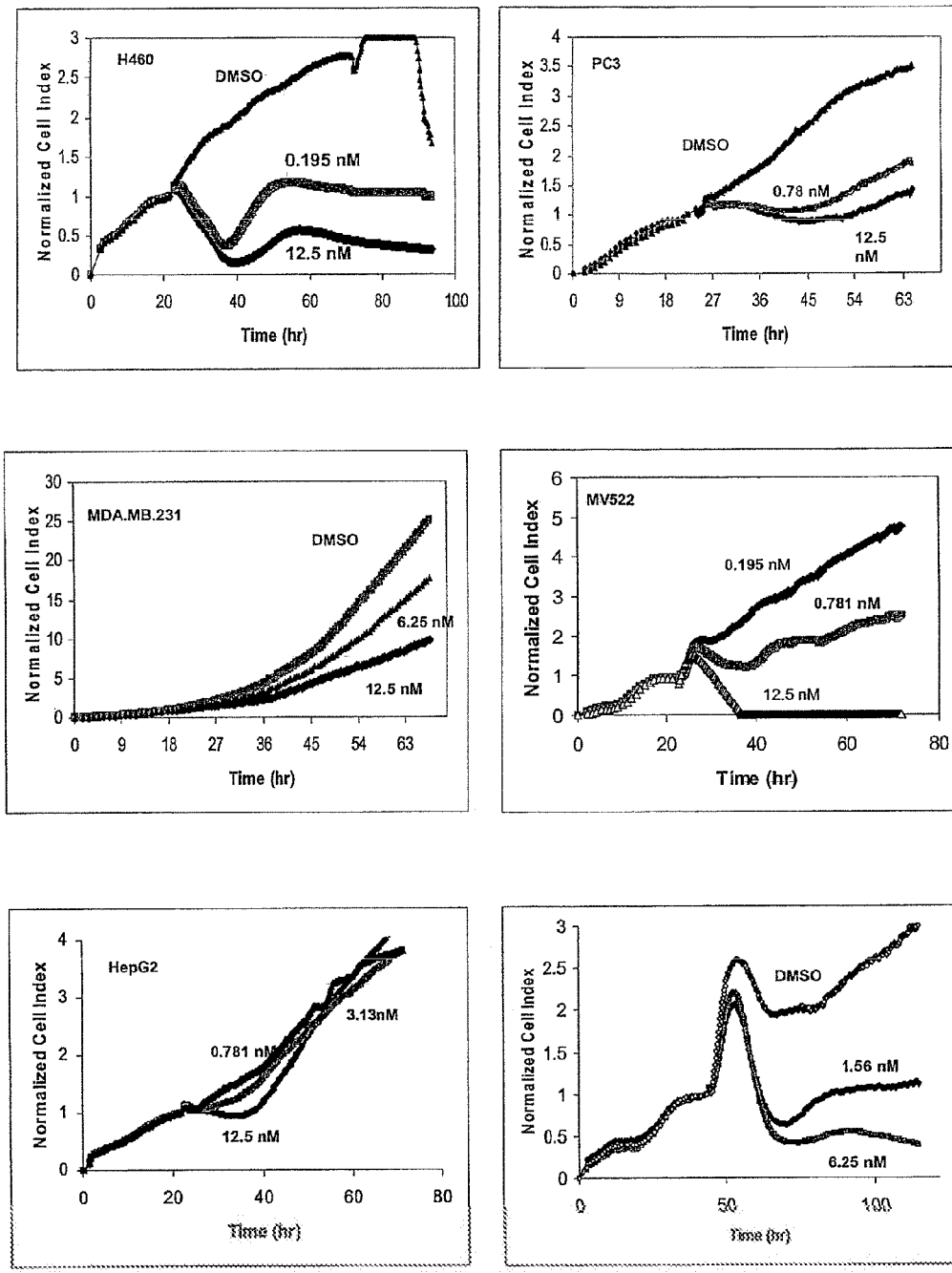
FIGS. 11A and 11B show the responses of various cell types (listed in Table 1) to paclitaxel treatment as monitored using a cell-substrate impedance monitoring system of the present invention. The indicated cell lines were seeded onto microtiter devices fabricated with electronic sensor arrays shown in FIG. 1B. The cellular responses were continuously monitored at 15 or 30 or 60 minutes time interval before and after treatment with paclitaxel.
Figure 11B:
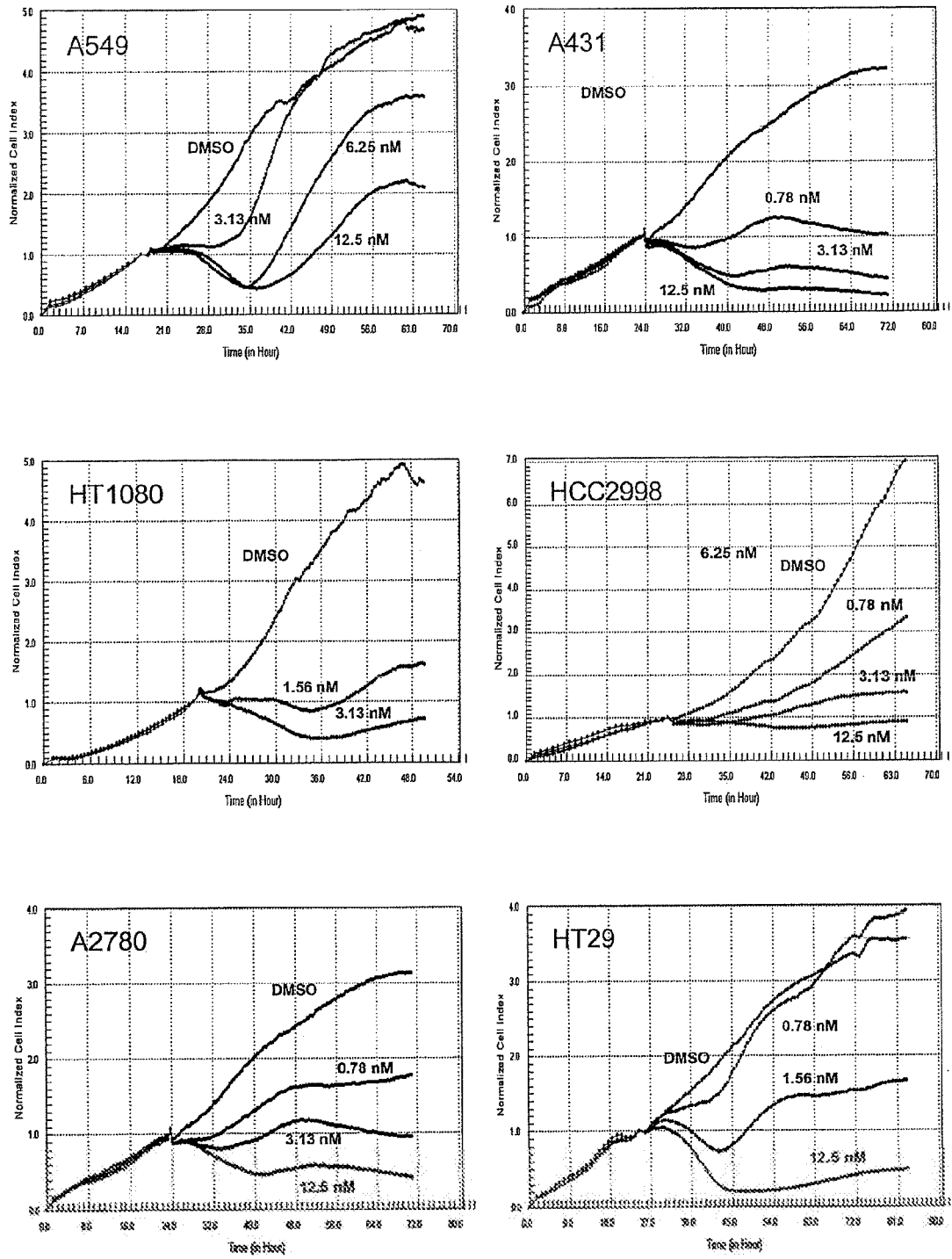
Figure 12A:
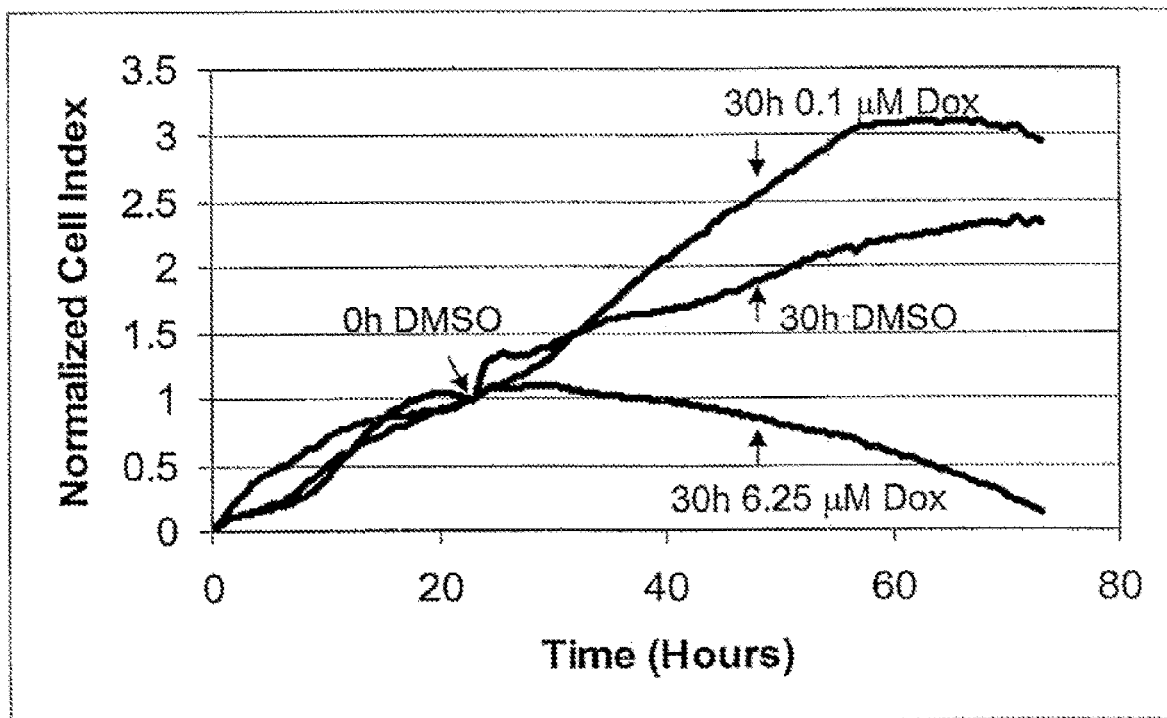
FIG. 12A shows the response of MV522 cells to doxorubicin treatment as monitored using a cell-substrate impedance monitoring system of the present invention. MV522 cells were seeded onto microtiter devices fabricated with electronic sensor arrays shown in FIG. 1B and were treated with either DMSO or doxorubicin at the indicated time and concentration.
Figure 12B:
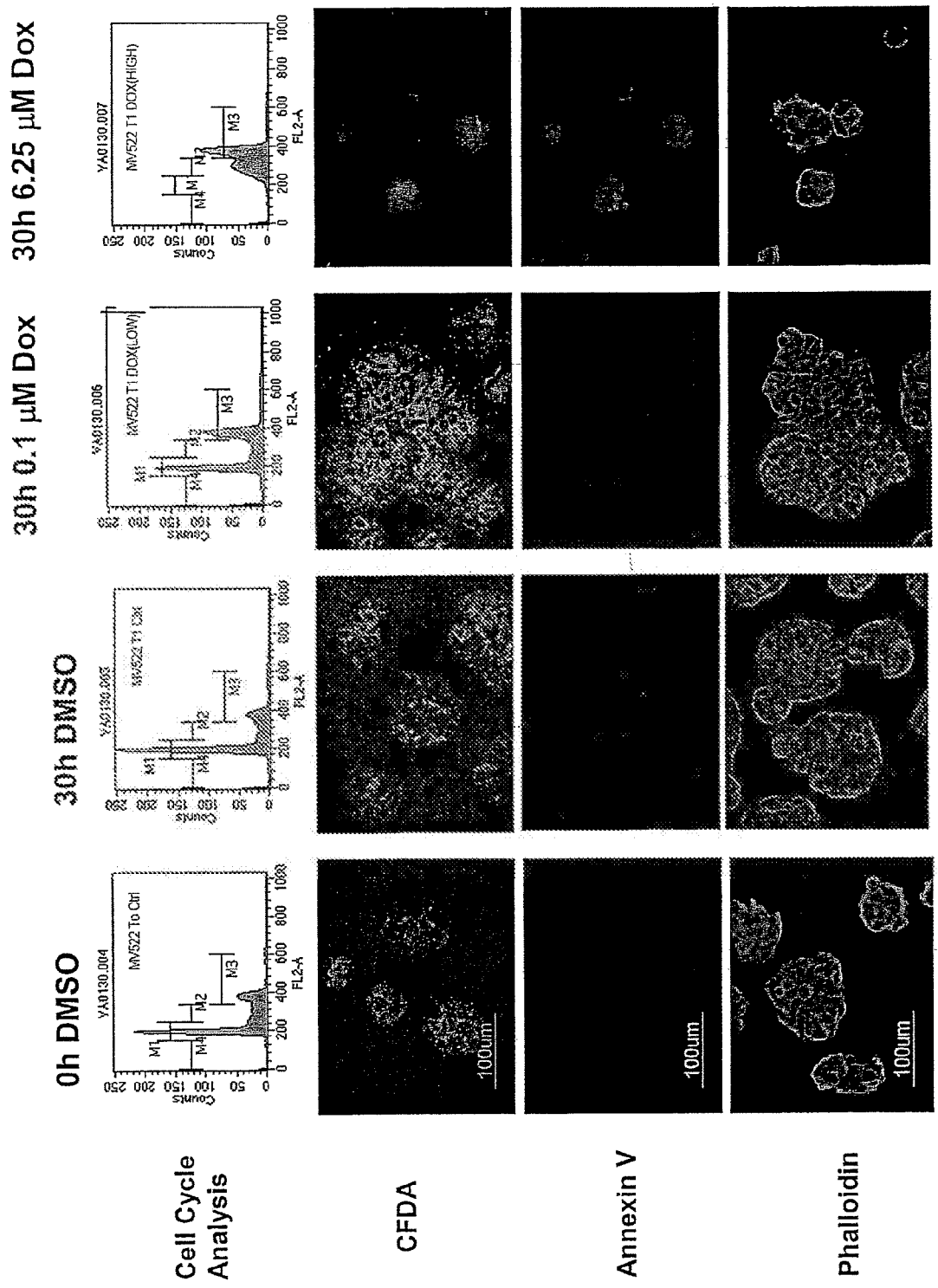
FIG. 12B shows the characterization of the cell biological effect of doxorubicin treatment on MV522 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 13A:
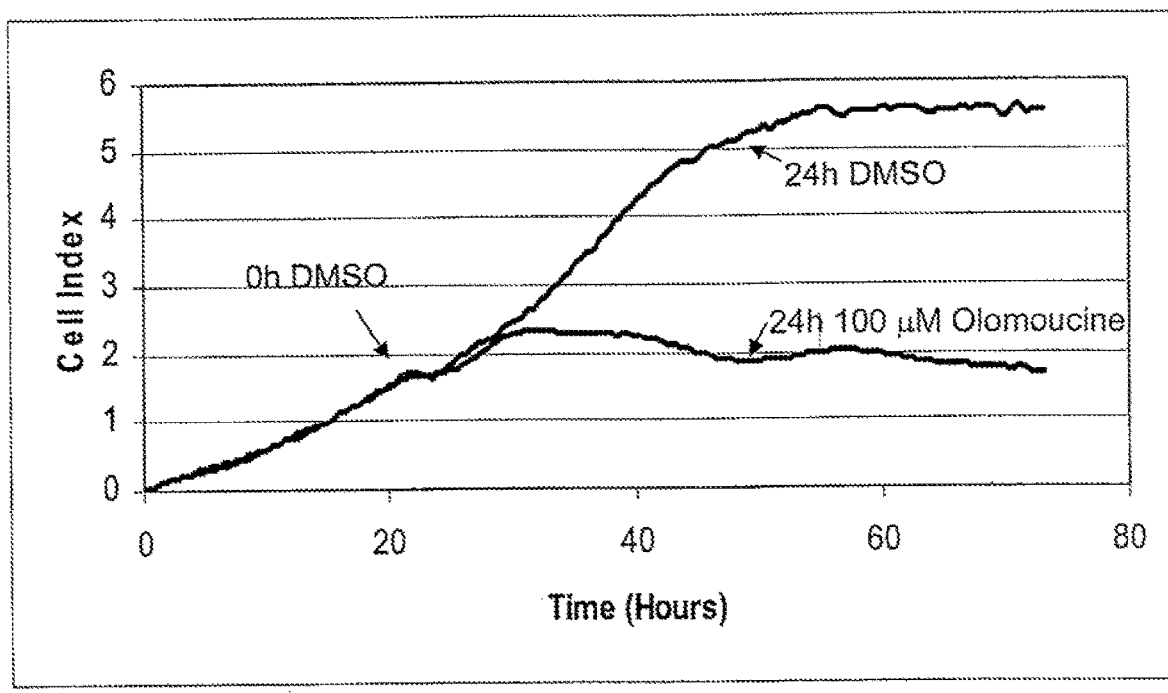
FIG. 13A shows the response of A549 cells to olomoucine treatment as monitored using a cell-substrate impedance monitoring system of the present invention. A549 cells were seeded onto microtiter devices fabricated with electronic sensor arrays shown in FIG. 1B and were treated with either DMSO or olomoucine at the indicated time and concentration.
Figure 13B:
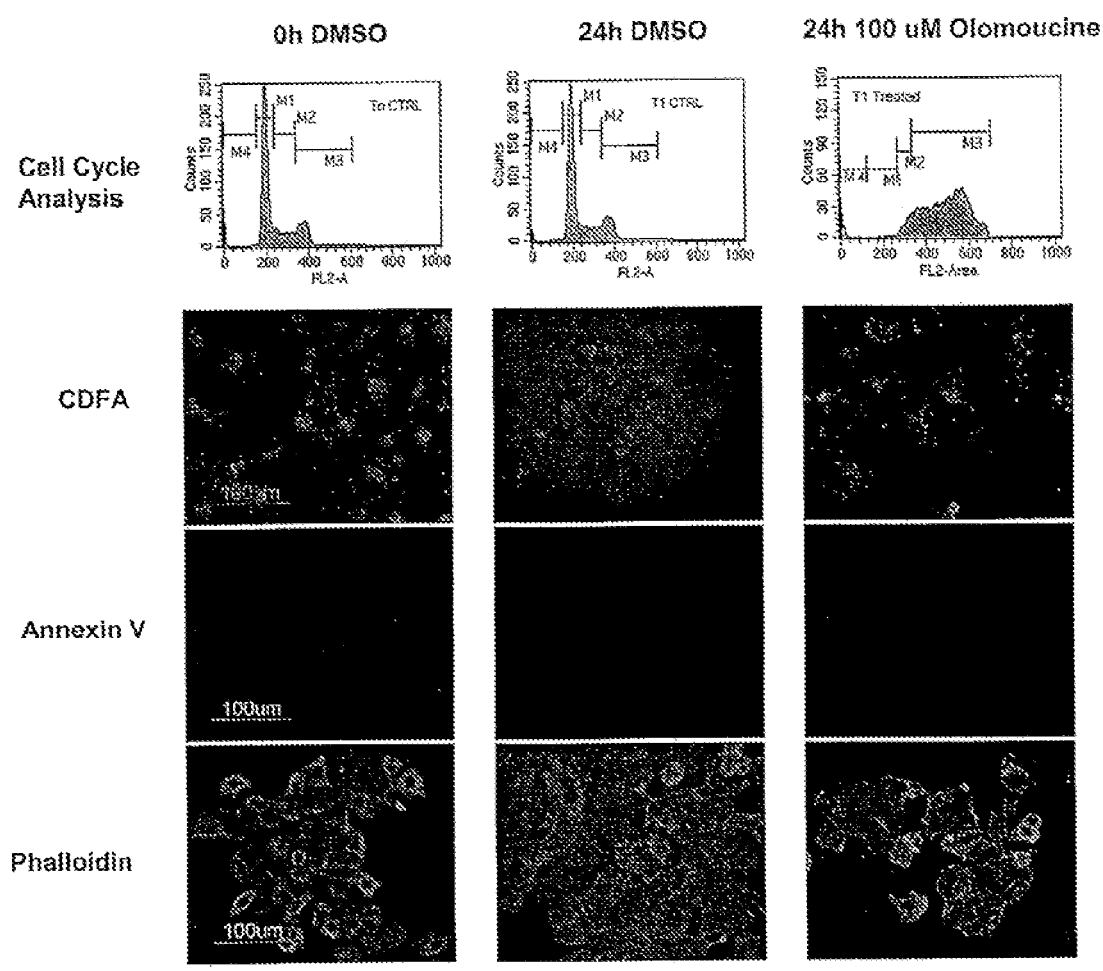
FIG. 13B shows the characterization of the cell biological effect of olomoucine treatment on MV522 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 14A:
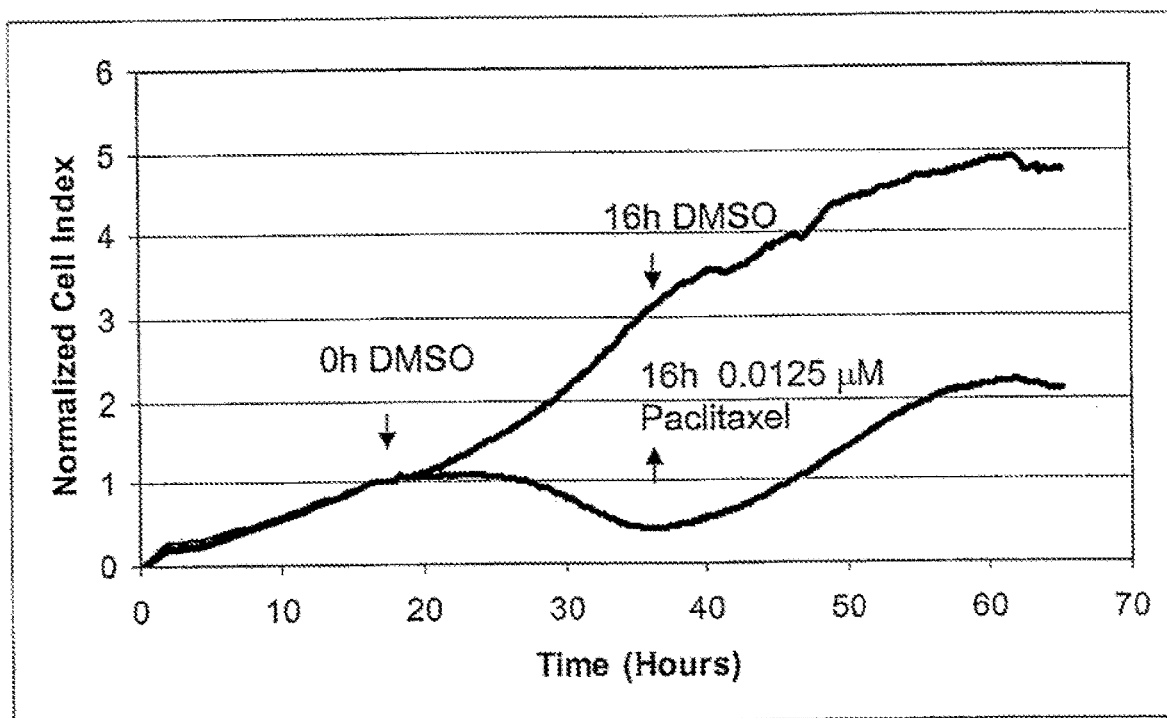
FIG. 14A shows the response of A549 cells to paclitaxel treatment as monitored using a cell-substrate impedance monitoring system of the present invention. A549 cells were seeded onto microtiter devices fabricated with electronic sensor arrays shown in FIG. 1B and were treated with either DMSO or paclitaxel at the indicated time and concentration.
Figure 14B:
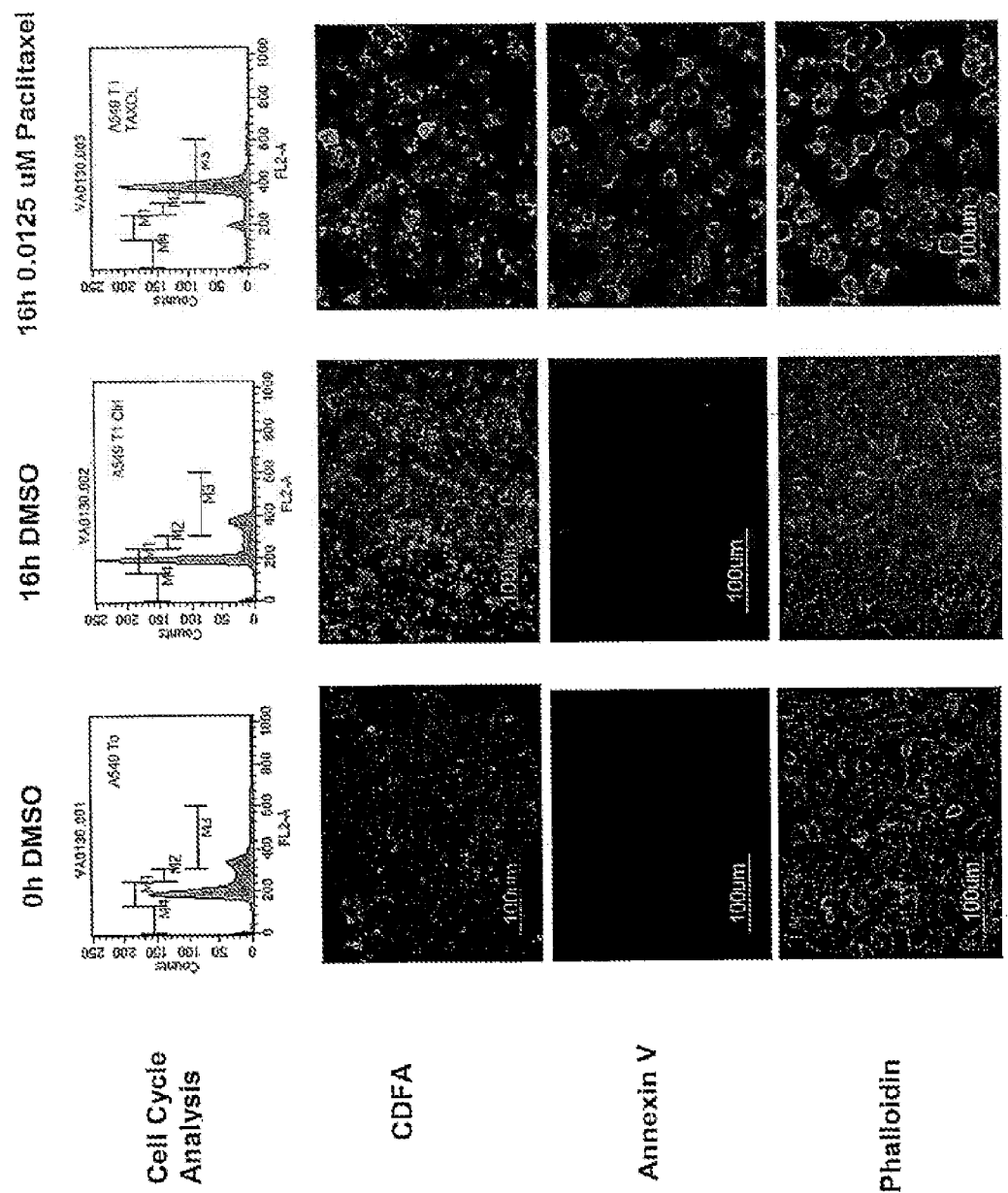
FIG. 14B shows the characterization of the cell biological effect of paclitaxel n treatment on A549 cells. The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 15A:
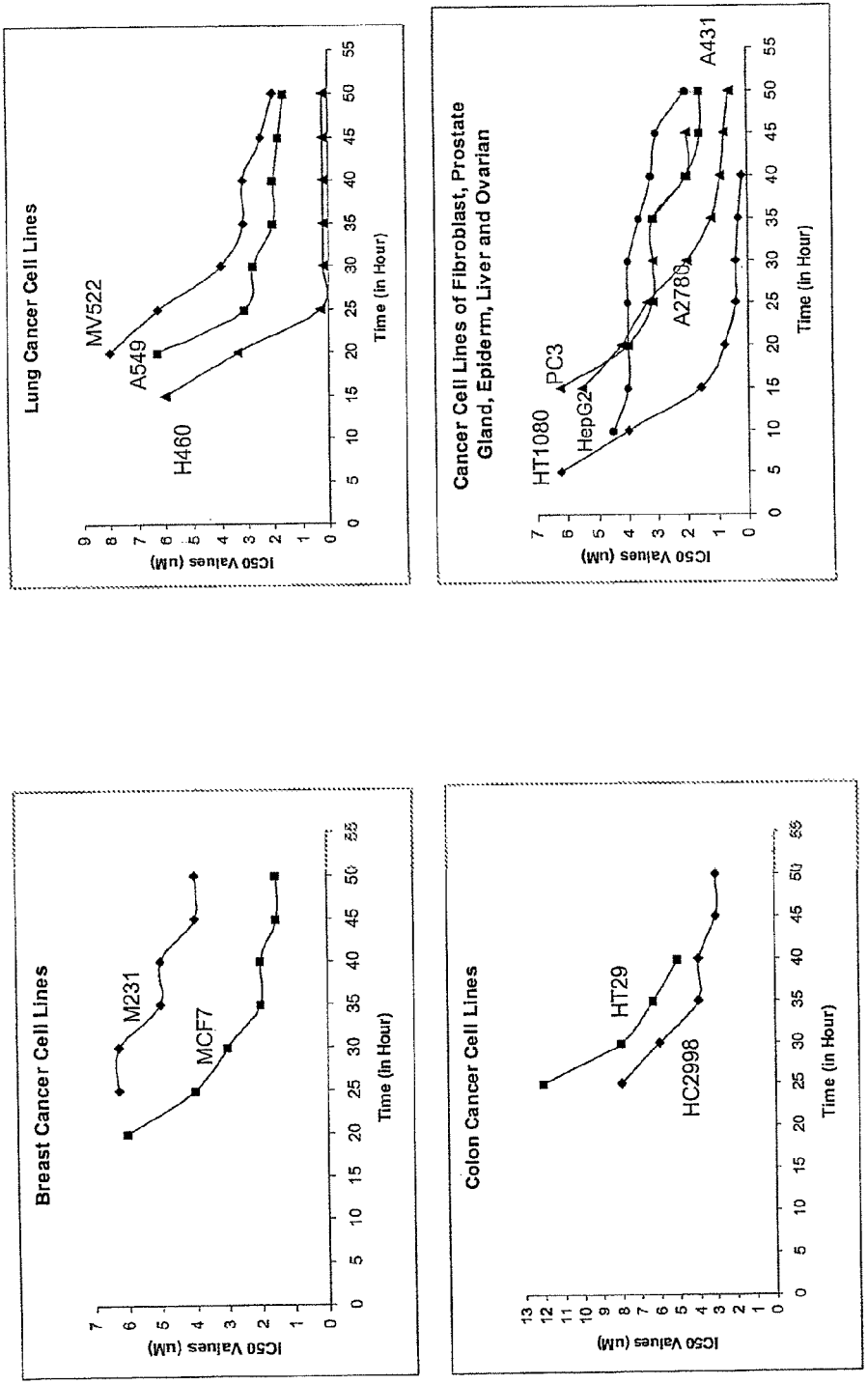
FIG. 15A-15D. The time dependent IC values for each compound (FIG. 15A: Doxorubicin.
Figure 15B:
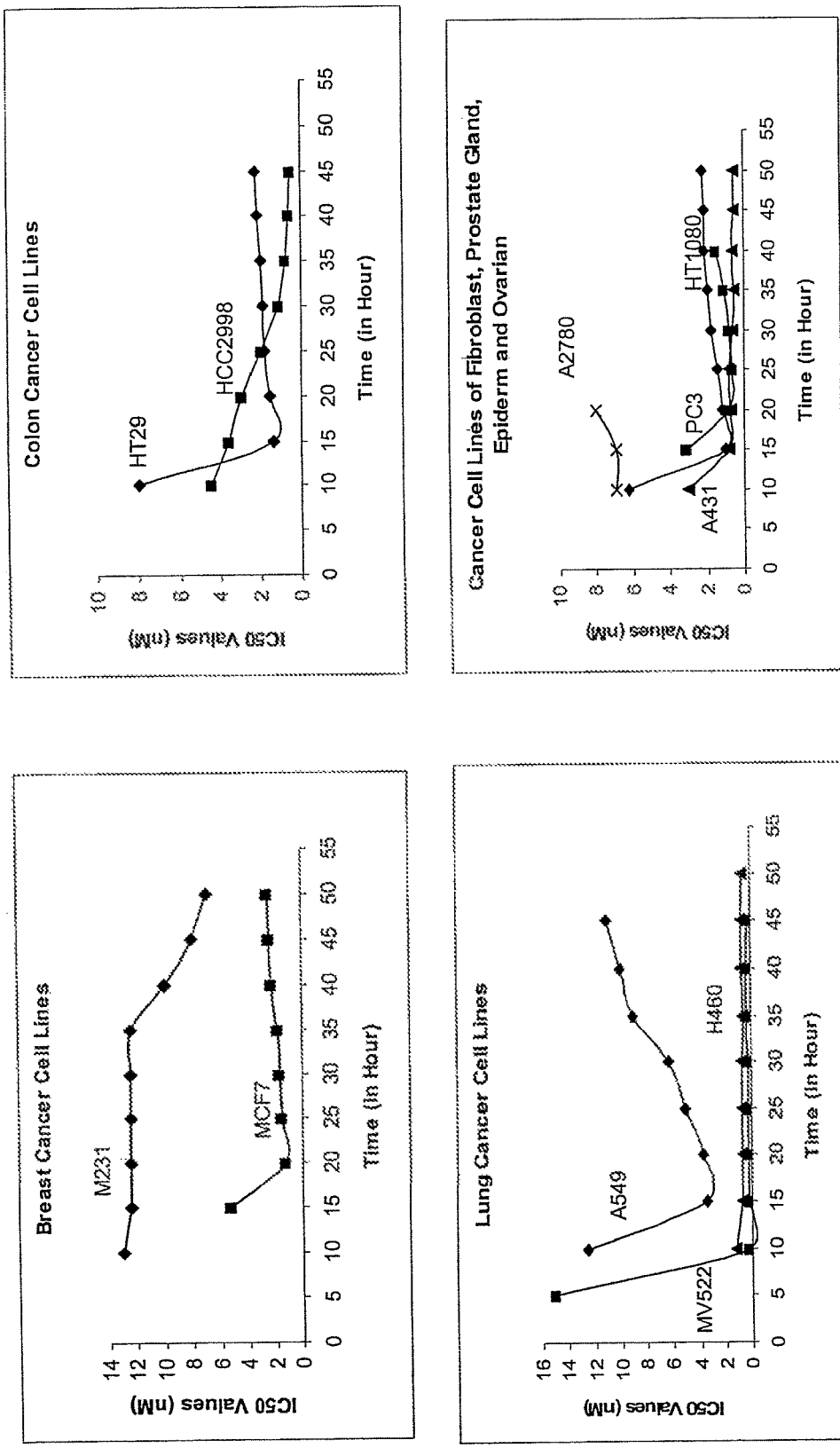
Figure 15C:
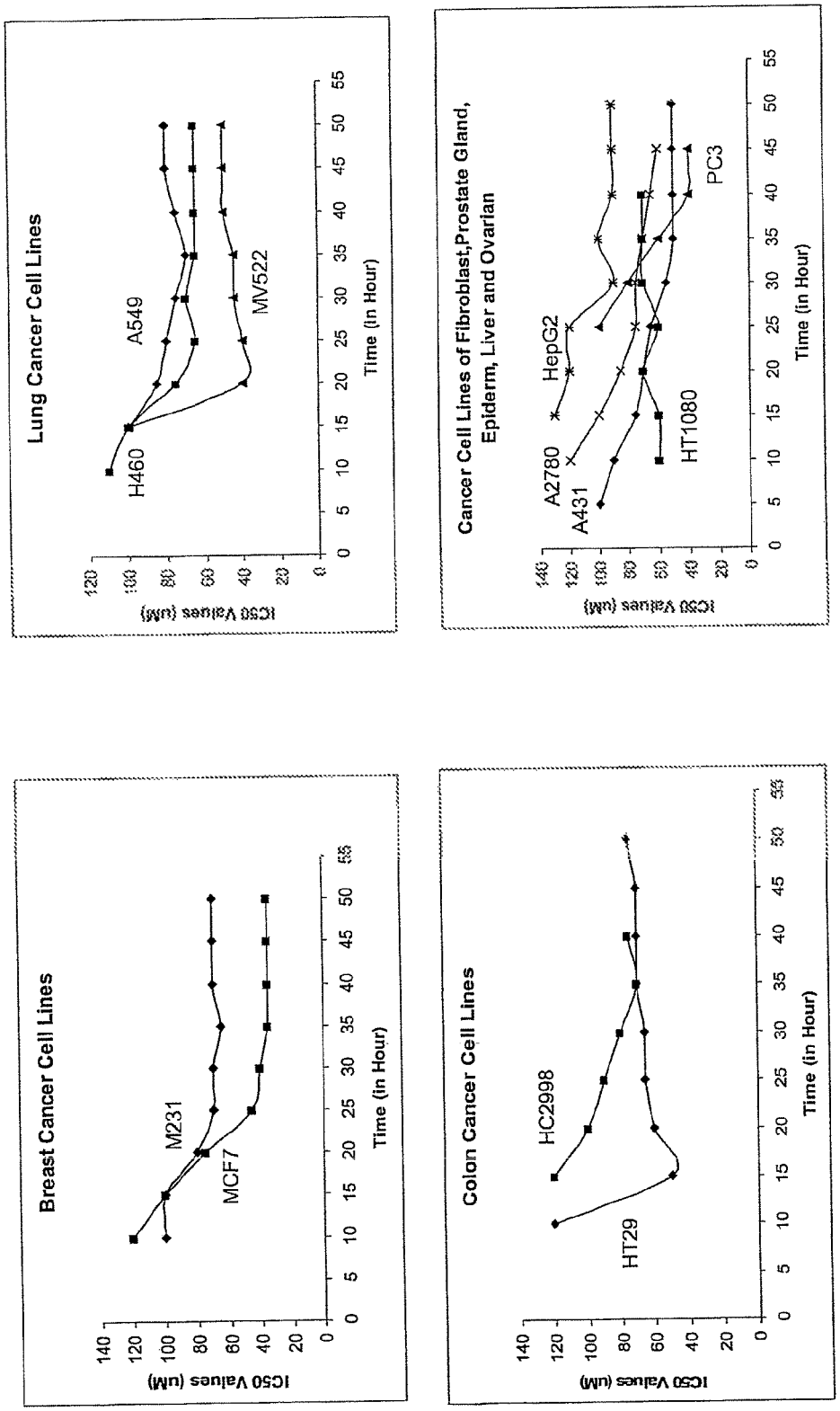
Figure 15D:
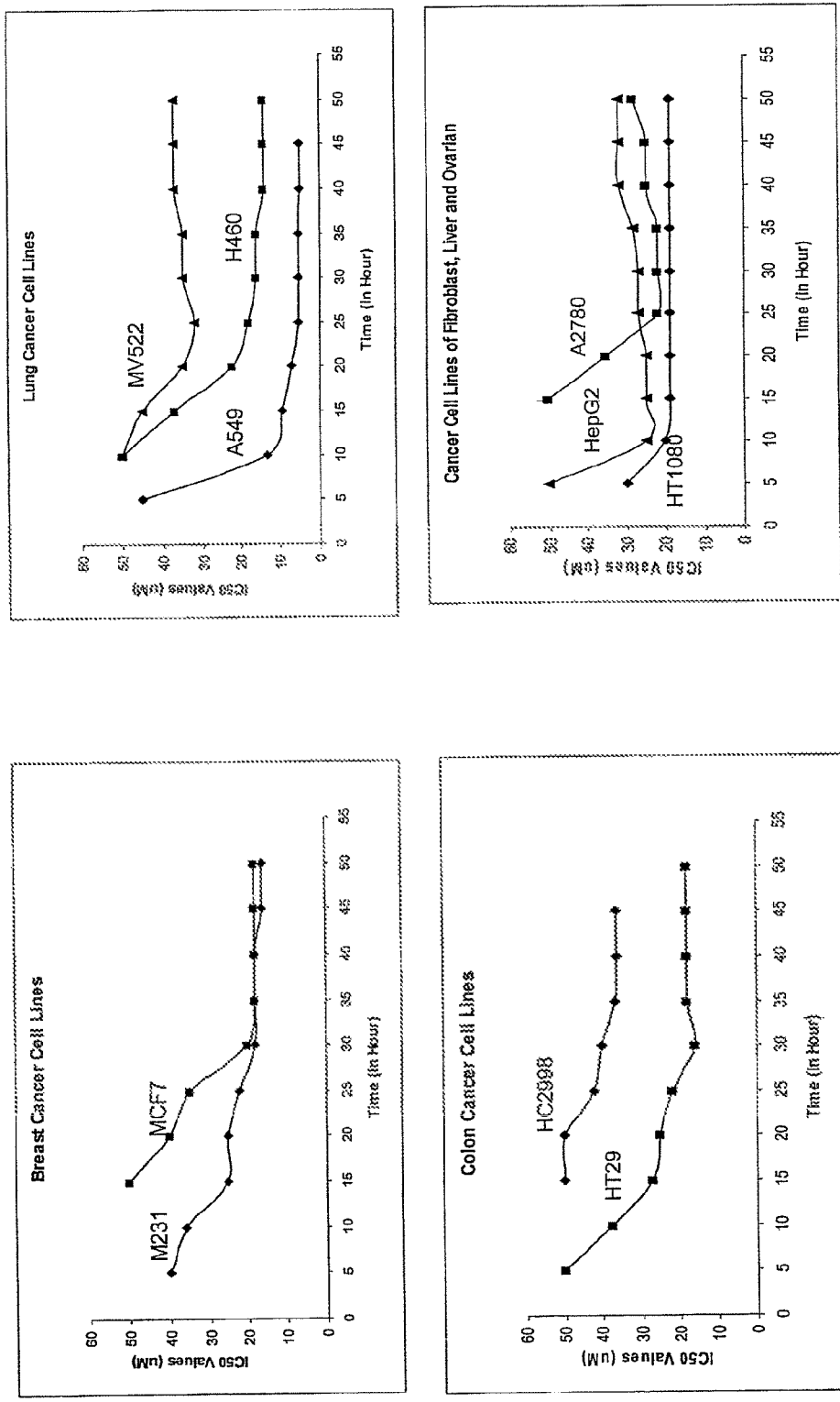

FIGS. 11A and 11B show the responses of various cell types (listed in Table 1) to paclitaxel treatment as monitored using a cell-substrate impedance monitoring system of the present invention. The indicated cell lines were seeded onto microtiter devices fabricated with electronic sensor arrays shown in FIGS. 1A-C. The cellular responses were continuously monitored at 15 or 30 or 60 minutes time interval before and after treatment with paclitaxel. Comparison among these cell index curves showed that certain similarity does exist. Take the treatment of palitaxel at 0.78-12.5 nM range as examples. Typically, such nM paclitaxel treatment resulted in an initial decrease in cell index for about 15-20 hrs. For one particular cell index curve, after the cell index reached a minimum, it then reversed its decreasing trend and started to increase. Such "going down and then going up" feature in cell index curves was also observed in cell index curves for cells treated with vinblastin or colcemid. Examples of cell index curve for vinblastin-treated cells are shown in FIG. 16A and FIGS. 22A-C. All these compounds—i.e., paclitaxel, vinblastin and colcemid, are so called mitotic poisons and follow similar mechanism of drug action. For example, both vinblastin and paclitaxel act on microtubule dynamics within a cell.

In addition, for a given assay time point, cell index (including normalized cell index or delta cell index), can be plotted versus compound concentration. Such dose response relationships can be used to derive a time-dependent IC5, IC10, IC20, IC30, IC40, IC50, IC60, IC70, IC80, IC90, or IC95. In some preferred embodiments, a time-dependent IC50 is calculated for a compound. Determining a range of time-dependent IC50s for a compound provides information on when the effect of the compound on cells is maximal.

The CI derived from impedance data from wells comprising different cell types and a test compound can be used to derive cell change index (CCI) values for assay time points. CCI values of particular cell types at assay time points can be compared. Such comparisons can indicate whether different cell types are responding similarly to a compound. CCI can also be plotted versus time, and CCI curves of cells of different types assayed with one or more test compounds can be compared to determine the similarities or differences in cellular responses of different cell types to a test compound.

For example, the time frame, magnitude, and duration of a difference in response as evidenced by the curves can indicate a difference in efficacy or mechanism of compounds. The impedance differences can reflect differences in, for example, cell attachment or adhesion, cell growth or proliferation; the number of viable cells or dead cells; cytoskeleton organization or function; or the number of cells going through apoptosis or necrosis in response to a test compound.

Preferably, data from impedance monitoring of wells that comprise different cell types are compared. In one preferred embodiment impedance monitoring is performed for different cell types exposed to multiple dose concentrations of a compound. In some embodiments, multiple compounds can be tested with multiple cell types. In some embodiments, multiple compounds at multiple concentrations can be tested with multiple cell types.

Cytotoxicity Profiling

In another aspect, the present invention provides a method for performing real-time cytotoxicity assay of a compound, comprising: a) providing an above described system; b) seeding cells to the wells of multiple-well devices; c) adding the compound to the wells containing cells; d) monitoring cell-substrate impedance before and after adding the compound at a regular or irregular time interval; wherein the time dependent impedance change provides information about time dependent cytotoxicity of the compound. In one embodiment, the cell-substrate impedance is monitored at regular time intervals. In exemplary embodiments, the impedance is measured at a regular 2 hour, 1 hour, 30 min or 15 min time interval before and after adding the compound.

In one embodiment of the above method, multiple wells with same cell types are used, wherein each well is added with the compound of different concentrations. The method provides the time-dependent and concentration-dependent cytotoxic responses.

In yet another aspect, the present invention provides a method for analyzing and comparing time-dependent cytotoxic effects of a first compound and a second compound on a cell type, comprising: a) performing a real-time cytotoxicity assay on a cell type with the first compound using the method described above; b) performing a real-time cytotoxicity assay on said cell type with the second compound using the method described above; c) comparing the time-dependent cytotoxic responses of the first compound and the second compound to see how similar or different the responses from the two compounds are. In one embodiment of this method, time-dependent cytotoxic responses are determined for the first compound at multiple dose concentrations. In another embodiment, time-dependent cytotoxic responses are determined for the second compound at multiple dose concentrations. In yet another embodiment, time-dependent cytotoxic responses are determined for both first compound and second compound at multiple dose concentrations.

In another embodiment of above methods, the first compound is a compound with a known mechanism for its cytotoxic effect and the second compound is a compound with an unknown mechanism for its cytotoxic effect. If the time dependent cytotoxic responses from the second compound are similar to that of the first one, the second compound may follow a similar mechanism for its cytotoxic effect to the first compound.

Various approaches may be used in comparing the cytotoxic responses of the compounds. A cell index (or cell number index) can optionally be calculated using the impedance values obtained. In one embodiment of the method described above, time dependent IC50 may be derived for the compounds and comparison between their cytotoxic responses is done by comparing their time dependent IC50 curves based on cell index values. If the IC50 curves follow a similar time-dependent trend, the two compounds may follow a similar mechanism for inducing cytotoxicty effects. In another embodiment of the method described, direct comparison of time-dependent cytotoxic responses of two compounds are done where the concentrations for the two compounds may be the same or may be different. Direct comparison between time-dependent cytotoxic responses may be done by analyzing the slope of change in the measured responses (that is equivalent to the first order derivative of the response with respect to time) and comparing the time-dependent slopes for the two compounds. In another approach, the time-dependent cytotoxic responses may be analyzed for their higher order derivatives with respect to time. Comparing such high order derivatives may provide additional information as for the mechanisms of compound-induced cytotoxicity.

In one embodiment of the method, analyzing real-time cytotoxicity response may include the derivation of time-dependent IC50 values for the compound on the multiple cell types. In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

In yet another embodiment, the above methods are applied to perform cytotoxicity profiling of multiple compounds on multiple cell types.

In another embodiment of the method, analyzing real-time cytotoxicity response may include derivation of the slope of change in the time dependent cytotoxicity response at a given compound concentration. In yet another embodiment of the method, analyzing real-time cytotoxicity response may include derivation of high-order derivatives of the time dependent cytotoxicity response with respect to time at a given compound concentration.

Some examples of compound assays that can be performed using a cell-substrate impedance system of the present invention are provided by way of illustration with reference to the figures. In these examples, cell index is calculated using the same method as the Cell Index calculation method (A) as described in Section C of the present application. In some of the figures of the present application, Normalized Cell Index was plotted. The Normalized Cell Index at a given time point is calculated by dividing the Cell Index at the time point by the Cell Index at a reference time point. Thus, the Normalized Cell Index is 1 at the reference time point.

As described in the present application, if the cell attachment conditions remain unchanged or exhibit little change over the course of an assay that uses impedance monitoring, then the larger the cell index, the larger the number of the cells in the wells. A decrease in cell index suggests that some cells are detaching from the substrate surface or dying under the influence of the compound. An increase in cell index suggests that more cells are attaching to the substrate surfaces, indicating an increase in overall cell number.

Figure 5:
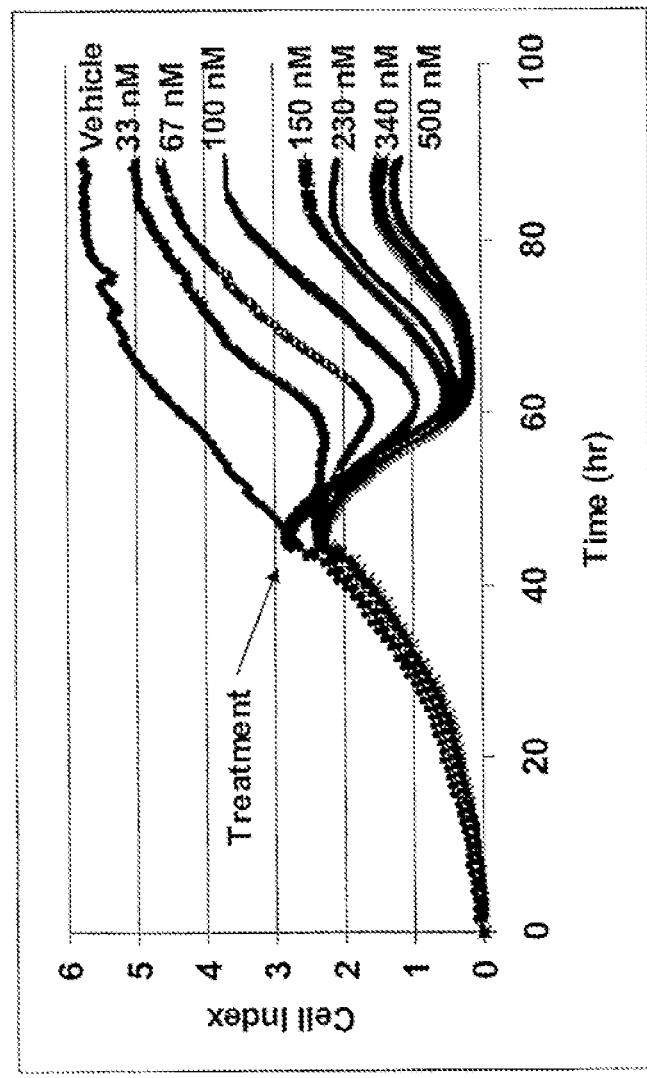
FIG. 5 shows time-dependent cell index for H460 cells treated by anticancer drug paclitaxel. Different wells of cultured H460 cells were treated at their exponential growth phase with different concentrations of Paclitaxel. The dynamic response of the cells to different doses of paclitaxel was monitored in real time every 15 minutes for 50 hours after treatment using a cell-substrate impedance monitoring system of the present invention. For paclitaxel concentration between 67 nM and 500 nM, H460 cells exhibited a gradual decrease in cell index initially after the compound addition. However, the cell index reached a minimum at a time dependent on the compound concentration between about 15 hours and 20 hours after compound addition. After that point, the cell index exhibited a gradual increase in cell index. The cell index for compound concentration of 33 nM exhibited a near-constant value for time up to about 15 hours after compound addition. After 15 hours following the compound addition, the cell index exhibited a gradual increase in cell index.

FIG. 5 shows curves that represent the time-dependent cell index for H460 cells treated with different concentrations of the anticancer drug paclitaxel. In this experiment, H460 cells were introduced into wells of a 16× cell-substrate impedance monitoring device. The device was positioned on a device station that was located in an incubator maintaining conditions of 37 degrees C. and 5% $CO_2$. The cells were cultured and treated at their exponential growth phase with different concentrations of paclitaxel. The dynamic response of the cells to different doses of paclitaxel was monitored by monitoring cell-substrate impedance in real time every 15 minutes for 50 hours after treatment using a cell-substrate impedance monitoring system. The cell-substrate impedance monitoring system calculated the cell index at each time point monitored and plotted the cell index as a function of time. For paclitaxel concentrations between 67 nanomolar and 500 nanomolar, H460 cells exhibited a gradual decrease in cell index after compound addition. However, the cell index reached a minimum at a time dependent on the compound concentration, between about 15 hours and 20 hours after compound addition. After that point, there was a gradual increase in cell index in these wells. The cell index for compound concentration of 33 nanomolar exhibited a near-constant value for up to about 15 hours after compound addition. After 15 hours following compound addition, the cell index exhibited a gradual increase.

Information about cell responses to the compound includes, but is not limited to, information about cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. Information about cell status may also include any compound-cell interaction leading to any change to one or more of above cell status indicators. For example, if the compound binds to a receptor on the cell surface and such binding leads to a change in cell morphology, then the binding of compound to the receptor can be assayed by the monitored cell-substrate impedance. The cell-based assays that be performed with above methods include, but not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, cell-based assay for screening and measuring ligand-receptor binding.

Figure 6:
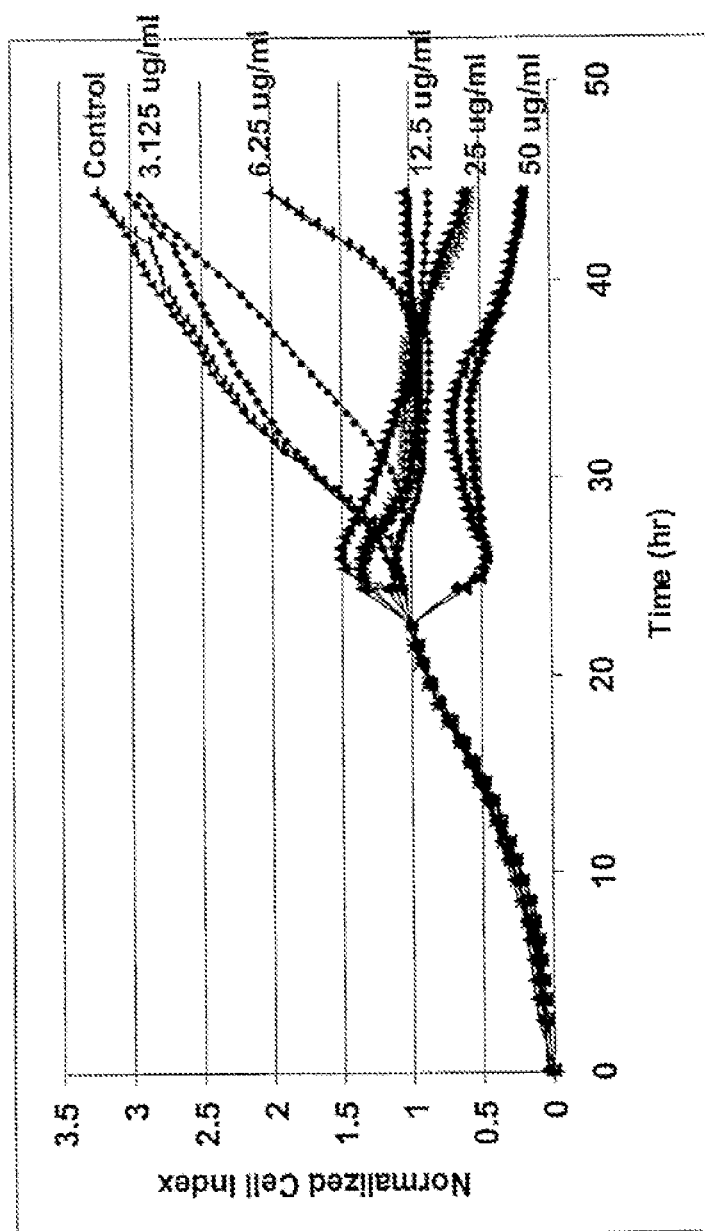
FIG. 6 shows time-dependent cell index for H460 cells treated by anticancer drug AC101103. Different wells of cultured H460 cells were treated at their exponential growth phase with different concentrations of AC 101103. The dynamic response of the cells to different doses of AC 101103 was monitored in real time every 30 minutes for about 20 hours on a cell substrate impedance monitoring system of the present invention. The time-dependent cell index in FIG. 6 is significantly different from those shown in FIG. 5. For compound concentrations at 3.125 μg/ml, 6.25 μg/ml and 12.5 μg/ml, the cell index exhibited a near-constant value for about 5 hrs, about 15 hrs and >20 hrs respectively. For compound concentrations at 3.125 μg/ml and 6.25 μg/ml, the cell index started to increase after about 5 hrs and about 15 hrs following compound addition. For the compound concentration of 25 μg/ml, there was a gradual, yet slow decrease in the cell index after compound addition. For the compound concentration of 50 μg/ml, there was an about 10 hr time period over which the cell index remained near-constant, and after that, the cell index decreased steadily.

FIG. 6 shows curves that represent the time-dependent cell index for H460 cells treated with anticancer drug AC101103. H460 cells were introduced into wells of a 16× cell-substrate impedance monitoring device. The device was positioned on a device station that was located in an incubator maintaining conditions of 37 degrees C. and 5% $CO_2$. The cells were cultured and treated at their exponential growth phase with different concentrations of AC 101103. The dynamic response of the cells to different doses of AC101103 was monitored by measuring impedance in real time every 30 minutes for about 20 hours after treatment on the cell-substrate monitoring system.

Notably, the time-dependent cell index in FIG. 6 is significantly different from those shown in FIG. 5. For compound concentrations at 3.125 microgram/ml, 6.25 microgram/ml and 12.5 microgram/ml, the cell index exhibited a near-constant value for about 5 hrs, about 15 hrs and >20 hrs respectively. For compound concentrations at 3.125 microgram/ml and 6.25 microgram/ml, the cell index started to increase after about 5 hrs and about 15 hrs following compound addition. For the compound concentration of 25 microgram/ml, there was a gradual, yet slow decrease in the cell index after compound addition. For the compound concentration of 50 microgram/ml, there was an about 10 hr time period over which the cell index remained near-constant, and after that, the cell index decreased steadily.

Figure 7:
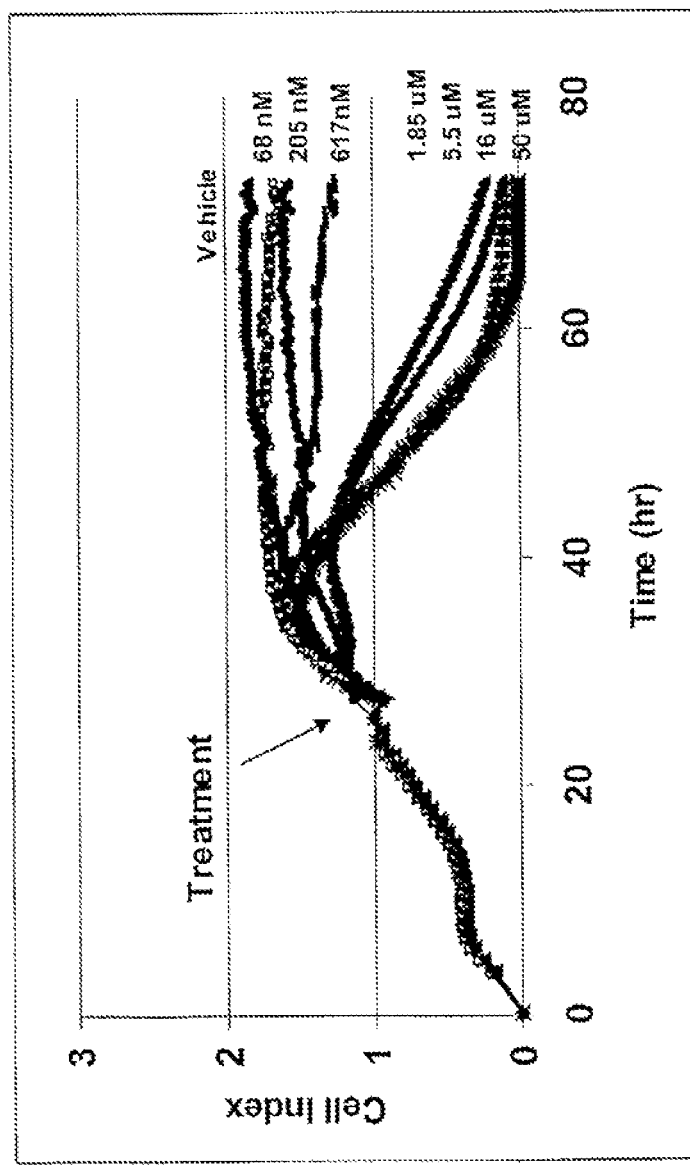
FIG. 7 shows dynamic drug response curves of A549 cells treated with doxorubicin. 10,000 A549 cells were seeded in each well of a 16× device. The cell attachment and cell growth were monitored on the cell-substrate impedance monitoring system of the present invention in real time before treatment. When the cells were in exponential growth phase, doxorubicin at different concentration was added to the cells. Same volume of a solvent used for dissolve the drug was served as vehicle control. The time, and drug dose dependent cell response to doxorubicin was recorded in real time.

FIG. 7 shows dynamic drug response curves of A549 cells treated with doxorubicin. 10,000 A549 cells were seeded into each well of a 16× device. The device was positioned on a device station that was located in an incubator maintaining conditions of 37 degrees C. and 5% $CO_2$. Cell attachment and cell growth were monitored on a cell-substrate impedance system in real time before treatment by monitoring impedance at regular intervals. When the cells were in exponential growth phase, doxorubicin at different concentrations was added to the wells. The same volume of the solvent used to dissolve the drug was added to some wells as a control. The time, and drug dose dependent cell response (calculated as cell index) to doxorubicin was recorded in real time on the cell-substrate impedance monitoring system as shown in this figure.

D.4. Real-Time Cell Based Assays to Identify a Compound Capable of Interacting with a G-Protein Coupled Receptor (GPCR)

The methods described in the present invention may be applied to identifying one or more compounds that are capable of interacting with a G-protein coupled receptor. More specifically the methods may be applied to identify compounds that affect a GPCR such as but not limited to stimulation or inhibition of the GPCR. The methods may identify GPCR agonists, inverse agonists, antagonists and the like. The methods of the present invention may be used to identify compounds that affect known GPCRs and orphan GPCRs.

The present invention includes cell-impedance technology to assess and quantify the morphological changes that occur in cells or cell lines that are expressing appropriate GPCR in response to their cognate ligand or agonist using cell-substrate impedance technology. It has been shown that multiple GPCRs and GPCR-mediated signaling pathways converge upon and induce rearrangement of the actin cytoskeleton at the periphery or an increase in stress fiber formation. GPCR-mediated actin cytoskeleton rearrangement has been shown to be mediated by activation of tyrosine kinases and members of the rho family of GTPases (Luttrel, L M. Mol Cell (2002) 9:1152-4.). We have utilized the cell shape changes (the changes in cell morphology) that occur as a result of GPCR-mediated rearrangement of the actin cytoskeleton as readout for GPCR function using cell-substrate impedance technology.

In one aspect, the present invention is directed at a method to screen for natural ligands or agonists of the appropriate GPCR utilizing electronic measurement and sensing of cells. One approach for electronic measurement of cells is based on the measurement of cell-substrate or cell-electrode impedances. The approach features in the integration of cell biology with microelectronics and is based on the electronic detection of biological assay process. The details of this cell electronic sensing technology, called real-time cell electronic sensing (RT-CES), and associated devices, systems and methods of use have been provided in, PCT application number PCT/US03/22557, titled "Impedance based devices and methods for use in assays", filed on Jul. 18, 2003; U.S. patent application Ser. No. 10/705,447, titled "Impedance based devices and methods for use in assays", filed on Nov. 10, 2003; PCT Application No. PCT/US04/037696, entitled "Real time electronic cell sensing system and application for cell based assays", filed on Nov. 12, 2004; U.S. patent application Ser. No. 10/987,732, entitled "Real time electronic cell sensing system and application for cell based assays" filed Nov. 12, 2004; PCT Application No. PCT/US05/004481, entitled "Real time electronic cell sensing system and applications for cytotoxicity profiling and compound assays", filed on Feb. 9, 2005; U.S. patent application Ser. No. 11/055,639, entitled "Real time electronic cell sensing system and applications for cytotoxicity profiling and compound assays" filed Feb. 9, 2005. All the above applications are incorporated by reference.

For measurement of cell-substrate or cell-electrode impedance using RT-CES technology, microelectrodes having appropriate geometries are fabricated onto the bottom surfaces of microtiter plate or similar device, facing into the wells. Cells are introduced into the wells of the devices, and make contact to and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue electronic readout signals are measured automatically and in real time, and are converted to digital signals for processing and for analysis. In a RT-CES system, a cell index is automatically derived and provided based on measured electrode impedance values. The cell index obtained for a given well reflects: 1) how many cells are attached to the electrode surfaces in this well, 2) how well cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

The method of the present invention is to screen for ligands or agonists of GPCR being expressed by appropriate cell lines using measurement of cell-substrate impendence. The method is based on quantification in real time of the cytoskeletal changes and/or morphological changes that arise as a response to ligand or agonist binding to the exogenous or endogenous GPCR being expressed on the surface of an appropriate cell line or primary cells. Because the electronic assay readout relies on cytoskeletal dynamics and/or cell morphology and/or cell adhesion property, all of which are intrinsic cell responses to the activated GPCR, it precludes the need for establishing reporter cell lines or using any other reagent. Furthermore, since the assay is performed in real time, multiple treatments can be performed within the same experiment and receptor desensitization can be assessed.

In another aspect, the present invention is directed to method to use electronic impedance technology to screen for potential antagonists of GPCR expressed by an appropriate cell line and activated by a known ligand.

In another aspect, the present invention is directed to method to use electronic impedance technology for target validation purposes of key enzymes and proteins involved in the signaling pathway leading initiated by the activation of the GPCR expressed and displayed at the cell surface.

In another aspect, the present invention is directed to method to use electronic impedance technology for screening of small molecular inhibitors of key enzymes and proteins involved in the signaling pathway leading from binding and activation of the GPCR at the cell surface.

For example, the present invention provides a method of identifying a compound capable of interacting with a G-Protein Coupled Receptor (GPCR) including: (a) providing a device capable of measuring cell-substrate impedance; wherein the device comprises at least two wells, further wherein the device is operably connected to an impedance analyzer; (b) adding test cells to at least two wells, wherein the test cells express a GPCR; (c) measuring first impedances of the at least two wells immediately preceding step (d) and optionally determining first cell indices from the first impedances; (e) adding a compound to at least one well containing the test cells to form at least one compound well and adding a vehicle control to at least another well containing test cells to form at least one control well; (f) measuring second impedances of the at least one compound well and of the at least one control well after step (d) and optionally determining second cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the at least one control well; (h) comparing the change in impedance or cell index between the at least one compound well and the at least one control well; and (i) identifying the compound interacts with the GPCR if the comparison demonstrates a significant difference between the change in impedance or cell index of the at least one compound well and the change in impedance or cell index of the at least one control well.

Devices for Measuring Cell-Substrate Impedance

The devices used with the present invention include devices capable of measuring or monitoring cell-substrate impedance. The cell-substrate (or cell-electrode) impedance is related to not only to the number of the cells but also to the morphology and adhesion quality of the cells on the electrode surfaces. The higher the cell number on the electrode surface is, the larger the cell-substrate impedance (resistance). Similarly, the more spread out the cells are on the electrode surfaces, the larger the cell-substrate impedance (resistance). Likewise, the tighter the cell adhesion to the electrode surfaces, the larger the cell-substrate impedances (resistance). In one aspect of the present invention, the methods are provided for monitoring the activation of GPCR or RTK in living cells based on a change in cell morphology and/or cell adhesion occurred when GPCR or RTK are activated.

Examples of suitable devices for monitoring or measuring cell-substrate impedance are previously described in the present application. In preferred embodiments the devices frequently contain at least two wells, at least one well forming a test well or a compound well and at least one well forming a control well or a confirmation well. One skilled in the art would recognize that multiple wells may be utilized for one or more assays. For example the device may be in the format of a multi-well plate. In this embodiment multiple assays may be performed simultaneously. Each of the wells may contain a conductive electrode array. As a non-limiting example, a multi-well plate usable with the present invention may be a 16 well plate, a 24 well plate, a 96 well plate, a 384 well plate, and a 1536 well plate.

As another nonlimiting example, a device capable of monitoring or measuring substrate impedance may include but is not limited to a nonconducting substrate, two or more electrode arrays fabricated on the substrate, wherein each of the two or more electrode arrays includes two electrode structures; the two or more wells on the substrate, wherein each of the two or more arrays is associated with one of the two or more wells, and at least two connection pads, each of which is located on an edge of the substrate, wherein for each of the two or more electrode arrays, each of the two electrode structures includes multiple electrode elements and the first of the two electrode structures of each of the at least two electrode arrays is connected to one of the at least two connection pads, and the second of the two electrode structures of each of the at least two electrode arrays is connected to another of the at least two connection pads, further wherein at least two of the two or more electrode arrays share one common connection pad, further wherein each electrode array has an approximately uniform electrode resistance distribution across the entire array, and further wherein said substrate has a surface suitable for cell attachment or growth, wherein the cell attachment or growth on the substrate can result in a detectable change in impedance between or among the electrode structures within each electrode array.

The GPCR Superfamily

The present invention may be used to identify compounds that affect a variety of GPCRs. The human genome project has identified a number of proteins which can be categorized into GPCRs based on sequence. The number of GPCRs encoded by the human genome is estimated to be between 800-1000 and thus far approximately 650 GPCR have been identified from the effort of the human genome project, 200 of which are classified as known GPCRs because the activating ligands for these receptors are known (Nambi, P and Nambi, A. Assay and Drug Development Technologies (2003) 1, 305-310). The remaining receptors for which the ligands are not known are considered "orphan receptors" and they are the subject of intense scrutiny as potential medically relevant targets. There are a number of in vitro and cell-based assays available which are used to screen for potential agonist or antagonist of GPCRs. The in vitro assays are based on binding studies with labeled ligand and receptor. (Nambi, P and Nambi, A. Assay and Drug Development Technologies (2003) 1, 305-310) The cell-based assays are based on engineering cell lines to express exogenous GPCRs alone or together with a reporter plasmid. Calcium sensitive dyes have been used extensively to screen for GPCRs that increase intracellular calcium levels in response to agonists challenge. Alternatively, a fluorescent or luminescent-based reporter assay co-transfected with the appropriate GPCR and G-protein has also been used to identify potential agonists or antagonists of the transfected GPCR (Nambi, P and Nambi, A. Assay and Drug Development Technologies (2003) 1, 305-310). While these assays are extremely useful in high throughput screening to identify potential agonists and antagonists, they do involve pre-labeling the cells with fluorescent dyes in the case of calcium-based assays or lysing the cells to measure the activity of reporter genes.

The present invention addresses a variety of difficulties in identifying compounds that affect GPCRs or the GPCR pathway. As a nonlimiting example, the present invention is useable with a recombinant GPCR, an endogenous GPCR, an orphan GPCR, a constitutively active GPCR, a chimeric GPCR, or other chimeric receptors containing a GPCR property.

Test Cells

The present invention refers to adding test cells to at least one well of a device capable of monitoring or measuring cell-substrate impedance. Test cells refer to cells that express the receptor of interest. In the instance of the methods of identifying a compound that affects a GPCR, the test cells would express the GPCR of interest. Test cells may express a variety of receptors such as but not limited to a recombinant GPCR, an endogenous GPCR, an orphan GPCR, a constitutively active GPCR, a chimeric GPCR, or other chimeric receptors containing a GPCR property.

Test cells may be added to the wells using any suitable method known in the biological arts for cell transfer or high throughput cell transfer such as but not limited to aliquoting, pipetting or transferring cells. Test cells may be added at a predetermined concentration or not.

Compound Added to Test Wells

The present invention includes adding one or more compounds to test cells, control cells and the like to determine the effect of the compound on a GPCR or GPCR pathway. A well containing a compound may be referred to as a compound well for clarity. The compound may be a particular compound of interest or may be a compound from a library of compounds. As nonlimiting examples, the compound may be believed to be a potential ligand, an agonist, an inverse agonist or an antagonist or inhibitor for a GPCR. The compound may be added at a single concentration or at a variety of concentrations. In some embodiment dose-response curves are obtained by adding a compound in more than one concentration and correlating the response in cell-substrate impedance or a cell index (as obtained from the cell-substrate impedance measurement) to the compound concentration. Cell responses to a compound may result in a change (for example, increase or decrease) in cell-substrate impedance or in cell index. Furthermore, the EC50 or IC50 of a compound may be determined by identifying the concentration of compound that results in approximately 50% of maximum responses in cell-substrate impedance or cell index.

Measuring or Monitoring Impedance (Cell-Substrate Impedance)

The present invention monitors impedance over time while adding one or more compounds to test cells, control cells, confirmation cells and the like. As previously described impedance may be monitored continually or at desired time intervals or time points. In some embodiments, the present invention describes an impedance as a first impedance, a second impedance, a third impedance and the like. Each of the referenced impedance measurements may be a single impedance measurement or a series of impedance measurements. For example a first impedance measurement may be taken after adding test cells to at least two wells and before adding a compound or a vehicle control to the wells. In this instance the first impedance measurement may function as a type of control to determine the change in impedance of a single well upon the addition of a compound or vehicle control. Thus, multiple impedance measurements may be taken prior to adding a compound, and may be referred to as a first impedance measurement. Since a cell index may be determined for an impedance measurement, a series of cell indexes (i.e., cell indices) may be determined corresponding to the series of impedance measurements, where each of the first cell indexes corresponds to a distinct impedance measurement. Similarly, a second impedance may be measured or monitored after adding a compound to the at least one well containing a test cell (frequently referred to as forming a compound well). In this instance, the second impedance measures the cellular response or detects changes corresponding to the addition of a compound. The second impedance measurement may therefore reflect an impedance measurement at a time point after addition of a compound. Depending on the desired assay, the second impedance measurement may contain one or more measurements. A series of three or more impedance measurements at three or more time points may be performed to provide a time-dependent, impedance curve or cell index curve that may depict the time dependent changes to the test cells or control cells due to the addition of the compound (or maybe due to the interaction of the compound with a GPCR). When multiple measurements at multiple time-points are taken or the impedance is routinely monitored, a peak in cell-substrate impedance (cell-substrate resistance) or a peak in cell index or a peak in normalized cell index or a peak in delta cell index may be identified. The peak may be a maximum or a minimum impedance (e.g. resistance) out of all the impedance values measured after addition of the compound. Or, the peak may be a maximum change (e.g, relative change or absolute change) in cell-substrate impedance with respect to the impedance before addition of the compound. Or the peak may be a maximum change in cell index or normalized cell index or delta cell index out of all the cell indexes or normalized cell indexes determined from the measurement of cell-substrate impedance after addition of the compound. For each concentration of the compound, such a peak may be identified and may be plotted versus the compound concentration to determine a dose-response curve. Thus, the second impedance measurement may be a series of impedance measurements optionally taken to identify a dose curve. Alternatively, the area under the cell-index or impedance curve for each concentration of the compound can also be determined and used in generating a dose-response curve. Here cell-index curve or impedance curve refers to time-dependent cell-index (or time-dependent impedance) plotted versus time after addition of the compound. In a nonlimiting example, the second impedance may be taken at a time point including but not limited to a time point such as more than 1 minute, more than 5 minute, more than 30 minute, more than 1 hour, more than 2 hours, more than 5 hours, more than 10 hours, and more than 24 hours after adding the compound or vehicle control.

Measuring or monitoring impedance at a given time point does not mean that the impedance measurement took place at a single time moment. Indeed, measuring an impedance may take a short period of time, for example, 1 second, or 100 milli-second, or one milli-second, or a one micro-second, or even less than one micro-second. Thus, such a measurement time is not taken into account and measuring impedance at a given time point may refer to a time point just before the starting moment of the impedance measurement, or just after the end of the impedance measurement, or any time moment in between.

Impedance may be monitored using the methods previously disclosed in the present application. Monitoring impedance may include performing one or more impedance measurements at one or more time points or a series of measurements at a series of time points. Monitoring impedance may include performing impedance measurements at multiple frequencies. Impedance measurement includes the measurement of resistance and/or reactance. Depending on the desired assay, impedance may be monitored or measured at regular or irregular time intervals during an assay period.

In some embodiments an impedance measurement is performed at a time point or time points before adding a compound or a vehicle control or immediately prior to adding a compound or a vehicle control to the cells. In one exemplary embodiment, impedance measurement may be performed at a time point of less than less than 30 minutes, less than 1 hour, less than 2 hours, less than 4 hours, or less than 10 hours, or less than 24 hours, or other time length prior to adding a compound or vehicle control to the cells. In another exemplary embodiment, impedance measurement may be performed at a time point immediately preceding or prior to adding a compound or a vehicle control, such as less than 20 minutes, less than 10 minutes, less than 5 minutes, less than 2 minutes, or less than 1 minute prior to adding the compound or vehicle control. A vehicle control in this context refers to a medium or solution or solvent that has the same composition as the medium or solution or solvent in which a test compound is placed, but without the test compound.

In still another exemplary embodiment, impedance measurement may be performed at regular or irregular time intervals prior to addition of a test compound or a vehicle control. As can be envisioned, a series of two, three, four or more measurements may be desired after adding a compound. In one exemplary embodiment, impedance measurement may be performed at regular time intervals (for example, every 15 seconds, or every minute, or every 15 minutes) after adding a compound. In another exemplary embodiment, impedance measurement may be performed at irregular time intervals (for example, initially every 2 minutes up to 1 hour and followed by every 30 minutes up to 24 hours) after adding a compound. In still another exemplary embodiment, impedance measurement may be performed at a time point of more than 15 seconds, more than 1 minute, more than 5 minute, more than 30 minutes, more than 1 hour, more than 2 hours, more than 5 hours, more than 10 hours after adding a compound.

A method of the present invention is to identify a compound capable of interacting with a G-Protein Coupled Receptor (GPCR) in test cells using measurement of cell-substrate impedance. It is based on impedance-based quantification of change in cell morphology (and/or cell adhesion) which arise as a response to compound interacting with (for example, binding to) a GPCR, causing cellular changes, including but not limited cytoskeleton re-arrangement. Because the impedance readout relies on the interaction of the test cells with the sensor electrodes, the change in cell morphology and or cell adhesion due to the compound interacting with a GPCR leads to a time-dependent change (for example, increase or decrease) in the cell-substrate impedance which correlates with the interaction of the compound with the GPCR, or with GPCR activation.

Determining Cell Index

The methods of the present invention may include comparing one or more impedance measurements or comparing one or more cell indices (i.e., cell indexes) or cell index values. In one embodiment, a cell index is determined by calculating, for each measurement frequency, the relative-change in resistance (a component of impedance) of a well when the cells are present in the well with respect to that of the well when no cell is present, and then finding the maximum relative-change in resistance for all frequencies measured. The maximum relative-change in resistance is used as cell index (see equation (4) in Section C. Methods for Calculating Cell Index (CI) and Cell Change Index (CCI) of the present invention). If impedance is measured at a single frequency, then the relative change in resistance (a component of impedance) of a well when compounds are present in the well with respect to that of the well when no compound is present, or when only test cells or only control cells are present. Other methods for calculating cell index have been disclosed in a previous Section C. Methods for Calculating Cell Index (CI) and Cell Change Index (CCI). Since the cell index or cell indexes correspond to an impedance measurement or impedance measurements, the present invention envisions comparing cell indexes for the same well measured at different time points to determine a change in cell index. For example, one may compare cell indexes derived at time points before and after adding a compound that interacts with or is suspected to interact with a GPCR in the cells to determine the change in cell index as a result of adding the compound. The present invention also envisions comparing changes in cell indexes between different wells, for example, a compound well and a control well. As with impedance measurements, a first cell index may be one or more cell indexes, a second cell index may be one or more cell indexes, a third cell index may be one or more cell indexes and the like. When determining a series of cell indexes, a single cell index may be utilized for a distinct cell impedance or impedance measurement.

As previously demonstrated, cell indexes may be normalized for comparison. Normalization may take into account the number of cells in a particular well, variables in detecting impedance and the like. Although methods of normalization may vary, in some embodiments, the normalization is performed at a time point a short time before doing a treatment on cells, for example, adding compound or a vehicle control. As nonlimiting examples, a short time may be less than 1 minute, less than 2 minutes, less than 5 minutes, less than 10 minutes, less than 30 minutes, less than 1 hour, less than 2 hours, less than 5 hours, less than 10 hours and less than 24 hours.

Determining Changes in Impedance or Cell Index

The present invention compares one or more impedance measurements and optionally determining a cell index before and after adding a compound suspected of being capable of affecting a GPCR. In preferred embodiments the change in impedance of a single well is determined. As nonlimiting examples, a change in impedance may be determined for a compound well, a test well, a control well, a confirmation well and the like. Determining the change in impedance may be performed by comparing a second impedance or second cell index of a particular well measured or derived at a second time point to the first impedance or first cell index of the same well measured or derived at a first time point.

In one embodiment of the methods of the present invention, the change in impedance or cell index may be derived by subtracting the first impedance or first cell index of a particular well measured at a first time point from the second impedance or second cell index of the same well measured at a second time point. The change in impedance or cell index derived this way is referred as "absolute change" in impedances or cell indices (cell indexes). In one example of this embodiment, a particular well is a compound well, the first time point is a time point immediately preceding adding a compound to the cells in the compound well and the second time point is a time point after adding the compound. For this example, the "absolute" change in impedance or cell index for the compound well reflects the cell responses to the addition of the compound. In another example of this embodiment, a particular well is a control well, the first time point is a time point immediately preceding adding a vehicle control to the cells in the control well and the second time point is a time point after adding the vehicle control. For this example, the "absolute" change in impedance or cell index for the control well reflects the cell responses to the addition of the vehicle control. The absolute change in cell index may also be referred as "delta cell index" if the first time point is a standard time point and the cell index at the standard time point is used for calculating "absolute change in cell index" for multiple second time points. Furthermore, cell index in embodiment here may be a normalized cell index.

In another embodiment of the methods of the present invention, the change in impedance or cell index may be derived by two subsequent steps: (1) determining "absolute change" in impedances or cell indexes by subtracting the first impedance or first cell index of a particular well measured at a first time point from the second impedance or second cell index of the same well measured at a second time point; (2) dividing the "absolute change" in impedance or cell indexes by the first impedance or cell index of the same well measured at the first time point. The change in impedances or cell indices (cell indexes) derived this way is referred as "relative change" in impedances or cell indexes. In one example of this embodiment, a particular well is a compound well, the first time point is a time point immediately preceding adding a compound to the cells in the compound well and the second time point is a time point after adding the compound. For this example, the "relative" change in impedance or cell index for the compound well reflects the cell responses to the addition of the compound. In another example of this embodiment, a particular well is a control well, the first time point is a time point immediately preceding adding a vehicle control to the cells in the control well and the second time point is a time point after adding the vehicle control. For this example, the "relative" change in impedance or cell index for the control well reflects the cell responses to the addition of the vehicle control.

As described previously in the present invention, monitoring impedance may include performing impedance measurements at multiple frequencies. Impedance measurement includes the measurement of resistance and/or reactance. Thus, a change in impedance may refer to a change in impedance at a particular measurement frequency, or may refer to a maximum change in impedance for multiple measurement frequencies, or may refer other parameters that may be derived from the change in the frequency spectrum of the impedance. Furthermore, a change in impedance may be a change in resistance, or reactance, or resistance and reactance.

Comparing Changes in Impedance or Cell Index

Changes in impedance or cell index are compared between test samples and control samples. For example, a change in impedance or cell index for a compound well as a result of adding a compound to the cells in the compound well may be compared to the change in impedance or cell index for a control well as a result of adding a vehicle control to the cells in the control well. If such a comparison demonstrates a significant difference (for example, more than 0.5%, or more than 1%, or more than 10%) between the compound well and the control well, then change in impedance or cell index for the compound well is significantly different from the change in impedance or cell index for the control well. We may identify that the compound may interact with the cells. If the cells express a GPCR, we may identify that the compound may interact with the GPCR in the cells.

In another example, a change in impedance or cell index for a test well as a result of adding a compound to the test cells in the test well may be compared to the change in impedance or cell index for a control well as a result of adding the same compound to the control cells in the control well. If such a comparison demonstrates a significant difference (for example, more than 0.5%, or more than 1%, or more than 10%) between the test well and the control well, then change in impedance or cell index for the test well is significantly different from the change in impedance or cell index for the control well. We may identify that the compound may interact with the test cells differently from the interaction of the compound with the control cells. If the test cells express a GPCR whilst the control cells do not express the GPCR or express the GPCR at a significantly lesser level than the test cells, we may identify that the compound may interact with the GPCR in the test cells.

In another example, a change in impedance or cell index for a test well as a result of adding a compound to the test cells in the test well may be compared to the change in impedance or cell index for a confirmation well as a result of adding a vehicle control to the test cells in the confirmation well. In still another example, a change in impedance or cell index may be compared between multiple compound wells such as multiple compound wells containing the compound at a variety of dilutions or concentrations.

Identifying Compounds of Interest

Compounds that interact with GPCRs are identified by determining which compound(s) cause significant changes in impedance or cell index. For example, when screening or identifying a compound capable of affecting a GPCR, a compound may be identified if a significant change is observed between the change in impedance or cell index of the compound well in comparison to the change in impedance or cell index of a control well. Here both compound well and control well have the same test cells expressing a GPCR. The compound is added to the compound well whilst a vehicle control is added to the control well. For the compound well, the change in impedance or cell index refer to the change occurred after adding the compound. For the control well, the change in impedance or cell index refer to the change occurred after adding the vehicle control. As a nonlimiting example, a compound may be identified as an agonist to a GPCR if the comparison indicates a significant change including an increase or a decrease in impedance or cell index for the compound well after the compound is added to the test cells that express the GPCR, as relative to the control well. A compound may be identified as an inverse agonist if the comparison indicates a significant change including a decrease or increase in impedance or cell index for the compound well after the compound is added as relative to the control well, and the significant change in impedance or cell index for the compound well is in the OPPOSITE direction compared to the change of a known agonist. For example, a known agonist of a GPCR may result in a significant increase in impedance or cell index after addition of the agonist to the cells expressing the GPCR. For this GPCR in the same cells, a compound is identified as an inverse agonist if the compound results in a significant decrease in impedance or cell index after addition of the compound. In another example, an agonist may result in a significant decrease in impedance or cell index and an inverse agonist may result in a significant increase in impedance or cell index.

As previously disclosed in the present invention, compounds may be added to multiple wells to determine a dose curve or dose response curve. Each concentration of a compound results in a change in impedance or cell index after addition of the compound. Such a change in impedance or cell index may be determined or derived at multiple time points. Thus, a time-dependent change of impedance or cell index (a trace of impedance change or a trace in cell index change) may be derived for each concentration of the compound. To provide a dose-response curve, one may define or derive a single parameter to reflect the cellular response or cellular change for each concentration of the compound. In one preferred embodiment a single parameter for reflecting the cellular response or cellular changes is the maximum change in impedance (resistance) or cell index after addition of the compound and a dose-response curve may be constructed by plotting a maximum change in impedance or cell index for each concentration of the compound versus the concentration of the compound. In another embodiment, the area under the cell-index or impedance curve for each concentration of the compound may also be determined and used in generating a dose-response curve. Here cell-index curve or impedance curve refers to time dependent cell-index (or time dependent impedance) plotted versus time after addition of the compound.

In another preferred embodiment, the single parameter for reflecting the cellular response or cellular change is a change in impedance or cell index at one particular time point after the compound addition. This particular time point may correspond to the time point at which a maximum change in impedance or cell index for the highest concentration of the compound occurs.

With a dose-response curve or a dose curve, one may be able to derive EC50 or IC50 of a compound. In one embodiment, an EC50 is a concentration of a compound capable of inducing 50% of the maximum response in impedance or cell index. The maximum response in impedance or cell index refers to the maximum change in cell impedance or cell index for all concentrations of the compound, as derived from the dose-response curve or dose curve. Various formula or methods may be used to derive EC50 or IC50 from a dose response curve for a compound. Those skilled in biostatistics or in the analysis of biological data may readily choose appropriate formula or methods to calculate an EC50 or IC50 from a dose curve. For example, experimental dose curve may be fitted into a sigmoid curve and an EC50 or IC50 may be derived from the curve fitting.

Alternative Methods of Identifying Compounds that Affect the GPCR

The present invention includes a method of identifying a compound capable of interacting with a G-Protein Coupled Receptor (GPCR) including: (a) providing a device capable of measuring cell-substrate impedance; wherein the device comprises at least two wells, further wherein the device is operably connected to an impedance analyzer; (b) adding test cells to at least one of the at least two wells to form at least one test well, and adding control cells to at least another well to form at least one control well, wherein the test cells express a GPCR and the control cells do not express the GPCR or express the GPCR at a significantly lesser level that the test cells; (c) measuring first impedances of the at least one test well and of the at least one control well immediately preceding step (d) and optionally determining first cell indices from the first impedances; (d) adding a compound to the at least one test well and to the at least one control well; (e) measuring second impedances from the at least one test well and from the at least one control well after step (d) and optionally determining second cell indices from the second impedances; (f) determining the change in the impedance or cell index of the at least one test well by comparing the second impedance or the second cell index of the at least one test well to the first impedance or the first cell index of the at least one test well, and determining the change in the impedance or cell index of the at least one control well by comparing the second impedance or the second cell index of the at least one control well to the first impedance or the first cell index of the at least one control well; (g) comparing the changes in impedance or in cell index between the at least one test well and the at least one control well; and (h) identifying the compound interacts with the GPCR if the comparison demonstrates a significant difference between the change in impedance or cell index for the at least one test well and the change in impedance or cell index for the at least one control well.

Compounds that interact with GPCRs are identified by determining which compound(s) cause significant changes in impedance or cell index. For example, when screening or identifying a compound capable of affecting a GPCR, a compound may be identified if a significant change is observed between the change in impedance or cell index of the test well in comparison to the change in impedance or cell index of a control well. Here test well has the test cells expressing a GPCR and control well has control cells not expressing the GPCR or expressing GPCR at a significantly low level. The compound is added to both the test well and the control well. For the test well, the change in impedance or cell index refer to the change occurred after adding the compound to the test cells. For the control well, the change in impedance or cell index refer to the change occurred after adding the compound to the control cells. As a nonlimiting example, a compound may be identified as an agonist to a GPCR if the comparison indicates a significant change including an increase or a decrease in impedance or cell index of the test well after the compound is added to the test cells that express the GPCR, as relative to the control well. A compound may be identified as an inverse agonist if the comparison indicates a significant change including a decrease or increase in impedance or cell index of the test well after the compound is added as relative to the control well, and the significant change in impedance or cell index for the test well is in the OPPOSITE direction compared to the change of a known agonist. For example, a known agonist of a GPCR may result in a significant increase in impedance or cell index after addition of the agonist to the cells expressing the GPCR. For this GPCR in the same cells, a compound is identified as an inverse agonist if the compound results in a significant decrease in impedance or cell index after addition of the compound. In another example, an agonist may result in a significant decrease in impedance or cell index and an inverse agonist may result in a significant increase in impedance or cell index.

The provided methods have particular utility to identifying agonists or antagonists for orphan GPCRs. As provided earlier it is predicted that there are between 800-1000 potential GPCR that are coded by the genome and only 200 of which have known ligands. Therefore, in order to identify potentially relevant pharmaceutical targets the pharmaceutical industry has invested extensively in trying to identify the ligands for the orphan GPCR. The present invention provides methods to screen for potential ligands or agonist of an orphan GPCR using-substrate impedance technology. The methods may include test cells engineered to express the appropriate orphan GPCR seeded in either ACEA's 16× or 96× microtiter plates (E-Plates) at a pre-determined cell density, treating the test cells with appropriate ligand concentration from a ligand library or with potential agonist using a compound library. As a control cells that are not expressing the receptor may also be treated with the ligands or potential agonist library. The transient morphological changes of the cells due to ligand or agonist stimulation may be electronically monitored using the RT-CES system. Plotting the ligand concentration against the maximal change in cell-substrate impedance response or maximal change in cell index at each ligand concentration will result in a dose-response curve. The maximal change in this context refers to the maximum change in impedance (resistance) or cell index after addition of the compound with respect to the impedance or cell index before adding the compound. Alternatively, the area under the cell-index curve or impedance curve for each concentration of the ligand or agonist can also be determined and used in generating a dose-response curve. The cell-index curve or impedance curve refers to time dependent cell-index (or time dependent impedance) plotted versus time after addition of the ligand or agonist. The dose-response curve can be used to calculate the EC50 value, which is the molar concentration of the ligand or agonist that produces half of the maximum biological response or half of the maximum response in impedance or cell index. The maximum response in impedance or cell index refers to the maximum change in cell impedance or cell index for all concentrations of the compound, as derived from the dose-response curve or dose curve. If the actual ligand for the receptor is known, it may be used as a positive control in the assay and the EC50 value of the potential agonists may be compared to the EC50 of the natural ligand. Compounds that do not induce any cell-electrode impedance response (with respect to the response of the control cells) will not be considered as agonists. Compounds that induce a response at the concentration being screened may be further evaluated at different doses to determine their relative EC50 value. Those compounds that illicit an EC50 response which is equal to or less than that of the natural ligand are considered as agonists. Also, compounds that do reach maximum response even at much higher EC50 values may still be considered as potential agonists. Compounds that only induce a partial response (a fraction of the maximum response) may be considered as partial agonists.

Methods of Screening for an Antagonist for a G-Protein Coupled Receptor (GPCR) with a Known Ligand The methods of the present invention may be adapted to screen for an antagonist for a GPCR with a known ligand. In these aspects and embodiments, impedance is measured before and after stimulation of the GPCR. The potential antagonist is added prior to stimulation of the GPCR. More specifically the present invention provides a method for screening for an antagonist, including (a) providing a device capable of measuring cell-substrate impedance, wherein the device comprises at least two wells, further wherein the device is operably connected to an impedance analyzer; (b) adding test cells to each of at least two of the at least two wells, wherein the test cells express a GPCR; (c) adding a compound suspected of being a GPCR antagonist to at least one of the at least two wells to form at least one compound well, adding a vehicle control to at least another well of the at least two wells to form at least one control well; (d) measuring first impedances of the at least one compound well and the at least one control well immediately preceding step (e), and optionally determining first cell indices (cell indexes) from the first impedances; (e) adding a GPCR ligand to the at least one compound well and to the at least one control well; (f) measuring second impedances of the at least one compound well and the at least one control well after step e) and optionally determining second cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the the at least one control well; (h) comparing the change in impedance or cell index between the at least one compound well and the at least one control well; and (i) identifying the compound is an antagonist for the GPCR if the comparison demonstrates a significant difference between the change in impedance or cell index of the at least one compound well and the change in impedance or cell index of the at least one control well.

In one embodiment of the above method, the method further comprise identifying the compound as an antagonist for the GPCR if the change in impedance or cell index of the at least one compound well is significantly smaller than the change in impedance or cell index of the at least one control well. In another word, a compound is identified as an antagonist for the GPCR if the compound inhibits or reduces the impedance response of the cells to the stimulation of an agonist or a GPCR ligand.

In an exemplary embodiment, the method for screening for a potential antagonist of GPCRs with known ligands using cell-substrate impedance technology may include the following steps. (1) Cells expressing the appropriate GPCR will be obtained or engineered to express the appropriate GPCR at adequate levels of expression. (2) The cells will be seeded on ACEA's 16× or 96× microtiter plates (E-Plates) at a predetermined concentration. The attachment and proliferation of the cells will be monitored continuously on the RT-CES system. (3) The cells will be pre-incubated with a pre-determined concentration of potential antagonists or compounds from a library and then stimulated with an appropriate amount of ligand or agonist that will result in optimal response on the RT-CES. As a control, the cells will be pre-incubated with vehicle alone and then stimulated with the appropriate ligand and also the cells will be treated with the compounds, but not stimulated with the ligand or agonist. The cell response will be continuously monitored on the RT-CES. (4) An antagonist may be identified if (a) the cells pre-incubated with vehicle alone and then stimulated with the appropriate ligand give a significant change in impedance or cell index as a result of ligand stimulation; (b) the cells pre-incubated with a potential antagonist and then stimulated with the appropriate ligand gives a significantly smaller change in impedance or cell index as a result of ligand stimulation (i.e., the antagonist reduces or inhibits the ligand-induced cell responses).

Once potential antagonists that block the agonist or ligand response has been identified, the IC50 values of the potential antagonists, which are the molar concentration of the antagonist which results in 50% inhibition of the maximal cell-electrode impedance response (i.e., leading to that the maximal cell electrode impedance response is reduced by 50%), will be determined. The IC50 will be determined by preincubating the cells which express the appropriate receptors with increasing concentration of the potential antagonist and then stimulating the cells with the appropriate ligand or agonist. As a control, the cells will only be incubated with media or vehicle alone. In addition, if there are any known antagonists for the receptor of interest, those may also be included in the assay as a positive control. Those compounds that block the agonist or ligand maximal response in a dose dependent manner and cause the cells to return to baseline will be considered as potential antagonists. A dose response curve may be constructed by plotting the ligand-induced or agonist-induced cell-impedance response for cells pre-incubated with each concentration of the potential antagonist versus concentration of the potential antagonist. Alternatively, the area under the cell-index curve or impedance curve for each concentration of the potential antagonist can also be determined and used in generating a dose-response curve. Here cell-index curve or impedance curve refers to time dependent cell-index (or time dependent impedance) plotted versus time after addition of the compound. The dose response curves may show that the potential antagonist inhibits or reduces the ligand-induced (or agonist-induced) cell-substrate impedance responses in a dose-dependent manner. From such a dose-response curve, IC50 may be derived or calculated. Those who are skilled in the biostatistics or in the analysis of biological data may readily choose appropriate formula or methods to calculate an IC50 from a dose-response curve of an antagonist. For example, experimental dose curve may be fitted into a sigmoid curve and an IC50 may be derived from the curve fitting.

Methods of Identifying a Compound that Affects a G-Protein Coupled Receptor (GPCR) Pathway The methods of the present invention may be adapted to screen or identify a compound that affects a GPCR pathway. For example, the present invention provides a method of identifying a compound that affects a GPCR pathway including: (a) providing a device capable of measuring cell-substrate impedance, wherein the device comprises at least two wells, further wherein the device is operably connected to an impedance analyzer; (b) adding test cells to at least two of the at least two wells, wherein the test cells express a GPCR; (c) adding a compound suspected of being capable of affecting a GPCR pathway to at least one of the at least two wells containing the test cells to form at least one compound well, adding a vehicle control to at least another well of the at least two wells containing the test cells to form at least one control well; (d) measuring first impedances of the at least one compound well and the at least one control well immediately preceding step (e), and optionally determining first cell indices from the first impedances; (e) adding a GPCR activating compound to the at least one compound well and to the at least one control well; (f) measuring second impedances of the at least one compound well and the at least one control well after step (e) and optionally determining second cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the at least one control well; (h) comparing the change in impedance or cell index between the at least one compound well and the at least one control well; and (i) identifying the compound effects the GPCR pathway if the comparison demonstrates a significant difference between the change in impedance or cell index of the at least one compound well and the change in impedance or cell index of the at least one control well.

In one embodiment of the above method, the method further comprise identifying the compound as an inhibitor for the GPCR pathway if the change in impedance or cell index of the at least one compound well is significantly smaller than the change in impedance or cell index of the at least one control well. In another word, a compound is identified as an inhibitor for the GPCR pathway if the compound inhibits or reduces the impedance response of the cells to the stimulation of a GPRC activating compound (for example, an agonist or a GPCR ligand). One may determine a dose-response curve for such a compound that is capable of inhibiting GPCR pathway and determine the IC50 values using the approach similar to that used for deriving IC50 for an antagonist for a G-protein coupled receptor (GPCR) with a known ligand described previously in the present invention.

Methods of Validating Molecular Targets Involved in the GPCR Signaling Pathway Leading from GPCR Activation The intracellular signaling pathway that is stimulated by activation of the GPCR by its cognate ligand leads to activation or inactivation of key enzymes such as kinases, phosphatases and phospholipases amongst others, which may lend themselves as key potential targets for pharmaceutical drug discovery. However, prior to screening for potential inhibitors of these target proteins and enzymes, the target proteins and enzymes must be validated to ascertain that they can interfere with the GPCR-mediated signaling.

This can be achieved either by introducing into cells expressing the appropriate GPCR by transfection, electroporation or viral infection the DNA encoding for the dominant negative versions of these signaling proteins or siRNA that target and reduce the expression of these proteins or introducing known and specific inhibitors of key enzymes or proteins. Once this has been achieved, then the RT-CES system can be used to assess the effect of these key proteins on GPCR-mediated signaling. An example of a suitable assay includes introduce into cells either the DNA for the dominant negative version of the protein, a genetic knockout or siRNA targeting the protein of interest by the various methods into cells which express the appropriate GPCR. The cells may be transferred to ACEA 16× or 96× microtiter plates and the attachment and growth of the cells monitored as previously described. Alternatively, the dominant interfering reagents can also be directly introduced into the cells in ACEA's 16× or 96× microtiter plates. The cells may then be stimulated with appropriate ligand or agonist and the cellular response recorded by RT-CES™ system as previously described in the present invention. If the GPCR-mediated events induced by the ligand or agonist are affected in these cell lines containing either the DNA for the dominant negative version of the protein or siRNA targeting the protein of interest, as determined from the impedance measurements, then it means that interference with the function or expression of the protein or enzyme of interest would prevent the GPCR-mediated event to occur. Such proteins or enzymes will be considered as a potential validated target for drug discovery and can also be confirmed by other cell-based assays.

The present invention also includes methods of validating molecular targets involved in the GPCR signaling pathway leading from GPCR activation including: (a) providing a device capable of measuring cell-substrate impedance, wherein the device comprises two or more wells, further wherein the device is operably connected to an impedance analyzer; (b) adding test cells to at least one well to form a test well and adding confirmation cells to at least another well to form a confirmation well, wherein the test cells express a GPCR and the confirmation cells comprise (1) a dominant negative version of a protein of interest, or (2) an siRNA targeting a protein of interest, (3) a gene knockout of a protein of interest, or (4) a chemical or protein inhibitor of the protein of interest; (c) measuring first impedances of the at least one test well and the at least one confirmation well immediately preceding step (d), and optionally determining first cell indices from the first impedances; (d) adding a GPCR activating compound to the at least one test well and to the at least one confirmation well; (e) measuring second impedances of the at least one test well and the at least one confirmation well after step (d) and optionally determining second cell indices from the second impedances; (f) determining the change in the impedance or cell index for the at least one test well by comparing the second impedance or the second cell index of the at least one test well to the first impedance or the first cell index of the at least one test well, and determining the change in the impedance or cell index of the at least one confirmation well by comparing the second impedance or the second cell index of the at least one confirmation well to the first impedance or the first cell index of the at least one confirmation well; (g) comparing the change in impedance or cell index between the at least one test well and the at least one confirmation well; and (h) validating the protein of interest as a molecular target if the comparison demonstrates a significant difference between the change in impedance or cell index of the at least one test well and the change in impedance or cell index of the at least one confirmation well.

A GPCR pathway may be activated using the appropriate activating compound. In one embodiment the activating compound is the appropriate GPCR ligand or GPCR agonist provided in an appropriate amount.

Methods of Monitoring Dose-Dependent Functional Activation of a GPCR

The present invention also includes method of monitoring dose-dependent functional activation of a GPCR. The provided methods include (a) providing a device capable of measuring cell-substrate impedance; wherein the device comprises at least two wells, further wherein the device is operably connected to an impedance analyzer; (b) adding test cells to the at least two wells, wherein the test cells express a GPCR; (c) measuring first impedances from the at least two wells immediately preceding step (d) and optionally determining first cell indices from the first impedances; (d) adding a compound capable of activating the GPCR to at least two wells in at least at two different concentrations forming compound wells 1 through x, wherein x equals the number of the at least two different concentrations; (e) measuring a series of impedances for each of the compound wells 1 through x after step (d) and optionally determining a series of cell indices from the series of impedances, wherein the series comprise at least three impedance measurements; (f) determining the change in the impedance or cell index for each of the compound wells 1 through x by comparing the series of impedances or the series of cell indices for each of the compound wells 1 through x to the first impedance or the first cell index of each well corresponding to the compound wells 1 through x; and (g) comparing the changes in impedances or in cell indices between the compound wells 1 through x at a given time point.

The provided methods may also include establishing a dose curve. The dose curve may include a display of a series of different concentrations versus a corresponding maximum change in impedance or cell index for each of the provided concentrations, as derived from the time-dependent changes in impedance or cell index after adding the compound at each concentration to the test cells. The EC50 of the compound may be determined from such dose curves. EC50 of a compound is a concentration of the compound capable of inducing 50% of the maximum response in impedance or cell index. The maximum response in impedance or cell index refers to the maximum change in cell impedance or cell index for all concentrations of the compound, as derived from the dose-response curve or dose curve.

Methods of Determining Desensitization of a GPCR

The present invention also provides methods of determining desensitization of a GPCR. The methods may include: (a) providing a device capable of measuring cell-substrate impedance of a test cell expressing a GPCR, wherein the device comprises at least one well, further wherein the device is operably connected to an impedance analyzer; (b) adding test cells to the at least one well, wherein the test cells expresses a GPCR; (c) measuring a first impedance of the at least one well immediately preceding step d) and optionally determining a first cell index; (d) introducing an agonist to the at least one well; (e) measuring a second impedance of the at least one well and optionally determining a second cell index; (f) comparing the second impedance or the second cell index to the first impedance or the first cell index; (g) allowing the cell-substrate impedance to return about to the first impedance; (h) washing the test cells with an appropriate wash solution; (i) introducing an agonist to the at least one well after the washing the test cells; (j) measuring a third impedance of the at least one well and optionally determining a third cell index; (k) comparing the third impedance or the third cell index to the first impedance or the first cell index; (l) comparing the third impedance or the third cell index to the second impedance or the second cell index; and (m) determining the GPCR is fully desensitized if the third impedance or the third cell index does not significantly vary from the first impedance or the first cell index, or determining the GPCR is not desensitized if the third impedance or third cell index does not significantly vary from the second impedance or the second cell index, or determining the GPCR is partially desensitized if the third impedance or third cell index does vary from the first impedance or the first cell index.

In the above method of the present invention for determining desensitization of a GPCR, the method may further include repeating steps (h) through (m) if the GPCR is not fully desensitized.

In one embodiment of the above method of the present invention, if the third impedance or cell index differs from the first impedance or cell index by less than 5%, or 2%, or 1%, then the third impedance or cell index does not significantly vary from the first impedance or cell index and the GPCR is fully desensitized. In another embodiment of the above method of the present invention, if the third impedance or cell index differs from the second impedance or cell index by less than 5%, or 2%, or 1%, then the third impedance or cell index does not significantly vary from the second impedance or cell index and the GPCR is not desensitized. In one embodiment of the above method of the present invention, if the third impedance or cell index differs from the first impedance or cell index by more than 1%, more than 2%, more than 5%, then the third impedance or cell index does vary from the first impedance or cell index and the GPCR is partially desensitized. In still another embodiment, the GPCR is partially desensitized if the third impedance or cell index does vary from the first impedance or cell index, and the difference between the third impedance or cell index and the first impedance or cell index is smaller in magnitude than the difference between the second impedance or cell index and the first impedance or cell index.

D.5. Real-Time Cell Based Assays to Identify a Compound Capable of Interacting with a Receptor Tyrosine Kinase (RTK)

The devices, methods and procedures described above for assaying GPCR activation, for identifying a compound capable of interacting with a GPCR, for screening for an antagonist for a GPCR with a known ligand, for identifying a compound that affects a GPCR pathway, validating molecular targets involved in a GPCR signaling pathway leading from GPCR activation or for monitoring dose-dependent functional activation of a GPCR, and for determining desensitization of a GPCR also apply to the assays for activation of a receptor tyrosine kinase (RTK).

Methods of Identifying a Factor Capable of Interacting with a Receptor Tyrosine Kinase (RTK)

Over 500 different protein kinases have been identified, constituting ~1.7% of the human genome, of this 11% are known to be receptor tyrosine kinases (RTKs) (1). RTK and their growth factor ligands mediate important cellular processes including proliferation, survival, differentiation, metabolism, motility and gene expression. Loss of regulation of RTK expression or activity has been implicated in initiation and progression of cancer, inflammation, diabetes and cardiovascular disease. Their central role in these cellular processes and disease states has made RTK an attractive and important target for the development of inhibitors as therapy for these diseases. Several antibody and small molecule-based inhibitors specific for various RTKs have been approved by the FDA for the treatment of different cancers.

RTKs are membrane receptors that contain an intracellular kinase domain, which transfers a phosphate group from an ATP molecule to the hydroxyl group on tyrosine residues. Upon ligand binding, RTKs dimerize or oligomerize resulting in autophosphorylation and increased activation of its intrinsic kinase activity. This leads to phosphorylation of several downstream effector proteins resulting in activation of multiple signaling pathways. These pathways include the activation of Ras/MAPK, phosphoinositide-3 kinase and PLC pathways. Another pathway activated as a result of growth factor binding to their cognate RTKs is the phosphorylation of effector proteins such as Src, Paxillin and FAK. Activation or phosphorylation of these proteins as a result of RTK activation leads to cytoskeletal changes including membrane ruffling, lamelipodia and filopodia formation (2). These cellular changes as a result of actin remodeling are mediated by the activities of small GTPases Rac, Rho and Cdc42 (3).

ACEA Biosciences has developed a cell sensor array electrodes integrated on the bottom of the wells of microtiter plate (E-PLATE). The sensors are arrayed in a novel design that covers approximately 80% of the wells surface area, allowing for sensitive and quantitative detection of cellular changes. Signals from these sensors are relayed to a real time cell electronic sensing (RT-CES) system that allows for monitoring and analysis of the kinetic aspects of cellular behavior. The signals relayed are impedance changes in the ionic environment created by the application of an electric field. Disruption of this ionic environment on the sensor surface due to the presence of cells or changes in the cells morphology can lead to changes in measured impedance, which is then converted to a cell index value. The extent of the cell-electrode impedance response is dependent on the attachment quality and the sensor area covered by the cell. An increase in measured impedance value due to an increase in cell number or degree of attachment results in an increase in observed cell index. This system has been successfully used in monitoring cell proliferation and cytotoxicity, cell adhesion, and G-protein coupled receptor function.

It is known that growth factor binding to RTK results in immediate morphological changes, as exemplified by membrane ruffling, filopodia and lamellipodia formation. Using this technology we are able to quantitatively detect these cellular changes as a measure of receptor tyrosine kinase activity and function. Characterization of these measured cell response on the RT-CES system show that the response is specific, robust, reproducible and in concurrence with other RTK cell-based assays, such as ELISA.

Therefore, the RT-CES system was used to screen a small diverse library of inhibitors and a collection of kinase inhibitors, enabling the identification of a specific and potent EGFR inhibitor. This assay was also used to further characterize the hit by generating dose response curves. Compared to existing RTK assays, this assay does not suffer from interference from assay components, nor require expensive reagents, such as purified antibody or peptides. Furthermore, this assay platform provides high content information regarding the signaling pathways being activated. Since the readout is non-invasive and carried out on live cells, multiple treatments can be carried out in the same well with the same cells and can also be used in conjunction with existing endpoint assays such as ELISA. The ACEA RT-CES system therefore offers an alternative to or complements existing RTK assays, and can be used for both primary and secondary screens.

Stimulation of receptor tyrosine kinases such as EGF receptor, PDGF receptor, fibroblast growth factor (FGF) receptor, vascular endothelial growth factor (VEGF) receptor and c-Met receptor for hepatocyte growth factor with their cognate ligand leads to dramatic remodeling of the actin cytoskeleton. These receptor tyrosine kinases have also been linked to the progression of different kinds of cancers. Because the RT-CES system can detect transient changes in morphology and adhesive capacity of the cells, it can be used to monitor growth factor-induced remodeling of actin cytoskeleton in adherent mammalian cells through their associated receptor tyrosine kinase. The RT-CES assay provides a convenient label-free, real-time and quantitative method for functional activation of the receptor tyrosine kinases.

The steps involved in using the RT-CES system for measurement of cytoskeletal changes associated with receptor tyrosine kinase may include: seeding adherent mammalian cells which are endogenously expressing the appropriate receptor protein tyrosine kinase in the wells of ACEA e-plate, alternatively, the receptor of interest can be transiently or stably expressed in an appropriate cell line and then seeded in ACEA e-plate, monitor the growth and proliferation of the cells using the RT-CES system for approximately 16 hours, removing the media from the wells and wash the cells once with phosphate buffered solution (PBS), replacing with media devoid of serum and allow the cells to continue growth for an additional 8-20 hours, stimulating the cells with the appropriate growth factor ligand for the receptor protein tyrosine kinase of interest. Monitor the morphological changes due to actin cytoskeleton remodeling every five minutes using the RT-CES system for a total of 5-6 hours.

In one aspect, the method of the present invention is to devise a cell-based assay method for assaying receptor protein tyrosine kinase activity and also for screening for inhibitors of the receptor protein tyrosine kinase. The method is based on quantification in real time of cytoskeletal changes and/or morphological change and/or cell adhesion change that arise as a response to growth factor stimulation of its associated receptor on the surface of cells growing in the E-Plates. Because the electronic assay readout relies on cytoskeletal dynamics and/or cell morphology and/or cell adhesion property which are intrinsic cell responses to stimulation of receptor protein tyrosine kinase it precludes the need for establishing reporter cell lines or using any other reagent. Furthermore, since the assay is performed in real time, the entire kinetics receptor protein tyrosine kinase activation and its effect on the cell can be assessed.

The present invention also includes additional methods of identifying a factor capable of interacting with a receptor tyrosine kinase (RTK). These methods may include: (a) providing a device capable of measuring cell-substrate impedance; wherein the device comprises at least two wells, further wherein the device is operably connected to an impedance analyzer; (b) adding test cells to at least two wells, wherein the test cells express a RTK either endogenously or as a recombinant protein; (c) measuring first impedances of the at least two wells immediately preceding step (d) and optionally determining first cell indices from the first impedances; (d) adding a compound suspected of being a factor capable of interacting with a RTK to at least one well containing the test cells to form at least one compound well and adding a vehicle control to at least another well containing test cells to form at least one control well; (e) measuring second impedances of the at least one compound well and of the at least one control well after step (d) and optionally determining second cell indices from the second impedance; (f) determining the change in the impedance or cell index for the at least one compound well by comparing the second impedance or the second cell index of the at least one compound well to the first impedance or the first cell index of the at least one compound well, and determining the change in the impedance or cell index for the at least one control well by comparing the second impedance or the second cell index of the at least one control well to the first impedance or the first cell index of the at least one control well; (g) comparing the changes in impedances or in cell indices between the at least one compound well and the at least one control well; and (h) identifying the compound is a factor that interacts with the RTK if the comparison demonstrates a significant difference between the change in impedance or cell index for the at least one compound well and the change in impedance or cell index for the at least one control well.

In a preferred embodiment of the above method for identifying a factor capable of interacting with a receptor tyrosine kinase (RTK), the test cells are in a serum free medium.

In one example of the above method, a compound may be identified as a factor capable of interacting with a receptor tyrosine kinase if a significant change is observed between the change in impedance or cell index of a compound well in comparison to the change in impedance or cell index of a control well. Here both compound well and control well have the same test cells expressing a RTK. The compound is added to the compound well whilst a vehicle control is added to the control well. For the compound well, the change in impedance or cell index refer to the change occurred after adding the compound. For the control well, the change in impedance or cell index refer to the change occurred after adding the vehicle control. As a nonlimiting example, a compound may be identified as a factor capable of interacting with a RTK if the comparison indicates a significant change including an increase or a decrease in impedance or cell index of the compound well after the compound is added to the test cells that express the RTK, relative to the control well.

Another method of identifying a factor capable of interaction with a receptor tyrosine kinase (RTK) includes: (a) providing a device capable of measuring cell-substrate impedance; wherein the device comprises at least two wells, further wherein the device is operably connected to an impedance analyzer; (b) adding test cells to at least one well to form at least one test well, wherein the test cells express a RTK, and adding control cells to at least another well to form at least one control well, wherein the control cells do not express the RTK or express the RTK at a significantly lesser level that the test cells; (c) measuring first impedances from the at least one test well and from the at least one control well immediately preceding step d) and optionally determining first cell indices from the first impedances; (d) adding a compound to the at least one test well and to the at least one control well; (f) measuring second impedances from the at least one test well and from the at least one control well after step d) and optionally determining second cell indices from the second impedances; (g) determining the change in the impedance or cell index for the at least one test well by comparing the second impedance or the second cell index of the at least one test well to the first impedance or the first cell index of the at least one test well, and determining the change in the impedance or cell index for the at least one control well by comparing the second impedance or the second cell index of the at least one control well to the first impedance or the first cell index of the at least one control well; (h) comparing the changes in impedance or in cell index between the at least one test well and the at least one control well; and (i) identifying the compound interacts with the RTK if the comparison demonstrates a significant difference between the change in impedance or cell index for the at least one test well and the change in impedance or cell index for the at least one control well.

In one example of the above method, a compound may be identified as a factor capable of interacting with a receptor tyrosine kinase if a significant change is observed between the change in impedance or cell index of a test well in comparison to the change in impedance or cell index of a control well. Here test well has the test cells expressing a RTK and control well has control cells not expressing the RTK or expressing RTK at a significantly low level. The compound is added to both the test well and the control well. For the test well, the change in impedance or cell index refer to the change occurred after adding the compound to the test cells. For the control well, the change in impedance or cell index refer to the change occurred after adding the compound to the control cells. As a nonlimiting example, a compound may be identified as a factor capable of interacting with a RTK if the comparison indicates a significant change including an increase or a decrease in impedance or cell index of the test well after the compound is added to the test cells that express the RTK, as relative to the control well.

The devices, methods and procedures described previously in Section D.4 for identifying a compound capable of interacting with a GPCR, including but not limited to, Devices for measuring cell-Substrate Impedance, Compound added to test wells, Measuring or monitoring impedance (cell-substrate impedance), Deriving cell index, Determining changes in impedance or cell index, Comparing changes in impedance or cell index and Identifying compounds of interest, may be applied here to the methods of identifying a factor capable of interacting with a receptor tyrosine kinase (RTK).

Method of for an Inhibitor for a Receptor Tyrosine Kinase (RTK) in Response to Activation of RTK with a Stimulating Factor The present invention also provides a method of screening for an inhibitor of a receptor tyrosine kinase (RTK) with a known RTK stimulating factor. Examples of potential inhibitor are but not limited to a compound, a protein, and antibody and the like. The method for screening for an inhibitor for a RTK includes: (a) providing a device capable of measuring cell-substrate impedance, wherein the device comprises at least two wells, further wherein the device is operably connected to an impedance analyzer; (b) adding test cells to each of at least two of the at least two wells, wherein the test cells expresses a RTK; (c) adding a compound suspected of being a RTK inhibitor to at least one of the at least two wells containing test cells to form at least one compound well, adding a vehicle control to at least another well of the at least two wells containing test cells to form at least one control well; (d) measuring first impedances of the at least one compound well and the at least one control well immediately preceding step e), and optionally determining first cell indices from the first impedances; (f) adding a RTK stimulating factor to the compound well and the control well; (g) measuring second impedances of the at least one compound well and the at least one control well after step e) and optionally determining third cell indices from the second impedances; (h) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the at least one control well; (i) comparing the change in impedance or cell index between the at least one compound well and the at least one control well; and (j) identifying the compound is an inhibitor for the RTK if the comparison demonstrates a significant difference between the change in impedance or cell index for the at least one compound well and the change in impedance or cell index for the at least one control well.

The devices, methods and procedures described previously in Section D.4 for identifying a compound capable of interacting with a GPCR, including but not limited to, Devices for measuring cell-Substrate Impedance, Compound added to test wells, Measuring or monitoring impedance (cell-substrate impedance), Deriving cell index, Determining changes in impedance or cell index, Comparing changes in impedance or cell index, Identifying compounds of interest and Methods of screening for an antagonist for a G-protein coupled receptor (GPCR) with a known ligand may be applied here to the method of screening for an inhibitor for a receptor tyrosine kinase (RTK) with a known RTK stimulating factor.

Thus, as provided above, the present invention provides an effective method of screening for inhibitors of receptor protein tyrosine kinases. One way to assess the effect of the inhibitor and to determine the changes in impedance or cell index for an inhibitor well (i.e., a compound well) is to assess and analyze the peak amplitude and duration of the cell-electrode impedance response. Alternatively, the area under the cell-index curve or impedance curve of the test well and the control well can also be determined as a measure of the inhibitor potency. The cell-electrode impedance response here refers to the time dependent cell-electrode impedance (or cell index) variation after the addition of RTK stimulating factor to the cells. Increasing concentrations of a RTK-inhibitor should lead to a dose-dependent decrease in the amplitude of the response or the area under the cell-index curve or impedance curve for each compound concentration, indicating that the receptor is inhibited in a specific manner. Some inhibitors may affect not only the peak amplitude of the response, but also the duration of the response as well. The duration is defined as the time it takes from the time point of the stimulation with the RTK-stimulating factor to the time point when the cell-electrode impedance or cell index returns to the cell-electrode impedance or cell index prior to the addition of RTK-stimulating factor. If certain inhibitors do affect the duration of the cell-electrode impedance response, then perhaps in addition to inhibiting the receptor tyrosine kinase of interest, there are other inhibitory mechanisms which need to be evaluated using biochemical methods.

Method of Screening for a Compound that Affects a Receptor Tyrosine Kinase (RTK) Pathway The present invention also provides a method of identifying a compound that affects a receptor tyrosine kinase (RTK) pathway. The method includes (a) providing a device capable of measuring cell-substrate impedance, wherein the device comprises at least two wells, further wherein the device is operably connected to an impedance analyzer; (b) adding test cells to at least two of the at least two wells, wherein the test cells expresses a RTK; (c) adding a compound suspected of being capable of effecting a RTK pathway to at least one of the at least two wells to form at least one compound well, adding a vehicle control to at least another well of the at least two wells to form at least one control well; (d) measuring first impedances of the at least one compound well and the at least one control well immediately preceding step (e), and optionally determining first cell indices from the first impedances; (e) adding a RTK stimulating factor to the at least one compound well and to the at least one control well; (f) measuring second impedances of the at least one compound well and the at least one control well after the adding the RTK stimulating factor and optionally determining second cell indices from the second impedances; (g) determining the change in the impedance or cell index for the at least one compound well by comparing the second impedance or the second cell index of the at least one compound well to the first impedance or the first cell index of the at least one compound well, and determining the change in the impedance or cell index of the at least one control well by comparing the second impedance or the second cell index of the at least one control well to the first impedance or the first cell index of the the at least one control well; (h) comparing the change in impedance or cell index between the at least one compound well and the at least one control well; (i) identifying the compound effects the RTK pathway if the comparison demonstrates a significant difference between the change in impedance or cell index for the at least one compound well and the change in impedance or cell index for the at least one control well.

The methods of the present invention include activating or stimulating the RTK. Any method of activating or stimulating the RTK may be used. In some embodiments, the RTK is activated by adding a growth factor capable of activating the RTK. Examples of suitable growth factors may include epidermal growth factor (EGF), platelet derived growth factor (PDGF), a nerve growth factor (NGF), and an antibody capable of activating RTK.

In one embodiment of the above method, the method further comprise identifying the compound as an inhibitor for the RTK pathway if the change in impedance or cell index of the at least one compound well is significantly smaller than the change in impedance or cell index of the at least one control well. In another word, a compound is identified as an inhibitor for the RTK pathway if the compound inhibits or reduces the impedance response of the cells to the stimulation of a RTK activating compound. One may determine a dose-response curve for such a compound that is capable of inhibiting RTK pathway and determine the IC50 values using the approach similar to that used for deriving IC50 for an antagonist for a G-protein coupled receptor (GPCR) with a known ligand described previously in the present invention.

Method of Validating a Molecular Target Involved in the Receptor Tyrosine Kinase (RTK) Signaling Pathway The intracellular signaling pathway that is stimulated by engagement of the receptor tyrosine kinases by their cognate ligand leads not only to the activation of the receptor but also activation of key enzymes such as kinases, phosphatases and phospholipases amongst others which lend themselves as key potential targets for pharmaceutical drug discovery. However, prior to screening for potential inhibitors of these target proteins and enzymes, the target proteins and enzymes must be validated to ascertain that they can interfere with receptor tyrosine kinase-mediated signaling. This can be achieved either by introducing into cells by transfection, electroporation or viral infection the DNA encoding for the dominant negative versions of these proteins, genetic knockouts or siRNA that target and reduce the expression of these proteins. Also, specific chemical and protein inhibitors of the target proteins or enzymes may also be introduced to the cells to assess target validation. Once this has been achieved, then the cell-electrode impedance measurement method can be used to assess the effect of these key proteins on receptor-mediated signaling.

As an example an assay may be performed using the following procedure: introducing into cells either the DNA for the dominant negative version of the protein, a genetic knockout or siRNA targeting the protein of interest by various methods known to those skilled in the biological arts, transferring the cells to the wells of ACEA E-Plates, and assessing the effect of interfering agents in one or two ways. First, the cells may be stimulated with growth factors (RTK activation factors, or RTK stimulating factors) and the cellular response monitored by the RT-CES system. If the target protein does participate in the receptor-mediated signaling pathway, then its abrogation by the methods described above is expected to either reduce or completely block growth factor mediated cytoskeletal changes (and/or morphological changes), which can be measured and monitored by cell-electrode impedance sensing. The target is then a good candidate for participation in the receptor-mediated signaling pathway. Alternatively, the effect of interfering with the target protein can be examined in the context where the receptor tyrosine kinase participates in the growth and proliferation of the cells. If inhibition or down regulation of the target protein interferes with growth and proliferation of the cells, then it is a candidate for participating in the signaling pathway initiated by activation of the receptor tyrosine kinase.

The present invention also includes a method of validating a molecular target involved in the receptor tyrosine kinase (RTK) pathway leading from RTK activation. The methods may include: (a) providing a device capable of measuring cell-substrate impedance, wherein the device comprises at least two wells, further wherein the device is operably connected to an impedance analyzer; (b) adding test cells to at least one well to form a test well and adding control cells to at least another well to form a control well, wherein the control cells express a RTK and the test cells comprise: (i) a dominant negative version of protein of interest, (ii) an siRNA targeting a protein of interest, (iii) a gene knockout of a protein of interest or or (iv) a chemical or protein inhibitor specific for the protein of interest; (c) measuring first impedances of the at least one test well and the at least one control well immediately preceding step (d), and optionally determining first cell indices from the first impedances; (d) adding a compound to the at least one test well and to the at least one control well; (e) measuring second impedances of the at least one test well and the at least one control well after step (d) and optionally determining second cell indices from the second impedances; (f) determining the change in the impedance or cell index for the at least one test well by comparing the second impedance or the second cell index of the at least one test well to the first impedance or the first cell index of the at least one test well, and determining the change in the impedance or cell index of the at least one control well by comparing the second impedance or the second cell index of the at least one control well to the first impedance or the first cell index of the the at least one control well; (g) comparing the change in impedance or cell index between the at least one test well and the at least one control well; and (h) validating the protein of interest as a molecular target if the comparison demonstrates a significant difference between the change in impedance or cell index of the at least one test well and the change in impedance or cell index of the at least one control well.

Method of Monitoring Dose-Dependent Functional Activation of a Receptor Tyrosine Kinase (RTK)

The present invention also includes a method of monitoring dose-dependent functional activation of a receptor tyrosine kinase (RTK). The methods may include: (a) providing a device capable of measuring cell-substrate impedance; wherein said device comprises at least two wells, further wherein said device is operably connected to an impedance analyzer; (b) adding test cells to said at least two wells, wherein said test cells express a RTK; (c) measuring first impedances from said at least two wells immediately preceding step (d) and optionally determining first cell indices from said first impedances; (d) adding a compound capable of activating said RTK to at least two wells in at least at two different concentrations forming compound wells 1 through x, wherein x equals the number of said at least two different concentrations; (e) measuring a series of impedances for each of said compound wells 1 through x after step (d) and optionally determining a series of cell indices from said series of impedances, wherein said series comprise at least three impedance measurements; (f) determining the change in the impedance or cell index for each of said compound wells 1 through x by comparing said series of impedances or said series of cell indices for each of said compound wells 1 through x to said first impedance or said first cell index of each well corresponding to compound wells 1 through x; and (g) comparing said changes in impedances or in cell indices between said compound wells 1 through x at a given time point.

The provided methods may also include establishing a dose curve. The dose curve may include a display of a series of different concentrations versus a corresponding maximum change in impedance or cell index for each of the provided concentrations, as derived from the time-dependent variation of impedance or cell index after adding the compound at each concentration to the test cells. The provided methods may also include determining an EC50 of the compound from such dose curve, where EC50 is the molar concentration of a compound capable of inducing 50% of a maximum response in impedance or cell index for all concentrations of the compound. The maximum response in impedance or cell index refers to the maximum change in cell impedance or cell index for all concentrations of the compound, as derived from the dose-response curve or dose curve.

Method of Identifying a Compound Capable of Affecting Receptor Tyrosine Kinase (RTK) Cancer Cell Proliferation In addition to morphological changes, stimulation of receptor tyrosine kinases via their cognate ligand can induce cell growth and proliferation. It has been shown that stimulation of cells via growth factors such as EGF can induce signaling pathways which induces the entry of the cells into the cell cycle and proliferation. Therefore, cellular proliferation is another method to assess the functional role of growth factor receptor tyrosine kinases. The RT-CES system can be readily used to monitor cellular proliferation, especially those of breast and lung cancer, where receptor tyrosine kinases have been shown to play an important role.

The following steps need to be followed to monitor the proliferation of cancer cells using the RT-CES system: (1) Seed cancer cells at an appropriate density in ACEA E-Plates; (2) Monitor the growth and proliferation of the cells using the RT-CES system until the cells reach the log growth phase; (3) Add specific inhibitors of the receptor tyrosine kinase of interest (compound, antibody or protein) and monitor its effect on cell growth and proliferation for 24 to 48 hours; (4) Alternatively, at 24 hours after seeding the cells, remove the serum from the media and only include the cognate growth factor for the receptor of interest to determine its relevant contribution to cell growth and proliferation. If the growth factor alone (without serum) can support cell growth, then specific inhibitor of the receptor tyrosine kinase of interest can be added and its effect on cell proliferation can be monitored using the RT-CES system.

Thus, in one aspect of the present invention, a method is provided for identifying a compound capable of affecting cancer cell proliferation. The disclosed methods have particular use when the cancer cell proliferation involves a receptor tyrosine kinase (RTK). The methods measure impedance over a longer period of time than methods that monitor cell morphology. Whereas, changes in morphology cause short term increases or decreases in impedance, methods to monitor cancer cell proliferation typically require greater time to identify effective compounds. Thus, immediate spikes in impedance may be due to morphological changes and longer term impedance increases may monitor cellular proliferation.

A method for identifying a compound capable of affecting cancer cell proliferation by inhibiting activity of a receptor tyrosine kinase is provided in the present invention. The method may include: (a) providing a device capable of measuring cell-substrate impedance, wherein the device comprises at least two wells, further wherein the device is operably connected to an impedance analyzer; (b) adding cancer cells expressing a receptor tyrosine kinase (RTK) to at least two of the at least two wells; (c) measuring first impedances of the at least two wells before step (d) and optionally determining first cell indices; (d) introducing a compound suspected of being an RTK inhibitor to the at least one well to form at least one compound well and adding a vehicle control to at least another well to form a control well; (e) measuring a series of second impedances of the compound well and the control well after step (d) and optionally determining second cell indices; (f) determining the change in the impedance or cell index for the at least one compound well by comparing the series of second impedances or the second cell indices of the at least one compound well to the first impedance or the first cell index of the at least one compound well, and determining the change in the impedance or cell index of the at least one control well by comparing the series of second impedances or the second cell indices of the at least one control well to the first impedance or the first cell index of the at least one control well; (g) comparing the change in impedance or cell index between the at least one compound well and the at least one control well; and (h) identifying the compound is capable of affecting cancer cell proliferation if the comparison demonstrates the change in impedance or cell index of the at least one control well is greater than the change in impedance or cell index at least one compound well.

For the above method, the cells in the control well are expected to grow and proliferate. Thus, the change in impedance or cell index for the control well after adding the vehicle control is expected with the increasing the impedance (resistance) or cell index with time for the control well. If the compound inhibits the activity of the receptor tyrosine kinase of interest, then it may inhibit or partially inhibit the cell proliferation. Thus, the increase in impedance or cell index for the compound well with time may be slower than that for the control well, and the change in impedance or cell index for the compound well is expected to smaller than that for the control well.

In a preferred embodiment of the above method, the second impedances are measured during a period occurring after an initial spike in impedance. In another preferred embodiment of the above method, the method include adding a RTK stimulating factor after step (d) and before step (e), wherein the cancer cells are in serum-free medium in the at least compound well and in the at least one control well.

EXAMPLES

Figure 16A:
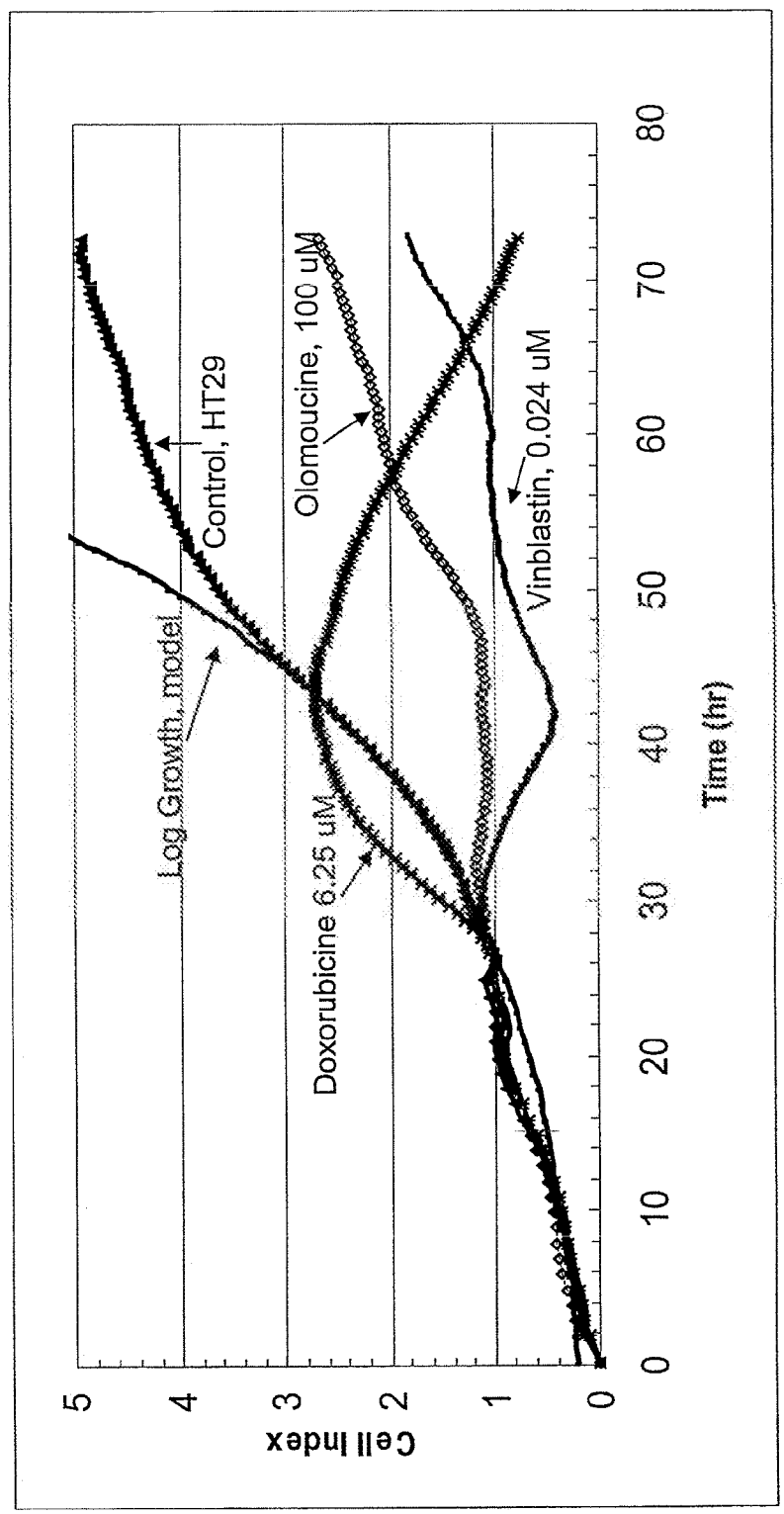
FIG. 16A shows the cell index curves of HT29 cells before and after treatment with various compounds. Also shown is a theoretical exponential increase of cell index with time (labeled as "Log-growth, model") and cells treated with DMSO vehicle control (labeled as "Control, HT29").
Figure 16B:
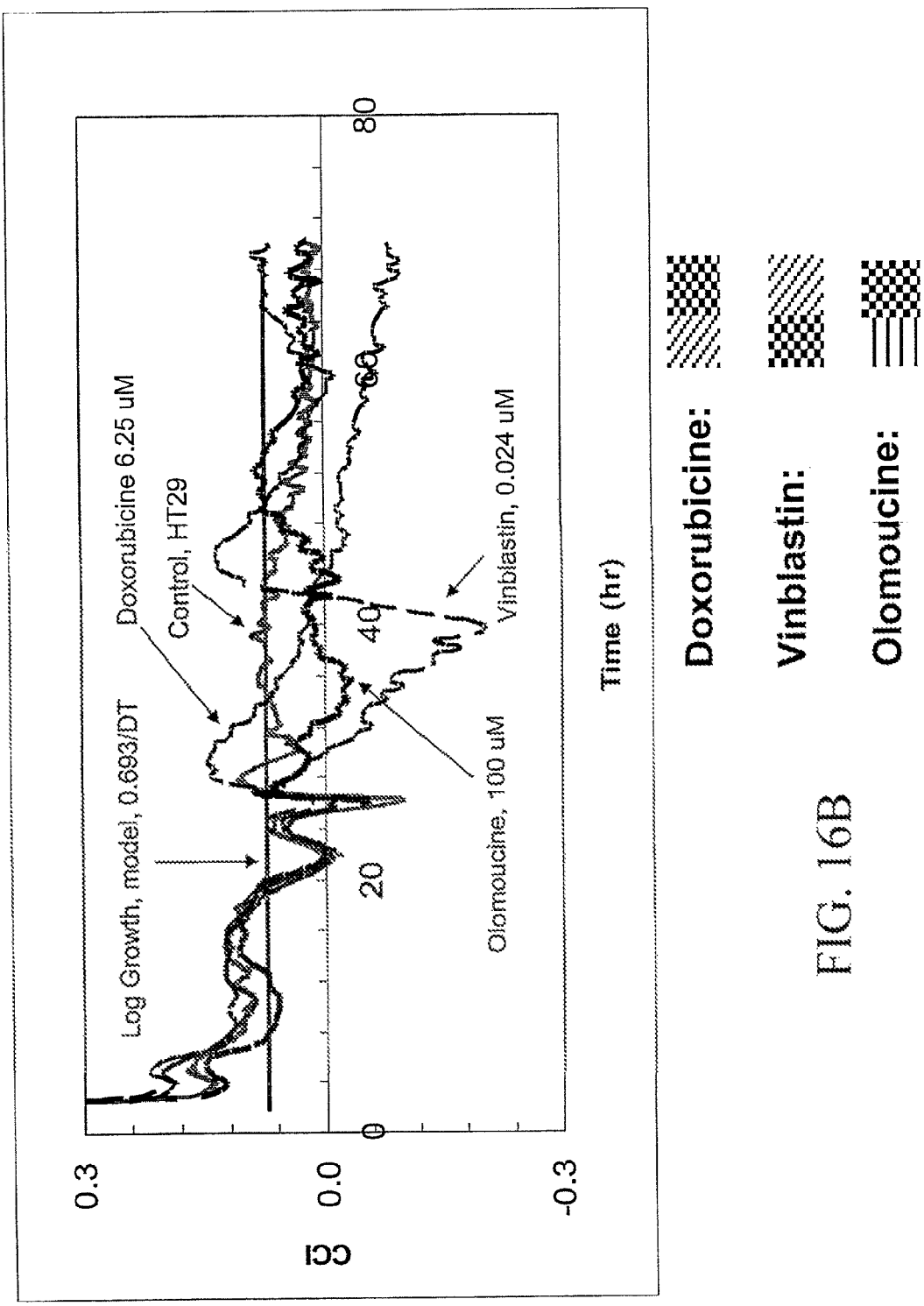
FIG. 16B shows the derived cell change index (CCI) from the cell index curves shown in FIG. 16A. Also shown is the "black-white shading codes" used for different responses based on the convention shown in FIG. 16C.
Figure 16C:
FIG. 16C shows the color-coding scheme used for representing the CCI curves. If the DT is the doubling time for the cells undergoing exponential growth in the cell culture media used, then CCI having different values relative to 0.7/DT indicates the different cell change status. If CCI>>0.7/DT, cell index increases faster than that expected for an exponential growth (or log growth) of the cells (such region n the CCI curve is represented a ▦ Rectangle). If CCI is about 0.7/DT, cell index increases in the same rate as that expected for an exponential growth of the cells (such region in the CCI curve is represented as ▦ Rectangle). If CCI is more than zero but somewhat smaller than 0.7/DT, then cell index increases in the rate slowed than that expected for an exponential growth (such region of the CCI curve is represented as ▦ Rectangle). If CCI is about zero, then cell index shows a near constant value (such region of the CCI curve is represented as ≡ Rectangle). If CCI is negative, then the cell index is decreasing with time, showing the cells losing attachment to the electrode surface or changing their morphology (such region of the curve is shown as ▦ Rectangle). If CCI is very negative, then the cell index decreases rapidly with time, showing that either cells lose attachment to the electrode surfaces quickly or cells change their morphology very quickly (such region of the CCI curve is represented as ▥ Rectangle). The transient, quick noise in the CCI values are removed so that the whole CCI curve is represented after compound addition by one, two or three black/white-shaded rectangles.
Figure 16C:
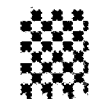
Figure 16C:
Figure 16C:
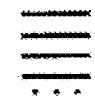
Figure 16C:
Figure 16C:
Figure 17:
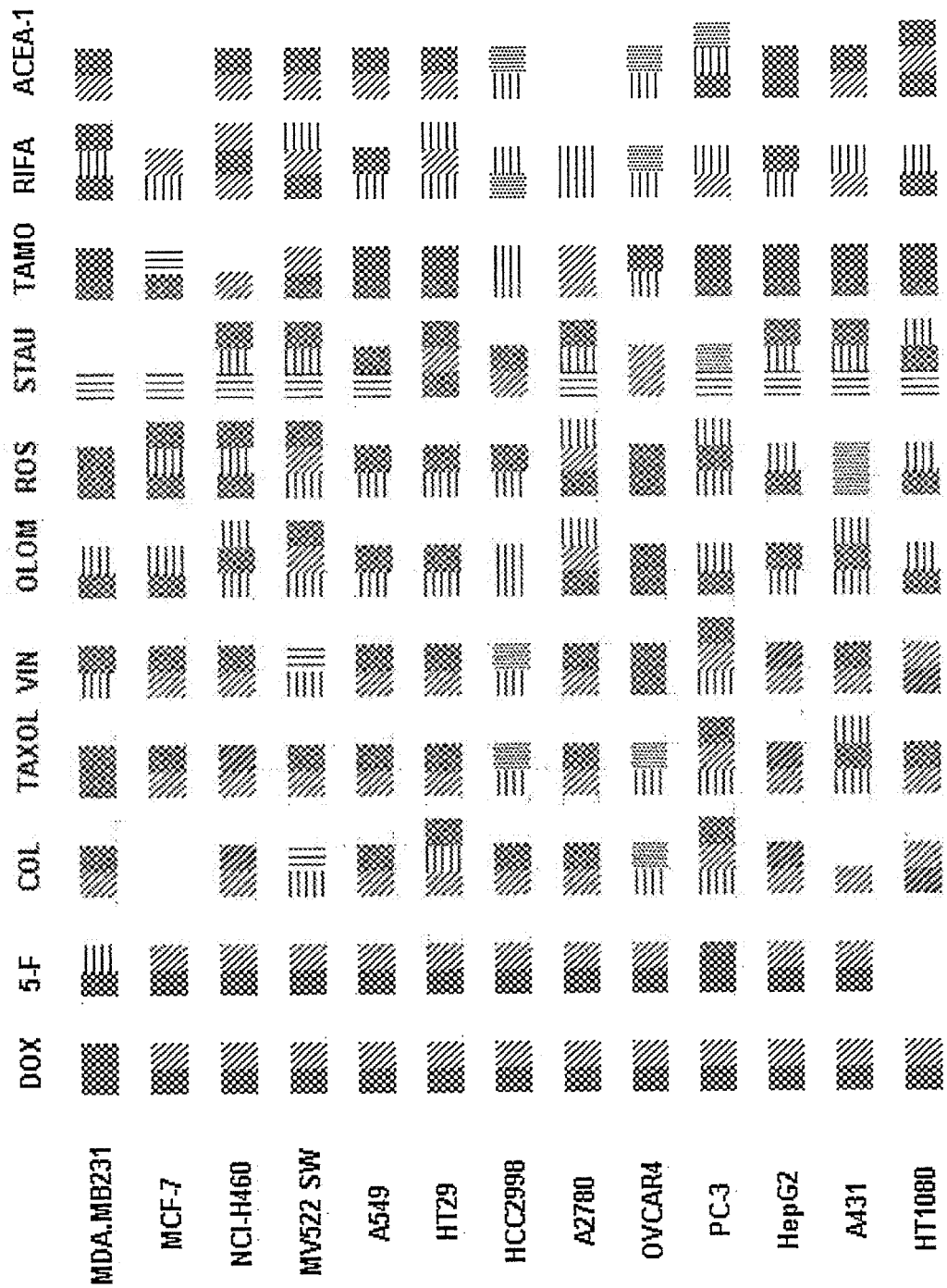
FIG. 17 shows the cell response profile of each cell line tested against the indicated chemotherapeutic agents. For each cell line and compound, the time-dependent cell change index (CCI) was calculated from their corresponding RT-CES responses at an IC50 concentration. (IC 50 is time dependent so that the IC50 concentration at 30 h, or the concentration closest to that, after drug addition is used). The specific CCI curves as related to specific cellular responses were coded according to the convention described in FIG. 16C and displayed in groups of compounds with similar mechanism of action. DOX: doxorubicin; 5-F: 5-Fluorouracil; COL: Colcemid; TAXOL: paclitaxel; VIN: vinblastin; OLOM: Olomoucine; ROS: Roscovitine; STAU: Staurosporine; TAMO: Tamoxifan; RIFA: Rifampicin; ACEA-1: an ACEA test compound.

Example 1. Profiling of Dynamic Cell Responses to Anti-Cancer Drugs Using ACEA RT-CES System In this study, we used the RT-CES system to dynamically monitor cancer cell responses to chemotherapeutic compounds with characterized mechanisms, and to profile the specific cell response patterns. Thirteen cancer cell lines including cancers of breast, prostate, lung, colon, ovary, kidney, fibroblast, and central nervous system were tested (Table 1). Each cancer cell type was treated with 11 chemotherapeutic compounds, classified as DNA damaging agents, protein kinase inhibitors, anti-mitotic drugs, cell cycle specific inhibitors, protein synthesis inhibitors plus a compound of unknown category (Table 2). Dynamic and dose dependent cell-compound interaction patterns were characterized and summarized for all the tested cell lines and compounds. The profiles for three drugs, doxorubicin, olomoucine and paclitaxel against a panel of 12 different cell lines are presented in FIGS. 9A-B, 10A-B and 11A-B. respectively. In addition, we characterized the biological effect of these compounds on cells by monitoring cell cycle progression, cell viability and morphological status of the cells in an attempt to correlate specific cellular response to the shape of the cell index trace (FIGS. 12A-B, 13A-B and 14A-B). Furthermore we calculated the time-dependent IC-50 values for each compound against the various cell lines (FIG. 15A-D) and developed an algorithm to calculate Cell Change Index to profile the dynamic cell response of the different chemotherapeutic agents across the different cell lines. Cell Change Index was calculated for the dynamic RT-CES responses of different cell lines to different chemotherapeutic agents using the definitions described above. Based on the time-dependent values of CCI, each CCI value region across the time scale is represented by black-white shading-based coding. For example, if after compound addition, the CCI value (for a particular cell line under a specific compound treatment at the concentration of IC50 value) is nearly zero for certain period of time and then becomes positive, attaining a value about 0.7/DT (DT is doubling). Then the cell response to this compound is represented as a ▤ rectangle followed by a ▩ rectangle. Examples of such analysis is shown in FIG. 16B-C. The overall black-white shading-based coding map representing the cell dynamic responses to various compounds is shown in FIG. 17.

In summary of this study, we note that using the RT-CES system to screen chemotherapeutic agents results in unique activity patterns that is dependent on the compound itself, the concentration, length of incubation and the cell type. The "signature" patterns of each drug correlates with specific biological phenomenon such as log growth, cell cycle rest, morphology change and cell death. Cell Change Index was a good parameter derived from RT-CES data to mathematically describe cell changes. Cell response profiling based on CCI value indicates that drugs with similar mechanism of action displays similar patterns. Thus, the similarity in the dynamic cell-compound interaction patterns may indicate similarity in mechanism of action, mode of resistance and possibly molecular targets. The RT-CES system can be readily adapted to high throughput dynamic screening and analysis of anti-cancer compounds and the information-intensive approach presented in this study can be applied to profile existing cancer chemotherapeutic agents, screen new compounds and provide insight into the mechanism of action of anti-cancer agents.

TABLE I

List of cancer cell lines tested against a number of chemical compounds.

| Cancer Cell Line | Organ or Tissue Origin |
| --- | --- |
| MDA.MB231 | Breast Cancer |
| MCF7 | Breast Cancer |
| NCI-H460 | Non-Small Cell Lung Cancer |
| MV522 SW | Non-Small Cell Lung Cancer |
| A549 | Non-Small Cell Lung Cancer |
| HT29 | Colon cancer |
| HCC2998 | Colon cancer |
| A2780 | Ovarian Cancer |
| OVCAR4 | Ovarian Cancer |
| PC-3 | Prostate Cancer |
| HepG2 | Human Hepatosarcoma |
| A431 | Epidermoid Cancer |
| HT1080 | Fibrosarcoma |

TABLE II

List of chemical compounds used in the study of profiling cell dynamic responses to a number of anti-cancer compounds.

| Machanisms of Compound Action Effect on DNA replication or Topology | Chemical Compounds | concentration From High to Low (dilution factor: 2) |
| --- | --- | --- |
| Mitotic Poisons | Doxorubincin | 6.25 uM-0.098 uM |
| | 5-Fluorouracil | 50 uM-0.78 uM |
| | Colcemid | 3.125 uM-0.049 uM |
| | Paclitaxol | 0.0125 uM-0.00019 uM |
| | Vinblastin | 1.56 uM-0.024 uM |
| Cell Cycle Arrest | Olomoucine | 100 uM-1.56 uM |
| | Roscovitine | 50 uM-0.78 uM |
| Kinase Inhibitors | Staurosporine | 5 uM-0.078 uM |
| | Tamoxifan | 50 uM-0.78 uM |
| Protein synthesis Inhibitor | Rifampicin | 100 uM-1.56 uM |
| Unknown type | ACEA-1 | |

Example 2. Cytotoxicity Profiling

Methods

Cells.

All the cells used in this study were obtained from ATCC and maintained at 37° C. incubator with 5% $CO_2$ saturation. H460, HepG2 and HT1080 cells were maintained in RPMI media containing 5% FBS and 1% penicillin and streptomycin. NIH3T3 cells were maintained in DMEM media containing 10% FBS and 1% penicillin and streptomycin.

Cell Proliferation Assays.

For each of the cell type, the indicated number of cells was seeded per well in 96× microtiter plates (e-Plate™) with incorporated electrode structures in individual wells device in 100 μL of media. The attachment, spreading and proliferation of the cells were continuously monitored every 30 minutes using the RT-CES™ system (a cell-substrate impedance monitoring system. Cell proliferation was monitored for a period of 48-72 hours depending on the experiment. The electronic readout, cell-sensor impedance is displayed as a parameter called Cell Index.

Drug Treatment and Cytotoxicity Assessment.

Figure 18:
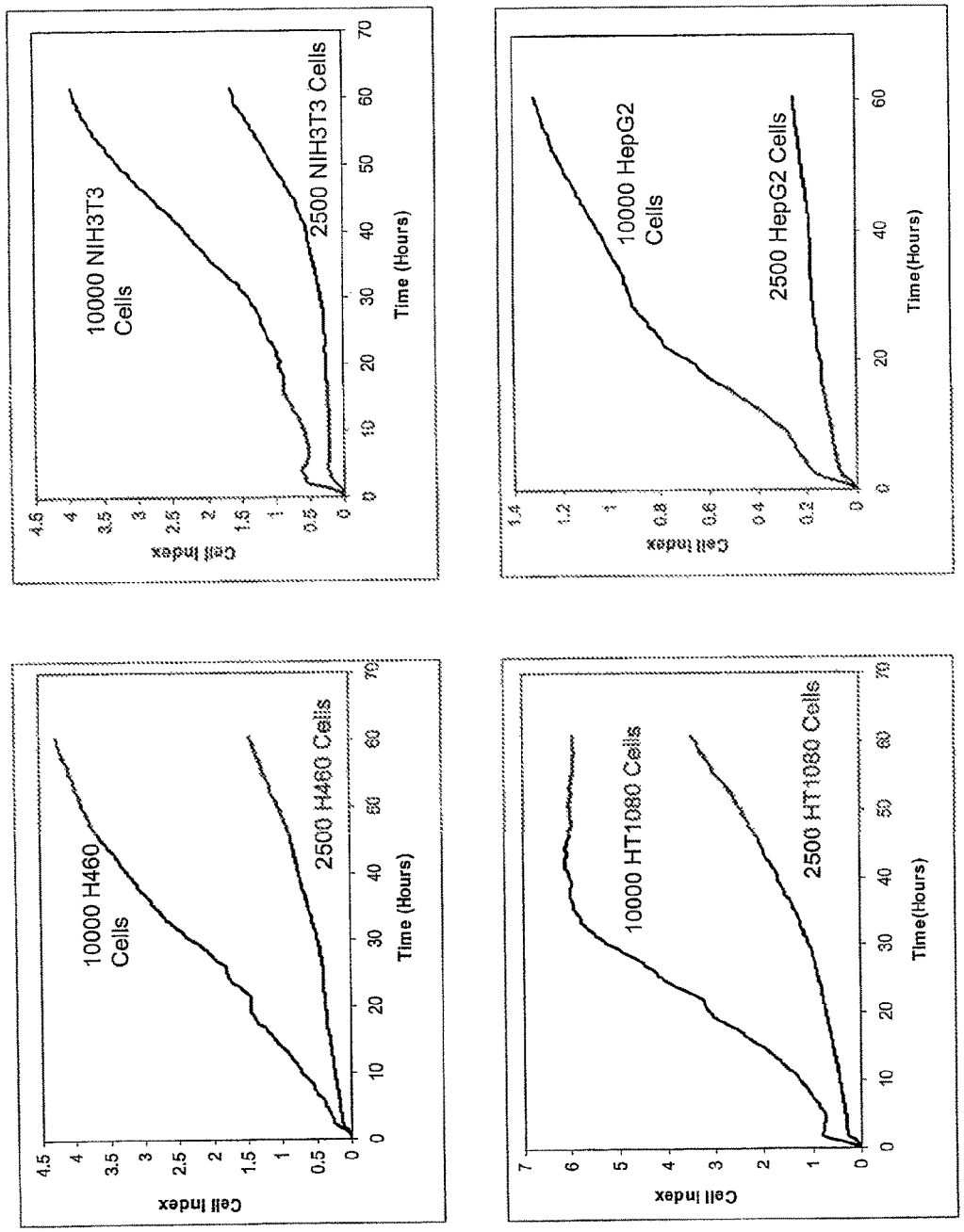
FIG. 18. Dynamic monitoring of cell proliferation. H1080 fibrosarcoma cells, H460 lung cancer cells, HepG2 hepatosarcoma cancer cells and NIH3T3 mouse fibroblast cell lines were seeded at a density of 2500 and 10,000 cells per well of ACEA 96× e-Plate device. The adhesion, spreading and proliferation of the cells were dynamically monitored every 30 minutes using a cell-substrate impedance monitoring system of the present invention.

For each cell type the optimum cell concentration was chosen based on their respective proliferation pattern (FIG. 18). The indicated cell numbers were seeded per well of ACEA's 16× or 96× E-PLATE (exemplary devices of the present invention) in 100 μL final volume. The attachment, spreading and proliferation of the cells were continuously monitored every 30 minutes using the RT-CES system (an exemplary system of the present invention). Approximately 24 hours after seeding, when the cells were in the log growth phase, the cells were treated with 100 μL of the indicated compounds dissolved in cell culture media. The cells were also treated with DMSO, which served as vehicle control. Depending on the experiment, the final DMSO concentration in the media was in the range of 0.25%-0.5%.

MTT Assay.

Increasing numbers of NIH3T3 cells were seeded in 16× e-plate and monitored by RT-CES to obtain the corresponding Cell Index. The media was immediately aspirated and the cells were then assayed by using the standard MTT assay according to the manufacturer's protocol.

Flow Cytometry.

A549 cells were seeded at a density of 500,000 cells/well in 60 mm tissue culture dishes. Approximately, 24 hours after seeding, the cells were treated with the indicated final concentration of Olomoucine and 16 hours later the cells were washed with PBS, trypsinized, washed twice with PBS and fixed in 70% methanol and stored at 4° C. until the staining step. The cells were stained with propidium iodide and analyzed by FACS using a wavelength of 488 nm.

Monitoring Dynamic Cell Proliferation in Real-Time Using the RT-CES

In order to assess dynamic cell proliferation using the RT-CES system, H460 human lung cancer cells, H1080 fibrosarcoma cells, HepG2 human hepatosarcoma cells and NIH3T3 mouse fibroblasts were seeded at 2500 and 10,000 cells per well in triplicate in ACEA's 96× e-Plate™. The cells were continuously monitored every 30 minutes using the RT-CES system for the indicated period of time (FIG. 18). As shown in FIG. 18, each cell type has its own characteristic kinetic trace, based on the number of cells seeded, the overall size and morphology of the cells and the degree to which the cells interact with the sensor surface. Also, the adhesion and spreading kinetics as well as time when the cells enter the log growth phase is characteristic of each of the indicated cell lines and therefore offers an excellent internal control and a way to standardize and validate stock cultures during different phases of the manufacturing process.

Figure 19A:
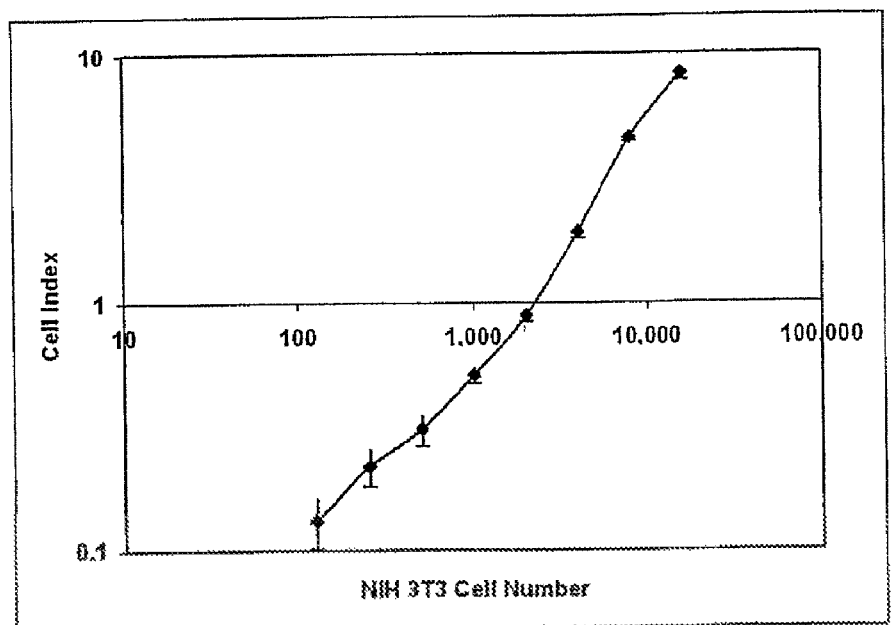
FIGS. 19A-B. Correlation between cell-substrate impedance measurement (as shown here, Cell Index) and number of cells seeded and comparison of Cell Index with MTT.
Figure 19B:
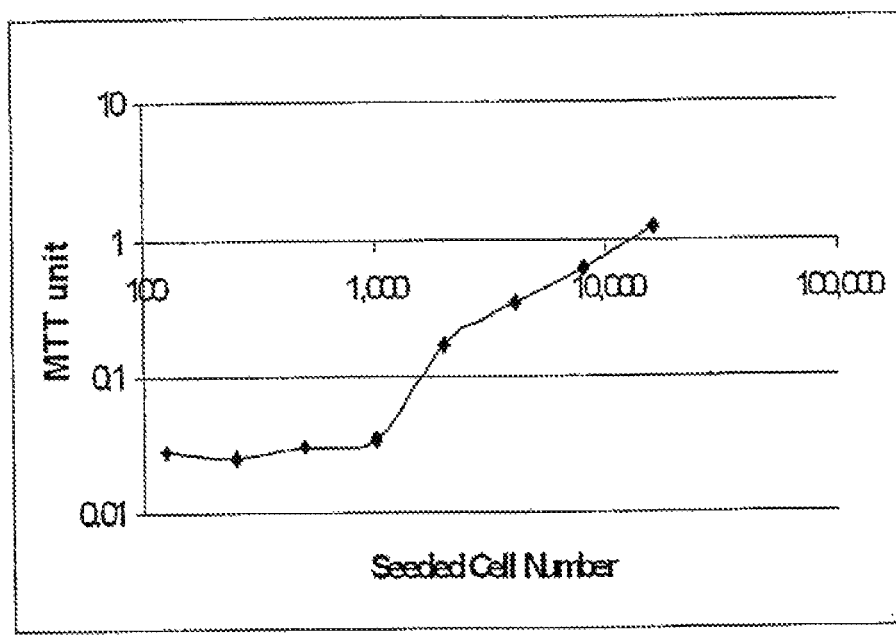

To ascertain that the RT-CES units of Cell Index correlates with the number of the cells in the well, increasing numbers of NIH3T3 cells were seeded in ACEA 16× e-Plate™ and were monitored for up to 10 hours, at which time the Cell Index was acquired. FIG. 19A shows a plot of Cell number seeded versus the Cell Index obtained and indicates that for this particular cell type the RT-CES system could detect as little as 100 cells and the readout is linear by two orders of magnitude all the way up to 10000 cells. In addition, at the end of the experiment described in FIG. 19A, the cells were also assayed by the MTT assay. As shown in FIG. 19B, even at up to 1000 cells the MTT assay is not appreciably different than background values and for cell numbers exceeding 1000, then the MTT units correlates with the number of cells seeded in a linear fashion. However, it is important to remember that while the RT-CES system is capable of dynamic and continuous measurements, for comparative reasons the experiment described in FIGS. 19A-B was only conducted at a single point, since MTT is a single point assay.

Assessment of Drug Interaction with Target Cells Using the RT-CES™ System

To assess drug potency using the RT-CES system, the IC-50 value of Tamoxifen was determined for different cell lines and compared with MTT assay at 48 hours after Tamoxifen addition. According to Table III, the IC-50 values obtained for Tamoxifen for the different cell lines using the RT-CES system is very consistent with the values obtained by the MTT assay, indicating that the RT-CES system can be used to assess the potency of various drugs against different adherent cell lines.

Figure 20A:
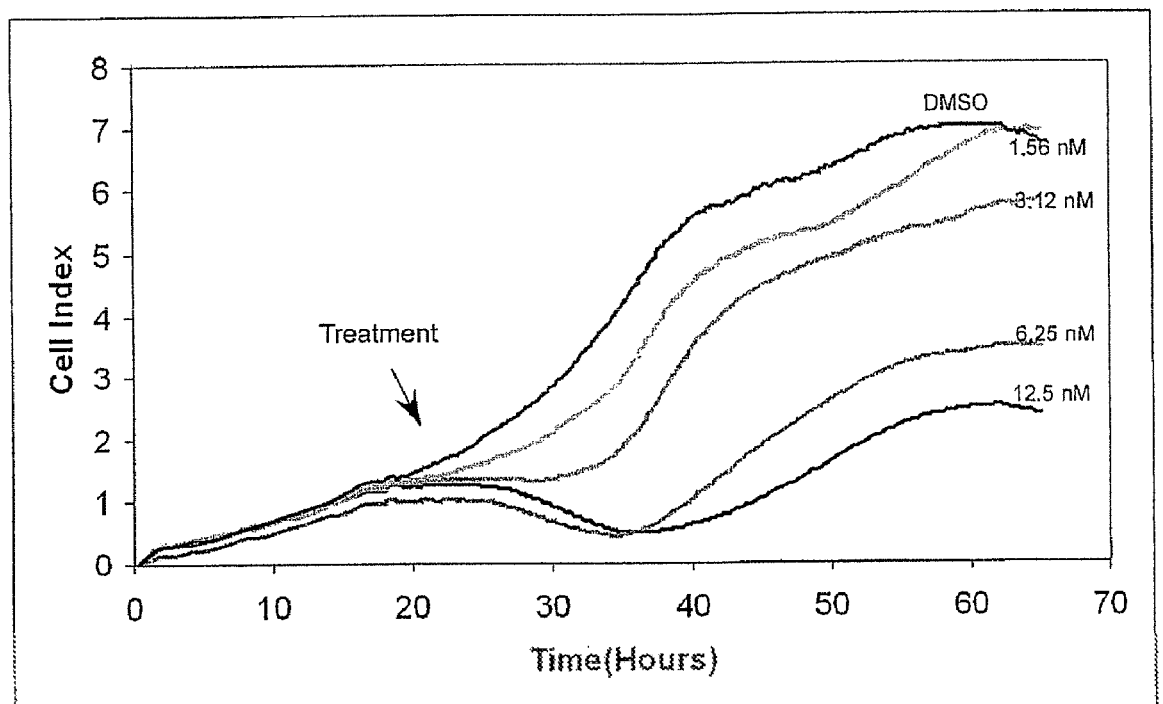
FIGS. 20A-B. Dynamic monitoring of drug interaction with target cells using a cell-substrate impedance monitoring system of the present invention.
Figure 20B:
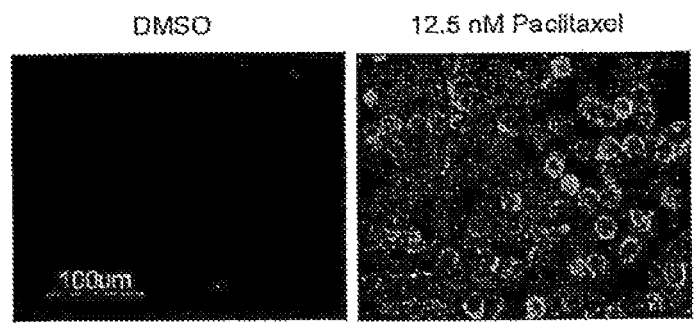

In order to observe the kinetics of drug interaction with target cells, A549 non-small lung cancer cells were seeded in ACEA 96× E-PLATE and continuously monitored until the cells reached the log growth phase at which point different concentrations of paclitaxel were added to the cells at the indicated final concentration. As shown in FIG. 20A, paclitaxel at the highest concentration initially induces a cytotoxic effect which is mainly due to cell death as judged by Annexin V staining (FIG. 20B). Remarkably, the cells recover from the initial cytotoxic effect of the drug and start to re-proliferate. While it remains to be determined if this phenomenon is due to metabolism and inactivation of paclitaxel or due to the emergence of paclitaxel-resistant sub-population, this experiment clearly exemplifies the tremendous advantage of real-time measurement which is offered by the RT-CES system and allows the user to the opportunity to observe and assess the entire history of drug interaction with the target cells which provides further information in addition to cell viability or cytotoxicity. The phenomenon observed in FIG. 20A would've been easily missed by traditional single-point assays such as MTT.

Figure 21A:
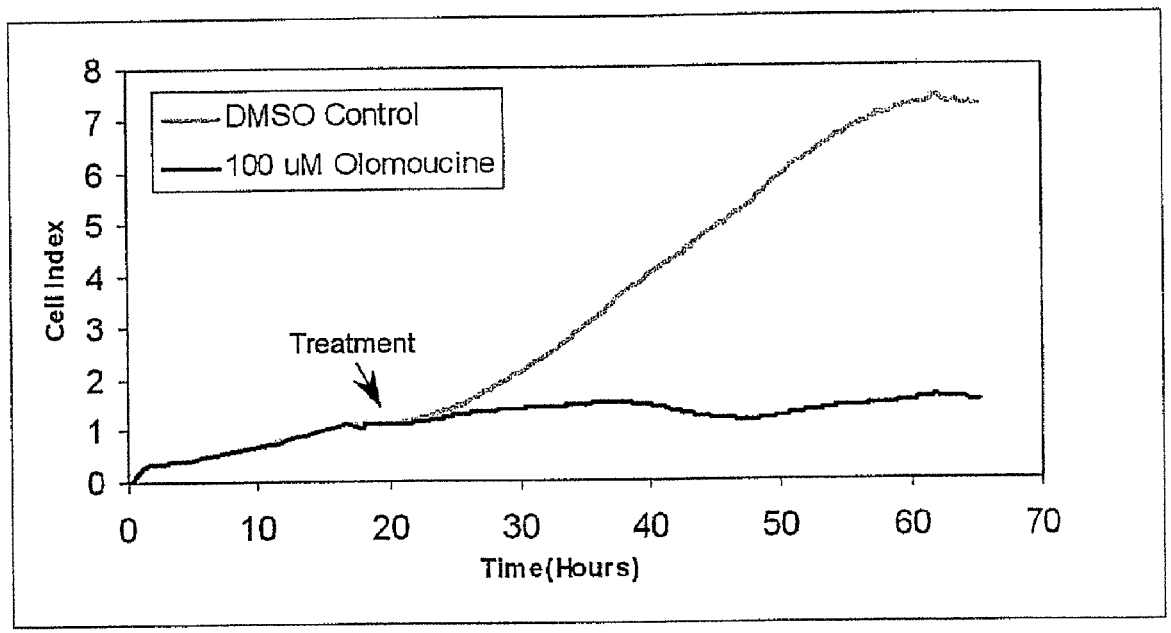
FIGS. 21A-B. Dynamic monitoring of cell cycle arrest using a cell-substrate impedance monitoring system of the present invention. A549 cells were seeded in a device of present invention at 10,000 cells per well and continuously monitored using the RT-CES. The cells were treated with either (FIG. 21A) DMSO or 100 µM Olomoucine (FIG. 21B) A549 cells growing on tissue culture dishes for 20 hours were treated with DMSO or 100 µM Olomoucine. Cell cycle analysis was performed by flow cytometry.
Figure 21B:
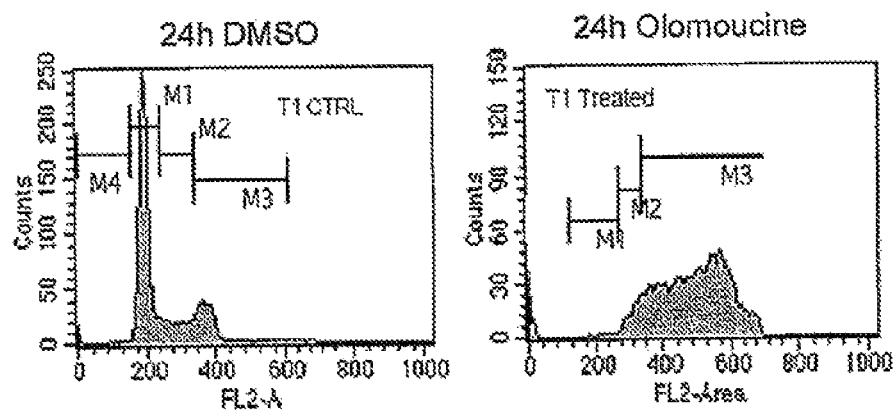

Yet another major advantage of using the RT-CES system to continually monitor the interaction of drugs with target cells is that the user can obtain insight into the mechanism of action of the drug of interest. To demonstrate this point, A549 cells were seeded in ACEA 96× microtiter device and continually monitored by the RT-CES. The cells were treated with either DMSO as the vehicle control or with 100 µM Olomoucine which is a CDK inhibitor and induces cell cycle arrest either at G1→S transition or at the G2→M transition, depending on the cell line. As shown in FIG. 21A addition of Olomoucine to exponentially growing A549 cells causes the trace of the Cell Index recordings of the cells to level off and remain in a steady state that is reminiscent of cell cycle block, where the cells are neither proliferating nor dying off. The control cells treated with DMSO continue to proliferate until they reach confluence, at which time they are contact inhibited and the Cell Index recording levels off. To demonstrate that the effect of Olomoucine on A549 cells as monitored by the RT-CES was indeed due to an arrest of the cell cycle, A549 cells growing on tissue culture dish were treated with the same concentrations of DMSO and Olomoucine and subjected to flow cytometry analysis. As shown in FIG. 21B, the flow cytometry analysis indicates that treatment of A549 cells with the indicated concentration of Olomoucine induces cell cycle arrest at the G2→M transition, where CDKs such as CDK2 is active. Taken together, using the RT-CES system to dynamically monitor drug interaction with the target cells offers the user the opportunity to understand the mechanism of drug action and its mode of interaction with the target cell.

Figure 22A:
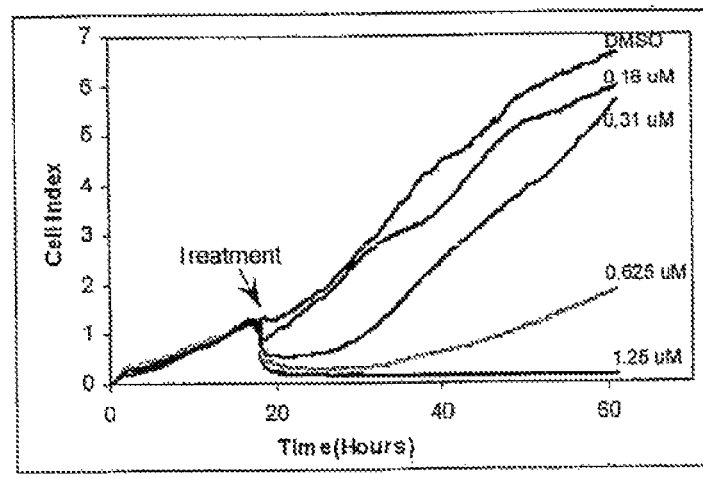
FIGS. 22A-C. Dynamic monitoring of cytotoxic compounds with target cells using a cell-substrate impedance monitoring system of the present invention. A549 cells were seeded in a device of the present invention and continuously monitored using the RT-CES system. The cells were treated with the indicated final concentrations of (FIG. 22A) staurosporine, (FIG. 22B) vinblastine and (FIG. 22C) 5-flourouracil.
Figure 22B:
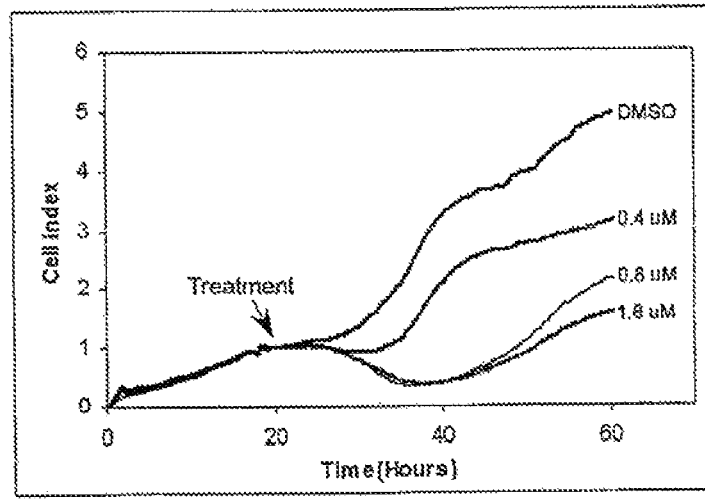
Figure 22C:
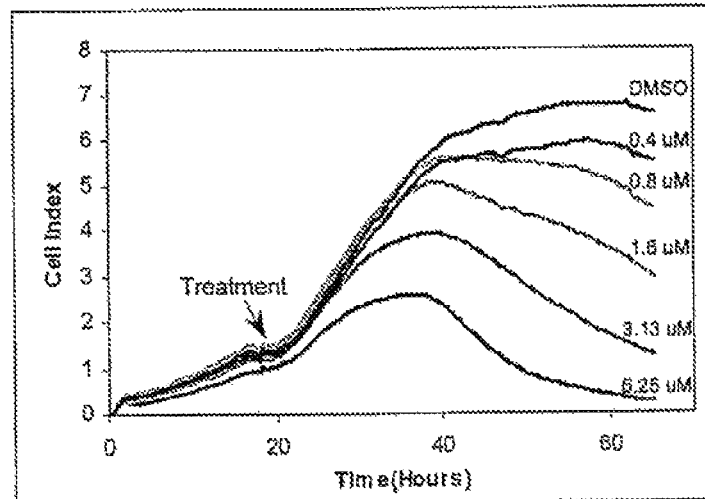
Figure 23A:
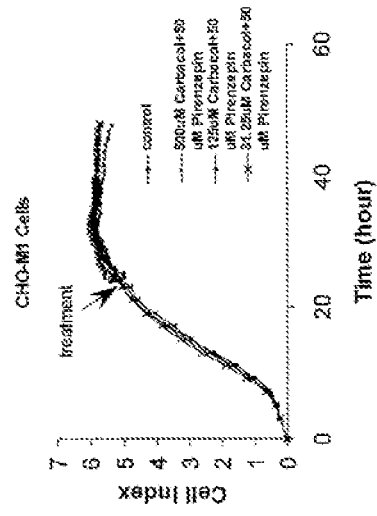
FIGS. 23A-B.
Figure 23B:
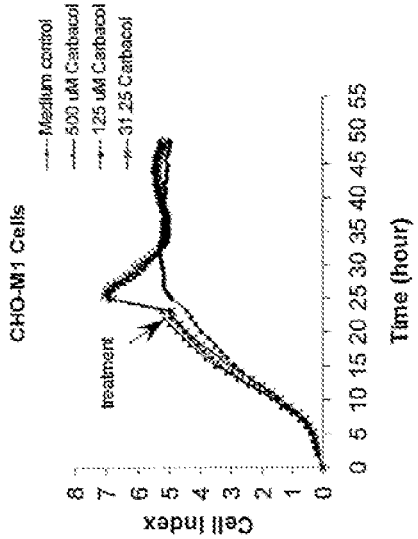
Figure 24A:
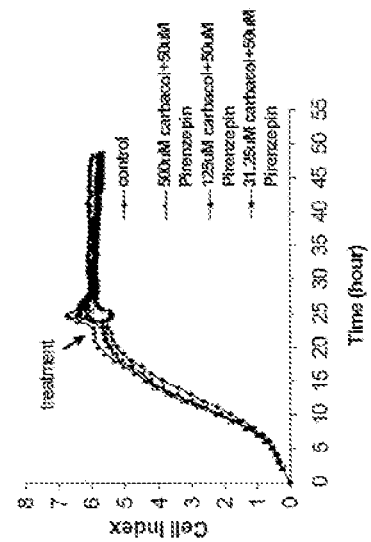
FIGS. 24A-B. CHO-M3 cells were seeded on ACEA 16× devices (16× E-Plate), grown and stimulated with the indicated doses of carbacol as described in FIGS. 23A-B and monitored by RT-CES system.
Figure 24B:
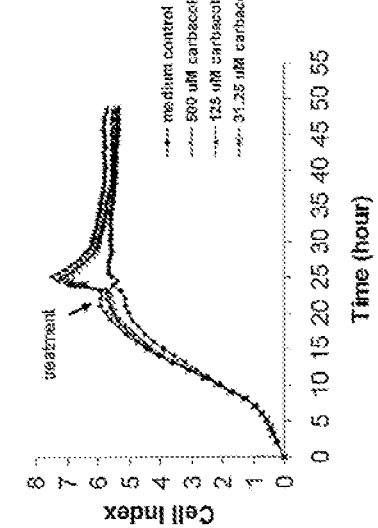

In order to assess the RT-CES system for analysis of cytotoxicity, the interaction of A549 cells was examined with cytotoxic agents with different mechanism of action. FIGS. 22A-C shows the characteristic trace of A549 cells monitored by RT-CES and treated with different concentrations of 5-fluorouracil, vinblastine and staurosporine. According to FIGS. 22A-C, dynamic monitoring of the interaction of the indicated cytotoxic agents leads to the generation of characteristic kinetic patterns that is dependent on the cellular background, the concentration of the drug, the duration of exposure and the mechanism of drug action. Since each compound has its own characteristic pattern, these kinetic traces could potentially be used to determine the mechanism of action of compounds with unknown targets by comparing the kinetic profile to the profile of compounds with known mechanism of action.

Label-free and dynamic monitoring of cell proliferation, viability and cytotoxicity using the RT-CES system offers very distinct and important advantages over traditional end-point assays. It allows for built in internal quality control to assure consistency and reproducibility between the different assays. Dynamic monitoring allows for observation of the entire episode of drug interaction with target cells and the user can therefore have a better understanding of the mode and mechanism of drug interaction. Furthermore, the actual kinetic trace of the drug interaction with the target cell is very significant because it can offer clues as to the mechanism of drug interaction with the target cell. Finally, since each compound or drug has its own characteristic profile with respect to its interaction with target cells, the RT-CES system can be used as a way to determine the mechanism of action of drugs with unknown targets.

Table III.

Comparison of IC-50 values for Tamoxifen treatment of different cancer cell lines using the RT-CES system versus MTT assay. The indicated cell lines were seeded in ACEA 16× devices and monitored by RT-CES. Approximately 24 hours later, the cells were treated with increasing concentrations of Tamoxifen and then continually monitored by RT-CES. The experiment was stopped about 48 hours later and the cells in the 16× devices were assayed by using MTT. The IC-50 values derived from RT-CES system are time-dependent. In the table, the IC-50 values at about 48 hrs after compound treatment are shown for RT-CES system determination and MTT assay.

| Cell Type | RT-CES ™ | MTT Assay |
|---|---|---|
| HT1080 | 22.4 µM | 30.0 µM |
| NIH3T3 | 16.0 µM | 19.0 µM |
| HepG2 | 15.2 µM | 16.2 µM |
| HUEVEC | 7.5 µM | 8.0 µM |

Example 3: Measuring and Monitoring the Morphological Changes Occurring in Chinese Hamster Ovary (CHO) Cells Upon Stimulation of the Muscarinic M1 and M3 Receptors As an example, we describe here the use of the ACEA RT-CES™ system to measure and monitor the morphological changes that occur as a result of carbacol treatment of Chinese hamster ovary (CHO) cells which express the muscarinic M1 and M3 receptor.

CHO cells expressing the muscarinic M1 receptor (CHO-M1) or the muscarinic M3 receptor (CHO-M3) were seeded in ACEA's 16× device (E-Plate) at 20,000 cells/well and the attachment and growth of the cells in the 37° C. tissue culture incubator were monitored in real-time using RT-CES™ system (which includes, for example, a 16× device station or 16× E-Plate station, RT-CES impedance analyzer and integrated software for controlling the impedance analyzer and device station). Cell index curves measured on the RT-CES system are shown in FIGS. 23A-B and FIGS. 24A-B. After 22 hours the cells were treated with different doses of carbacol which is an agonist for both the M1 and M3 receptors. As a control, the cells were treated with media alone. The device chambers were returned to the incubator and recording was resumed. In addition, as a measure of specificity, the cells were also treated with carbacol in the presence of excess amount of pirenzipine, which is an antagonist of the M1 and M3 receptors.

Figures 25A, 25B:
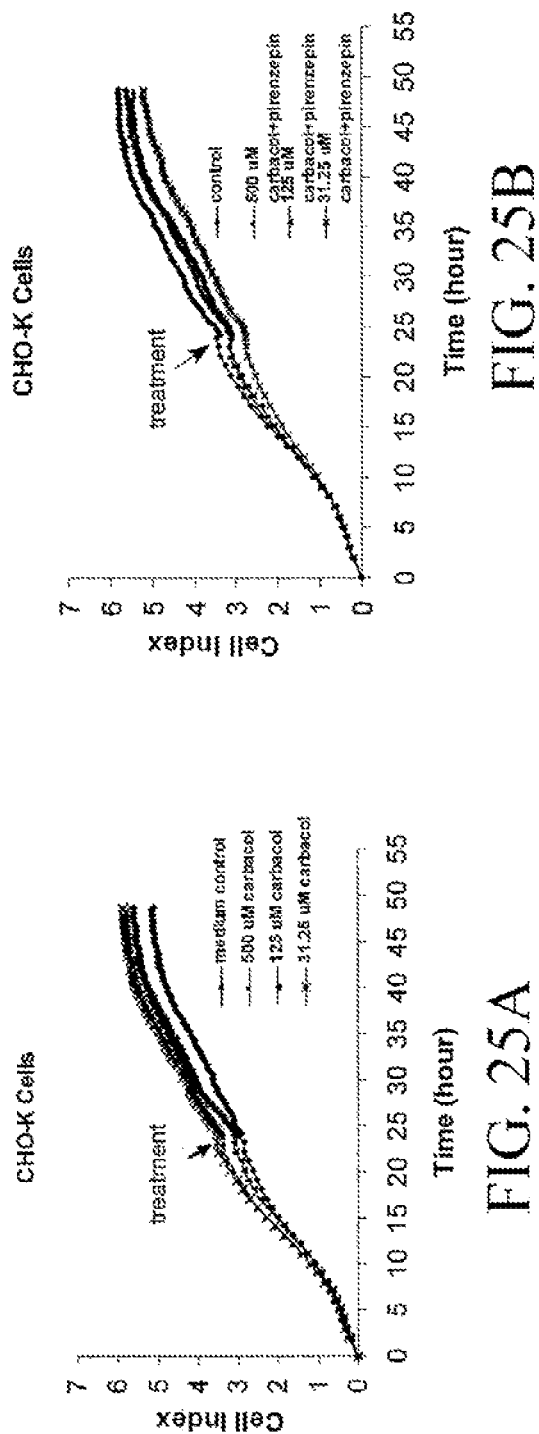
FIG. 25A-B. CHO cells which do not express the M1 and M3 receptors were seeded on ACEA 16× device (16× E-Plate) and were treated with carbacol and pirenzipine as described in FIGS. 23A-24B. The cells do not respond to the agonist carbacol (FIG. 25A) or the antagonist pirenzepine (FIG. 25B).
Figure 26:
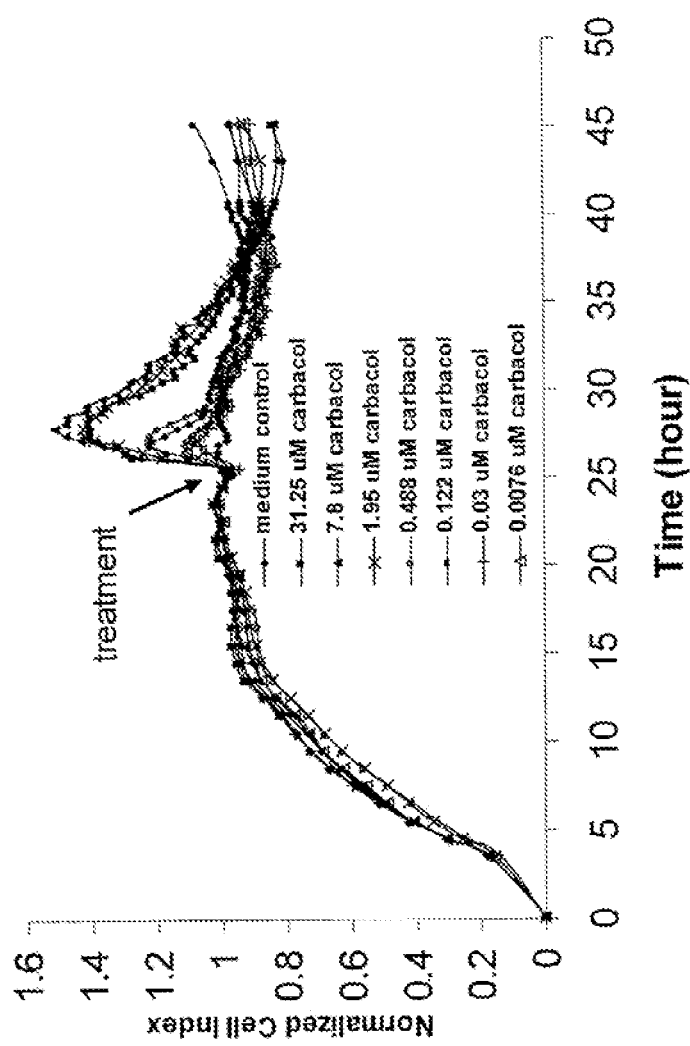
FIG. 26. CHO-M1 cells growing on ACEA 16× microtiter devices were stimulated with the indicated doses of carbacol and the dose-dependent cell-electrode impedance response was monitored by RT-CES.

The effect of carbacol on CHO-M1 cells and CHO-M3 cells in the presence or absence of pirenzipine is shown in FIGS. 23A-B and FIGS. 24A-B. The effect of carbacol is seen as a transient and abrupt shift in the trace of the cell index number at 22 hours, immediately after treatment with different doses of carbacol. The duration of the signal for the carbacol-mediated affect lasts approximately 4 hours and then returns to baseline. The vehicle control did not have any effect on the recording. However, as expected, pirenzipine blocked the effect of carbacol on both CHO-M1 and CHO-M3 cells indicating that the effect of carbacol is indeed mediated through the M1 and M3 receptors, respectively. Furthermore, carbacol and pirenzipine did not have any effect on CHO-K cells which do not express the M1 and M3 muscarinic receptors (FIGS. 25A-B), indicating that the response is dependent on the expression of the muscarinic M1 or M3 receptors. In addition CHO-M1 cells were stimulated with increasing concentration of carbacol and the cell-electrode impedance response was continually monitored by RT-CES system. As shown in FIG. 26, the cell-electrode impedance response is dependent on the concentration of carbacol which is maximal at 31.25 nM. This experiment shows that the RT-CES system can be used to assess the effect of GPCR stimulation on cells and furthermore, it illustrates that this assay can be used to screen for antagonist of specific GPCRs. The assay can be performed in high-throughput format, in real time and without the need for any other reagents or cellular manipulation.

Figure 27A:
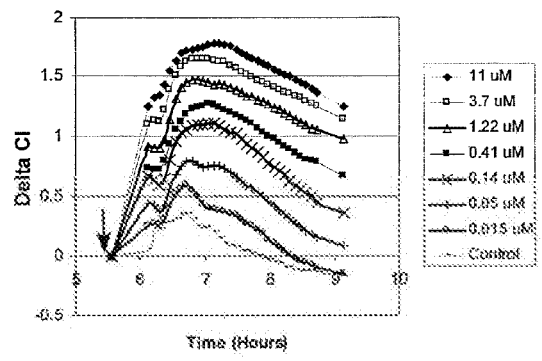
FIG. 27A-F depict the pharmacological characterization of carbachol-evoked CI increases in Muscarinic 1 Receptor (M1) And Muscarinic 3 Receptor (M3) expressed in CHO cells: blockage by M1 selective antagonist pirenzepine. M1 and M3 muscarinic receptor cell lines were seeded at 50,000 cells per well of ACEA E-plates (E-plates are microtiter plates that have incorporated microelectrode arrays at the bottom of the wells). The cells were continuously monitored using the RT-CES system. At the indicated time point of treatment, increasing concentrations of carbachol (from 0 to 11 µM) were added to the cells and the cell response was monitored every 3 minutes by the RT-CES system. Carbachol leads to a dose-dependent and transient increase in CI in M1 (FIG. 27A) and M3 (FIG. 27C). Delta cell index shown in (FIG. 27A) and (FIG. 27C) at a given time point was calculated by subtracting the cell index at a standard time point from the cell index at the given time point. Here the standard time point was the last time point of the measurement before adding carbachol to the CHO cells (the first time point on the traces in FIG. 27A and FIG. 27C). Plotting the peak Delta cell index responses versus the corresponding log concentration allows for calculation of the $EC_{50}$ (0.59 uM and 0.67 M) of carbachol for M1 (FIG. 27B) and M3 (FIG. 27D). For antagonist study, increasing concentrations of pirenzepine (from 0 to 33 uM), a selective M1 antagonist, were added to the cells 10 min prior to the application of a fixed concentration carbachol (10 uM) and the cell response was monitored every 3 minutes by the RT-CES system. Delta cell index shown in (FIG. 27E) at a given time point was calculated by subtracting the cell index at a standard time point from the cell index at the given time point. Here the standard time point was the last time point of the measurement before adding carbachol to the cells (the first time point on the traces in FIG. 27E). Pirenzepine blocked carbachol-induced Delta CI increases in a concentration-dependent manner as shown in traces (FIG. 27E). Plotting the maximal blocking effects on cell index response versus the corresponding log concentration allows for calculation of the $IC_{50}$ (~0.6 uM) of pirenzepine (FIG. 27F).
Figure 27B:
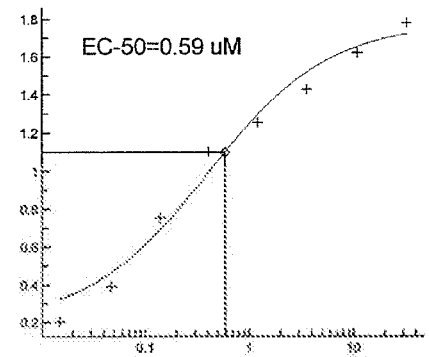
Figure 27C:
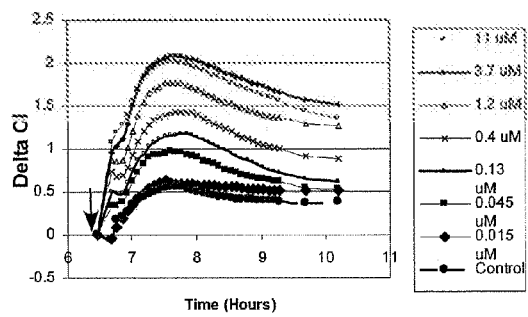
Figure 27D:
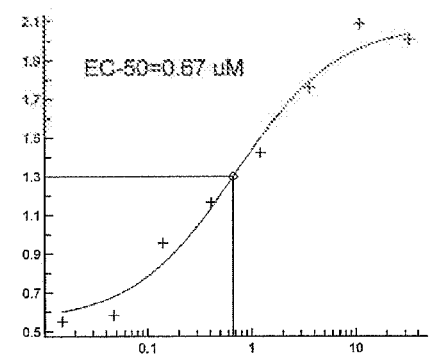
Figure 27E:
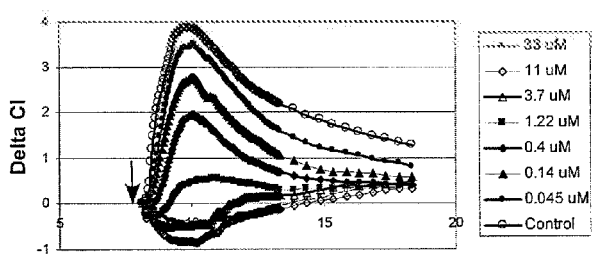
Figure 27F:
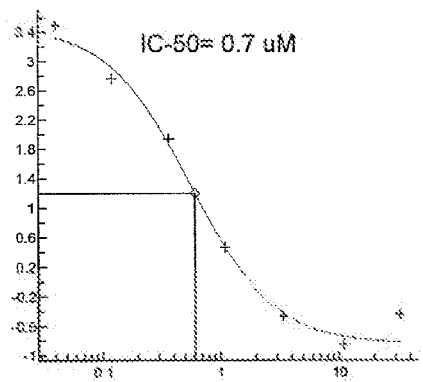

Example 4: Monitoring Dose-Dependent Functional Activation of the Muscarinic M1 and M3 Receptors in Chinese Hamster Ovary (CHO) Cells and Pharmacological Characterization by a Selective M1 Agonist M1 and M3 muscarinic receptors are linked to a modulation of cell function via Gq class of heterotrimeric G-proteins. We used CHO cells stably expressing the M1 and M3 muscarinic receptors to test their responses to carbachol, a non-hydrolysable analogue of acetylcholine. The cells were continuously monitored using the RT-CES system. At the indicated time point, increasing concentrations of carbachol were added to the cells and the cell response was monitored every 3 min. As shown in FIGS. 27A-F, carbachol ranging from 15 nM to 11 uM leads to a concentration-dependent increase in cell index in M 1 cells (FIG. 27A) and M3 cells (FIG. 27C). The dynamic of the cell responses demonstrates that maximal cell responses were achieved one hour after the application of carbachol and the cell index gradually decrease to lower levels. Plotting the peak cell index response versus the corresponding log concentration allows for calculation of the $EC_{50}$ values of carbachol for M1 cells (FIG. 27B) and M3 cells (FIG. 27D). Both the M1 and M3 muscarinic receptors are coupled to Gq subclass of Gα proteins so that their response patters on the RT-CES system are highly similar. To examine the pharmacology of carbachol on M1 cells, we started with a selective M1 antagonist, pirenzepine, to confirm the specificity of carbachol. As shown in FIG. 27 D, pirenzepine attenuates carbachol-induced cell responses in a concentration-dependent manner with IC50 of 0.7 uM. These results indicate that the effects of carbachol observed are caused by M1 receptors overexpressed in the host cell line.

B. Monitoring Dose-Dependent Functional Activation of the Muscarinic M3 and M2 Receptors Expressed in RBL-2H3 Cell Line Parallelly Parallelly, we compared two distinct muscarinic receptors which preferentially interact with specific G proteins. In general, odd numbered muscarinic receptors interact with a subunit of Gq class while even numbered muscarinic receptors are coupled to a subunit of Gi class. In turn, activation of Gq stimulates phospolipase C and activation Gi decreases cAMP production. Clearly as indicated in FIG. 28A-C, activation of M3 (FIG. 28A) and M2 (FIG. 28C) by carbachol reveals two unique profiles of cell index dynamics. Similar but not identical to M3 expressed in CHO cell line (FIG. 27C), M3 expressed in RBL-2H3 cell line demonstrates that maximal cell responses were achieved one hour after the application of carbachol and the cell index stay high for a relative longer period of time. On the contrary, M2 expressed in RBL-2H3 cell line reveals a complete different pattern to carbachol application. Cell Index increase sharply and reached the maximal levels with 1-2 hours and then quickly tapered off and the cell index stay lower close to basal levels afterwards.

C. Monitoring Dose-Dependent Functional Activation of the Human Histamine H1 Receptor (hH-C1) Stably Expressed in CHO Cell Line Another category of GPCR coupled to Gq has been investigated. We choose cell line overexpress human recombinant H1 receptors (hH1-C1) to substantiate what have been found in our previous described results. hH1-C1 cells were tested by various concentrations of histamine. As shown in FIG. 29A-D, histamine produce concentration-dependent increases in cell index and the $EC_{50}$ of histamine is 1.7 nM (B). Brompheniramine (a selective H1 antagonist) completely blocks histamine-induced CI increases with IC50 of 12 nM indicating that histamine-induced CI increases in hH1-C1 cells were specifically mediated by H1 receptors.

D. Monitoring Dose-Dependent Functional Activation of the Human Vasopressin Receptor 1a (V1a-C1) Stably Expressed in 1321-N1 Cells and Characterization of Pharmacology Vasopressin 1a receptor (V1a) together with V1b and V2, are a member of a family of related GPCRs which are activated by neurohypophysial peptide hormones including vasopressin (AVP). V1a is coupled to Gq and activation of the receptors leads to PLC activation and mediates a plethora response to AVP. We tested the V1a-C1 cell lines in RT-CSE system for the purpose of characterization of pharmacology. We used the natural ligand of Via, namely AVP, to monitor the change of CI as the read-outs of functional activation of the V1a receptors. We tested various concentrations AVP ranging from 1 pM to 10 uM. The traces for concentrations between 30 pM and 0.3 uM are shown in FIG. 30A-B. AVP-induced CI increases were transient in nature and CI gradually approached to basal levels after 5-6 hour of AVP application. Maximal effects of each tested-concentration were use to generate a concentration-dependent curve shown in FIG. 30C-D and $EC_{50}$ of AVP is 155 pM. [β-Mercapto-β,β-cyclopentamethylene-propionyl1, O-Et-Tyr$^2$, Val$^4$, Arg$^8$]Vasopressin (βM AVP) was used a blocker for AVP. The IC50 of βM AVP is 761 nM.

Example 5: Monitoring the Functional Activation of GPCRs Expressed Endogenously in a Variety of Cell Lines A. Using the RT-CES System to Monitor the Functional Activation of Endogenous Histamine Receptor in HeLa Cells and Characterization of Pharmacology.

HeLa cells were tested by application of histamine to monitor the activation of the endogenous histamine receptors. As demonstrated in FIGS. 31A, 31B, histamine produced concentration-dependent increases of CI and the EC50 of histamine is 146 nM. The effects of histamine can be attenuated by brompheniramine with $IC_{50}$ of 406 nM (FIGS. 31C, 31D).

B. Using the RT-CES System to Monitor the Functional Activation of Endogenous Endothelin Receptor in Hela Cells HeLa cells were tested by application of endothelin 1 to monitor the activation of the endogenous endothelin receptors. As demonstrated in FIGS. 32A-B, endothelin 1 produced concentration-dependent increases of CI and the EC50 of endothelin 1 is 0.9 nM.

Figure 33C:
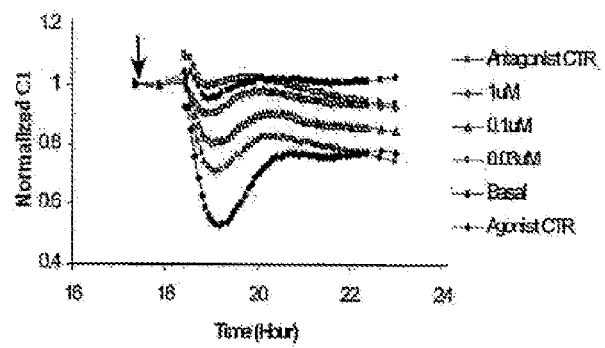
FIGS. 33A-G depict isoproterenol-evoked decreases of cell index (CI) of C6 glioma cells which express the endogenous B-adrenergic receptors: Demonstration Of The Involvement Gs And Adenylate Cyclase. C6 cells were seeded at 50,000 cells per well of ACEA E-plates. The cells were continuously monitored using the RT-CES system. At the indicated time point, increasing concentrations of isoproterenol were added to the cells and the cell response was monitored every 3 minutes by the RT-CES system. Isoproterenol leads to a dose-dependent and transient decrease in CI in C6 cells shown in traces (FIG. 33A). Plotting the peak cell index response versus the corresponding log concentration allows for calculation of the $EC_{50}$ of isoproterenol (FIG. 33B). For the antagonist study, increasing concentrations of alprenolol were added to the cells 10 min prior to the application of a fixed concentration isoproterenol (10 uM) and the cell response was monitored every 3 minutes by the RT-CES system. alprenolol blocked isoproterenol-induced CI decreases in a concentration-dependent manner as shown in traces (FIG. 33C). Plotting the maximal blocking effects on cell index response versus the corresponding log concentration allows for calculation of the $IC_{50}$ of alprenolol (FIG. 33D). The effects of isoproterenol can be mimicked by dibutyl-cAMP, a cell membrane permeable analogue of cAMP, and forskolin, an adenylate cyclase activator, shown in traces (FIG. 33E, FIG. 33G) and curves (FIG. 33F, FIG. 33H), respectively. Normalized cell index shown in (FIG. 33A, FIG. 33C, FIG. 33E and FIG. 33G) at a given time point was calculated by dividing the Cell Index at the time point by the Cell Index at a reference time point. Here the reference time point was the last time point of the measurement before adding Isoproterenol to the cells.
Figure 33D:
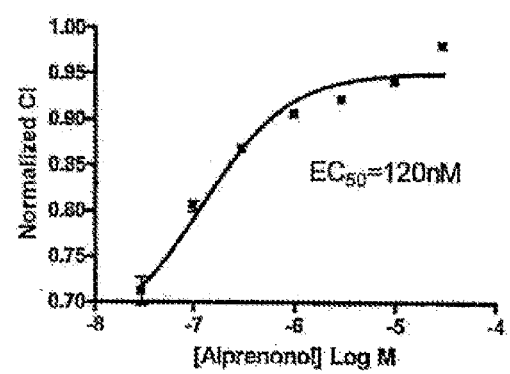
Figure 33E:
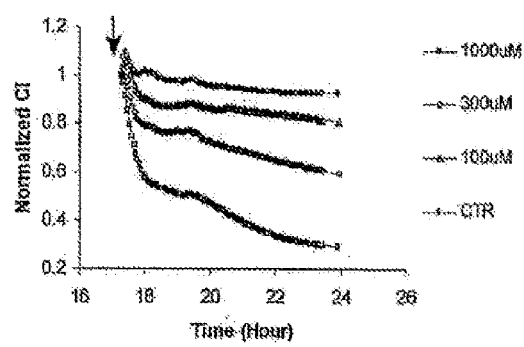
Figure 33F:
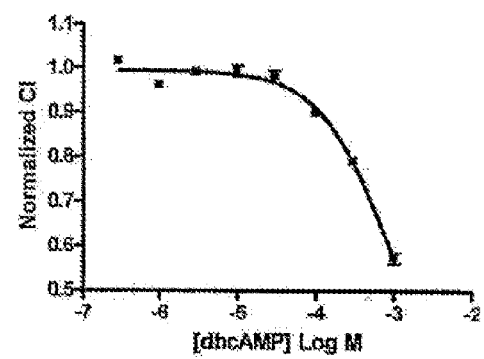
Figure 33G:
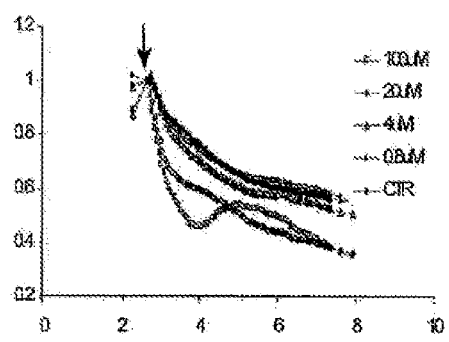
Figure 33H:
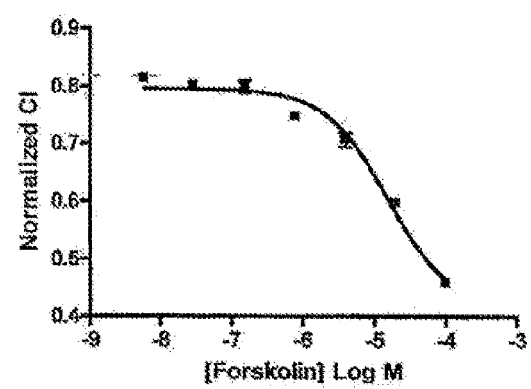

C. Using the RT-CES System to Monitor the Functional Activation of Endogenous B-Adrenergic Receptors in C6 Glioma C6 cells were tested by application of isoproterenol, a β-adrenergic agonist. Unlike activation of other category of G protein subunits, activation of 3-adrenergic receptors produced the dynamics of decreased CI. Isoproterenol produced a concentration-dependent and transient decrease of CI (FIG. 33A) with EC50 of 24 nM (FIG. 33B). The effects of isoproterenol can be blocked by β-adrenergic receptors antagonist alprenolol (FIG. 33C) with an IC50 of 120 nM (FIG. 33D) indicating the involvement of β-adrenergic receptors for this phenomenon. To substantiate the involvement of Gs, we take the advantage of dibutyl cAMP, a cell membrane permeable analogue of cAMP (FIGS. 33E, 33F), and forskolin (FIGS. 33G, 33H), an adenylate cyclase activator; both mimic the increase of intracellular cAMP as the consequence of Gs activation. Both compounds demonstrated the profiles of decreased CI supporting the results of isoproterenol.

Figures 34A, 34B:
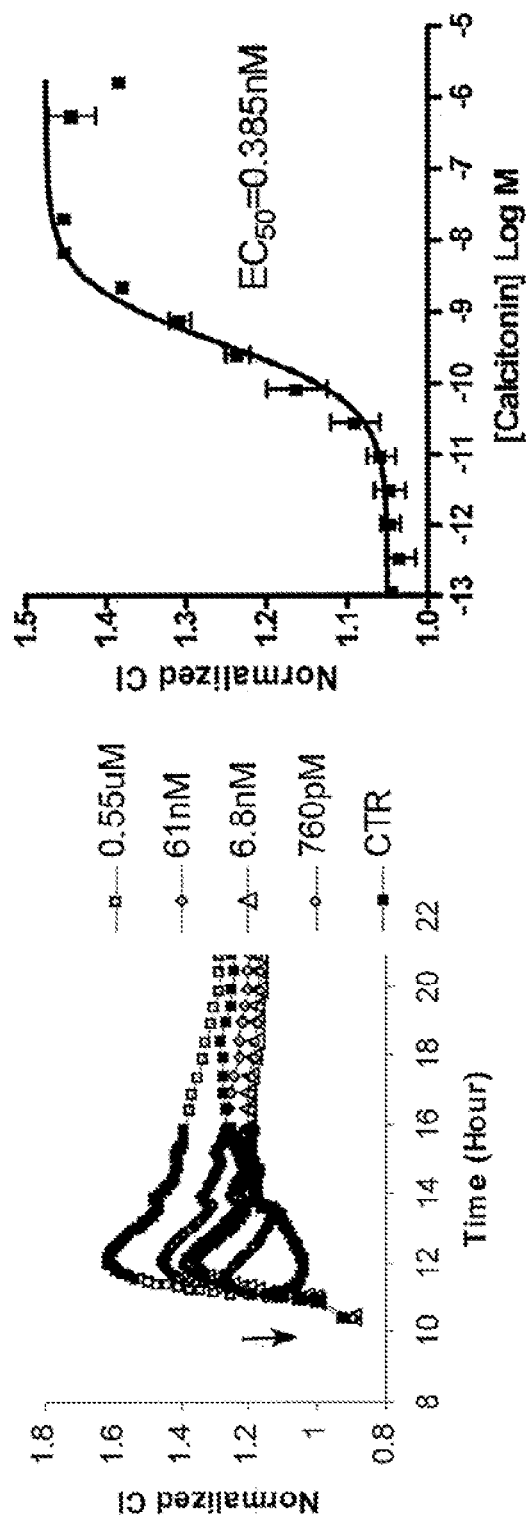
FIGS. 34A-B depict Calcitonin-evoked increases of Cell Index (CI) of CHO cells which express the endogenous calcitonin receptors. CHO cells were seeded at 50,000 cells per well of ACEA E-plates. The cells were continuously monitored using the RT-CES system. At the indicated time point, increasing concentrations of calcitonin were added to the cells and the cell response was monitored every 3 minutes by the RT-CES system. Calcitonin leads to a dose-dependent and transient decrease in CI in CHO cells shown in traces (FIG. 34A). Plotting the peak cell index response versus the corresponding log concentration allows for calculation of the $EC_{50}$ (0.385 nM) of calcitonin (FIG. 34B). Normalized cell index shown in (FIG. 34A) at a given time point was calculated by dividing the Cell Index at the time point by the Cell Index at a reference time point. Here the reference time point was the last time point of the measurement before adding Calcitonin to the cells.

D. Using the RT-CES System to Monitor the Functional Activation of the Calcitonin Receptor in CHO-K1 Cell Another pair of ligand-receptor coupled to Gs, calcitonin on CHO cells, has been tested by RT-CES system. In contrast to the activation of Gs in C6 cells, activation of Gs in CHO by calcitonin generated the increased CI. As shown (FIGS. 34A, 34B), the effects of calcitonin is concentration-dependent with $EC_{50}$ of 0.385 nM.

Example 6: Monitoring the GPCR Activation Pathway Using the RT-CES System

Figure 35:
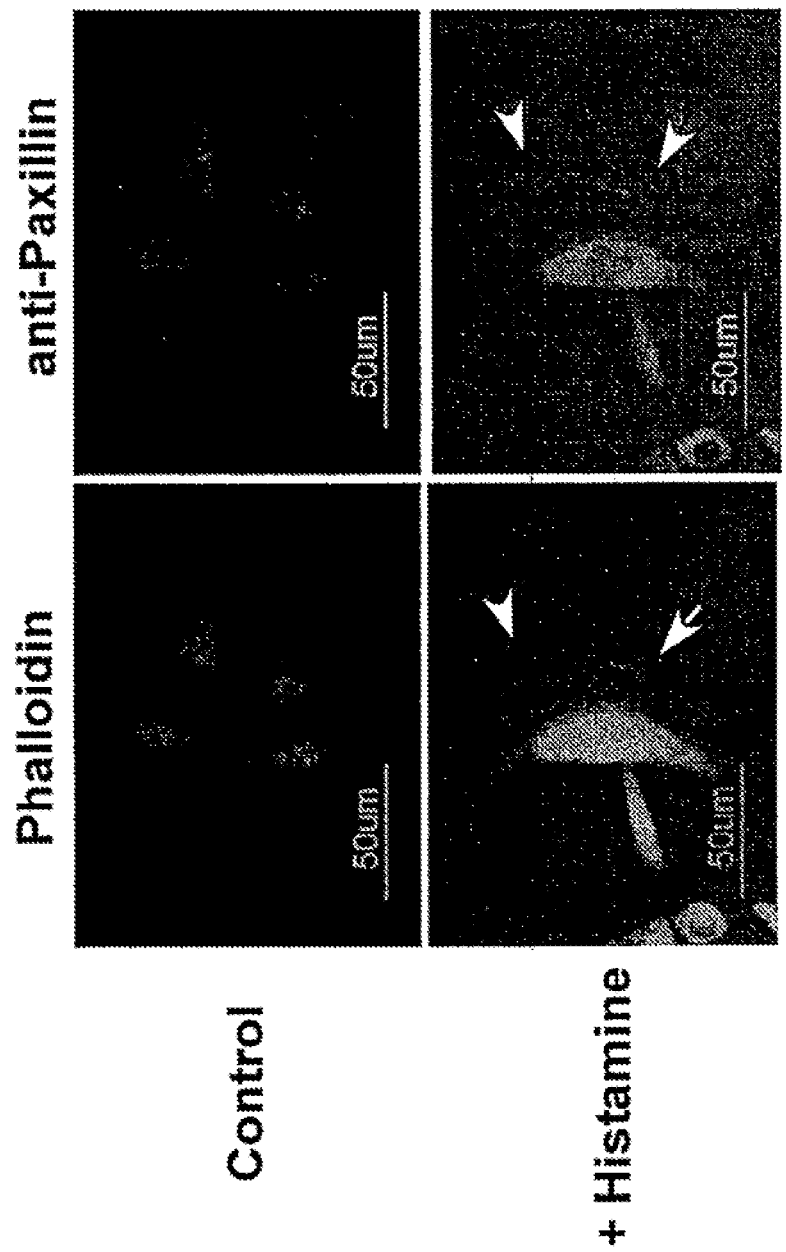
FIG. 35 depicts an example where Histamine induces focal adhesion assembly and membrane ruffling in hH1-C1 cells. The hH1-C1 cells were seeded on eight-well chamber slides with the density of 10,000 cells per well for one day. After an overnight incubation in serum-free medium, the cells were treated with 100 nM Histamine for 5 minutes. The cells were fixed, stained with FITC-Phalloidin and anti-Paxillin antibody and visualized by using an immunofluorescence microscope. Membrane ruffling can be observed (arrows).
Figure 36:
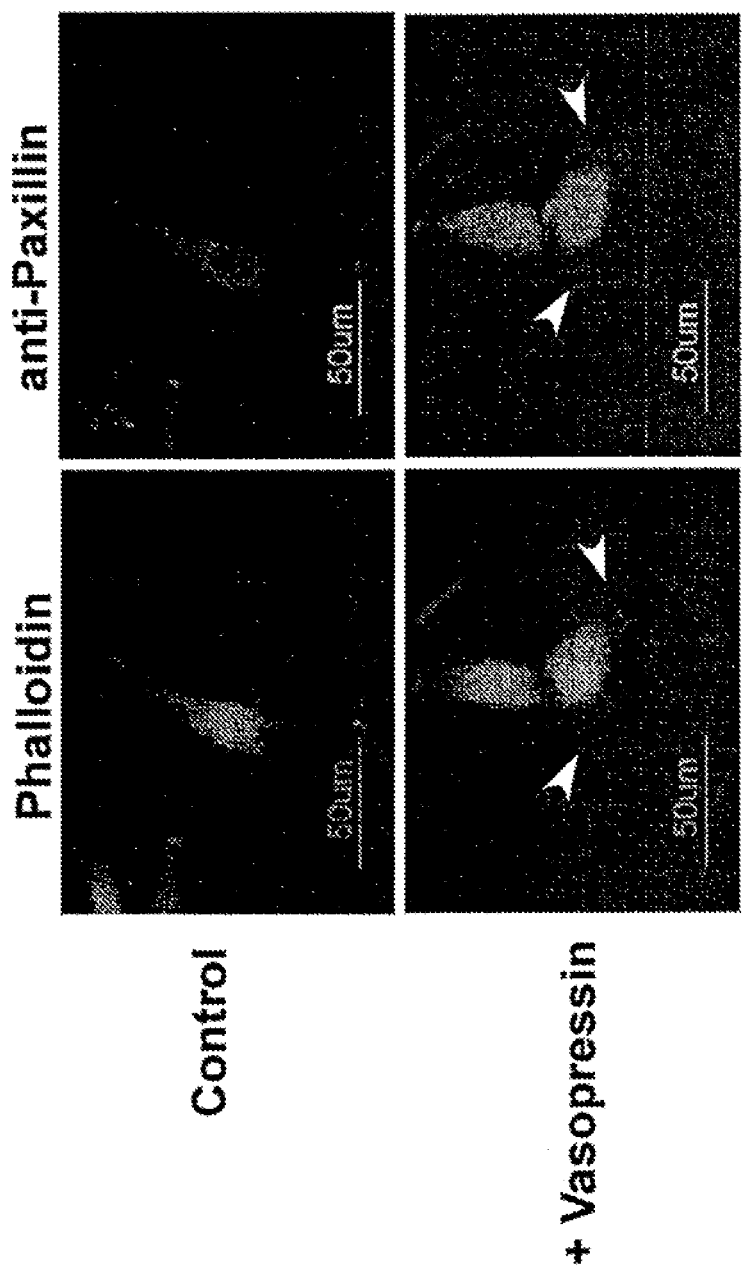
FIG. 36 depicts an example where AVP induces focal adhesion assembly and membrane ruffling in V1a-C1 cells. The V1a-C1 cells were seeded on eight-well chamber slides with the density of 10,000 cells per well for one day. After an overnight incubation in serum-free medium, the cells were treated with 1 μM AVP for 5 minutes. The cells were fixed, stained with FITC-Phalloidin and anti-Paxillin antibody and visualized by using an immunofluorescence microscope. Membrane ruffling can be observed (arrows).

A. Activation of GPCRs in hH-C1 Cells and V1a-C1 Cells by their Respective Ligands Cause Membrane Ruffling and Focal Adhesion Assembly As the cell-electrode impedance reading is primarily associated with number, shape and strength of the adhesion of the cells on the surface of electrodes, we utilized there are indeed a morphological changes of the cells after the application of the ligand, which are associated with the changes of CI we observed in RT-CES system. We choose hH1-C1 and V1a-C1 cells stimulated by their respective ligands. After the addition of the ligand, f-actin was visualized by FTIC-phalloidin and a focal adhesion protein paxillin was co-stained by its antibody. As shown in FIG. 35, after a brief exposure to histamine (100 nM, 5 min), membrane ruffling as indicated by phalloidin and increased focal adhesion assembly reflected by paxillin become apparent (arrows in lower panels of FIG. 35). The similar phenomenon was found in V1a-C1 cells stimulated by AVP (arrows in lower panels of FIG. 36).

B. Utilization of Various Signal Transduction Blockers to Dissect the Mechanisms of Histamine-Induced CI Changes in hH-C1 Cells.

Figure 37A:
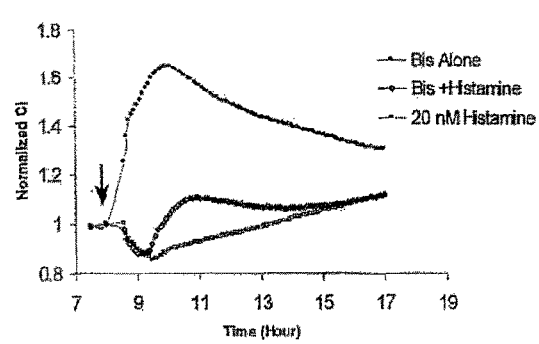
FIGS. 37A-F. Mechanistic studies of Histamine-induced increases of CI in hH1-C1 cells by various reagents ranging from pathway blockers and toxins. Cell lines were seeded at 50,000 cells per well of ACEA E-plates. The cells were continuously monitored using the RT-CES system. Bisindolylmalemide (Bis, 10 μM), a PKC inhibitor (FIG. 37A); PP2 (10 uM), a Src inhibitor (FIG. 37B); latrunculin (1 uM), a cell adhesion blocker (FIG. 37C); ROCK (10 uM), a Rho kinase inhibitor (FIG. 37D); PD98059 (PD, 10 μM), a MEK inhibitor (FIG. 37E) and U73122 (10 μM), a PLC inhibitor (FIG. 37F) were added alone or 10 min before the addition of histamine (20 nM). The cells were continuously monitored by the RT-CES system to the end of the experiment. Normalized CI traces are shown respectively. Normalized cell index shown in (FIGS. 37A-37F) at a given time point was calculated by dividing the Cell Index at the time point by the Cell Index at a reference time point. Here the reference time point was the last time point of the measurement before adding histamine (20 nM) to the cells.
Figure 37B:
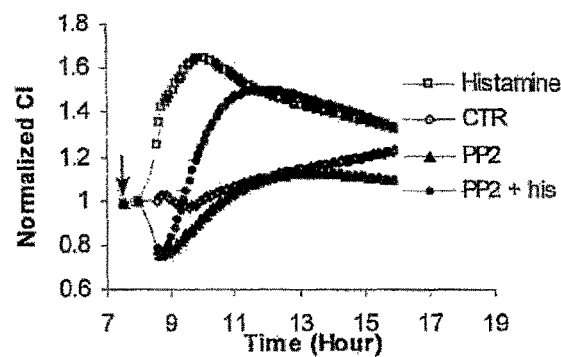
Figure 37C:
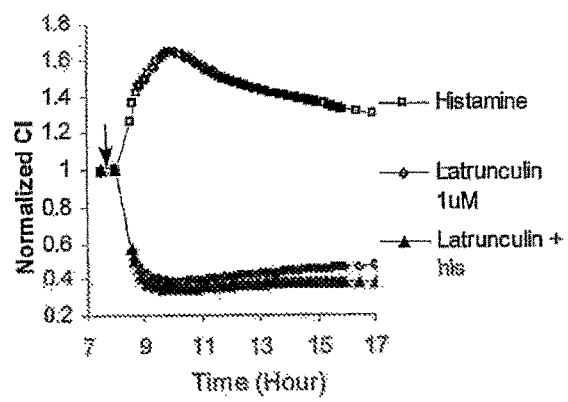
Figure 37D:
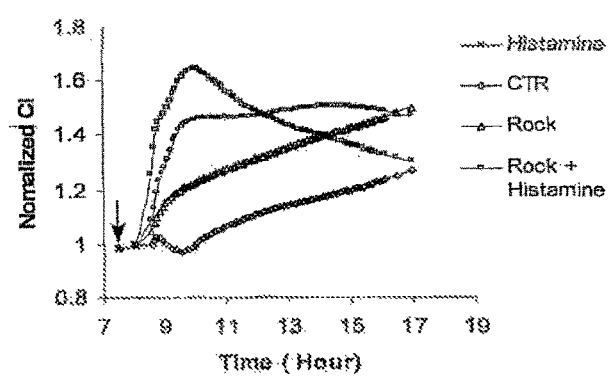
Figure 37E:
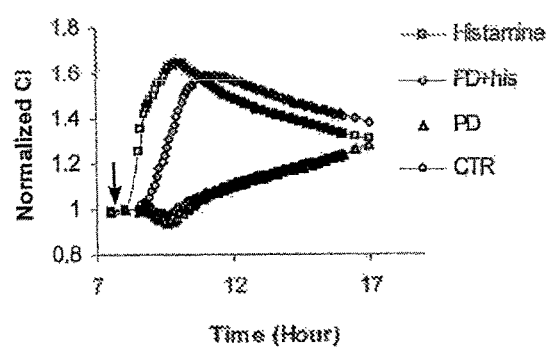
Figure 37F:
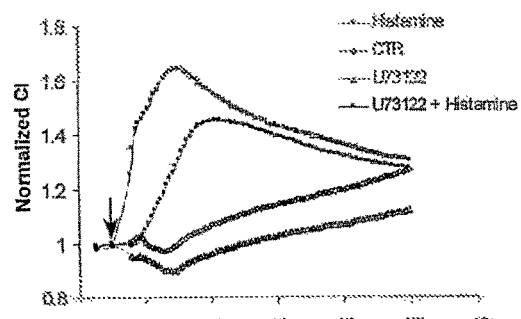

In order to fully understand the intracellular events after activation of H1 receptors, various pathway blockers or toxins were applied to the hH1-C1 cells before the addition of histamine. The CI was continuously monitored by RT-CES system. We demonstrated that protein kinas C inhibitor, bisindolylmalemide (10 uM) completely inhibits the effects of histamine (FIG. 37A). Src inhibitor, PP2 delays and attenuates the effects of histamine the effects histamine (FIG. 37B) implying that Src pathway might be involved in GPCRs mediated intracellular events. Cell adhesion blocker latrunculin completely eliminate the effects of histamine stressed the importance of cell adhesion in response to H1 activation by histamine (FIG. 37C). Rho kinase inhibitor ROCK partially reduced the magnitude of CI increases by histamine and slightly delayed the effects of histamine. histamine (FIG. 37D). MEK inhibitor PD98059 also delayed the effects of histamine but has little inhibition for the magnitude of histamine. histamine (FIG. 37E). PLC inhibitor U73122 significantly delayed onset and reduced the magnitude by histamine (FIG. 37F).

Figure 38:
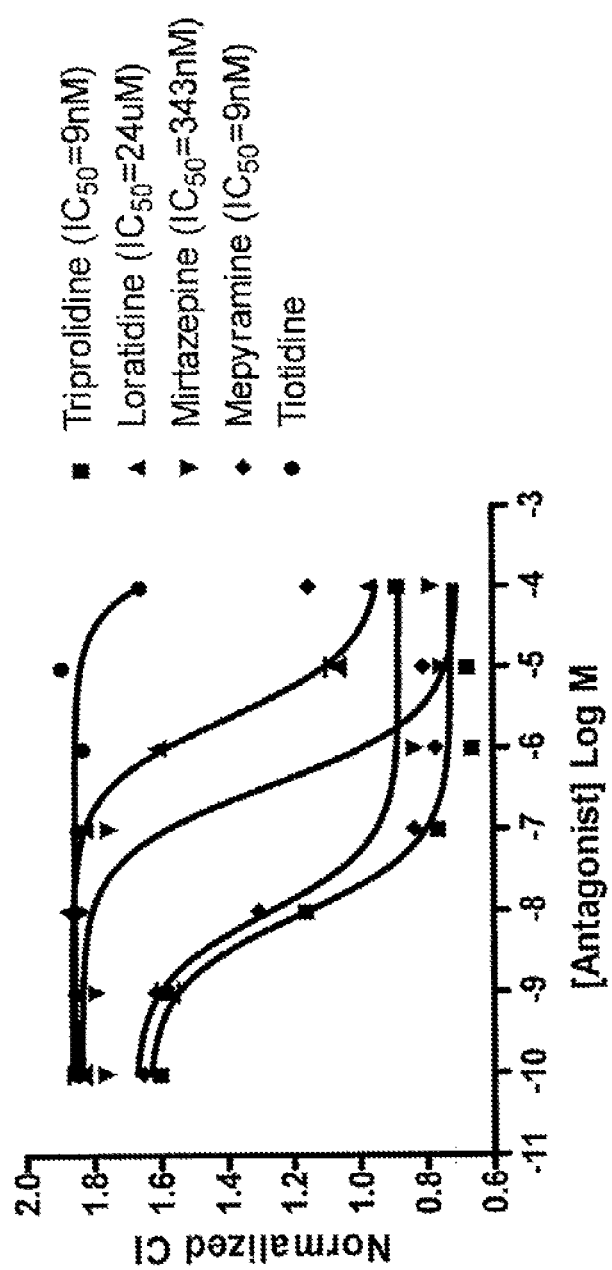
FIG. 38 depicts a application of RT-CES System to rank the potency of selective H1 antagonists on hH1-C1 cells. A panel of selective H1 antagonists and H2 antagonist (for negative control purpose) were chosen to test on hH1-C1 cells by using RT-CES system. The cell lines were seeded at 50,000 cells per well of ACEA E-plates. The cells were continuously monitored using the RT-CES system. At the indicated time point, increasing concentrations of a given antagonists were added to the cells 10 min prior to the addition of a fixed concentration of histamine (20 nM) and the cell response was monitored every 3 minutes by the RT-CES system. Four chosen H1 antagonists (triprolidine, loratidine, mirtazepine and mepyramine) blocked histamine-induced CI increases in a concentration-dependent manner with different potencies as reflected by $IC_{50s}$ indicated. H2 selective antagonist tiotidine did not block histamine-induced CI responses at the highest concentration (10 μM) tested.

Example 7: Application of RT-CES System for Ranking the Potency of Antagonists and for Screening Inverse Agonists A. Using RT-CES System to Rank the Potencies of Antagonists: Potential Application of Compound Screening In order to further explore the possibilities of compound screening by RT-CES system, we used the hH1-C1/histamine pair to compare the potencies of a panel of selective H1 antagonists. As shown in FIG. 38, RT-CES system can readily rank the potencies of the antagonists. The order of potency ranking is loratidine>mirtazepine>triprolidine=mepyramine. Tiotidine, a selective H2 antagonist was used a negative control.

B. Using RT-CES System to Discovery Potential Inverse Agonists

Figure 39:
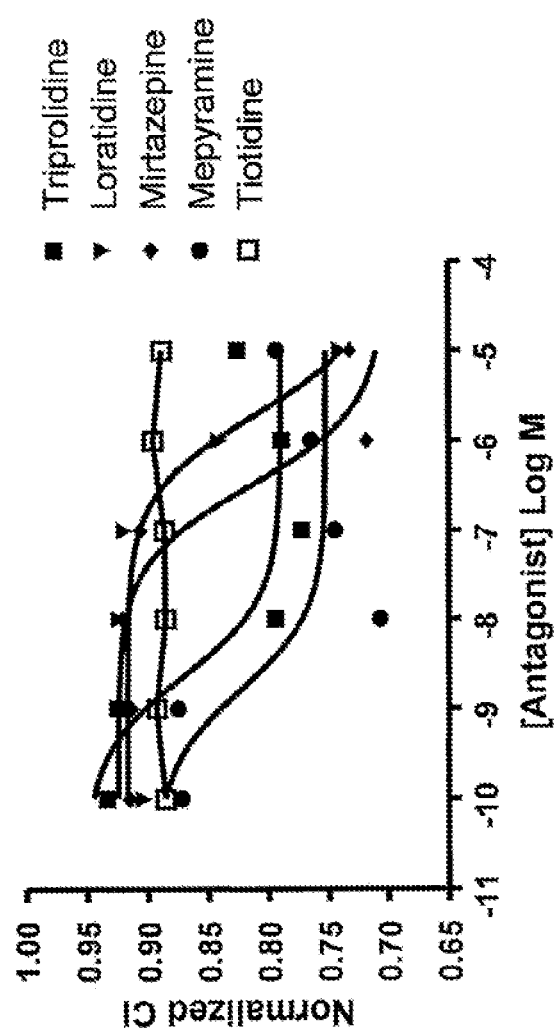
FIG. 39 depicts an application Of RT-CES System to rank the potency of selective H1 antagonists as inverse agonists. The cell lines were seeded at 50,000 cells per well of ACEA E-plates. The cells were continuously monitored using the RT-CES system. Increasing concentrations of a given antagonist were added to the cells and the cell response was monitored every 3 minutes by the RT-CES system. Four chosen H1 antagonists (triprolidine, loratidine, mirtazepine and mepyramine) alone causes a concentration-dependent decreases of CI with different potencies as indicated $EC_{50s}$ and while H2 antagonist (tiotidine) did not induce any changes in CI at the highest concentration (10 μM) tested.

One of the new applications of RT-CES system described in this application is its potential use for inverse agonist characterization. Recent literatures have revealed that some of the antagonist has the intrinsic activities of inverse agonist. We demonstrated here that application of selective H1 antagonist alone produced a CI profile opposite to what agonist generated; namely, agonist (histamine) increases the CI while inverse agonist decreases the CI. The RT-CES system can also rank the potencies of a panel of inverse agonists. As shown in FIG. 39, the order of potency ranking as the inverse agonists is loratidine>mirtazepine>triprolidine>mepyramine. Tiotidine, a selective H2 antagonist does not have the activities of inverse agonist.

Example 8: Dynamic Monitoring of G-Protein Couple Receptor (GPCR) in Living Cells Using the RT-CES System This example further expands on the utilization of the RT-CES technology to develop a label-free and real-time cell-based assay for monitoring functional activation of GPCRs in living cells. We demonstrate that this assay can be used with both engineered cell lines expressing recombinant GPCRs coupled to different G-proteins and more importantly with cell lines expressing endogenous levels of GPCRs. In addition, the non-invasive nature of the RT-CES readout makes it especially attractive as a tool for GPCR screening and research because multiple stimulations with the same agonist/antagonist or different agonist/antagonist in different combinations can be carried out in the same well. Also, the dynamic nature of the cell response to a particular agonist provides high content information regarding the signaling pathways being activated and can also be used to screen for antagonists and inverse agonists.

A. Materials and Methods

Cell Culture.

All the cells used in this study were purchased from ATCC unless indicated otherwise. The cells are cultured in a standard humidified incubator at 37° C. with 5% $CO_2$. C6 cells and HeLa cells were maintained in Dulbecco's modified Eagle's medium (DMEM) supplemented with 10% fetal calf serum, 2 mM glutamine and 1% penicillin/streptomycin. Chinese hamster ovary (CHO) cells were maintain in Ham's F12 medium supplemented with 10% fetal calf serum, 2 mM glutamine and 1% penicillin/streptomycin. Cell line stably expressing human recombinant histamine receptor 1 (H1), human vasopressin 1a (V1a) and human recombinant dopamine receptor 1 (D1) were obtained form Euroscreen and maintained in Ham's F12 medium supplemented with 10% fetal calf serum, 2 mM glutamine, 1% penicillin/streptomycin and 400 μg/mL G418. Cell line stably expressing human recombinant 5-hydroxytryptamine receptor 1A (5-HT1A) was obtained form Euroscreen and maintained in Ultra-CHO medium supplemented with 1% penicillin/streptomycin and 400 μg/mL G418.

Reagents.

All the reagents were purchased form Sigma (St. Louis, Mo.) unless indicated otherwise Loratidine, mirtazepine, mepyramine, triprolidine, tiotidine were purchased form Tocris (Ellisville, Mo.)

RT-CES Measurement of Cell-Electrode Impedance.

The detailed experimental procedures have been described previously (Abassi et al, Label-free, real-time monitoring of IgE-mediated mast cell activation on microelectronic cell sensor arrays, in J. of Immunological Methods. Vol: 292, pp 195-205, 2004; Solly et al., Application of real-time cell electronic sensing (RT-CES) technology to cell-based assays, in Assay and Drug Development Technologies. Vol: 2, pp 363-372, 2004.) Briefly, 50 μL of selective medium was added to wells of ACEA's 16× E-plates to obtain background readings followed by the addition of 150 μL of cell suspension containing the indicated number of cells. The E-plate containing the cells were allowed to incubate at room temperature for 10 minutes prior to being placed on the device station in the 37° C. $CO_2$ incubator for continuous recording of impedance as reflected by Cell Index (CI). The cells were allowed to attach and spread typically for 6-8 h to reach a stable base line before the addition of agonists. Typically, 5 μL of 40× stock solution of agonist was gently added to the well and recording was resumed. For pharmacological and mechanistic studies, antagonists or inhibitors were added to the cells 5-10 min prior to the agonist application. The results were expressed by normalized CI, unless indicated otherwise, which are derived from the ratio of CIs before and after the addition of the compounds. For concentration-dependent study, maximal response (usually 1-2 h after the ligand application) of a given concentration of the compound was used to plot the concentration-dependent curve and $EC_{50}$ or $IC_{50}$ were calculated by Prism (San Diego, Calif.).

Fluorescence Microscopy.

H1 cells and V1a cells were seeded in 16-well Lab-tec chamber slides and allowed to attach and spread for 24 h. The cells were stimulated by 100 nM histamine for 5 min and washed 3 times with PBS before fixation. The cells were fixed in 4% paraformaldehyde and permeabilized in PBS containing 0.2% Triton X 100. After washing, the fixed cells were blocked by PBS containing 0.5% BSA. The cells were stained with phalloidin conjugated with FTIC and a monoclonal anti-paxillin antibody from Sigma (St. Louis, Mo.). The cells were washed 3 times with PBS and visualized and imaged by using a Nikon E400 epifluorescence microscope and Nikon ACT software.

B. Dynamic Monitoring of GPCR Activation in Living Cells by RT-CES System.

The RT-CES system is composed of a 16× or 96× device station which fits inside the tissue culture incubator, an electronic analyzer and a computer which runs the software and operates the entire system. At the core of the system are 16× and 96× electronic plates (E-Plates™) with integrated microelectrodes in the bottom of the wells. Adherent cells are cultured on the surface of the sensors and the presence or absence of cells sensitively and precisely affects the electronic and ionic passage between cell culture media and the microelectrodes. Thus, interrogating the electrode impedance provides succinct information about the biological status of the cells such as proliferation, morphological changes and cell death.

In order to determine if the RT-CES system can be used to dynamically monitor the functional activation of GPCRs, CHO-K1 cells expressing the human H1 histamine receptor (H1) and 1321-N1 cells expressing the human vasopressin receptor (V1a) were seeded on the E-PLATES and stimulated with histamine and vasopressin, respectively (FIGS. 40A-D). Both histamine and vasopressin induced an immediate and transient increase in CI (FIGS. 40A and 40C). The maximal response for H1 cells was at 40 min after histamine addition while for V1a cells it was at 90 min (FIGS. 40A and 40C). Both histamine and vasopressin act through Gq and have also been shown to modulate the actin cytoskeleton and its regulatory proteins such as focal adhesion kinase (FAK) and paxillin. In order to determine if histamine and vasopressin lead to modulation of the actin cytoskeleton and its signaling proteins, H1 cells and V1a cells were stimulated with histamine and vasopressin, respectively, fixed, stained with FITC-Phalloidin and anti-paxillin mAb (FIG. 40B). Histamine treatment of H1 cells lead to an immediate (5 min) induction of membrane ruffles and translocation of paxillin to the site of membrane ruffles which is indicative of active actin remodeling (FIG. 40B). Similarly, vasopressin also induced formation of membrane ruffles and translocation of paxillin to these sites (FIG. 40D). In summary, the RT-CES system can detect the functional activation of GPCR based on its ability to modulate the actin cytoskeleton and cell adhesion.

C. Dynamic and Quantitative Monitoring of Recombinant GPCRs Coupled to Different Signaling Pathways.

Figure 42B:
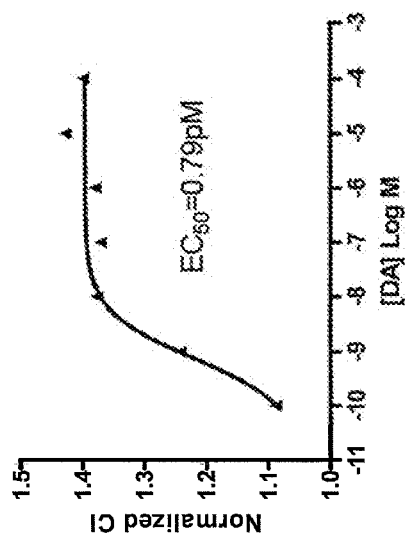
FIG. 42A-D depict a pharmacological study of D1 cell line (Gs) and 5-HT1A cell line (Gi): Generation of $EC_{50s}$. D1 or 5-HT1A cell lines were seeded at 25,000 or 12,000 cells per well of ACEA E-plates. The cells were continuously monitored using the RT-CES system. At the indicated time point (arrows), increasing concentrations of dopamine (FIG. 42A) or 5-HT (FIG. 42C) were added to the cells and the cell response was monitored every 3 min by the RT-CES system. CI traces were shown. Plotting the peak cell index responses versus the corresponding log concentrations allows for calculation of the $EC_{50s}$ of DA (FIG. 42B) and 5-HT (FIG. 42D). Normalized cell index shown in (FIGS. 42A and 42C) at a given time point was calculated by dividing the Cell Index at the time point by the Cell Index at a reference time point. Here the reference time point was the last time point of the measurement before adding dopamine (FIG. 42A) or 5-HT (FIG. 42C) to the cells.
Figure 42D:
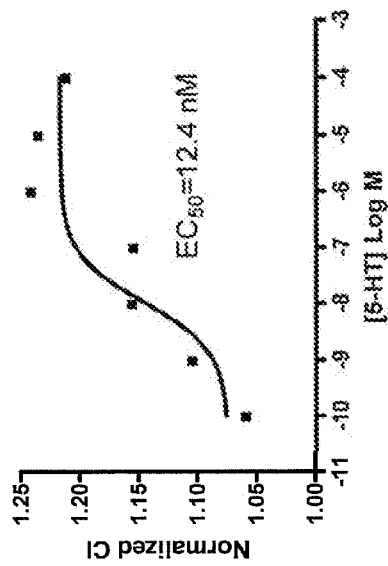
Figure 42A:
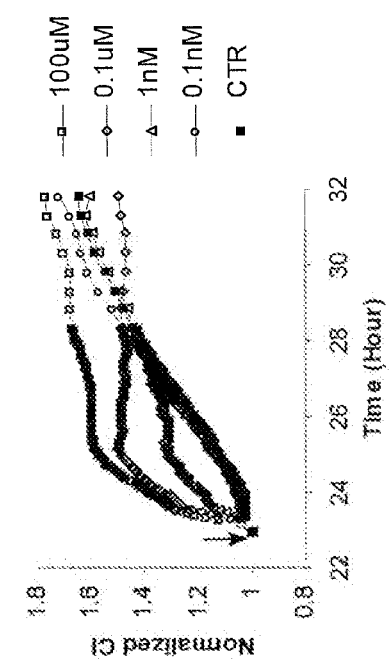
Figure 42C:
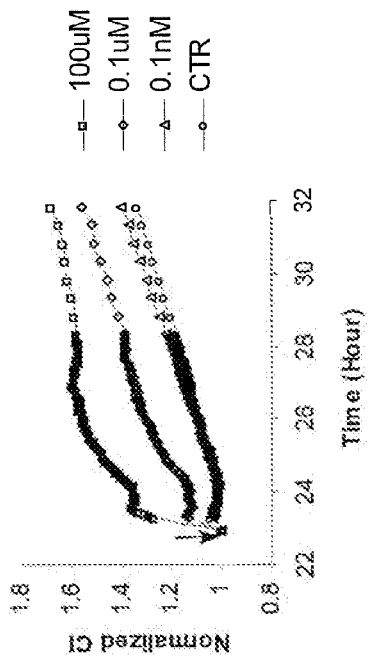

In order to further extend the findings discussed above, H1 cells were seeded in E-plates, treated with increasing concentration of histamine and continually monitored by RT-CES system. As depicted in FIG. 41A, histamine leads to a transient and dose-dependent increase in CI. To obtain a dose-response curve the log concentration of histamine was plotted against the normalized CI and the approximate $EC_{50}$ value obtained from this plot was 1.7 nM. Similarly, vasopressin causes a transient and dose-dependent increase in CI (FIG. 41C) with $EC_{50}$ of 155 pM (FIG. 41D). To determine if the functional activation of GPCRs coupled to other signaling pathways such as Gs or Gi can also be monitored on RT-CES system, CHO-K1 cells expressing the human dopamine 1 receptor (D1) coupled to Gs, or the human 5HT1A receptor (5-HT1A) coupled to Gi, were seeded on E-plates and stimulated with increasing concentrations of their respective ligands. As shown in FIGS. 42A and 42C, both cell types are activated in a dose-dependent manner. To generate a dose-response curve, the peak normalized CI value was plotted versus the log concentration of the agonist. Stimulation of D1 receptor by dopamine gave an $EC_{50}$ value of 0.79 pM (FIG. 42B), while 5-HT1A receptor by 5-HT stimulation gave an $EC_{50}$ value of 12.4 nM (FIG. 42D). In summary, the RT-CES system can detect the functional activation of GPCRs coupled to the different signaling pathways, which traditionally requires different detection technologies and instrumentation such as calcium or IP3 measurement (Gq) and cAMP measurements (Gs and Gi).

D. Dynamic Monitoring of Endogenously Expressed GPCR in Living Cells.

One of the challenges encountered by current label-based assays such as calcium measurements is that the cells have to be engineered to express promiscuous G proteins coupled to the calcium pathway. Alternatively, receptors may need to be overexpressed in order to obtain sufficient measurable signal. Once again all these artificial manipulations may ease the burden of screening large sets of compounds; however, physiological relevance of the findings will need to be supplemented with other experiments. The number of assays available to measure the functional activation of endogenous GPCRs in their natural and physiologically relevant settings is limited. We wanted to determine if RT-CES system can monitor the functional activation of endogenous GPCRs coupled to different signaling pathways. HeLa cells were seeded in E-plates and stimulated with increasing concentrations of histamine. As shown in FIG. 43A, histamine stimulation of HeLa cells leads to a dose-dependent and transient increase in cell index. The kinetics and amplitude of histamine-mediated response in HeLa cells are significantly different from those of H1 cells. Primarily, this can be explained by cell type specificity in terms of histamine signaling. Also, other histamine receptors in addition to H1 may be present in HeLa cells which can contribute to the amplitude and duration of the response. The calcitonin receptor is coupled to the Gs pathway. To determine if endogenous activation of calcitonin receptor can be detected by the RT-CES system, CHO-K1 cells were seeded on E-plates and stimulated with the indicated concentrations of calcitonin (FIG. 43C). As shown in FIG. 43C, calcitonin leads to a robust and transient increase in CI and plotting normalized CI versus log concentration of the ligand gives a dose-response curve with an $EC_{50}$ of 0.385 nM (FIG. 43D). On the contrary, 131 adrenergic receptor stimulation in C6 cells by isoproterenol reveals an opposite changes of CI. As shown in FIG. 43E, isoproterenol generated a dose-dependent decrease of CI with an $EC_{50}$ of 24 nM (FIG. 43F). In summary, it has been demonstrated that the RT-CES system can monitor the functional activation of GPCRs coupled to different signaling pathways for both endogenous receptors and recombinant receptors.

E. Quantitative Analysis and Ranking of Histamine Receptor Antagonists and Inverse Agonists.

In order to validate the GPCR assay using the RT-CES system we chose a panel of well-characterized and selective histamine antagonists to test and rank their potency in H1 cells stimulated with histamine. H1 cells were seeded in E-PLATES, pre-incubated with the indicated concentrations of selective H1 antagonists or H2 receptor antagonists as a control and then stimulated with a fixed concentration of histamine (20 nM). The peak normalized CI values were plotted versus the log concentrations of the antagonists. H1 receptor antagonist triprolidine, loratidine, mirtazepine and mepyramine led to a dose-dependent inhibition of histamine-mediated cellular response (previously shown as FIG. 38) with $IC_{50s}$ of 9 nM, 24 uM, 343 nM and 9 nM respectively while H2 selective antagonist tiotidine did not inhibit histamine-induced cell response at all the indicated concentrations tested. These results strongly indicate that RT-CES system can be used for the purpose of potency ranking of antagonists in a receptor subfamily specific manner. Interestingly, the H1 receptor antagonists alone gave rise to dose-dependent decreases of CI levels (previously shown as FIG. 39). This observation can be explained by the fact that all these H1 receptor antagonists have certain degrees of activities as inverse agonist (Fitzsimons et al., Mepyramine, a histamine H1 receptor agonist, binds preferentially to a G protein-coupled form of the receptor and sequesters G protein, in The Journal of Biochemical Chemistry, Vol: 279, pp 34431-34439, 2004), which impacts the basal activities of H1 receptor. Furthermore, selective H2 receptor antagonist tiotidine did not seem to affect histamine-mediated activation of the H1 cells nor did it have activity as inverse agonist indicating that the responses are specific. In summary, these results demonstrate that the RT-CES system can be used to screen selective antagonists or inverse agonists of GPCRs. Furthermore, the basal CI displayed prior to agonist addition is an actual reflection of the basal and cumulative signaling taking place inside the cell and any agent such as inverse agonists that perturb the basal signaling activity can be detected by the RT-CES system.

We have shown in this example that the RT-CES system can be used for functional screening of GPCR activity in cell-based assays. The main features which distinguish the RT-CES based assay described here from other cell-based functional assays for GPCRS are: (i) no pre- or post-labeling of the cells are necessary, saving expensive reagents and time; (ii) the readout is non-invasive and therefore cellular destruction is not required, allowing for multiple manipulations on the same cells in the same well, (iii) real-time kinetic readout which provides succinct and high content information regarding the pathways being activated, (iv) no compound interference with the detection method which can be a major problem in most optical-based assays and (v) since the readout monitors cell attachment and cell morphology which are integral components of cell viability, any compound that may be potentially cytotoxic or may have other adverse effects can be detected. Finally, the RT-CES system provides novel readouts for GPCR functions in living cells and provides another vantage point to increase our understanding of GPCR functions.

Example 9: Dynamic Monitoring of COS-7 Cells During Stimulation or Inhibition of a RTK The RT-CES™ system was used to dynamically monitor the inhibition and/or stimulation of a Receptor Tyrosine Kinase (RTK). Furthermore the RT-CES™ system allowed the determination of the EC50 and IC50 of the RTK.

Cell Culture and Reagents.

COS7 cells were acquired from ATCC. They were maintained in DMEM supplemented with 10% fetal bovine serum and incubated at 37 deg with 5% $CO_2$. From the time the cells were plated through the experimental process, cells were continually monitored with the RT-CES system. Cells were plated on sensor plates at $1 \times 10^4$ cells per well and incubated overnight. During the day of assay, cells were serum starved in DMEM supplemented with 0.25% BSA for a total of 4 hours. If treated with inhibitors, cells were preincubated with inhibitors during the last hour of serum starvation and stimulated with growth factors. Inhibitors (Calbiochem) and LOPAC enzyme inhibitor ligand set (Sigma) were resuspended and stored according to manufacturers instructions.

ELISA.

Cells were plated on sensor plates at $1\times10^4$ cells per well and incubated overnight. During the day of assay, cells were serum starved in DMEM supplemented with 0.25% BSA for a total of 4 hours. If pretreated with inhibitors, cells were preincubated with inhibitors during the last hour of serum starvation and then stimulated with growth factor for 15 minutes. After growth factor stimulation, cells were washed 2 times with cold PBS and lysed. ELISA (Biosource) assay was performed to detect total EGFR and phospho-EGFR (1068) and read at 450 nm.

Statistical and Data Analysis.

All dose response curves were generated by plotting the average of % control+/−standard deviation versus ligand or inhibitor concentrations. The average % control was calculated relative to samples treated with growth factor alone minus inhibitor of quadriplicate samples. The $EC_{50}$ for ligands and $IC_{50}$ for inhibitors were determined from fitted curve generated by XLfit 4.0.

Results and Discussion.

Figure 44A:
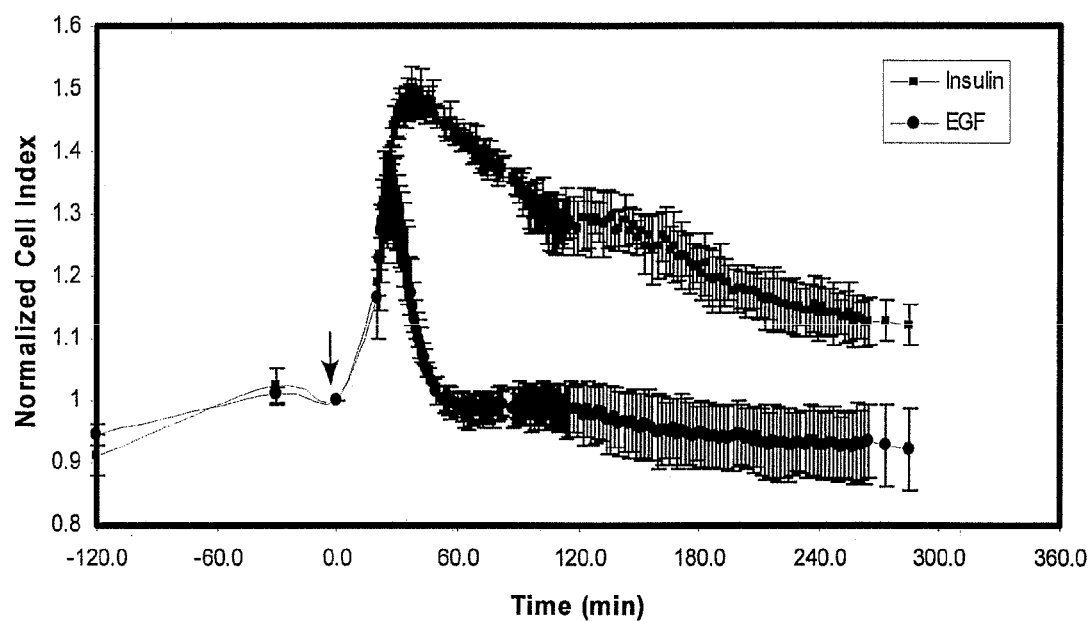
FIGS. 44A-B depict an assessment of specificity of cellular response to EGF and insulin treatments. COS7 cells were pretreated for 1 hour with either a specific EGFR inhibitor or vehicle. Cells were then stimulated with insulin or EGF.
Figure 44B:
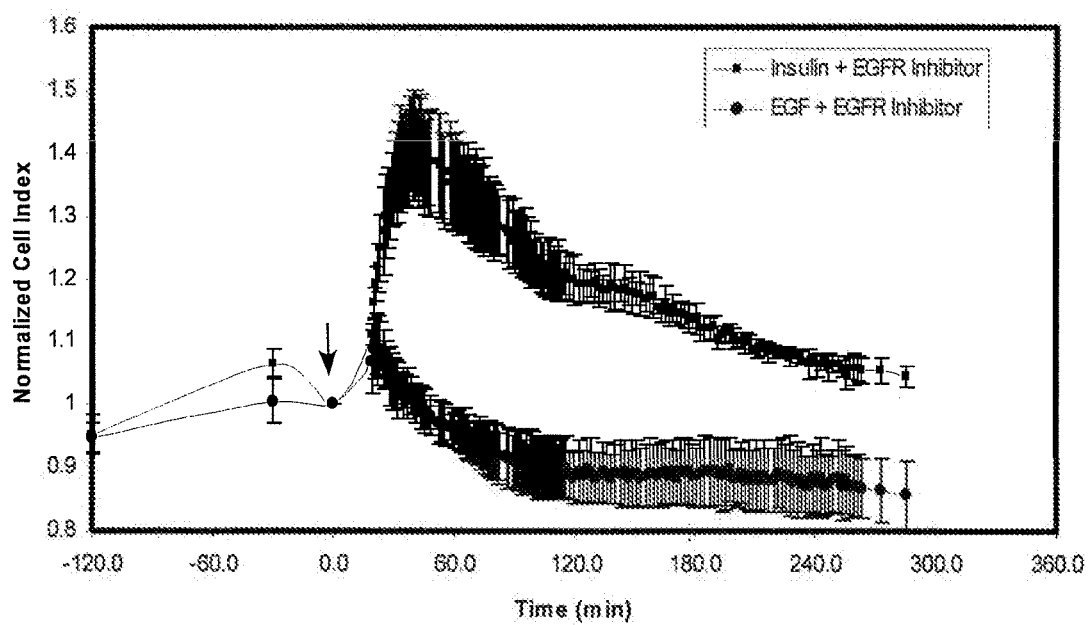

Cells plated on the ACEA RT-CES sensor plates (E-Plates™) were continuously monitored from the time of plating to the end of the experiment. This allows for continuous monitoring of cells and assay conditions for quality control before and during the time of experimentation. $1\times10^4$ COS7 cells plated on ACEA RT-CES sensor plates were serum starved for a total of 4 hours and stimulated with 25 ηg/mL EGF or insulin and monitored every minute from the time of ligand addition. Ligand addition results in a rapid and transient increase in cell index for both EGF and insulin treated cells (FIG. 44A). This increase was immediately followed by a decrease in cell index, with EGF showing a faster rate of decrease in cell index over time compared to insulin. The transient increase in cell index is a result of cytoskeletal rearrangements as a result of growth factor treatment. It is well documented that one of the intracellular signals RTKs activate are cytoskeletal changes resulting in membrane ruffling, lamellipodia and filopodia formation. To characterize the specificity of these responses to ligand treatment, cells were pretreated for one hour with 10 µM of the EGFR inhibitor (EGFRI), 4557 W, prior to addition of EGF or insulin. Since the inhibitor is specific to EGFR, application of the EGFRI should only affect cellular changes induced by EGF treatment. Indeed, after ligand addition, the transient increase in cell index was only detected on cells treated with insulin and not EGF (FIG. 44B). The absence of cell response in EGF treated cells was a result of the specific inhibition of EGFR and its signaling pathways by the EGFRI. The specificity of this inhibitor and ligand response is demonstrated by the lack of effect on the transient increase in cell index of insulin treated cells.

Figure 45A:
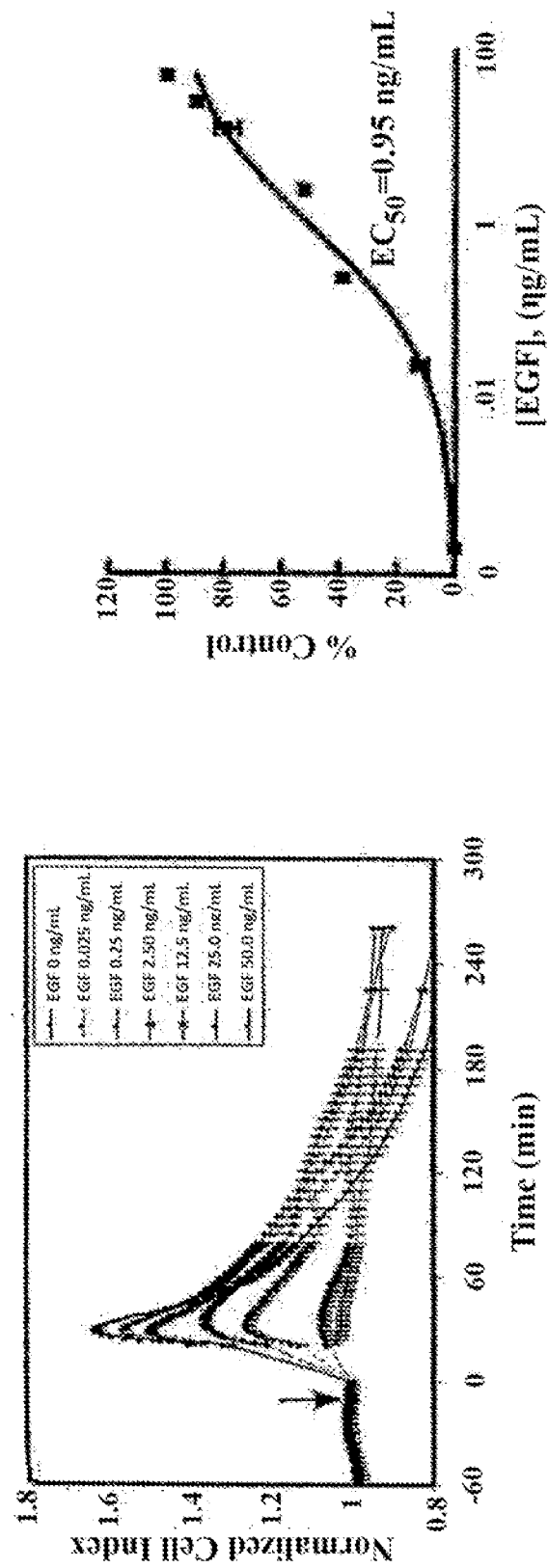
FIGS. 45A-C depict a characterization of COS7 cellular response to EGF and HGF treatments. Time-dependent normalized-cell-index traces are shown for COS7 cells treated with EGF (FIG. 45A) and HGF (FIG. 45B). Maximum cell indices (i.e., cell indexes) were determined from each trace corresponding to treatment of cells with one concentration of EGF or HGF and dose response curves were generated by plotting % control (relative to the normalized-cell-index response of the sample treated with maximum ligand concentration) versus ligand concentration.
Figure 45B:
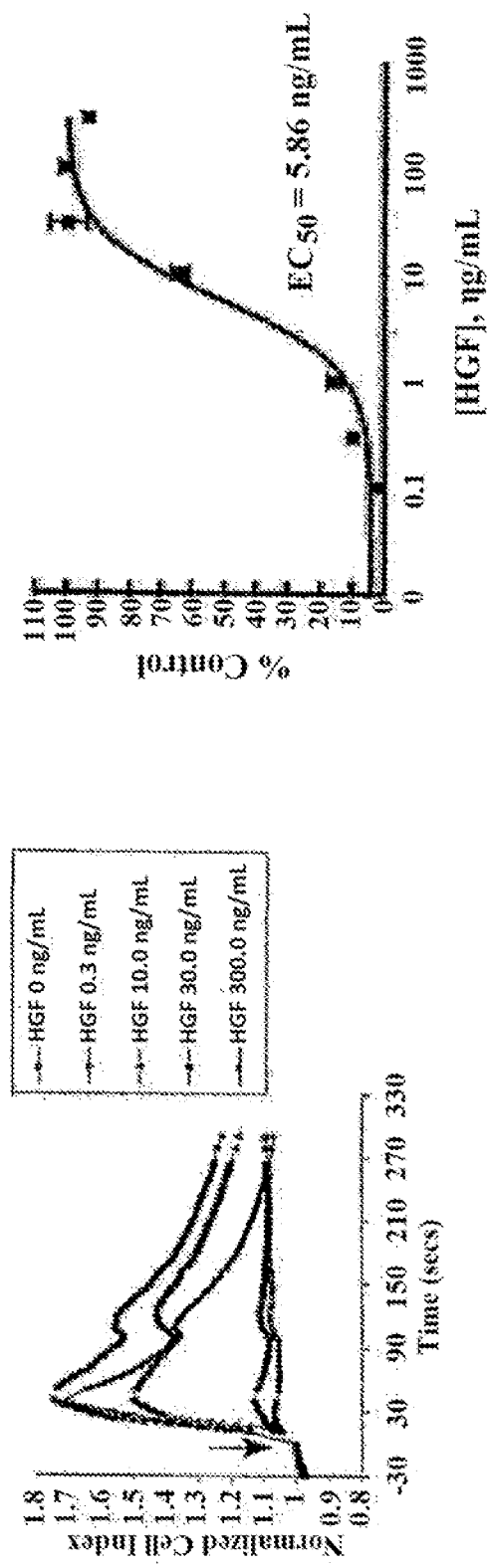
Figure 45C:
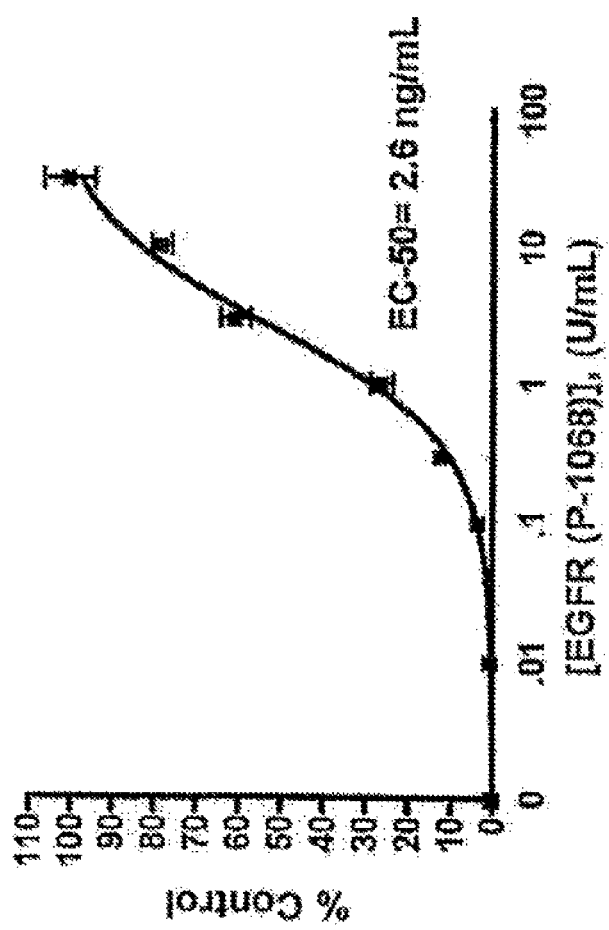

To further characterize this cellular response, a wide range of EGF and insulin concentrations were used to determine the ligand $EC_{50}$ (FIGS. 45A and 45B). The cell index was measured for each concentration every minute over several hours. Cells treated with low concentration of the ligand showed transient small changes in peak cell index, while an increasing concentration of ligand resulted in an increase in the amplitude of the peak of the cell index. The magnitude of the cell index was directly related to the concentration of ligand used and reached a saturable response. From these trace the maximum cell index for each ligand concentration were determined and the % control relative to the response of the sample treated with the maximum ligand concentration calculated and plotted versus ligand concentrations. From the fitted curves the EGF and insulin $EC_{50}$ were calculated to be 0.95 ng/mL and 8.5 ng/mL, respectively. An important consideration of the assay is to show that these results are consistent with other RTK assays. To compare the $EC_{50}$ values derived from ACEA RT-CES with a well-established assay used to monitor RTK activity, ELISA assays were performed to detect phosphorylated EGFR on COS7 cells treated with varying concentrations of EGF (FIG. 45C). From the fitted curve an $EC_{50}$ value of 2.6 ng/mL was calculated. This value was comparable to $EC_{50}$ values determined using the ACEA RT-CES demonstrating the use of this system as an alternative or complementary assay to existing RTK assays.

Figure 46A:
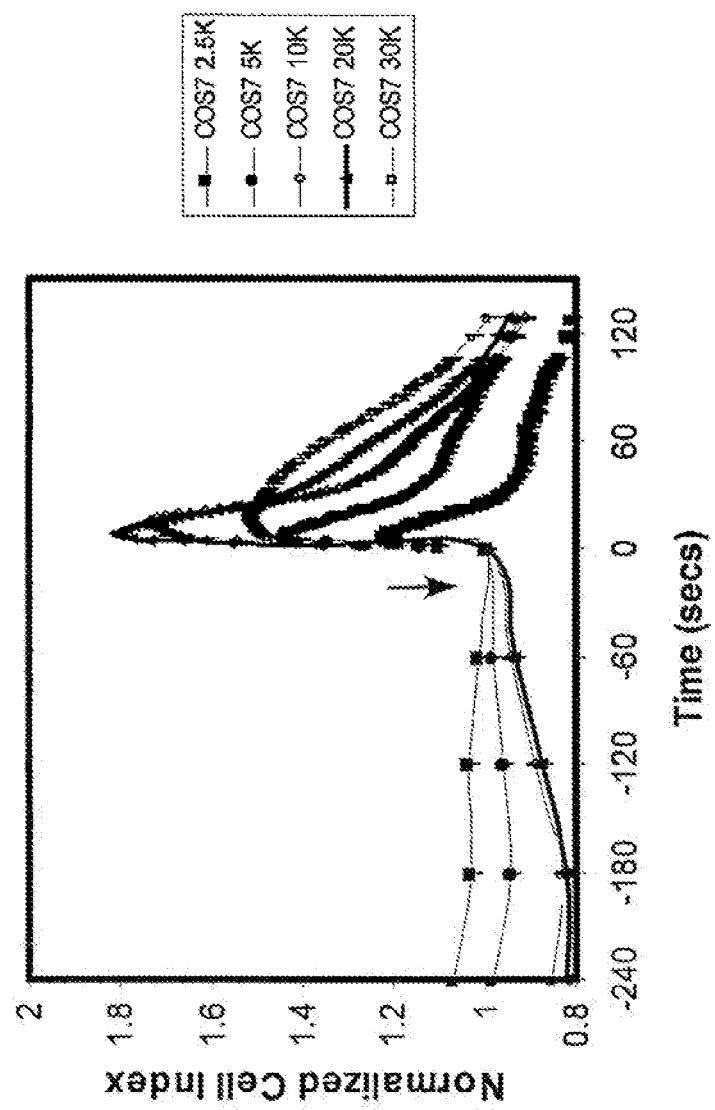
FIG. 46A-B depict an optimization of assay conditions for screening of inhibitors against RTKs.
Figure 46B:
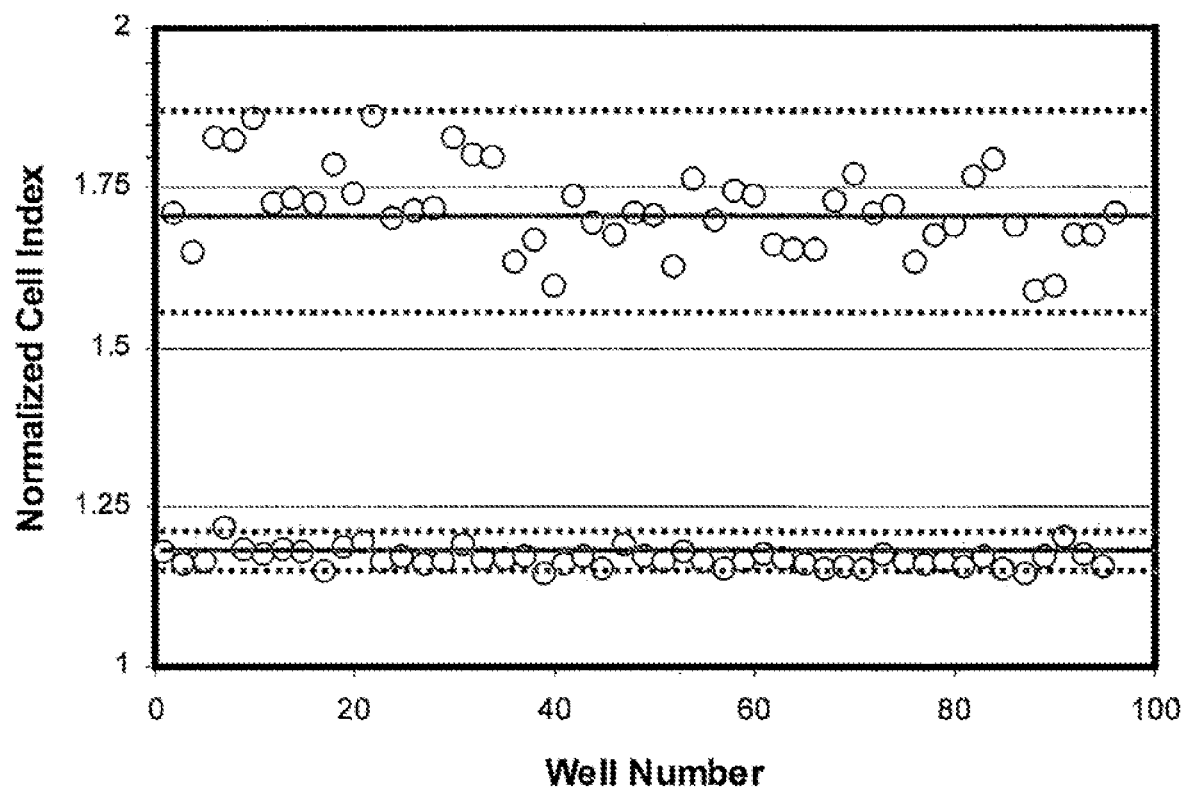

To determine the appropriate conditions to initiate a screen for EGFR inhibitors using the ACEA RT-CES system, a few parameters were optimized to maximize the signal to noise and the quality of the data. First, the optimum concentration of cells needed to achieve the maximum amount of signal was determined (FIG. 46A). A range of COS7 cells were plated and tested for response to EGF. The maximum peak in cell index as a result of EGF treatment was observed to increase with increasing number of cells plated. However, this response reached a critical cell density wherein further increase in cell number resulted in a decrease in cell index. This decrease is thought to be due to the absence of available space between the cells preventing the lateral expansion cell membrane over the sensors during ligand mediated cytoskeletal rearrangement. Second, it is also necessary to titrate the ligand concentration to determine the maximum amount of ligand needed to produce the highest signal and appropriate ligand concentration for the type of assay used (FIG. 46A). Having maximized these conditions, the statistical parameter in terms of Z' factor and S/N value of the assay was determined and evaluated to assess the quality of the assay (FIG. 46B). The Z' factor is a statistical characteristic for evaluating the assay quality. The Z' factor calculated showed a value of 0.6, which is above the acceptable limit for a robust and consistent assay, and the S/N value of 38.

Figure 47A:
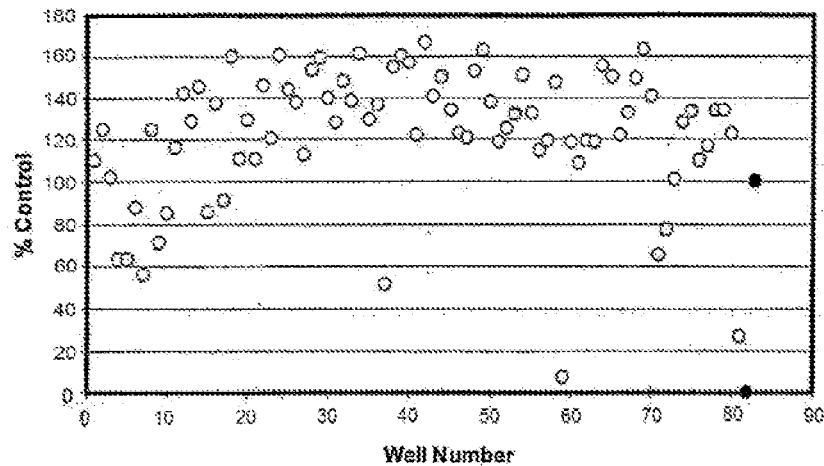
FIG. 47A is a graphical representation of a screen of 81 compounds mostly from Sigma's enzyme inhibitor Ligand Set. Compounds were screened in singlets at 5-10 µM concentrations. Red circle represents negative control and blue circle represent positive control.
Figure 47B:
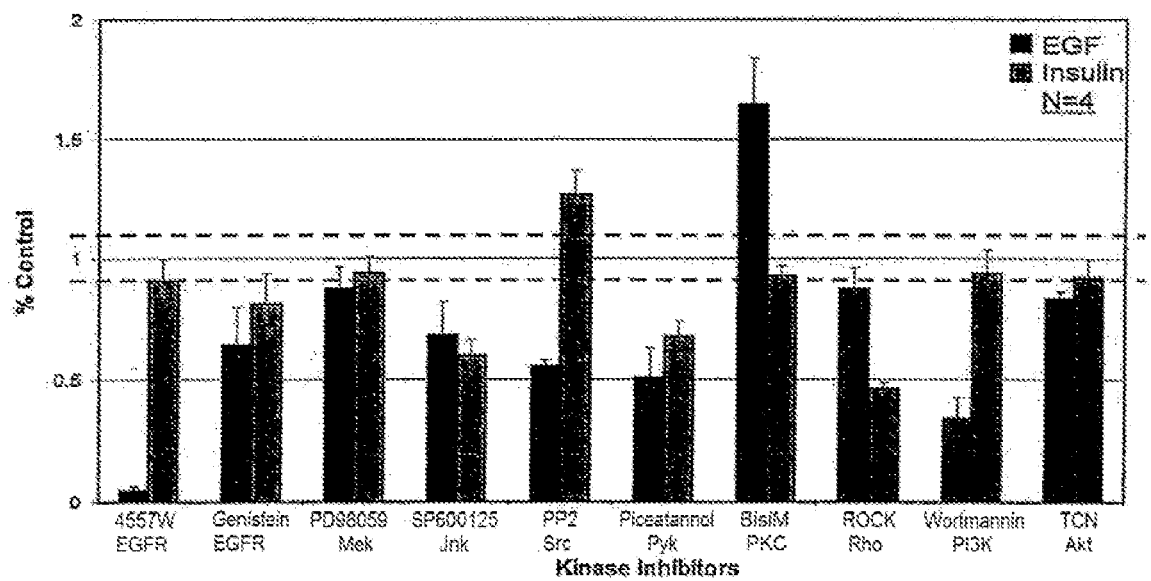
(FIG. 47B) A collection of kinase inhibitors were screened for inhibition of EGFR activity.
Figure 47C:
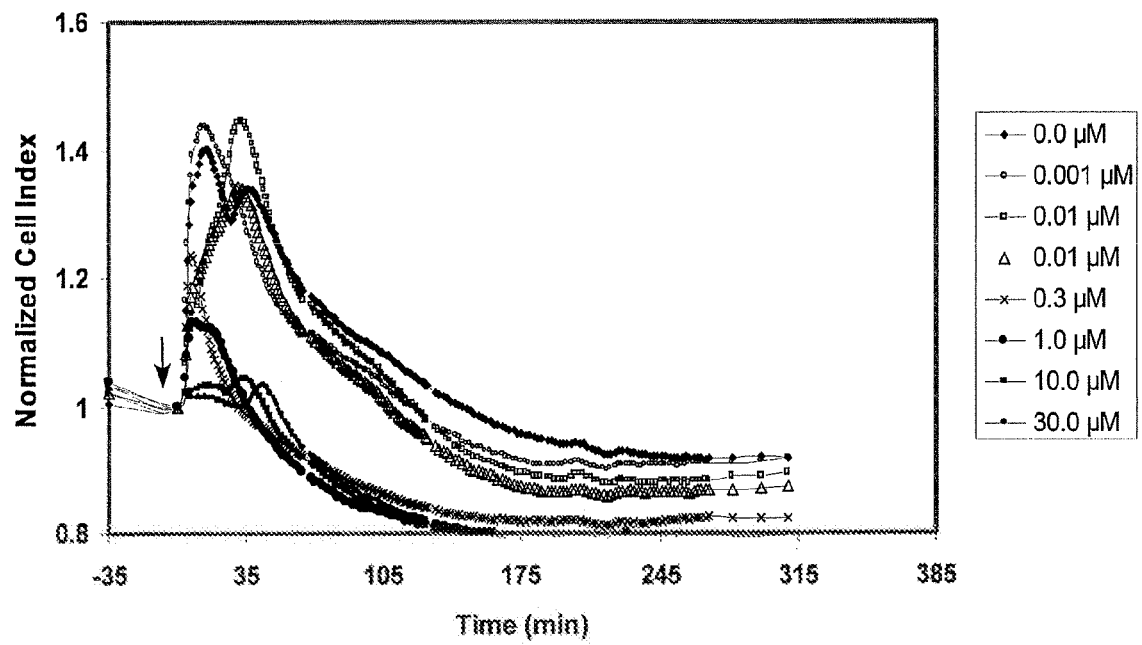
(FIG. 47C-D) EGFRI, 4557 W, was identified as potent inhibitor of EGFR signaling from both screens. Cellular response to EGF after pretreatment with varying concentration of inhibitor were measured and dose response curves generated by plotting % control of maximum cell index versus ligand concentration.
Figure 47D:
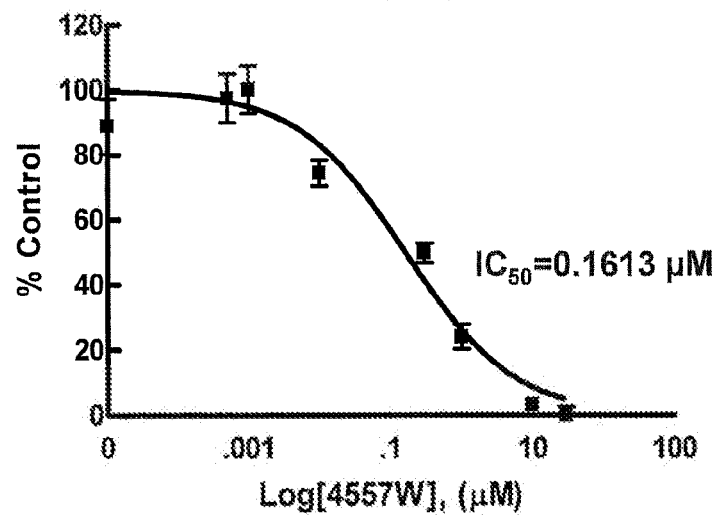

In order to validate this assay a screen was conducted of a diverse collection of small molecule inhibitors from Sigma (FIG. 47A). This library was supplemented to include a specific EGFRI. The library was arrayed in a 96-well format and contains several wells of full activity (positive) and zero activity (negative) reference controls. Sigma's inhibitor ligand set was screened at a single concentration between 5-10 µM. Maximum cell index as a result of EGF treatment was determined for each inhibitor treated samples and the % control relative to the positive reference, EGF treated cell without inhibitor, was calculated. Using 60% (or 40% inhibition) as the cutoff criteria for hit consideration, the screening study identified a single potent inhibitor. This inhibitor was the EGFRI, 4557 W, which was added to the library. The assay was also tested against a collection of kinase inhibitors and similarly identified only the EGFRI to produce the most significant inhibition (FIG. 47B-C). The inhibitor was further characterized and a dose response curve generated (FIG. 47D). From the fitted curve an IC50 of 161 ηM was calculated. This set of experiments demonstrates the ability of ACEA RT-CES system to identify a potent and selective inhibitor from a diverse library and chemically focused kinase library, and also to further characterize identified hits.

Figure 48A:
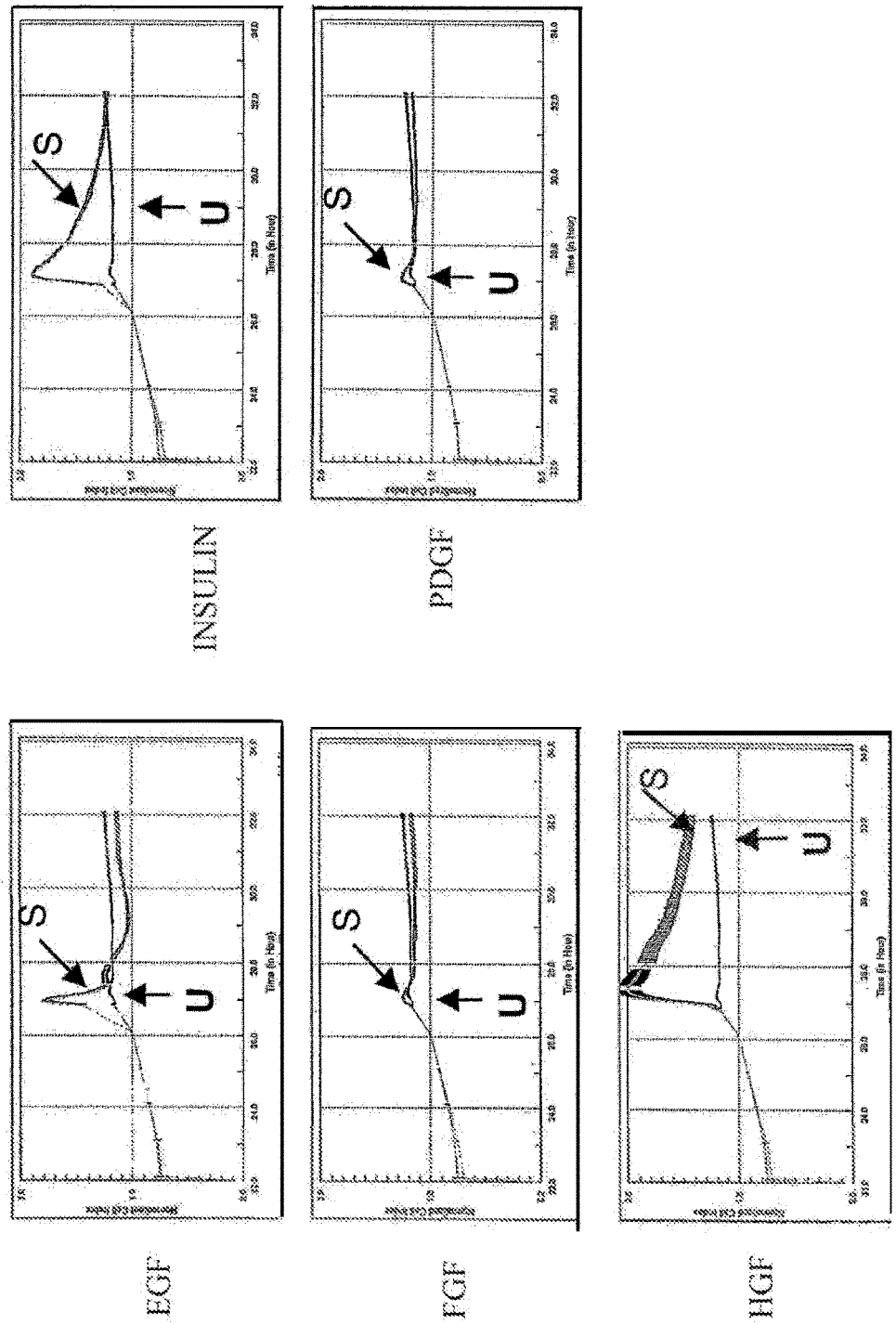
FIGS. 48A-C depict a comparison of unique signaling patterns of selected immortalized cell lines after treatment with various ligands for RTK. Cells were plated, serum starved and treated with ligands. Traces indicated with "S" represent cells treated or stimulated with ligand, and traces indicated with "U" represent cells treated with vehicle control (i.e., unstimulated). Response was measured every minute and data normalized to time point just before ligand addition. Error bars represent standard deviation of n=4. EGF=Epidermal Growth Factor; FGF=Fibroblast Growth Factor; HGF=Hepatocyte Growth Factor; PDGF=Platelet Derived Growth Factor.
Figure 48B:
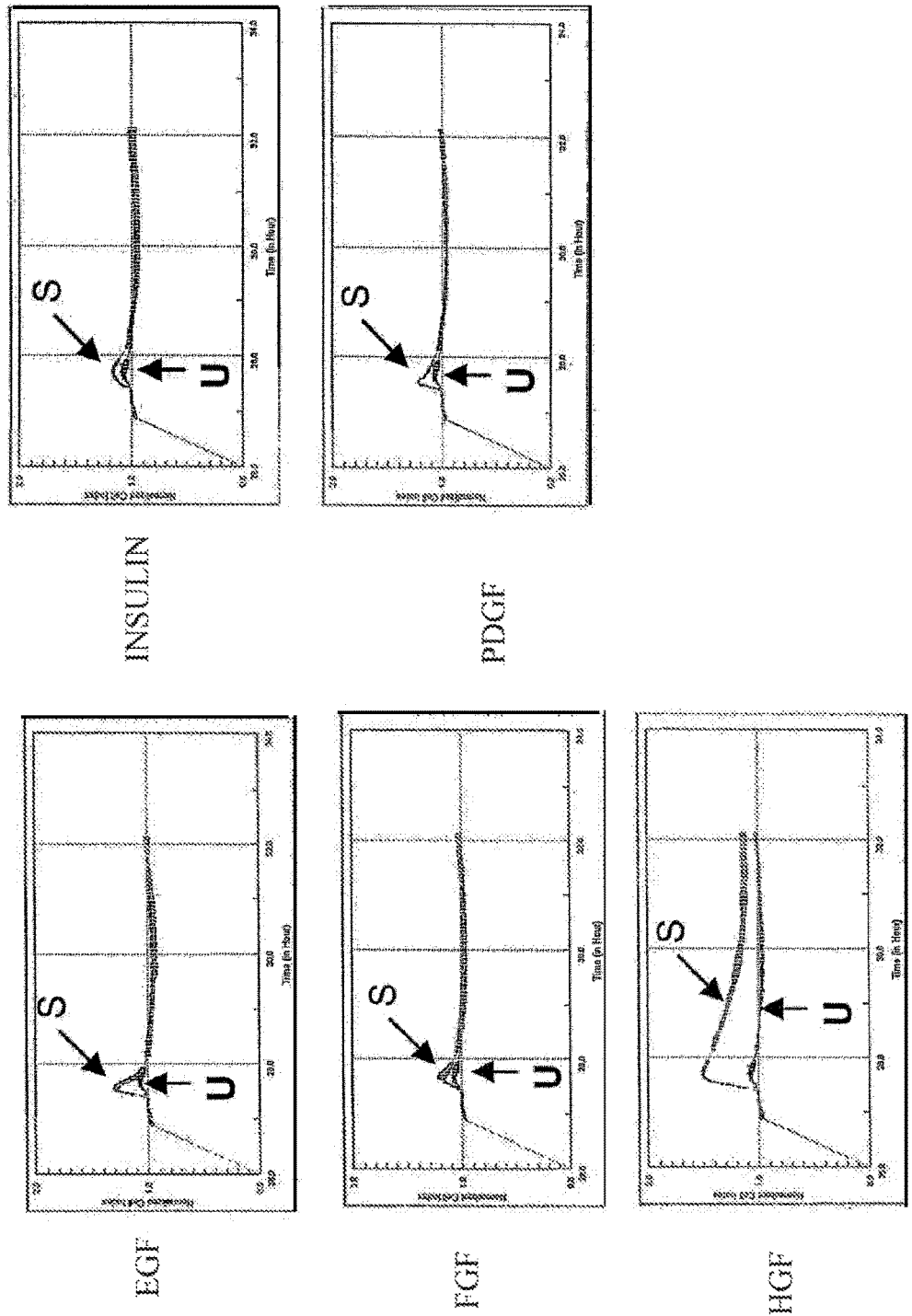
Figure 48C:
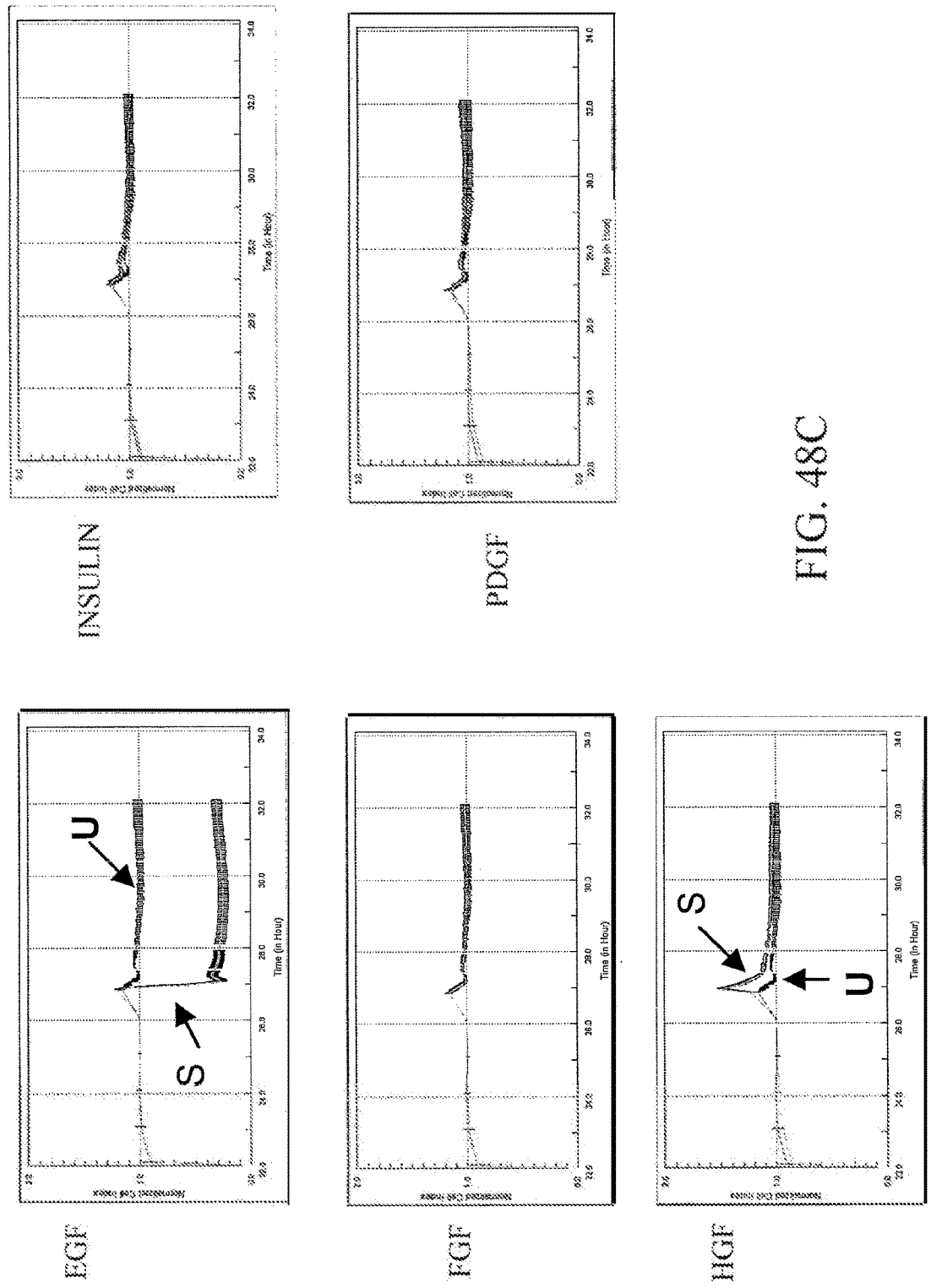

In addition to insulin and EGF, this cellular response can also be detected with treatment of HGF, FGF and PDGF in different mammalian cancer cells (FIGS. 48A-C). To explore the responses to these growth factors, several human cell lines were plated and treated with different growth factors. Cell lines such as A431 showed a robust response to EGF and HGF, while minimal response was observed to other growth factors.

In conclusion, these data demonstrate a facile and novel cell based assay for RTK activity and function. This assay quantifies morphological changes in response to growth factor treatment and therefore mimics proximal events in kinase activation. Unlike other RTK assay, this assay is cell-based, label-free and monitors cellular changes in real-time, therefore acquiring high content information regarding the state of the cell and the signaling pathways being activated. In addition, the RTK assay described here does not require expensive reagents nor suffer from assay component interference. Since the readout is non-invasive multiple treatments can be carried out in the same well and can also be used in conjunction with other existing cell-based assays for RTK. It requires very little optimization and user training, making this assay amenable for use in both primary and secondary screens.

Example 10: Method to Assess the Functional Contribution of Receptor Tyrosine Kinase Activity in Cancer Cell Proliferation In addition to morphological changes, stimulation of receptor tyrosine kinases via their cognate ligand can induce cell growth and proliferation. It has been shown that stimulation of cells via growth factors such as EGF can induce signaling pathways which induces the entry of the cells into the cell cycle and proliferation. Therefore, cellular proliferation is another method to assess the functional role of growth factor receptor tyrosine kinases. The RT-CES system can be readily used to monitor cellular proliferation, especially those of breast and lung cancer, where receptor tyrosine kinases have been shown to play an important role.

Figure 49:
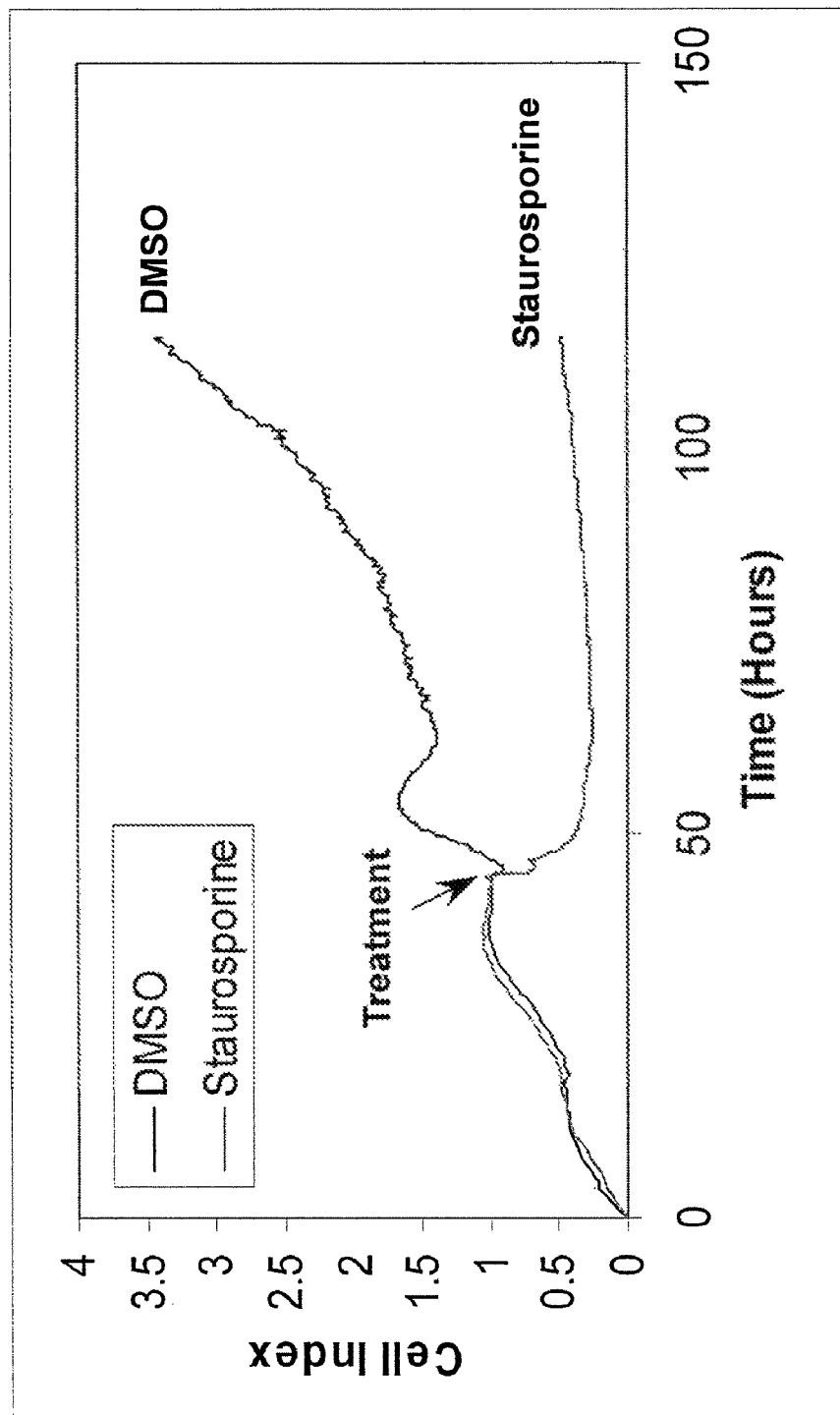
FIG. 49 depicts the monitoring of cancer cell proliferation and its inhibition by inhibitors of tyrosine kinases using the RT-CES system. MCF-7 breast cancer cells were seeded at a density of 8000 cells per well in ACEA e-plates. The cells were continuously monitored using the RT-CES system for about 48 hours at which time they were treated with staurosporine or DMSO as a control. Cellular proliferation was continually monitored by the RT-CES.

As an example we describe the monitoring of MCF-7 cancer cell proliferation and its inhibition by a general tyrosine kinase inhibitor, staurosporine. MCF-7 cells were seeded at a density of 8000 cells per well of ACEA e-plates. Cell proliferation was monitored using the RT-CES system for 48 hours at which point the cells were treated with either DMSO alone as a control or staurosporine at a final concentration of 2.5 µM (FIG. 49). The figure illustrates that the RT-CES system can be used to monitor the proliferation of cancer cells and furthermore, it can be used to assess the effect of tyrosine kinase inhibitors, which does affect EGF receptor as well as other tyrosine kinases on the proliferation of cancer cells. This method allows real-time monitoring of the effect of receptor tyrosine kinase inhibitors using the ACEA RT-CES system.

REFERENCES

1. Nambi, P and Aiyar N, 2003, G-protein coupled receptors in drug discovery, *Assay and Drug Development Technologies Vol:* 1, pp 305-310
2. Roberto E. Favoni and Alessandra De Cupis 2000, The role of polypeptide growth factors in human carcinomas: new targets for a novel pharmacological approach, *Pharmacological Reviews, Vol:*52, pp 179-205.
3. El-Rayes BF and LoRusso P M, 2004, Targeting the epidermal growth factor receptor, *British Journal of Cancer, Vol:* 91, pp: 418-424.
4. Abassi Y. A., Jackson J. A., Zhu J., O'Connell J., Wang X., Xu X 2004, Label-free, real-time monitoring of IgE-mediated mast cell activation on microelectronic cell sensor arrays. *Journal of Immunological Methods. Vol:* 292, pp 195-2$^{05}$.
5. Solly K., Wang X., Xu X., Struloviki B., Zheng W. 2004. Application of real-time cell electronic sensing (RT-CES) technology to cell-based assays, *Assay and Drug Development Technologies. Vol:* 2, pp 363-372.
6. Fitzsimons C. P., Monczor F., Fernandez N., Shayo C., Davio C. 2004, Mepyramine, a histamine H1 receptor agonist, binds preferentially to a G protein-coupled form of the receptor and sequesters G protein, *The Journal of Biochemical Chemistry. Vol:* 279, pp 34431-34439.

All of the references cited herein, including patents, patent applications, and publications, and including references cited in the Bibliography, are incorporated by reference in their entireties.

Headings are for the convenience of the reader and do not limit the scope of the invention.

What is claimed is:

1. A method of identifying a therapeutic compound for treating cancer in a human subject, the method comprising:
    a) providing a device that measures cell-substrate impedance, wherein the device comprises at least two wells, each well comprising an electrode array;
    b) culturing cancer cells in the at least two wells, wherein the cancer cells are obtained from a human subject and comprise a receptor tyrosine kinase (RTK) pathway;
    c) adding to a first well a proposed therapeutic compound that affects an RTK pathway and an RTK stimulating factor for the RTK pathway to form a test well, and adding to another well the RTK stimulating factor to form a control well;
    d) continuously monitoring cell-substrate impedance of the at least two wells and optionally determining cell indices from the monitored cell-substrate impedance; and
    e) determining a difference in impedance or optionally in cell index between the test well and control well; and if significantly different,
    f) concluding the proposed therapeutic compound is therapeutically active in the RTK pathway within the cancer cells of the human subject, thereby identifying the proposed therapeutic compound as a therapeutic compound for treating cancer in the human subject.

2. The method of claim 1, wherein the cancer cells are primary cells.

3. The method according to claim 1, wherein the cancer cells are selected from the group consisting of breast cancer cells, lung cancer cells, and colon cancer cells.

4. The method according to claim 1, wherein the cancer cells are selected from the group consisting of ovarian cancer cells, prostate cancer cells, hepatosarcoma cells, epidermoid cancer cells, and fibrosarcoma cells.

5. The method according to claim 1, wherein the cancer cells are cultured in serum-free media.

6. The method of claim 1, wherein the proposed therapeutic compound is a kinase inhibitor.

7. The method of claim 1, wherein the proposed therapeutic compound is Trastuzumab or 4-Quinazolinamine N-(3-chloro-4-fluorophenyl)-7-methoxy-6-[3-(4-morpholinyl) propoxy].

8. The method of claim 1, wherein the proposed therapeutic compound is added before the RTK stimulating factor.

9. The method of claim 1, wherein the RTK stimulating factor is a growth factor.

10. The method of claim 1, wherein the RTK stimulating factor is selected from the group consisting of epidermal growth factor (EGF), platelet derived growth factor (PDGF), a nerve growth factor (NGF), hepatocyte growth factor (HGF), and fibroblast growth factor (FGF).

11. The method of claim 1, wherein the method further comprises generating impedance-based curves for the at least two wells from the monitored impedance, wherein the impedance-based curves comprise monitored impedance values or cell index values.

12. The method of claim 11, wherein the step of determining a difference in impedance or optionally in cell index between the test well and control well is performed by comparing the impedance-based curves between the test well and the control well.

13. The method of claim 1, further comprising generating an impedance-based dose response curve of the proposed therapeutic compound.

14. The method of claim 13, further comprising determining an EC50 or IC50 of the proposed therapeutic compound from the dose response curve.

15. The method of claim 1, further comprising determining an IC50 of the proposed therapeutic compound.

\* \* \* \* \*